(12) United States Patent
Chakravarty et al.

US011292782B2

(10) Patent No.: US 11,292,782 B2
(45) Date of Patent: Apr. 5, 2022

(54) DIARYLHYDANTOIN COMPOUNDS AND METHODS OF USE THEREOF

(71) Applicant: Nuvation Bio Inc., San Francisco, CA (US)

(72) Inventors: Sarvajit Chakravarty, Edmond, OK (US); Son Minh Pham, San Francisco, CA (US); Jiyun Chen, San Francisco, CA (US); Jayakanth Kankanala, Saint Paul, MN (US); Jeremy D. Pettigrew, Vancouver (CA); Anjan Kumar Nayak, Noida (IN); Anup Barde, Noida (IN); Brahmam Pujala, Noida (IN)

(73) Assignee: Nuvation Bio Inc., San Francisco, CA (US)

( * ) Notice: Subject to any disclaimer, the term of this patent is extended or adjusted under 35 U.S.C. 154(b) by 0 days.

(21) Appl. No.: 16/698,486

(22) Filed: Nov. 27, 2019

(65) Prior Publication Data

US 2020/0199098 A1    Jun. 25, 2020

Related U.S. Application Data

(60) Provisional application No. 62/774,058, filed on Nov. 30, 2018.

(51) Int. Cl.
| | |
|---|---|
| *C07D 401/04* | (2006.01) |
| *C07D 401/14* | (2006.01) |
| *C07D 403/12* | (2006.01) |
| *C07D 471/04* | (2006.01) |
| *C07D 233/86* | (2006.01) |
| *C07D 417/12* | (2006.01) |
| *C07D 403/10* | (2006.01) |
| *C07D 413/12* | (2006.01) |
| *C07D 493/10* | (2006.01) |
| *C07D 235/02* | (2006.01) |
| *C07D 233/72* | (2006.01) |
| *A61P 35/00* | (2006.01) |
| *A61K 45/06* | (2006.01) |

(52) U.S. Cl.
CPC ............ *C07D 401/04* (2013.01); *A61P 35/00* (2018.01); *C07D 233/72* (2013.01); *C07D 233/86* (2013.01); *C07D 235/02* (2013.01); *C07D 401/14* (2013.01); *C07D 403/10* (2013.01); *C07D 403/12* (2013.01); *C07D 413/12* (2013.01); *C07D 417/12* (2013.01); *C07D 471/04* (2013.01); *C07D 493/10* (2013.01); *A61K 45/06* (2013.01)

(58) Field of Classification Search
CPC .. C07D 401/04; C07D 401/14; C07D 403/12; C07D 471/04; C07D 233/72; C07D 233/86; C07D 417/12; C07D 403/10; C07D 413/12; C07D 493/10; C07D 235/02; A61P 35/00; A61K 45/06

See application file for complete search history.

(56) References Cited

U.S. PATENT DOCUMENTS

| | | | |
|---|---|---|---|
| 4,465,836 A | 8/1984 | Buschhaus et al. | |
| 5,681,841 A | 10/1997 | Himmelsbach et al. | |
| 5,852,192 A | 12/1998 | Himmelsbach et al. | |
| 6,162,444 A | 12/2000 | Dubois | |
| 6,184,249 B1 | 2/2001 | Sovak et al. | |
| 6,331,552 B1 | 12/2001 | Wehner et al. | |
| 7,709,516 B2 | 5/2010 | Labrie et al. | |
| 7,709,517 B2 | 5/2010 | Sawyers et al. | |
| 7,875,636 B2 | 1/2011 | Barrow et al. | |
| 8,445,507 B2 | 5/2013 | Jung et al. | |
| 9,216,957 B2 | 12/2015 | Tong | |
| 9,963,433 B2 | 5/2018 | Qin | |
| 2007/0191336 A1 | 8/2007 | Flynn et al. | |
| 2007/0254933 A1 | 11/2007 | Jung et al. | |
| 2009/0082379 A1 | 3/2009 | Halley et al. | |
| 2009/0227588 A1 | 9/2009 | Fleck et al. | |
| 2009/0274632 A1 | 11/2009 | Li et al. | |
| 2010/0254916 A1 | 10/2010 | Karanewsky et al. | |
| 2014/0073636 A1 | 3/2014 | Kautz | |
| 2016/0130240 A1 | 5/2016 | Alig et al. | |
| 2016/0376263 A1 | 12/2016 | Patron et al. | |
| 2017/0087132 A1 | 3/2017 | Protter et al. | |
| 2017/0217903 A1 | 8/2017 | Qin et al. | |
| 2017/0327469 A1 | 11/2017 | Crew et al. | |
| 2020/0239433 A1 | 7/2020 | Chakravarty et al. | |

FOREIGN PATENT DOCUMENTS

| | | |
|---|---|---|
| CA | 2062655 A1 | 9/1992 |
| CN | 101032483 A | 9/2007 |
| CN | 101032483 B | 5/2011 |
| CN | 106146474 A | 11/2016 |
| CN | 107987055 A | 5/2018 |

(Continued)

OTHER PUBLICATIONS

Graff, J.N.,"Safety and effectiveness of enzalutamide in men with metastatic, castration-resistant prostate cancer." Expert Opinion on Pharmacotherapy 16.5 (2015): 749-754.*
Liu, J.K.H. "Anti-cancer vaccines—a one-hit wonder?." The Yale journal of biology and medicine 87.4 (2014): 481.*
Crawford, E. D., "Androgen receptor targeted treatments of prostate cancer: 35 years of progress with antiandrogens." The Journal of urology 200.5 (2018): 956-966.*
International Search Report & Written Opinion dated Mar. 24, 2020 for PCT/US2019/063742. 5 pages.

(Continued)

*Primary Examiner* — John M Mauro
(74) *Attorney, Agent, or Firm* — Sheppard Mullin Richter & Hampton LLP

(57) ABSTRACT

The disclosure relates to anti-cancer compounds derived from nuclear steroid receptor binders, to products containing the same, as well as to methods of their use and preparation.

39 Claims, 3 Drawing Sheets

(56) References Cited

FOREIGN PATENT DOCUMENTS

| | | | |
|---|---|---|---|
| CN | 110143925 A | 8/2019 |
| EP | 503548 A1 | 9/1992 |
| EP | 503548 B1 | 6/1997 |
| WO | WO 94/21607 A1 | 9/1994 |
| WO | WO 97/38984 A1 | 10/1997 |
| WO | WO 97/43351 A1 | 11/1997 |
| WO | WO 99/60015 A1 | 11/1999 |
| WO | WO 2001/058854 A1 | 8/2001 |
| WO | WO 2001/058855 A1 | 8/2001 |
| WO | WO 02/34753 A2 | 5/2002 |
| WO | WO 02/34753 A3 | 8/2002 |
| WO | WO 03/091258 A1 | 11/2003 |
| WO | WO 03/091259 A1 | 11/2003 |
| WO | WO 2004/009558 A2 | 1/2004 |
| WO | WO 03/091259 A8 | 2/2004 |
| WO | WO 2004/009558 A3 | 4/2004 |
| WO | WO 2005/023761 A2 | 3/2005 |
| WO | WO 2005/023761 A3 | 7/2005 |
| WO | WO 2006/010641 A2 | 2/2006 |
| WO | WO 2006/010642 A1 | 2/2006 |
| WO | WO 2006/014290 A2 | 2/2006 |
| WO | WO 2006/034441 A1 | 3/2006 |
| WO | WO 2006/014290 A3 | 4/2006 |
| WO | WO 2006/060318 A2 | 6/2006 |
| WO | WO 2006/060318 A3 | 7/2006 |
| WO | WO 2006/101521 A2 | 9/2006 |
| WO | WO 2006/010641 A3 | 10/2006 |
| WO | WO 2006/124118 A1 | 11/2006 |
| WO | WO 2006/101521 A3 | 12/2006 |
| WO | WO 2006/133567 A1 | 12/2006 |
| WO | WO 2007/012661 A1 | 2/2007 |
| WO | WO 2007/012661 A8 | 3/2007 |
| WO | WO 2007/115410 A1 | 10/2007 |
| WO | WO 2007/146712 A2 | 12/2007 |
| WO | WO 2008/030412 A2 | 3/2008 |
| WO | WO 2008/076754 A2 | 6/2008 |
| WO | WO 2007/146712 A3 | 11/2008 |
| WO | WO 2008/030412 A3 | 11/2008 |
| WO | WO 2008/076754 A3 | 12/2008 |
| WO | WO 2009/025793 A2 | 2/2009 |
| WO | WO 2009/026701 A1 | 3/2009 |
| WO | WO 2009/045314 A1 | 4/2009 |
| WO | WO 2009/025793 A3 | 5/2009 |
| WO | WO 2009/025793 A8 | 7/2009 |
| WO | WO 2010/037081 A1 | 4/2010 |
| WO | WO 2010/085522 A1 | 7/2010 |
| WO | WO 2010/085528 A1 | 7/2010 |
| WO | WO 2010/091176 A1 | 8/2010 |
| WO | WO 2010/118354 A1 | 10/2010 |
| WO | WO 2010/147776 A1 | 12/2010 |
| WO | WO 2011/029392 A1 | 3/2011 |
| WO | WO 2011/103202 A2 | 8/2011 |
| WO | WO 2011/106114 A1 | 9/2011 |
| WO | WO 2011/145669 A1 | 11/2011 |
| WO | WO 2011/103202 A3 | 1/2012 |
| WO | WO 2012/050868 A1 | 4/2012 |
| WO | WO 2012/119559 A1 | 9/2012 |
| WO | WO 2013/056547 A1 | 4/2013 |
| WO | WO 2013/066440 A1 | 5/2013 |
| WO | WO 2013/067131 A1 | 5/2013 |
| WO | WO 2013/067142 A1 | 5/2013 |
| WO | WO 2013/067151 A1 | 5/2013 |
| WO | WO 2013/066440 A9 | 7/2013 |
| WO | WO 2014/075387 A1 | 5/2014 |
| WO | WO 2015/018356 A1 | 2/2015 |
| WO | WO 2015/042170 A1 | 3/2015 |
| WO | WO 2015/049624 A1 | 4/2015 |
| WO | WO 2015/058047 A2 | 4/2015 |
| WO | WO 2015/058047 A3 | 6/2015 |
| WO | WO 2017/123542 A1 | 7/2017 |
| WO | WO 2018/007624 A1 | 1/2018 |
| WO | WO 2018/009694 A1 | 1/2018 |
| WO | WO 2018/037342 A1 | 3/2018 |
| WO | WO 2019/037742 A1 | 2/2019 |
| WO | WO 2019/120079 A1 | 6/2019 |
| WO | WO 2020/113088 A1 | 6/2020 |
| WO | WO 2020/113094 A1 | 6/2020 |

OTHER PUBLICATIONS

International Search Report & Written Opinion dated Mar. 24, 2020 for PCT/US2019/063734. 5 pages.

Caraculacu, et al. Polyhydrazides and Poly(1,3,4-Oxadiazole)s with Parabanic Structures. 1993; Eur. Polym. J. vol. 29, No. 8, pp. 1143-1147.

Jadhavar, et al. Targeting prostate cancer with compounds possessing dual activity as androgen receptor antagonists and HDAC6 inhibitors Bioorganic & Medicinal Chemistry Letters (2016), 26(21), 5222-5228.

Supplementary Material to Jadhavar et al., "Targeting prostate cancer with compounds possessing dual activity as androgen receptor antagonists and HDAC6 inhibitors," Bioorganic & Medicinal Chemistry Letters (2016), 26(21), 5222-5228, 59 pages.

* cited by examiner

Enza: Enzalutamide

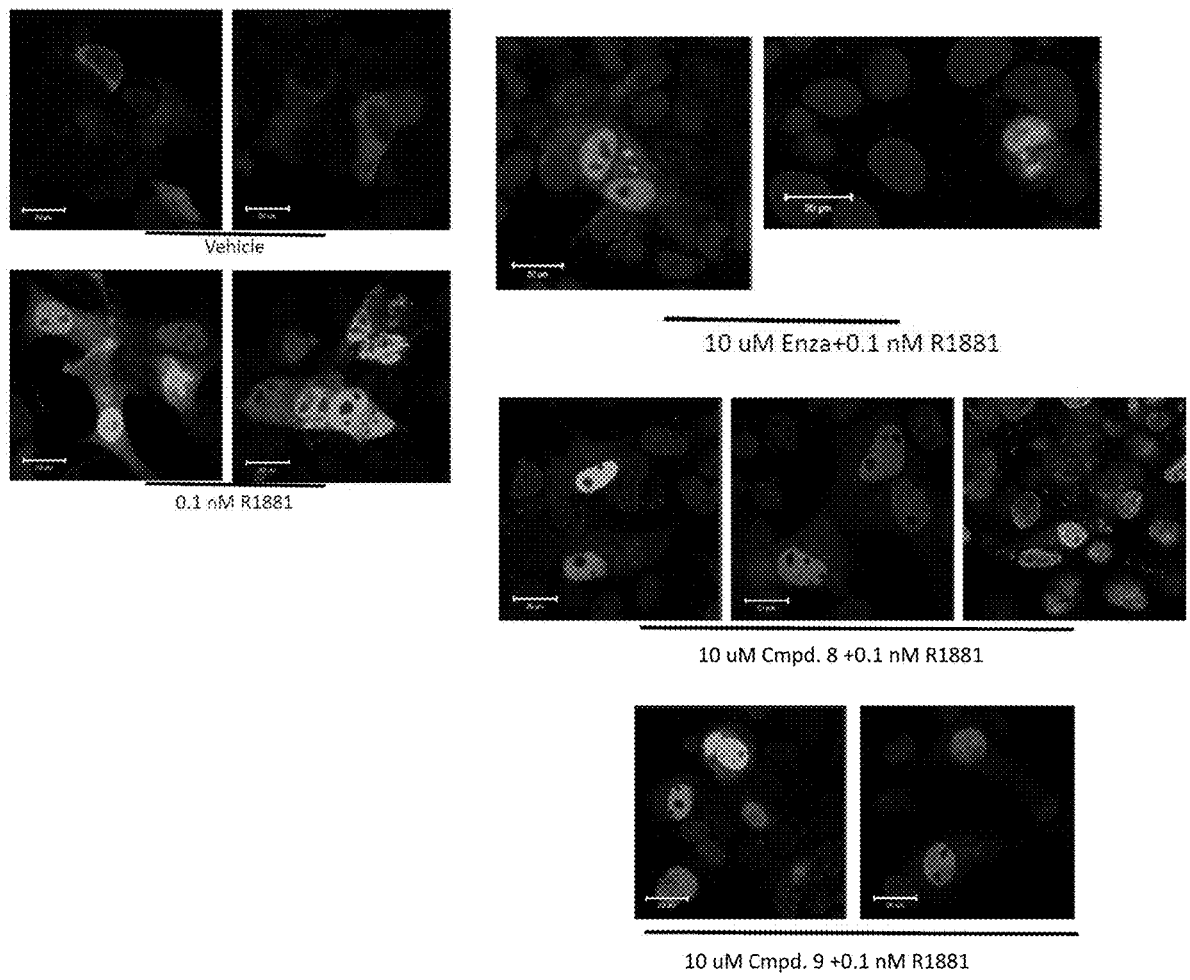

DIARYLHYDANTOIN COMPOUNDS AND METHODS OF USE THEREOF

CROSS REFERENCE TO RELATED APPLICATIONS

This application claims the benefit under 35 U.S.C. § 119(e) to U.S. Provisional Application No. 62/774,058, Nov. 30, 2018, which is hereby incorporated by reference in its entirety.

FIELD

The present disclosure relates to compounds, including diarylhydantoins, and methods for synthesizing and using the same in the treatment of cancer.

BACKGROUND

Nuclear hormone receptors (NHRs) constitute a superfamily of ligand-dependent and sequence-specific transcription factors. The androgen receptor (AR) is a member of the NHR family that is activated by binding of hormones including testosterone and dihydrotestosterone. It plays a fundamental role in the growth of prostate cancer cells. Androgen deprivation therapy serves as first-line treatment for prostate cancer. However, androgen deprivation therapy usually loses efficacy over time and prostate cancer progresses to hormone refractory prostate cancer, also known as castration-resistant prostate cancer (CRPC). Overexpression of AR has been identified and validated as a cause of hormone refractory prostate cancer. AR and its ligand binding are necessary for growth of hormone refractory prostate cancer.

A number of non-steroidal anti-androgens that inhibit AR have been developed for the treatment of prostate cancer. First-generation AR inhibitors include flutamide and bicalutamide. Second-generation AR inhibitors are enzalutamide and apalutamide. Enzalutamide was approved in the U.S. in August 2012 for patients with metastatic castration-resistant prostate cancer and in July 2018 for patients with non-metastatic castration-resistant prostate cancer. Apalutamide was approved in the U.S. in February 2018 for patients with non-metastatic castration-resistant prostate cancer. One drug in development is the non-steroidal anti-androgen darolutamide, which is in clinical trials for men with high-risk non-metastatic CRPC. It is known that bypass of AR signaling that results in resistance to AR inhibitors can occur by the overexpression of glucocorticoid receptor (GR) (Boudadi et al. Clin Med Insights Oncol (2016) 10:1-9; Crona et al. Cancers (Basel) (2017) 9:67). Although the physiological activities of androgens and glucocorticoids are diverse, GR and AR receptors are closely related members of the steroid nuclear-receptor superfamily Glucocorticoid signaling can be a major factor in the development of therapy resistance in prostate cancer. GR activation has been linked to chemotherapeutic agent resistance in other cancer types including ovarian cancer, breast cancer, non-small cell lung cancer and pancreatic cancer.

There remains a need for that newer therapies have significantly improved outcomes for prostate cancer patients.

SUMMARY

The present disclosure provides compounds having hormone receptor antagonist activity. These compounds can be useful in treating cancer, in particular those cancers which can be potentiated by AR and/or GR antagonism.

Provided herein is a compound of Formula I:

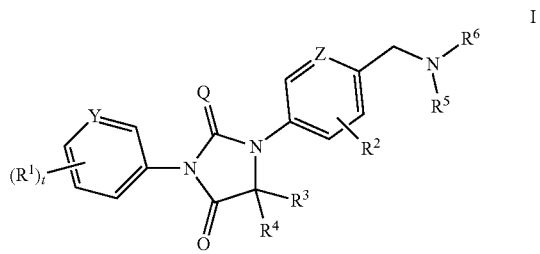

or a pharmaceutically acceptable salt, stereoisomer, mixture of stereoisomers, solvate, or tautomer thereof, wherein:
Y is N, CH, or $CR^1$;
Z is N or CH;
Q is O or S;
t is 0, 1 or 2;
each occurrence of $R^1$ is independently cyano, halo, $C_{1-6}$ alkyl, or $C_{1-6}$ haloalkyl; or two $R^1$ join to form a unsubstituted or substituted heteroaryl or unsubstituted or substituted aryl;
$R^2$ is hydrogen or halo;
$R^3$ and $R^4$ are each independently hydrogen, cyano, halo, or $C_{1-6}$ alkyl which may be further substituted with —OH, —$NH_2$, halo, or —$OCH_3$; or $R^3$ and $R^4$ join to form a $C_{3-10}$ cycloalkyl or 4-6-membered heterocyclyl;
$R^5$ is hydrogen or $C_{1-4}$ alkyl;
$R^6$ is —$C(O)R^7$, —$S(O)_2R^7$, —$C(CH_2)R^7$, —$CH_2R^7$, unsubstituted or substituted heteroaryl; or $R^5$ and $R^6$ join together to form a unsubstituted or substituted bicyclic heterocyclyl or unsubstituted or substituted heteroaryl; and
$R^7$ is unsubstituted or substituted $C_{1-6}$ alkyl, unsubstituted or substituted $C_{3-10}$ cycloalkyl, unsubstituted or substituted heterocyclyl, unsubstituted or substituted aryl, unsubstituted or substituted heteroaryl.

In certain embodiments, when $R^5$ is ethyl, then $R^7$ cannot be methyl. In certain embodiments, the compound is not (2E)-3-[1-[[4-[3-[4-cyano-3-(trifluoromethyl)phenyl]-5,5-dimethyl-4-oxo-2-thioxo-1-imidazolidinyl]-2-fluorophenyl]methyl]-1H-indol-5-yl]-N-hydroxy-2-propenamide; (2E)-3-[1-[[4-[3-[4-cyano-3-(trifluoromethyl)phenyl]-5,5-dimethyl-4-oxo-2-thioxo-1-imidazolidinyl]-2-fluorophenyl]methyl]-1H-indol-5-yl]-2-propenoic acid methyl ester; or (2E)-3-[1-[[4-[3-[4-cyano-3-(trifluoromethyl)phenyl]-5,5-dimethyl-4-oxo-2-thioxo-1-imidazolidinyl]-2-fluorophenyl]methyl]-1H-indol-5-yl]-2-propenoic acid.

Also provided is a method of treating or preventing an androgen receptor overexpressing cancer, comprising administering an effective amount of a compound as described herein, or a pharmaceutically acceptable salt, stereoisomer, mixture of stereoisomers, solvate, or tautomer thereof, to an individual in need thereof. In certain embodiments, the cancer is prostate, breast, triple negative breast cancer, bladder, or liver cancer.

Also provided is a method of treating or preventing a glucocorticoid receptor overexpressing cancer, comprising administering an effective amount of a compound as described herein, or a pharmaceutically acceptable salt, stereoisomer, mixture of stereoisomers, solvate, or tautomer thereof, to an individual in need thereof. In certain embodiments, the cancer is prostate, breast, uterine, or ovarian cancer.

Also provided is a method of treating or preventing cancer, comprising administering an effective amount of a compound or composition as described herein, or a pharmaceutically acceptable salt, stereoisomer, mixture of stereoisomers, solvate, or tautomer thereof, in combination with an additional chemotherapeutic agent, to an individual in need thereof.

Also provided is a method of treating or preventing an androgen receptor and/or glucocorticoid receptor overexpressing cancer, comprising administering an effective amount of a compound as described herein, or a pharmaceutically acceptable salt, stereoisomer, mixture of stereoisomers, solvate, or tautomer thereof, to an individual in need thereof.

The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated, at least in part, by hormone receptor antagonist activity.

Moreover, the disclosure provides uses of the compounds or compositions thereof in the manufacture of a medicament for the treatment of a disease, disorder, or condition that is mediated, at least in part, by hormone receptor antagonist activity.

BRIEF DESCRIPTION OF THE DRAWINGS

FIG. 2 shows the results of an AR immunofluorescence in nuclear translocation assay.

DETAILED DESCRIPTION

Figure 1A:
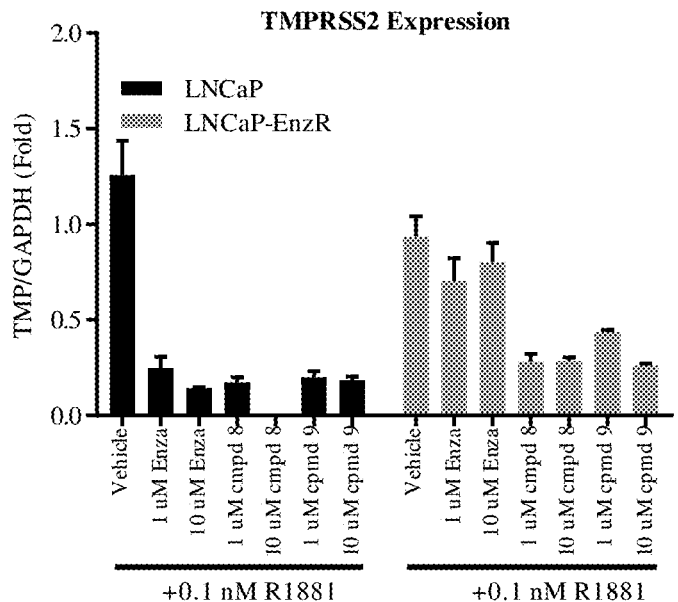
FIGS. 1A, 1B, 1C show compounds described herein significantly inhibited TMPRSS2, PSA and FKBP5 expression, respectively, at both 1 and 10 μM.

The following description sets forth exemplary embodiments of the present technology. It should be recognized, however, that such description is not intended as a limitation on the scope of the present disclosure but is instead provided as a description of exemplary embodiments.

Definitions

As used in the present specification, the following words, phrases and symbols are generally intended to have the meanings as set forth below, except to the extent that the context in which they are used indicates otherwise.

The term "about" refers to a variation of ±1%, ±3%, ±5%, or ±10% of the value specified. For example, "about 50" can in some embodiments includes a range of from 45 to 55. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. Also, the singular forms "a" and "the" include plural references unless the context clearly dictates otherwise. Thus, e.g., reference to "the compound" includes a plurality of such compounds and includes reference to one or more compounds and equivalents thereof known to those skilled in the art.

"Alkyl" refers to an unbranched or branched saturated hydrocarbon chain. As used herein, alkyl has 1 to 10 carbon atoms (i.e., $C_{1-10}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Haloalkyl" refers to an unbranched or branched alkyl group as defined above, wherein one or more (e.g., 1 to 6 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NH—, —O—, —S—, —S(O)—, —$S(O)_2$—, and the like. As used herein, heteroalkyl includes 1 to 8 carbon atoms, or 1 to 4 carbon atoms; and 1 to 3 heteroatoms, 1 to 2 heteroatoms, or 1 heteroatom.

"Alkoxy" refers to the group "—O-alkyl".

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy. "Amino" refers to the group —$NR^yR^z$ wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., C620 aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-40}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-42}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), and bicyclic heterocyclic groups, such as bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O$^-$) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ hetero-cyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. The term "heterocyclyl" also includes "spiroheterocyclyl" when there are two positions for substitution on the same carbon atom. In certain embodiments, the term "bicyclic heterocyclic" encompasses fused-heterocyclyl groups.

"Oxo" refers to =O.

"Halogen" or "halo" includes fluoro, chloro, bromo, and iodo.

The terms "optional" or "optionally" means that the subsequently described event or circumstance may or may not occur. The term "optionally substituted" refers to any one or more hydrogen atoms on the designated atom or group may or may not be replaced by a moiety other than hydrogen.

"Substituted" as used herein means one or more (e.g., 1 to 5 or 1 to 3) hydrogen atoms of the group is replaced with a substituent atom or group commonly used in pharmaceutical chemistry. Each substituent can be the same or different. Examples of suitable substituents include, but are not limited to, halo, —CN, —NO$_2$, hydrazide, azido, alkyl, alkenyl, alkynyl, haloalkyl, heteroalkyl, cycloalkyl, aryl, heterocyclyl, heteroaryl, —OR$^{56}$, —C(O)OR$^{56}$, —OC(O)R$^{56}$, —C(O)R$^{56}$, —OC(O)OR$^{56}$, —O-alkyl-OR$^{56}$, -alkyl-OR$^{56}$, —SR$^{56}$, —S(O)R$^{56}$, —S(O)$_2$R$^{56}$, —NR$^{56}$R$^{57}$, —C(O)NR$^{56}$R$^{57}$, NR$^{56}$C(O)R$^{57}$, —NR$^{56}$C(O)NR$^{56}$R$^{57}$, —NR$^{56}$C(O)OR$^{57}$, —OS(O)$_{1-2}$R$^{56}$, —S(O)$_{1-2}$OR$^{56}$, —NR$^{56}$S(O)$_{1-2}$NR$^{56}$R$^{57}$, or —S(O)$_{1-2}$NR$^{56}$R$^{57}$, including seleno and thio derivatives thereof, wherein each R$^{56}$ and R$^{57}$ are independently hydrogen, alkyl, alkenyl, alkynyl, haloalkyl, cycloalkyl, cycloalkyl-alkyl-, heterocyclyl, heterocyclyl-alkyl-, aryl, aryl-alkyl-, heteroaryl, or heteroaryl-alkyl-, and wherein each of the substituents can be optionally further substituted, such as with one or more (e.g., 1 to 5 or 1 to 3) halo, —CN, —NO$_2$, azido, alkyl, alkenyl, alkynyl, haloalkyl, cycloalkyl, heterocyclyl, aryl, heteroaryl, —NR$^g$R$^h$, —NR$^g$C(O)R$^h$, —NR$^g$C(O)NR$^g$R$^h$, —NR$^g$C(O)OR$^h$, —NR$^g$S(O)$_{1-2}$R$^h$, —C(O)R$^g$, —C(O)OR$^g$, —OC(O)OR$^g$, —OC(O)R$^g$, —C(O)NR$^g$R$^h$, —OC(O)NR$^g$R$^h$, —OR$^g$, —SR$^g$, —S(O)R$^g$, —S(O)$_2$R$^g$, —OS(O)$_{1-2}$R$^g$, —S(O)$_{1-2}$OR$^g$, —NR$^g$S(O)$_{1-2}$NR$^g$R$^h$, or —S(O)$_{1-2}$NR$^g$R$^h$, wherein R$^g$ and R$^h$ are each independently hydrogen, alkyl, alkenyl, alkynyl, alkoxy, haloalkyl, aryl, aryl-alkyl-, cycloalkyl, cycloalkyl-alkyl-, heterocyclyl, heterocyclyl-alkyl-, heteroaryl, or heteroaryl-alkyl-.

Provided also are stereoisomers, mixture of stereoisomers, tautomers, hydrates, solvates, isotopically enriched analogs, and pharmaceutically acceptable salts of the compounds described herein.

The compounds disclosed herein, or their pharmaceutically acceptable salts, may include an asymmetric center and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/ isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposeable mirror images of one another and "diastereomers," which refers to stereoisomers that have at least two asymmetric atoms, but which are not mirror-images of each other. Thus, all stereoisomers (for example, geometric isomers, optical isomers and the like) of the present compounds (including those of the salts, solvates and hydrates of the compounds), such as those which may exist due to asymmetric carbons on various substituents, including enantiomeric forms (which may exist even in the absence of asymmetric carbons), rotameric forms, atropisomers, and diastereomeric forms, are contemplated.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds disclosed herein, e.g., Formula I, may be atropisomers and are considered as part of this disclosure. Stereoisomers can also be separated by use of chiral HPLC.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any compound or structure given herein, is also intended to represent unlabeled forms as well as isotopically labeled forms of the compounds. These forms of compounds may also be referred to as an "isotopically enriched analog." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. Various isotopically labeled compounds of the present disclosure, for example those into which radioactive isotopes such as $^{3}H$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Such compounds may exhibit increased resistance to metabolism and are thus useful for increasing the half-life of any compound when administered to a mammal, particularly a human. Such compounds are synthesized by means well known in the art, for example by employing starting materials in which one or more hydrogens have been replaced by deuterium.

Certain compounds disclosed herein contain one or more ionizable groups (groups from which a proton can be removed (e.g., —COOH) or added (e.g., amines) or which can be quaternized (e.g., amines)).

All possible ionic forms of such molecules and salts thereof are intended to be included individually in the disclosure herein. With regard to salts of the compounds described herein, one of ordinary skill in the art can select from among a wide variety of available counterions those that are appropriate. In specific applications, the selection of a given anion or cation for preparation of a salt may result in increased or decreased solubility of that salt.

A "solvate" is formed by the interaction of a solvent and a compound. A "hydrate" is formed by the interaction of water and a compound. A solvate or hydrate of a salt of a compounds described herein are also provided.

The terms "inhibit," "inhibiting," and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

As used herein, by "combination therapy" is meant a therapy that includes two or more different compounds. Thus, in one aspect, a combination therapy comprising a compound detailed herein and anther compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the disclosure alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the disclosure which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the coadministered compounds may optionally be lowered due to the combined action (e.g., additive or synergistic effects) of the compounds.

The term "carrier," as used herein, refers to relatively nontoxic chemical compounds or agents that facilitate the incorporation of a compound into cells or tissues.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, J. Pharm. Sci. 1977 January; 66(1):1-19. Pharmaceutically acceptable salts can be prepared in situ in the manufacturing process, or by separately reacting a purified compound of the disclosure in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization.

Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Compounds

Provided herein is a compound of Formula I:

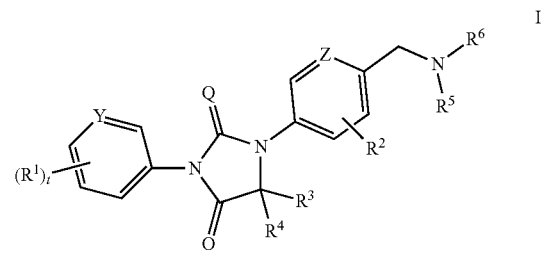

or a pharmaceutically acceptable salt, stereoisomer, mixture of stereoisomers, solvate, or tautomer thereof, wherein:

Y is N, CH, or $CR^1$;

Z is N or CH;

Q is O or S;

t is 0, 1 or 2;

each occurrence of $R^1$ is independently cyano, halo, $C_{1-6}$ alkyl, or $C_{1-6}$ haloalkyl; or two $R^1$ join to form a unsubstituted or substituted heteroaryl or unsubstituted or substituted aryl;

$R^2$ is hydrogen or halo;

$R^3$ and $R^4$ are each independently hydrogen, cyano, halo, or $C_{1-6}$ alkyl which may be further substituted with —OH, —NH$_2$, halo, or —OCH$_3$; or $R^3$ and $R^4$ join to form a $C_{3-10}$ cycloalkyl or 4-6-membered heterocyclyl;

$R^5$ is hydrogen or $C_{1-4}$ alkyl;

$R^6$ is —C(O)$R^7$, —S(O)$_2R^7$, —C(CH$_2$)$R^7$, —CH$_2R^7$, unsubstituted or substituted heteroaryl; or $R^5$ and $R^6$ join together to form a unsubstituted or substituted bicyclic heterocyclyl or unsubstituted or substituted heteroaryl; and $R^7$ is unsubstituted or substituted $C_{1-6}$ alkyl, unsubstituted or substituted $C_{3-10}$ cycloalkyl, unsubstituted or substituted heterocyclyl, unsubstituted or substituted aryl, unsubstituted or substituted heteroaryl.

In certain embodiments, provided is a compound of Formula I:

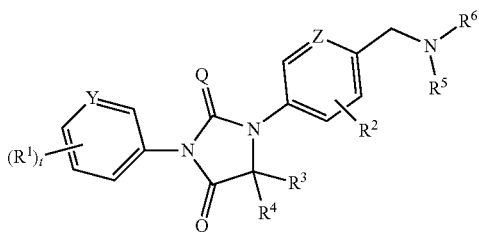

or a pharmaceutically acceptable salt, stereoisomer, mixture of stereoisomers, solvate, or tautomer thereof, wherein:
Y is N, CH, or $CR^1$;
Z is N or CH;
Q is O or S;
t is 0, 1 or 2;
each occurrence of $R^1$ is independently cyano, halo, $C_{1-6}$ alkyl, or $C_{1-6}$ haloalkyl; or two $R^1$ join to form a heteroaryl or aryl, wherein each heteroaryl or aryl is independently optionally substituted with 1-3 $R^{10}$;
$R^2$ is hydrogen or halo;
$R^3$ and $R^4$ are each independently hydrogen, cyano, halo, or $C_{1-6}$ alkyl which may be further substituted with —OH, —$NH_2$, halo, or —$OCH_3$; or $R^3$ and $R^4$ join to form a $C_{3-10}$ cycloalkyl or 4-6-membered heterocyclyl;
$R^5$ is hydrogen or $C_{1-4}$ alkyl;
$R^6$ is —$C(O)R^7$, —$S(O)_2R^7$, —$C(CH_2)R^7$, —$CH_2R^7$, or heteroaryl, wherein the heteroaryl is optionally substituted with 1-3 $R^{10}$; or
$R^5$ and $R^6$ join together to form a bicyclic heterocyclyl or heteroaryl, wherein the bicyclic heterocyclyl or heteroaryl is optionally substituted with 1-3 $R^{10}$;
$R^7$ is $C_{1-6}$ alkyl, $C_{3-10}$cycloalkyl, heterocyclyl, aryl, or heteroaryl, wherein the $C_{1-6}$ alkyl, $C_{3-10}$ cycloalkyl, heterocyclyl, aryl, or heteroaryl is optionally substituted with 1-3 $R^{10}$; and
each $R^{10}$ is independently halo, —CN, —$NO_2$, hydrazide, azido, $C_{1-6}$ alkyl, $C_{2-6}$ alkenyl, $C_{2-6}$ alkynyl, $C_{1-6}$haloalkyl, heteroalkyl, $C_{3-10}$cycloalkyl, aryl, heterocyclyl, heteroaryl, —$OR^{11}$, —$C(O)OR^{11}$, —$OC(O)R^{11}$, —$C(O)R^{11}$, —$OC(O)$ $OR^{11}$, —O—$C_{1-6}$ alkyl-$OR^{11}$, —$C_{1-6}$ alkyl-$OR^{11}$, —$S(O)$ $R^{11}$, —$S(O)_2R^{11}$, —$NR^{11}R^{12}$, —$C(O)NR^{11}R^{12}$, $NR^{11}C(O)$ $R^{12}$, —$NR^{11}C(O)NR^{11}R^{12}$, —$NR^{11}C(O)OR^{12}$, —$OS(O)_{1-2}$ $R^{11}$, —$S(O)_{1-2}OR^{11}$, —$NR^{11}S(O)_{12}NR^{11}R^{12}$, or —S $(O)_{12}NR^{11}R^{12}$, wherein each $R^{11}$ and $R^{12}$ are independently hydrogen, $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, or heteroaryl-$C_{1-6}$ alkyl-, and further wherein each $C_{1-6}$ alkyl, $C_{2-6}$alkenyl, $C_{2-6}$ alkynyl, $C_{1-6}$ haloalkyl, heteroalkyl, $C_{3-10}$ cycloalkyl, $C_{3-10}$cycloalkyl-$C_{1-6}$ alkyl-, heterocyclyl, heterocyclyl-$C_{1-6}$ alkyl-, aryl, aryl-$C_{1-6}$ alkyl-, heteroaryl, or heteroaryl-$C_{1-6}$ alkyl- of $R^{10}$, $R^{11}$ or $R^{12}$ is optionally further substituted with 1-3 substituents independently selected from halo, —CN, —$NO_2$, azido, $C_{1-6}$ alkyl, $C_{2-6}$ alkenyl, $C_{2-6}$ alkynyl, $C_{1-6}$ haloalkyl, $C_{3-10}$cycloalkyl, heterocyclyl, aryl, heteroaryl, —$NR^gR^h$, —$NR^gC(O)R^h$, —$NR^gC(O)NR^gR^h$, —$NR^gC(O)OR^h$, —$NR^gS(O)_{1-2}R^h$, —$C(O)R^g$, —$C(O)OR^g$, —$OC(O)OR^g$, —$OC(O)R^g$, —$C(O)NR^gR^h$, —$OC(O)NR^gR^h$, —$OR^g$, —$S(O)R^g$, —$S(O)_2R^g$, —$OS(O)_{1-2}R^g$, —$S(O)_{1-2}OR^g$, —$NR^gS(O)_{1-2}$ $NR^gR^h$, or —$S(O)_{12}NR^gR^h$, wherein $R^g$ and $R^h$ are each independently hydrogen, $C_{1-6}$ alkyl, $C_{2-6}$alkenyl, $C_{2-6}$ alkynyl, $C_{2-6}$ alkoxy, $C_{1-6}$haloalkyl, $C_{3-10}$cycloalkyl, $C_{3-10}$ cycloalkyl-$C_{1-6}$ alkyl-, heterocyclyl, heterocyclyl-$C_{1-6}$ alkyl-, aryl, aryl-$C_{1-6}$ alkyl-, heteroaryl, or heteroaryl-$C_{1-6}$ alkyl-.

In certain embodiments, when $R^5$ is ethyl, then $R^7$ cannot be methyl. In certain embodiments, the compound is not 5-(5-(4-((methyl(pyridin-4-ylmethyl)amino)methyl)phenyl)-8-oxo-6-thioxo-5,7-diazaspiro[3.4]octan-7-yl)-3-(trifluoromethyl)picolinonitrile; (2E)-3-[1-[[4-[3-[4-cyano-3-(trifluoromethyl)phenyl]-5,5-dimethyl-4-oxo-2-thioxo-1-imidazolidinyl]-2-fluorophenyl]methyl]-1H-indol-5-yl]-N-hydroxy-2-propenamide; (2E)-3-[1-[[4-[3-[4-cyano-3-(trifluoromethyl)phenyl]-5,5-dimethyl-4-oxo-2-thioxo-1-imidazolidinyl]-2-fluorophenyl]methyl]-1H-indol-5-yl]-2-propenoic acid methyl ester; or (2E)-3-[1-[[4-[3-[4-cyano-3-(trifluoromethyl)phenyl]-5,5-dimethyl-4-oxo-2-thioxo-1-imidazolidinyl]-2-fluorophenyl]methyl]-1H-indol-5-yl]-2-propenoic acid.

In certain embodiments, when $R^5$ and $R^6$ join together to form a unsubstituted or substituted bicyclic heterocyclyl or unsubstituted or substituted heteroaryl, then Y is CH or $CR^1$. In certain embodiments, when $R^5$ and $R^6$ join together to form a unsubstituted or substituted heteroaryl, then Y is CH or $CR^1$. In certain embodiments, when $R^5$ and $R^6$ join together to form a unsubstituted or substituted bicyclic heterocyclyl or unsubstituted or substituted heteroaryl, then Q is O. In certain embodiments, when $R^5$ and $R^6$ join together to form a unsubstituted or substituted heteroaryl, then Q is O.

In certain embodiments, Y is N or CH. In certain embodiments, Y is N. In certain embodiments, Y is CH.

In certain embodiments, Z is N or CH. In certain embodiments, Z is N. In certain embodiments, Z is CH.

In certain embodiments, Q is O or S. In certain embodiments, Q is S. In certain embodiments, Q is O.

In certain embodiments, t is 1 or 2. In certain embodiments, t is 1. In certain embodiments, t is 2.

In certain embodiments, each occurrence of $R^1$ is independently cyano, halo, or $C_{1-6}$haloalkyl; or two $R^1$ join to form a heteroaryl. In certain embodiments, each occurrence of $R^1$ is independently cyano, halo, or $C_{1-6}$haloalkyl. In certain embodiments, each occurrence of $R^1$ is independently cyano or $C_{1-6}$ haloalkyl. In certain embodiments, each occurrence of $R^1$ is independently cyano or halo. In certain embodiments, two $R^1$ join to form a heteroaryl.

In certain embodiments, $R^2$ is hydrogen or halo. In certain embodiments, $R^2$ is hydrogen or fluoro. In certain embodiments, $R^2$ is fluoro. In certain embodiments, $R^2$ is hydrogen.

In certain embodiments, $R^3$ and $R^4$ are each independently $C_{1-6}$ alkyl; or $R^3$ and $R^4$ join to form a $C_{3-10}$ cycloalkyl or 4-6-membered heterocyclyl. In certain embodiments, $R^3$ and $R^4$ are each independently $C_{1-6}$ alkyl. In certain embodiments, $R^3$ and $R^4$ are each methyl.

In certain embodiments, $R^3$ and $R^4$ join to form a $C_{3-10}$ cycloalkyl or 4-6-membered heterocyclyl.

In certain embodiments, $R^3$ and $R^4$ join to form a cyclopropyl, cyclobutyl, cyclopentyl, cyclohexyl, tetrahydrofuranyl, or oxetanyl.

In certain embodiments, $R^3$ and $R^4$ join to form a $C_{3-10}$ cycloalkyl. In certain embodiments, $R^3$ and $R^4$ join to form a cyclopropyl, cyclobutyl, cyclopentyl, or cyclohexyl.

In certain embodiments, $R^3$ and $R^4$ join to form a 4-6-membered heterocyclyl. In certain embodiments, $R^3$ and $R^4$ join to form a tetrahydrofuranyl or oxetanyl.

In certain embodiments, $R^5$ is hydrogen.

In certain embodiments, $R^5$ and $R^6$ join together to form a unsubstituted or substituted bicyclic heterocyclyl or unsubstituted or substituted heteroaryl. In certain embodiments, the heteroaryl is an optionally substituted monocyclic heteroaryl. In certain embodiments, the optionally substituted heteroaryl, contains one nitrogen and at least one additional heteroatom. In certain embodiments, the optionally substituted heteroaryl contains more than one nitrogen. In certain embodiments, the heteroaryl is an optionally substituted 6,6-bicyclic heteroaryl. In certain embodiments, the heteroaryl is an optionally substituted 5,6-bicyclic heteroaryl. In certain embodiments, $R^5$ and $R^6$ join together to form a bicyclic heterocyclyl.

In certain embodiments, $R^5$ is hydrogen or $C_{1-4}$ alkyl;
$R^6$ is —C(O)$R^7$, —S(O)$_2R^7$, —C(CH$_2$)$R^7$, —CH$_2R^7$, unsubstituted or substituted heteroaryl; and
$R^7$ is unsubstituted or substituted $C_{1-6}$ alkyl, unsubstituted or substituted $C_{3-10}$ cycloalkyl, unsubstituted or substituted heterocyclyl, unsubstituted or substituted aryl, unsubstituted or substituted heteroaryl.

In certain embodiments, $R^6$ is —C(O)$R^7$, —S(O)$_2R^7$, or —CH$_2R^7$.

In certain embodiments, $R^7$ is $C_{1-6}$ alkyl, $C_{3-10}$ cycloalkyl, aryl, or heteroaryl, wherein the $C_{1-6}$ alkyl, $C_{3-10}$ cycloalkyl, aryl, or heteroaryl is optionally substituted with 1-3 $R^{10}$; and
each $R^{10}$ is independently halo, $C_{1-6}$ alkyl, $C_{1-6}$ haloalkyl, $C_{3-10}$ cycloalkyl, aryl, or heteroaryl.

In certain embodiments, $R^5$ is hydrogen;
$R^6$ is —C(O)$R^7$, —S(O)$_2R^7$, or —CH$_2R^7$;
$R^7$ is $C_{1-6}$ alkyl, $C_{3-10}$ cycloalkyl, aryl, or heteroaryl, wherein the $C_{1-6}$ alkyl, $C_{3-10}$ cycloalkyl, aryl, or heteroaryl is optionally substituted with 1-3 $R^{10}$; and
each $R^{10}$ is independently halo, $C_{1-6}$ alkyl, $C_{1-6}$ haloalkyl, $C_{3-10}$ cycloalkyl, aryl, or heteroaryl.

In certain embodiments, Y is N or CH;
Z is N or CH;
Q is O or S;
t is 1 or 2;
each occurrence of $R^1$ is independently cyano, halo, or $C_{1-6}$ haloalkyl; or two $R^1$ join to form a heteroaryl;
$R^2$ is hydrogen or halo;
$R^3$ and $R^4$ are each independently $C_{1-6}$ alkyl; or $R^3$ and $R^4$ join to form a $C_{3-10}$ cycloalkyl or 4-6-membered heterocyclyl;
$R^5$ is hydrogen;
$R^6$ is —C(O)$R^7$, —S(O)$_2R^7$, or —CH$_2R^7$; or
$R^5$ and $R^6$ join together to form a bicyclic heterocyclyl;
$R^7$ is $C_{1-6}$ alkyl, $C_{3-10}$ cycloalkyl, aryl, or heteroaryl, wherein the $C_{1-6}$ alkyl, $C_{3-10}$ cycloalkyl, aryl, or heteroaryl is optionally substituted with 1-3 $R^{10}$; and
each $R^{10}$ is independently halo, $C_{1-6}$ alkyl, $C_{1-6}$ haloalkyl, $C_{3-10}$ cycloalkyl, aryl, or heteroaryl.

In certain embodiments, Y is N or CH;
Z is N or CH;
Q is O or S;
t is 1 or 2;
each occurrence of $R^1$ is independently cyano, fluoro, chloro, or —CF$_3$; or two $R^1$ join to form a heteroaryl;
$R^2$ is hydrogen or fluoro;
$R^3$ and $R^4$ are each independently methyl; or $R^3$ and $R^4$ join to form a cyclopropyl, cyclobutyl, cyclopentyl, cyclohexyl, tetrahydrofuranyl, or oxetanyl;
$R^5$ is hydrogen;
$R^6$ is —C(O)$R^7$, —S(O)$_2R^7$, or —CH$_2R^7$; or
$R^5$ and $R^6$ join together to form a bicyclic heterocyclyl;

$R^7$ is $C_{1-6}$ alkyl, $C_{3-10}$ cycloalkyl, aryl, or heteroaryl, wherein the $C_{1-6}$ alkyl, $C_{3-10}$ cycloalkyl, aryl, or heteroaryl is optionally substituted with 1-3 $R^{10}$; and
each $R^{10}$ is independently halo, $C_{1-6}$ alkyl, $C_{1-6}$ haloalkyl, $C_{3-10}$ cycloalkyl, aryl, or heteroaryl.

Also provided are compounds of Formula II:

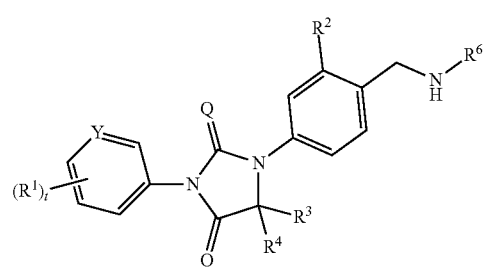

II or a pharmaceutically acceptable salt, stereoisomer, mixture of stereoisomers, solvate, or tautomer thereof, wherein Y, Q, t, $R^1$, $R^2$, $R^3$, $R^4$ and $R^6$ are as defined herein.

In certain embodiments, Q is S.
In certain embodiments, Q is O.
In certain embodiments, $R^3$ and $R^4$ are each independently hydrogen, cyano, halo, or $C_{1-6}$ alkyl which may be further substituted with —OH, —NH$_2$, halo, or —OCH$_3$.

In certain embodiments, $R^3$ and $R^4$ join to form a $C_{3-10}$ cycloalkyl or 4-6-membered heterocyclyl. In certain embodiments, $R^3$ and $R^4$ join to form a cyclopropyl, cyclobutyl, cyclopentyl, cyclohexyl, tetrahydrofuranyl, or oxetanyl. In certain embodiments, $R^3$ and $R^4$ join to form a cyclobutyl. In certain embodiments, $R^3$ and $R^4$ join to form a tetrahydrofuran.

Also provided are compounds of Formula III:

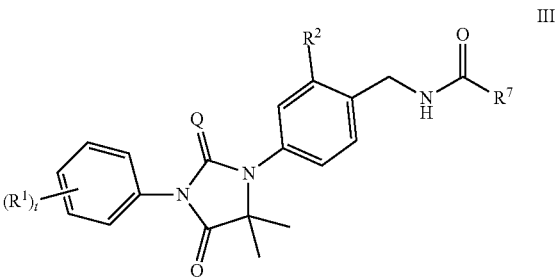

III or a pharmaceutically acceptable salt, stereoisomer, mixture of stereoisomers, solvate, or tautomer thereof, wherein Q, t, $R^1$, $R^2$ and $R^7$ are as defined herein.

Also provided are compounds of Formula IV:

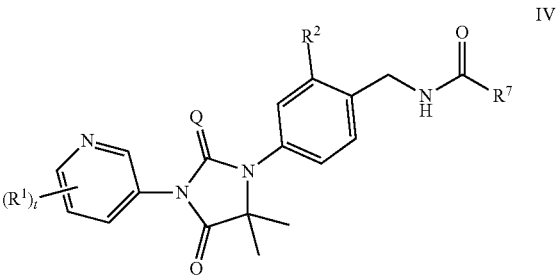

IV or a pharmaceutically acceptable salt, stereoisomer, mixture of stereoisomers, solvate, or tautomer thereof, wherein Q, t, $R^1$, $R^2$ and $R^7$ are as defined herein.

Also provided are compounds of Formula V:

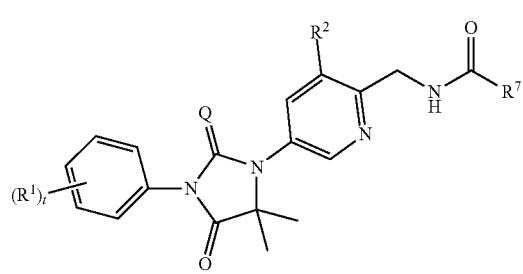

V or a pharmaceutically acceptable salt, stereoisomer, mixture of stereoisomers, solvate, or tautomer thereof, wherein Q, t, $R^1$, $R^2$ and $R^7$ are as defined herein.

Also provided are compounds of Formula VI:

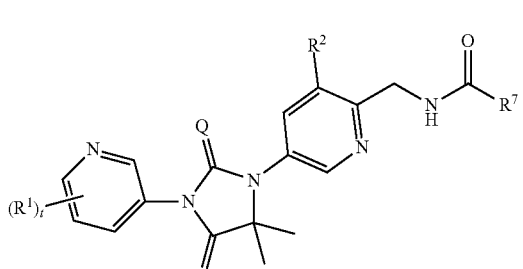

VI or a pharmaceutically acceptable salt, stereoisomer, mixture of stereoisomers, solvate, or tautomer thereof, wherein Q, t, $R^1$, $R^2$ and $R^7$ are as defined herein.

In certain embodiments, t is 1 or 2.

Also provided are compounds of Formula VII:

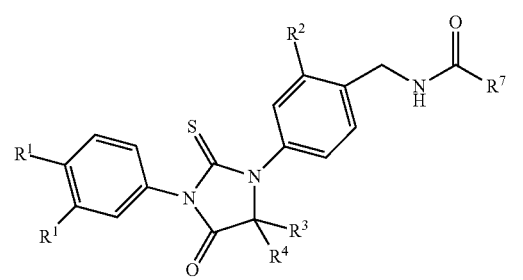

VII or a pharmaceutically acceptable salt, stereoisomer, mixture of stereoisomers, solvate, or tautomer thereof, wherein $R^1$, $R^2$, $R^3$, $R^4$ and $R^7$ are as defined herein.

Also provided are compounds of Formula VIII:

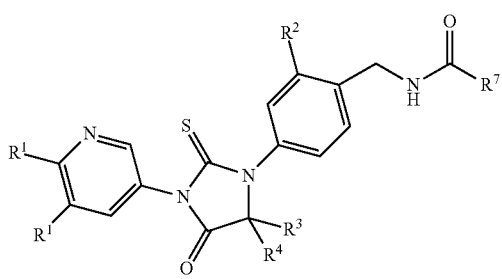

VIII or a pharmaceutically acceptable salt, stereoisomer, mixture of stereoisomers, solvate, or tautomer thereof, wherein $R^1$, $R^2$, $R^3$, $R^4$ and $R^7$ are as defined herein.

Also provided are compounds of Formula IX:

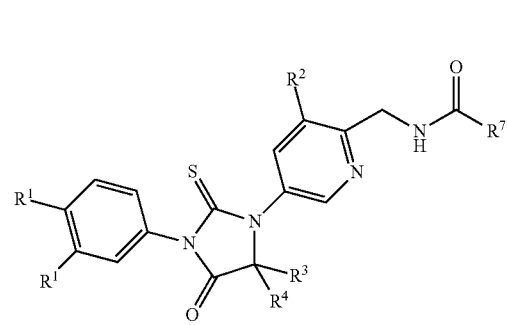

IX or a pharmaceutically acceptable salt, stereoisomer, mixture of stereoisomers, solvate, or tautomer thereof, wherein $R^1$, $R^2$, $R^3$, $R^4$ and $R^7$ are as defined herein.

Also provided are compounds of Formula X:

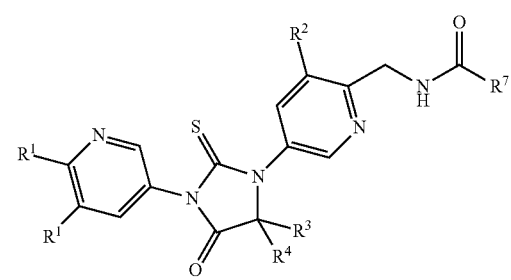

X or a pharmaceutically acceptable salt, stereoisomer, mixture of stereoisomers, solvate, or tautomer thereof, wherein $R^1$, $R^2$, $R^3$, $R^4$ and $R^7$ are as defined herein.

Also provided are compounds of Formula XI:

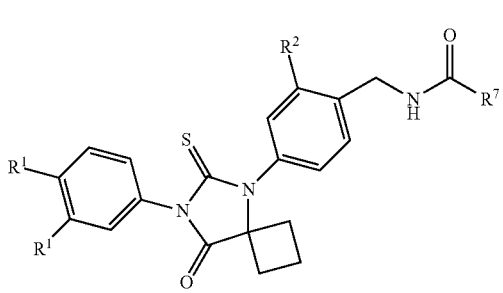

or a pharmaceutically acceptable salt, stereoisomer, mixture of stereoisomers, solvate, or tautomer thereof, wherein $R^1$, $R^2$, and $R^7$ are as defined herein.

Also provided are compounds of Formula XII:

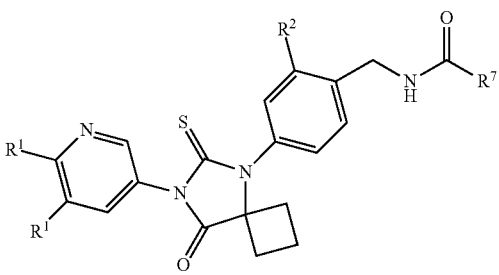

or a pharmaceutically acceptable salt, stereoisomer, mixture of stereoisomers, solvate, or tautomer thereof, wherein $R^1$, $R^2$, and $R^7$ are as defined herein.

Also provided are compounds of Formula XIII:

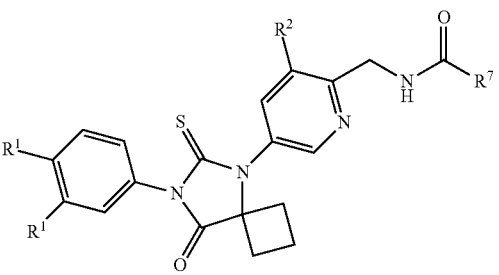

or a pharmaceutically acceptable salt, stereoisomer, mixture of stereoisomers, solvate, or tautomer thereof, wherein $R^1$, $R^2$, and $R^7$ are as defined herein.

Also provided are compounds of Formula XIV:

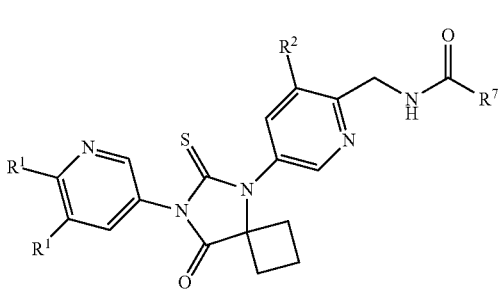

or a pharmaceutically acceptable salt, stereoisomer, mixture of stereoisomers, solvate, or tautomer thereof, wherein $R^1$, $R^2$, and $R^7$ are as defined herein.

Also provided are compounds of Formula XV:

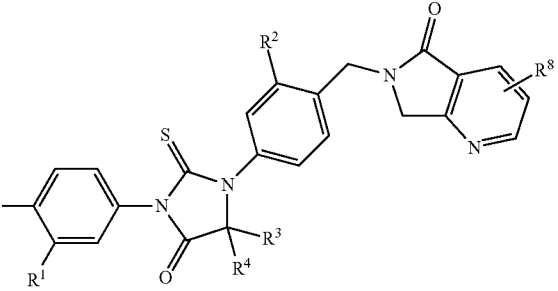

or a pharmaceutically acceptable salt, stereoisomer, mixture of stereoisomers, solvate, or tautomer thereof, wherein Y, Z, $R^1$, $R^2$, $R^3$, and $R^4$ are as defined herein; and $R^8$ is hydrogen, $C_{1-4}$ alkyl or halogen.

Also provided are compounds of Formula XVI:

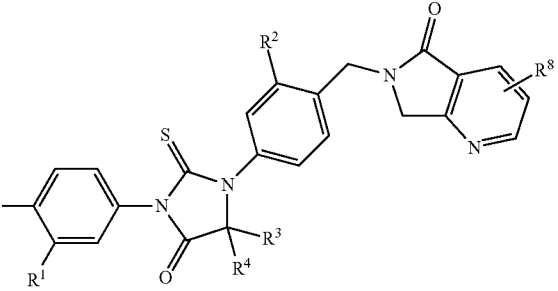

or a pharmaceutically acceptable salt, stereoisomer, mixture of stereoisomers, solvate, or tautomer thereof, wherein $R^1$, $R^2$, $R^3$, and $R^4$ are as defined herein; and $R^8$ is hydrogen, $C_{1-4}$ alkyl or halogen.

19

Also provided are compounds of Formula XVII:

20

Also provided are compounds of Formula XVIII:

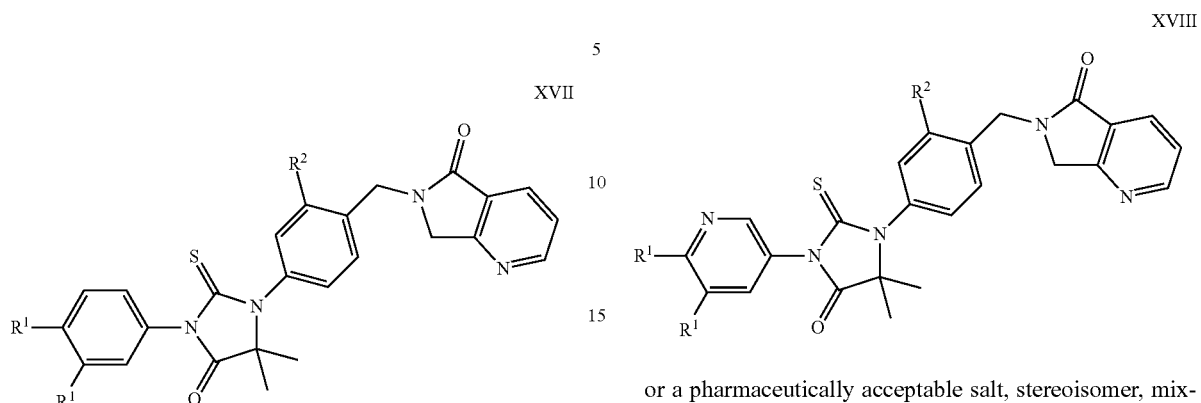

or a pharmaceutically acceptable salt, stereoisomer, mixture of stereoisomers, solvate, or tautomer thereof, wherein $R^1$ and $R^2$ are as defined herein.

or a pharmaceutically acceptable salt, stereoisomer, mixture of stereoisomers, solvate, or tautomer thereof, wherein $R^1$ and $R^2$ are as defined herein.

In certain embodiments, each $R^1$ is independently cyano, halo, $C_{1-6}$ alkyl, or $CF_3$.

Exemplary compounds provided by the present disclosure include, but are not limited to, a compound, shown in Table 1, or a stereoisomer, mixture of stereoisomers, hydrate, solvate, isotope or pharmaceutically acceptable salt thereof.

TABLE 1

| No. | Structure |
|---|---|
| 1 | 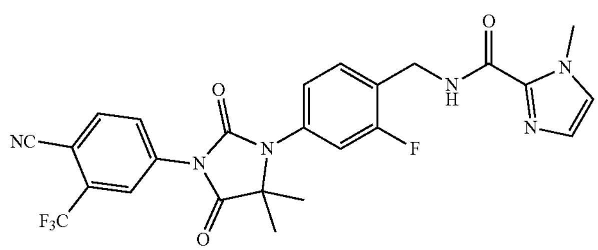 [SMILES: Cn1ccnc1C(=O)NCc1ccc(N2C(=O)N(c3ccc(C#N)c(C(F)(F)F)c3)C(=O)C2(C)C)cc1F] |
| 2 | 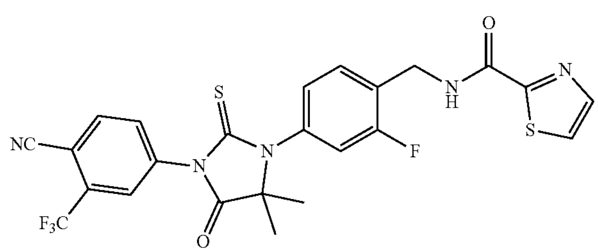 [SMILES: CC1(C)C(=O)N(c2ccc(C#N)c(C(F)(F)F)c2)C(=S)N1c1ccc(CNC(=O)c2nccs2)c(F)c1] |
| 3 | 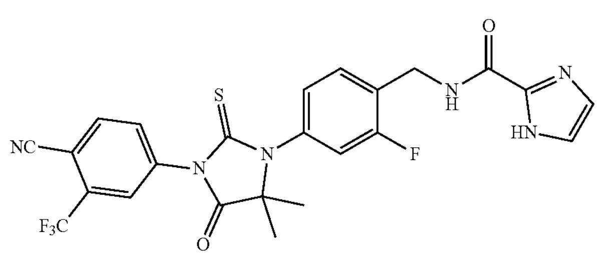 [SMILES: CC1(C)C(=O)N(c2ccc(C#N)c(C(F)(F)F)c2)C(=S)N1c1ccc(CNC(=O)c2ncc[nH]2)c(F)c1] |

TABLE 1-continued

| No. | Structure |
|---|---|
| 4 | *[chemical structure]* |
| 5 | *[chemical structure]* |
| 6 | *[chemical structure]* |
| 7 | *[chemical structure]* |
| 8 | *[chemical structure]* |
| 9 | *[chemical structure]* |

TABLE 1-continued

| No. | Structure |
|-----|-----------|
| 10  | 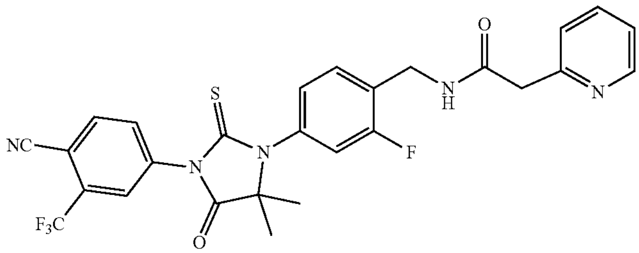 [SMILES: CC1(C)C(=O)N(c2ccc(C#N)c(C(F)(F)F)c2)C(=S)N1c1ccc(CNC(=O)Cc2ccccn2)c(F)c1]          |
| 11  | 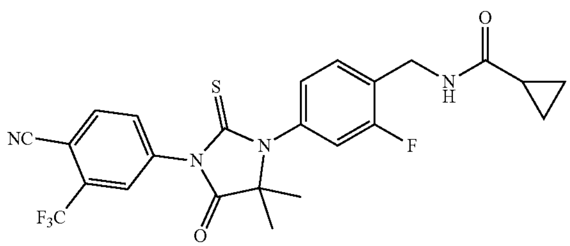 [SMILES: CC1(C)C(=O)N(c2ccc(C#N)c(C(F)(F)F)c2)C(=S)N1c1ccc(CNC(=O)C2CC2)c(F)c1]          |
| 12  | 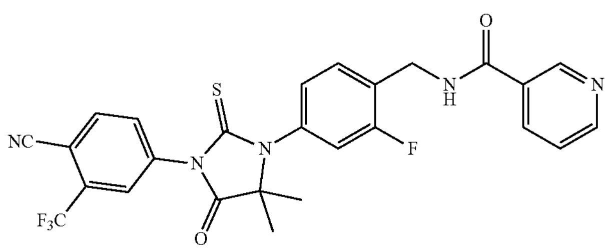 [SMILES: CC1(C)C(=O)N(c2ccc(C#N)c(C(F)(F)F)c2)C(=S)N1c1ccc(CNC(=O)c2cccnc2)c(F)c1]          |
| 13  | 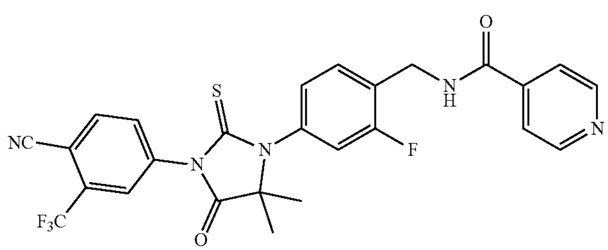 [SMILES: CC1(C)C(=O)N(c2ccc(C#N)c(C(F)(F)F)c2)C(=S)N1c1ccc(CNC(=O)c2ccncc2)c(F)c1]          |
| 14  | 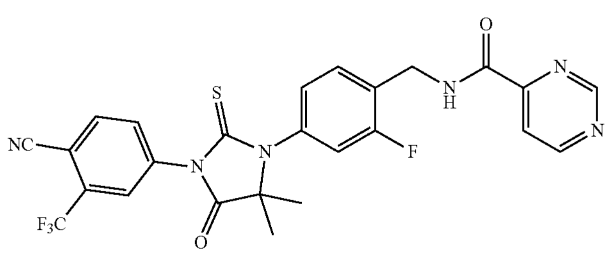 [SMILES: CC1(C)C(=O)N(c2ccc(C#N)c(C(F)(F)F)c2)C(=S)N1c1ccc(CNC(=O)c2ccncn2)c(F)c1]          |
| 15  | 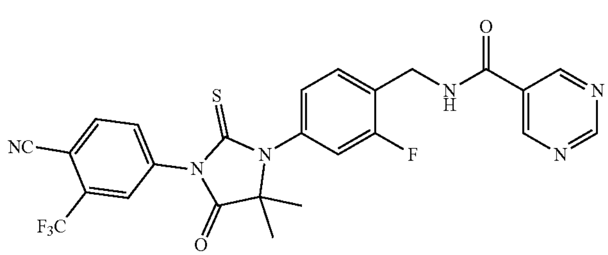 [SMILES: CC1(C)C(=O)N(c2ccc(C#N)c(C(F)(F)F)c2)C(=S)N1c1ccc(CNC(=O)c2cncnc2)c(F)c1]          |

TABLE 1-continued
| No. | Structure |
|---|---|
| 16 | 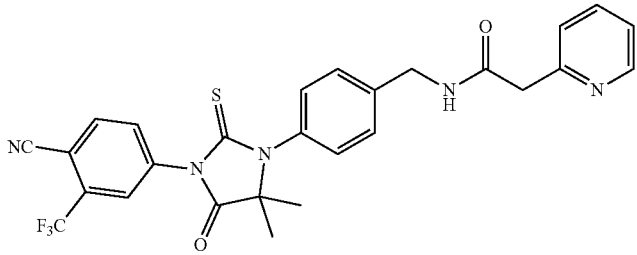 [SMILES: CC1(C)C(=O)N(c2ccc(C#N)c(C(F)(F)F)c2)C(=S)N1c1ccc(CNC(=O)Cc2ccccn2)cc1] |
| 17 | 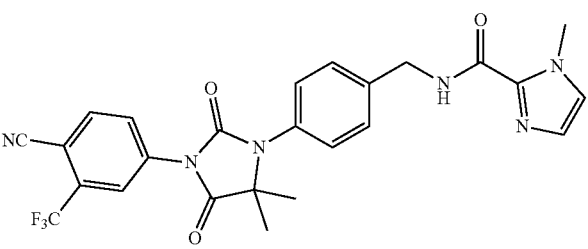 [SMILES: Cn1ccnc1C(=O)NCc1ccc(N2C(=O)N(c3ccc(C#N)c(C(F)(F)F)c3)C(=O)C2(C)C)cc1] |
| 18 | 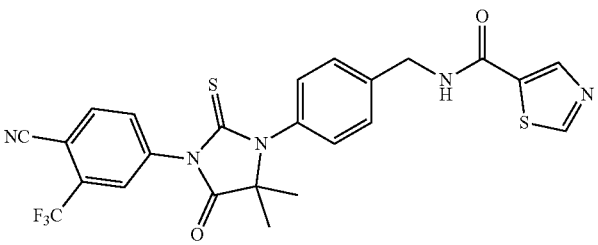 [SMILES: CC1(C)C(=O)N(c2ccc(C#N)c(C(F)(F)F)c2)C(=S)N1c1ccc(CNC(=O)c2cncs2)cc1] |
| 19 | 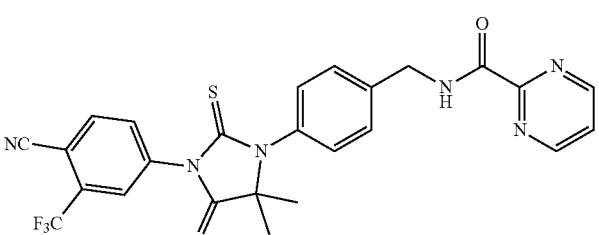 |
| 20 | 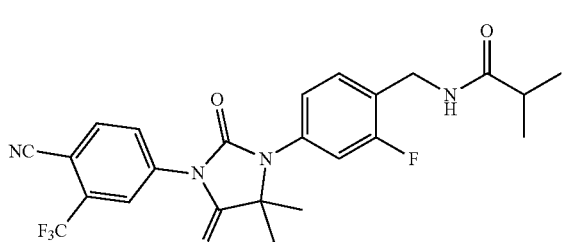 |
| 21 | 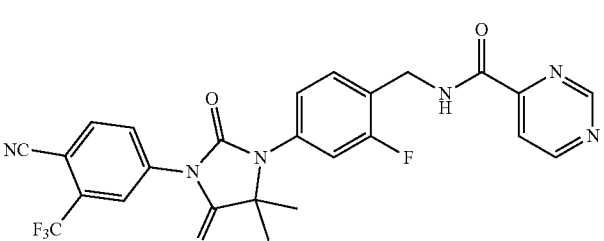 |

TABLE 1-continued

| No. | Structure |
|---|---|
| 22 | 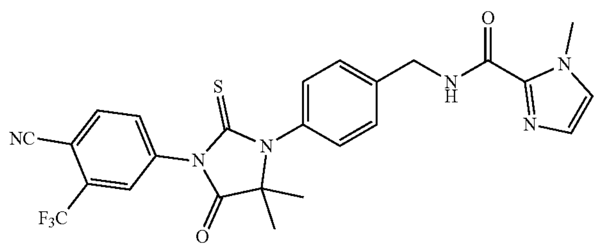 [SMILES: Cn1ccnc1C(=O)NCc1ccc(N2C(=S)N(c3ccc(C#N)c(C(F)(F)F)c3)C(=O)C2(C)C)cc1] |
| 23 | 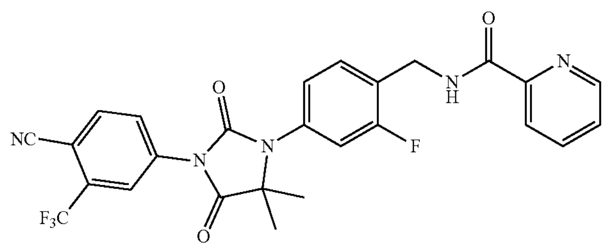 |
| 24 | 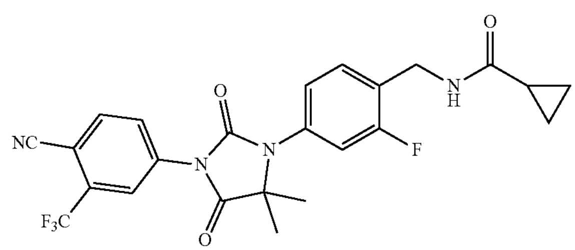 |
| 25 | 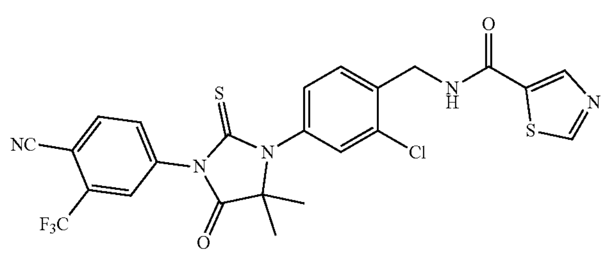 |
| 26 | 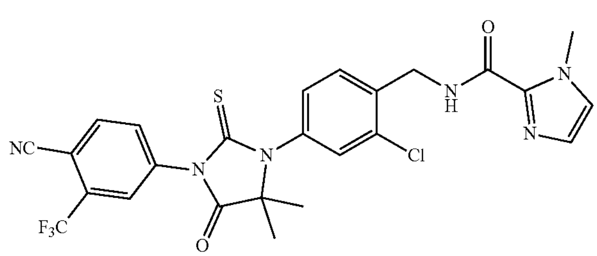 |
| 27 | 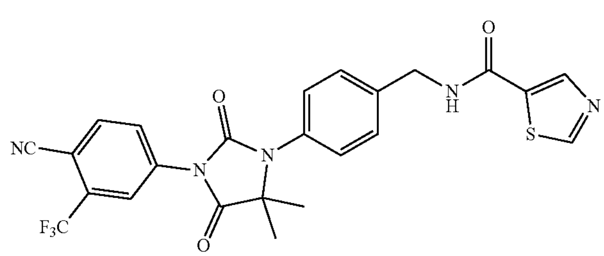 [SMILES: CC1(C)C(=O)N(c2ccc(C#N)c(C(F)(F)F)c2)C(=O)N1c1ccc(CNC(=O)c2cncs2)cc1] |

TABLE 1-continued

| No. | Structure |
|---|---|
| 28 | 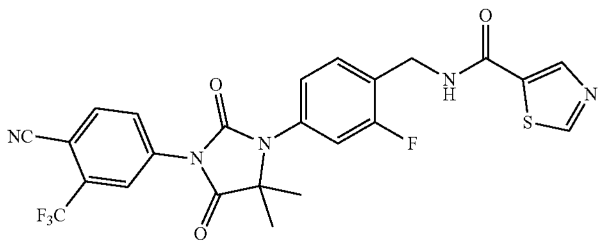 |
| 29 | 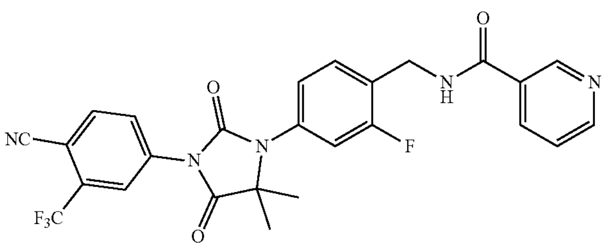 |
| 30 | 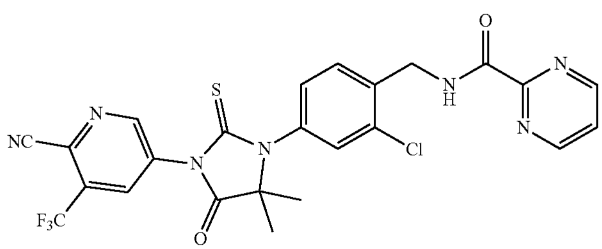 [SMILES: CC1(C)C(=O)N(c2cnc(C#N)c(C(F)(F)F)c2)C(=S)N1c1ccc(CNC(=O)c2ncccn2)c(Cl)c1] |
| 31 | 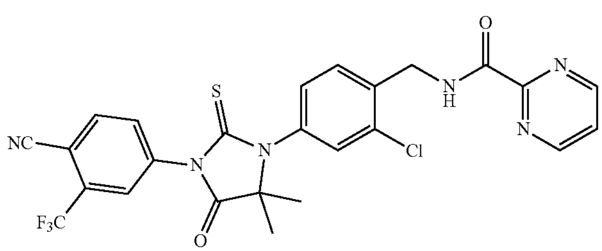 [SMILES: CC1(C)C(=O)N(c2ccc(C#N)c(C(F)(F)F)c2)C(=S)N1c1ccc(CNC(=O)c2ncccn2)c(Cl)c1] |
| 32 | 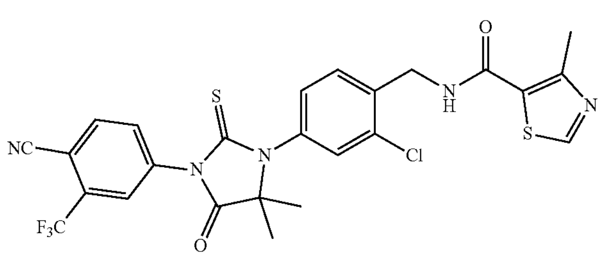 |
| 33 | 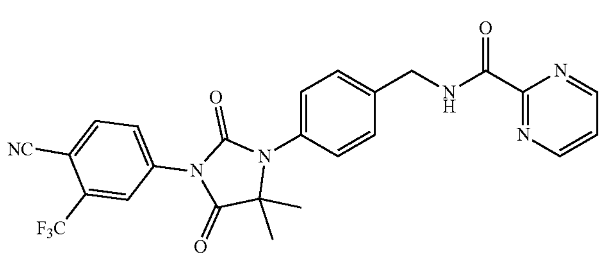 [SMILES: CC1(C)C(=O)N(c2ccc(C#N)c(C(F)(F)F)c2)C(=O)N1c1ccc(CNC(=O)c2ncccn2)cc1] |

TABLE 1-continued
| No. | Structure |
|---|---|
| 34 | 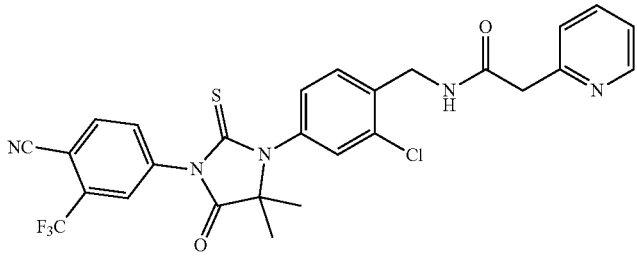 [SMILES: CC1(C)C(=O)N(c2ccc(C#N)c(C(F)(F)F)c2)C(=S)N1c1ccc(CNC(=O)Cc2ccccn2)c(Cl)c1] |
| 35 | 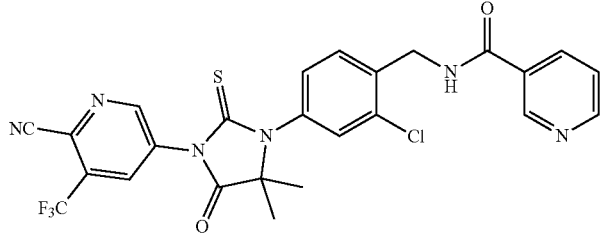 [SMILES: CC1(C)C(=O)N(c2cnc(C#N)c(C(F)(F)F)c2)C(=S)N1c1ccc(CNC(=O)c2cccnc2)c(Cl)c1] |
| 36 | 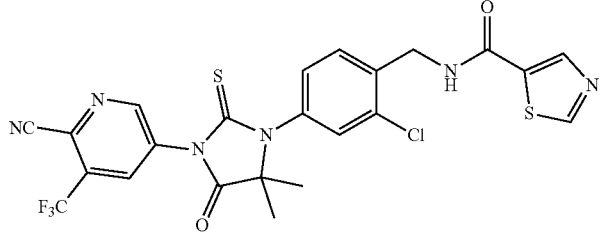 [SMILES: CC1(C)C(=O)N(c2cnc(C#N)c(C(F)(F)F)c2)C(=S)N1c1ccc(CNC(=O)c2cncs2)c(Cl)c1] |
| 37 | 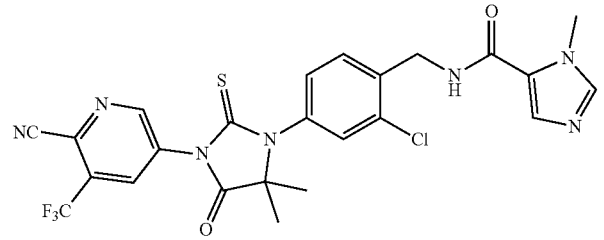 [SMILES: Cn1cncc1C(=O)NCc1ccc(N2C(=S)N(c3cnc(C#N)c(C(F)(F)F)c3)C(=O)C2(C)C)cc1Cl] |
| 38 | 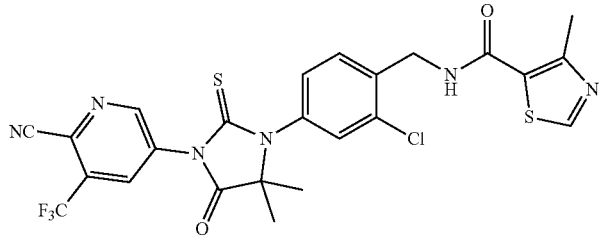 [SMILES: Cc1ncsc1C(=O)NCc1ccc(N2C(=S)N(c3cnc(C#N)c(C(F)(F)F)c3)C(=O)C2(C)C)cc1Cl] |
| 39 | 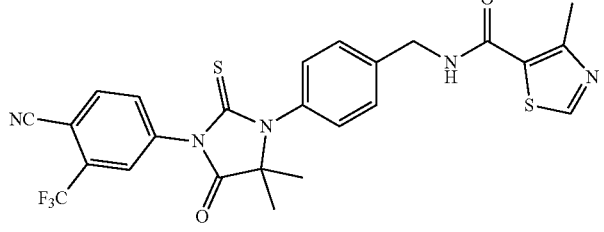 |

TABLE 1-continued

| No. | Structure |
|---|---|
| 40 | 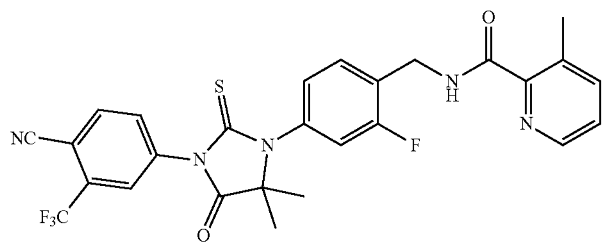 [SMILES: Cc1cccnc1C(=O)NCc1ccc(N2C(=S)N(c3ccc(C#N)c(C(F)(F)F)c3)C(=O)C2(C)C)cc1F] |
| 41 | 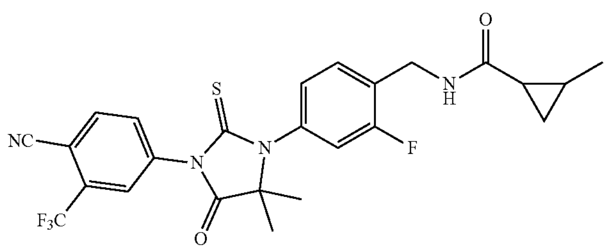 [SMILES: CC1CC1C(=O)NCc1ccc(N2C(=S)N(c3ccc(C#N)c(C(F)(F)F)c3)C(=O)C2(C)C)cc1F] |
| 42 | 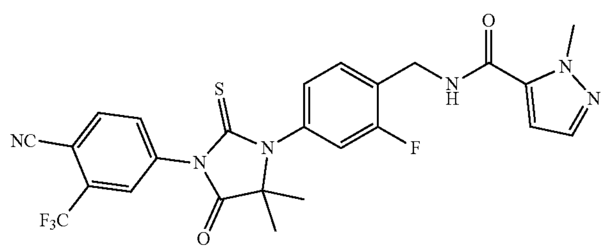 [SMILES: Cn1nccc1C(=O)NCc1ccc(N2C(=S)N(c3ccc(C#N)c(C(F)(F)F)c3)C(=O)C2(C)C)cc1F] |
| 43 | 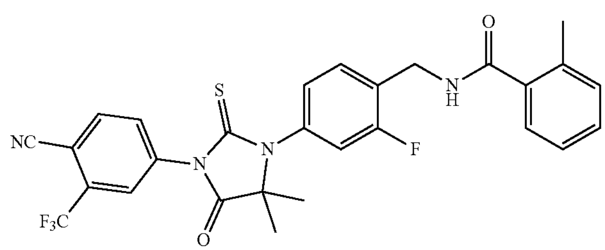 [SMILES: Cc1ccccc1C(=O)NCc1ccc(N2C(=S)N(c3ccc(C#N)c(C(F)(F)F)c3)C(=O)C2(C)C)cc1F] |
| 44 | 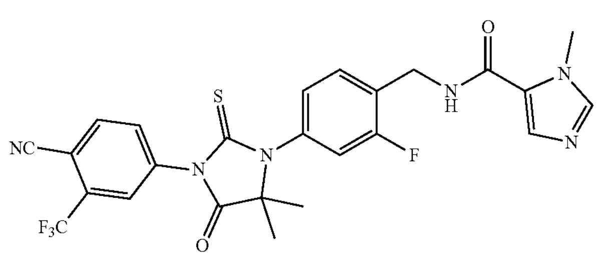 [SMILES: Cn1cncc1C(=O)NCc1ccc(N2C(=S)N(c3ccc(C#N)c(C(F)(F)F)c3)C(=O)C2(C)C)cc1F] |
| 45 | 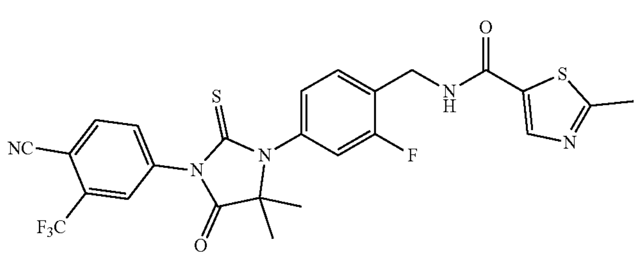 [SMILES: Cc1ncc(C(=O)NCc2ccc(N3C(=S)N(c4ccc(C#N)c(C(F)(F)F)c4)C(=O)C3(C)C)cc2F)s1] |

TABLE 1-continued

| No. | Structure |
|---|---|
| 46 | 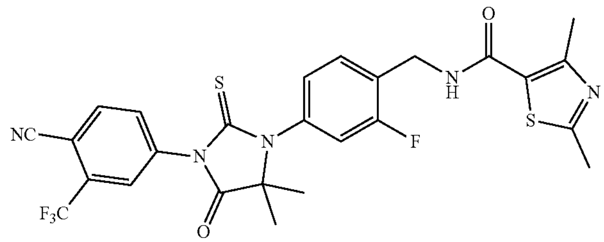 [SMILES: Cc1nc(C)c(C(=O)NCc2ccc(N3C(=S)N(c4ccc(C#N)c(C(F)(F)F)c4)C(=O)C3(C)C)cc2F)s1] |
| 47 | 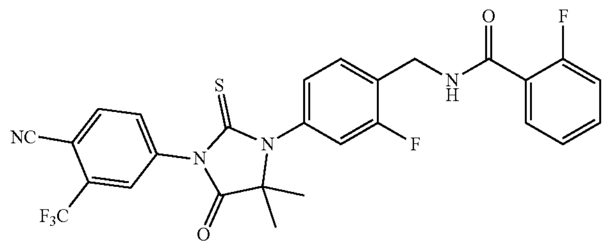 [SMILES: CC1(C)C(=O)N(c2ccc(C#N)c(C(F)(F)F)c2)C(=S)N1c1ccc(CNC(=O)c2ccccc2F)c(F)c1] |
| 48 | 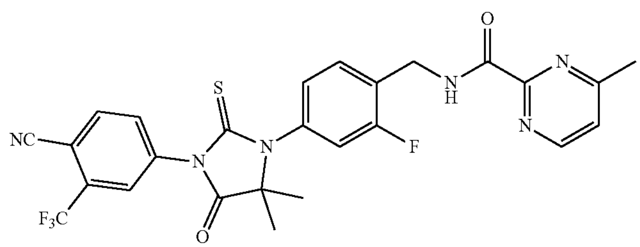 [SMILES: Cc1ccnc(C(=O)NCc2ccc(N3C(=S)N(c4ccc(C#N)c(C(F)(F)F)c4)C(=O)C3(C)C)cc2F)n1] |
| 49 | 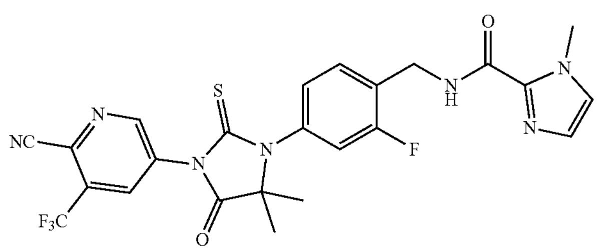 [SMILES: Cn1ccnc1C(=O)NCc1ccc(N2C(=S)N(c3cnc(C#N)c(C(F)(F)F)c3)C(=O)C2(C)C)cc1F] |
| 50 | 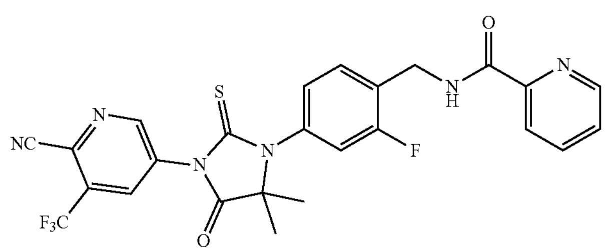 [SMILES: CC1(C)C(=O)N(c2cnc(C#N)c(C(F)(F)F)c2)C(=S)N1c1ccc(CNC(=O)c2ccccn2)c(F)c1] |
| 51 | 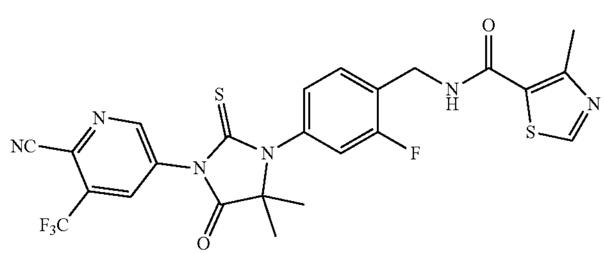 [SMILES: Cc1ncsc1C(=O)NCc1ccc(N2C(=S)N(c3cnc(C#N)c(C(F)(F)F)c3)C(=O)C2(C)C)cc1F] |

TABLE 1-continued
| No. | Structure |
|---|---|
| 52 | 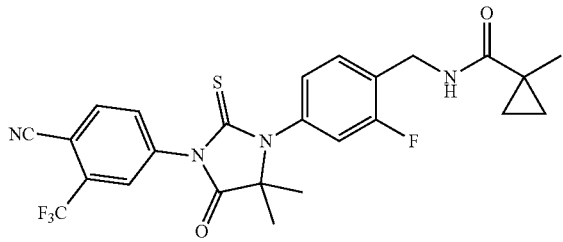 [SMILES: CC1(C(=O)NCc2ccc(N3C(=S)N(c4ccc(C#N)c(C(F)(F)F)c4)C(=O)C3(C)C)cc2F)CC1] |
| 53 | 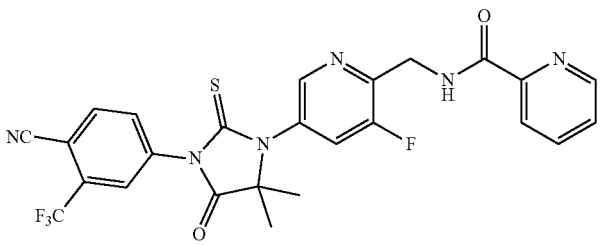 |
| 54 | 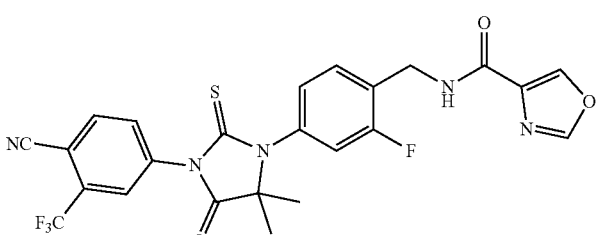 |
| 55 | 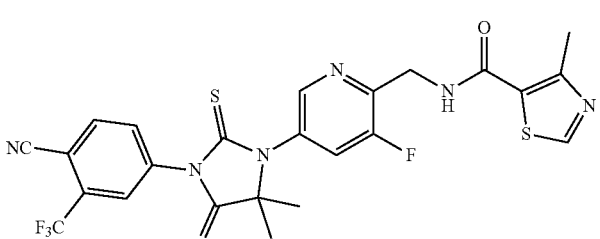 |
| 56 | 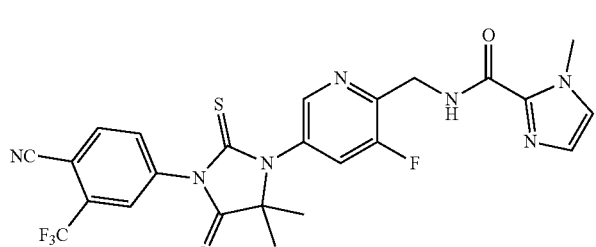 |
| 57 | 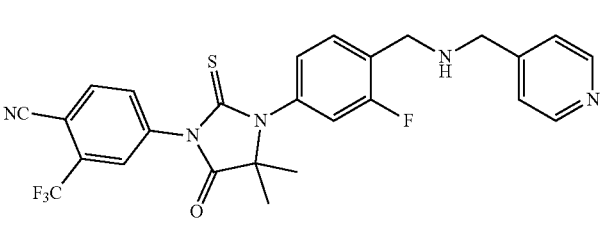 [SMILES: CC1(C)C(=O)N(c2ccc(C#N)c(C(F)(F)F)c2)C(=S)N1c1ccc(CNCc2ccncc2)c(F)c1] |

TABLE 1-continued

| No. | Structure |
|---|---|
| 58 | 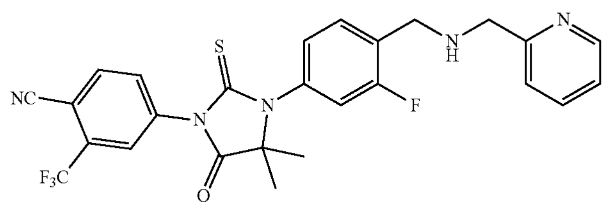 [SMILES: CC1(C)C(=O)N(c2ccc(C#N)c(C(F)(F)F)c2)C(=S)N1c1ccc(CNCc2ccccn2)c(F)c1] |
| 59 | 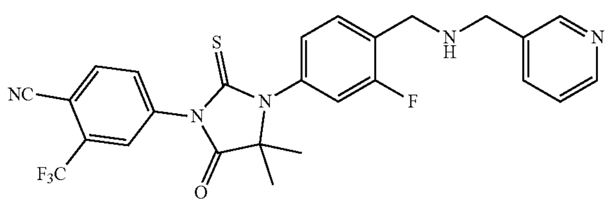 [SMILES: CC1(C)C(=O)N(c2ccc(C#N)c(C(F)(F)F)c2)C(=S)N1c1ccc(CNCc2cccnc2)c(F)c1] |
| 60 | 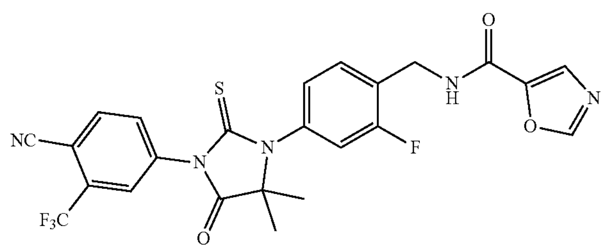 [SMILES: CC1(C)C(=O)N(c2ccc(C#N)c(C(F)(F)F)c2)C(=S)N1c1ccc(CNC(=O)c2cnco2)c(F)c1] |
| 61 | 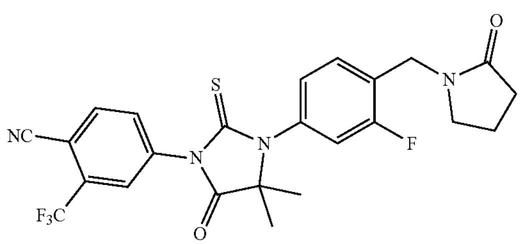 [SMILES: CC1(C)C(=O)N(c2ccc(C#N)c(C(F)(F)F)c2)C(=S)N1c1ccc(CN2CCCC2=O)c(F)c1] |
| 62 | 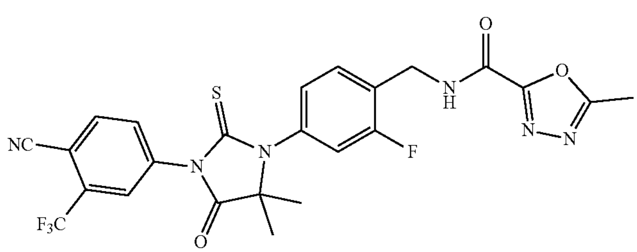 [SMILES: Cc1nnc(C(=O)NCc2ccc(N3C(=S)N(c4ccc(C#N)c(C(F)(F)F)c4)C(=O)C3(C)C)cc2F)o1] |
| 63 | 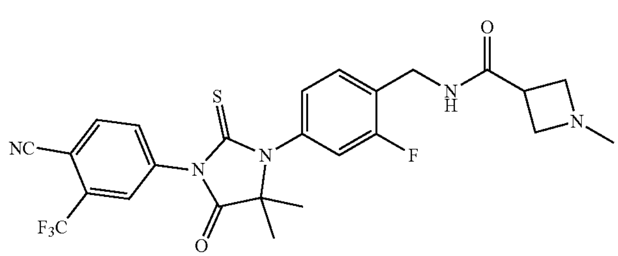 [SMILES: CN1CC(C(=O)NCc2ccc(N3C(=S)N(c4ccc(C#N)c(C(F)(F)F)c4)C(=O)C3(C)C)cc2F)C1] |

TABLE 1-continued

| No. | Structure |
|---|---|
| 64 | 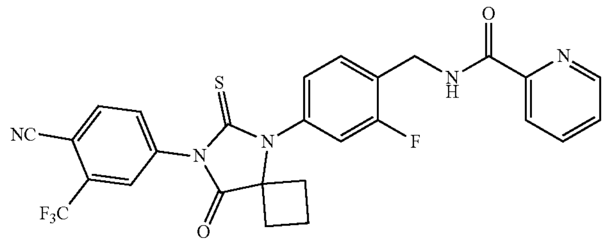 [SMILES: N#Cc1ccc(N2C(=O)C3(CCC3)N(c3ccc(CNC(=O)c4ccccn4)c(F)c3)C2=S)cc1C(F)(F)F] |
| 65 | 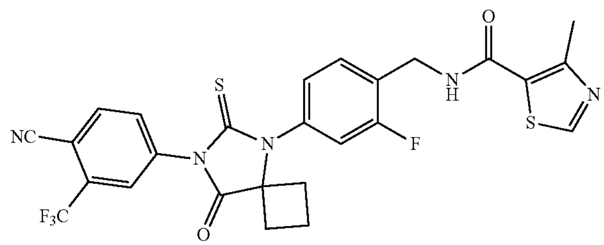 [SMILES: Cc1ncsc1C(=O)NCc1ccc(N2C(=S)N(c3ccc(C#N)c(C(F)(F)F)c3)C(=O)C23CCC3)cc1F] |
| 66 | 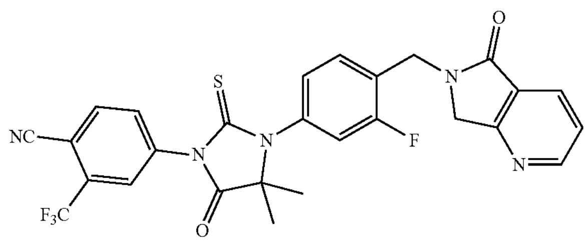 [SMILES: CC1(C)C(=O)N(c2ccc(C#N)c(C(F)(F)F)c2)C(=S)N1c1ccc(CN2Cc3ncccc3C2=O)c(F)c1] |
| 67 | 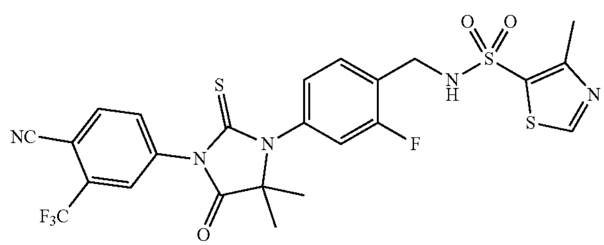 [SMILES: Cc1ncsc1S(=O)(=O)NCc1ccc(N2C(=S)N(c3ccc(C#N)c(C(F)(F)F)c3)C(=O)C2(C)C)cc1F] |
| 68 | 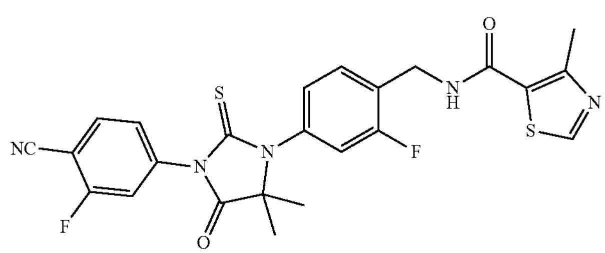 [SMILES: Cc1ncsc1C(=O)NCc1ccc(N2C(=S)N(c3ccc(C#N)c(F)c3)C(=O)C2(C)C)cc1F] |
| 69 | 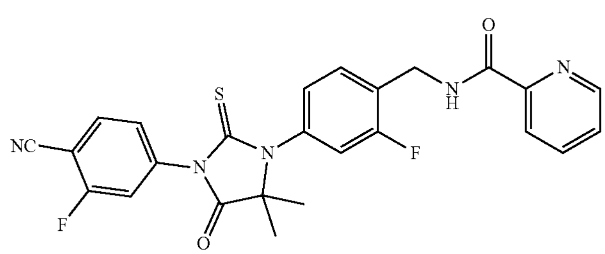 [SMILES: CC1(C)C(=O)N(c2ccc(C#N)c(F)c2)C(=S)N1c1ccc(CNC(=O)c2ccccn2)c(F)c1] |

TABLE 1-continued

| No. | Structure |
|---|---|
| 70 | 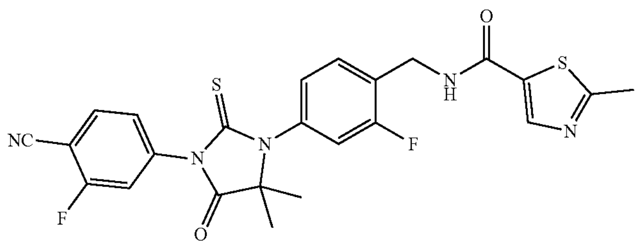 [SMILES: Cc1ncc(C(=O)NCc2ccc(N3C(=S)N(c4ccc(C#N)c(F)c4)C(=O)C3(C)C)cc2F)s1] |
| 71 | 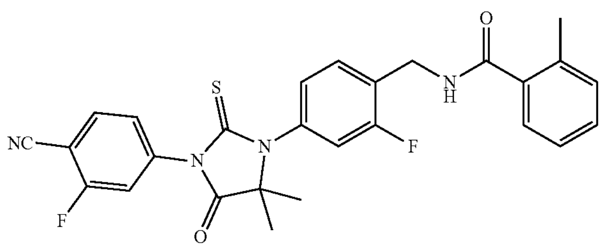 [SMILES: Cc1ccccc1C(=O)NCc1ccc(N2C(=S)N(c3ccc(C#N)c(F)c3)C(=O)C2(C)C)cc1F] |
| 72 | 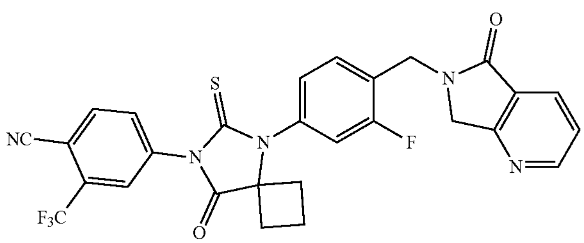 [SMILES: N#Cc1ccc(N2C(=O)C3(CCC3)N(c3ccc(CN4Cc5ncccc5C4=O)c(F)c3)C2=S)cc1C(F)(F)F] |
| 73 | 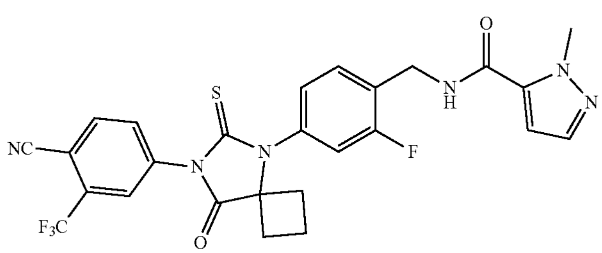 [SMILES: Cn1nccc1C(=O)NCc1ccc(N2C(=S)N(c3ccc(C#N)c(C(F)(F)F)c3)C(=O)C23CCC3)cc1F] |
| 74 | 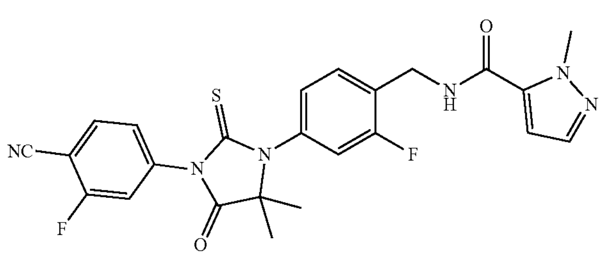 [SMILES: Cn1nccc1C(=O)NCc1ccc(N2C(=S)N(c3ccc(C#N)c(F)c3)C(=O)C2(C)C)cc1F] |
| 75 | 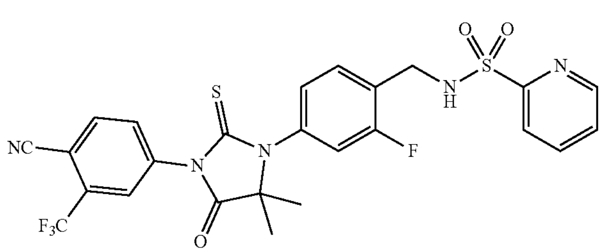 [SMILES: CC1(C)C(=O)N(c2ccc(C#N)c(C(F)(F)F)c2)C(=S)N1c1ccc(CNS(=O)(=O)c2ccccn2)c(F)c1] |

TABLE 1-continued
| No. | Structure |
|---|---|
| 76 | 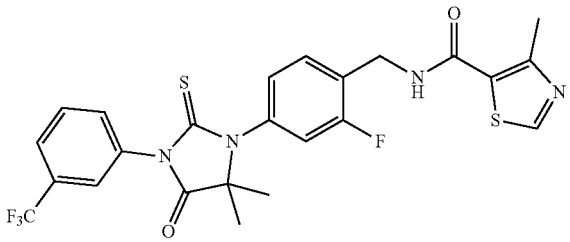 [SMILES: Cc1ncsc1C(=O)NCc1ccc(N2C(=S)N(c3cccc(C(F)(F)F)c3)C(=O)C2(C)C)cc1F] |
| 77 | 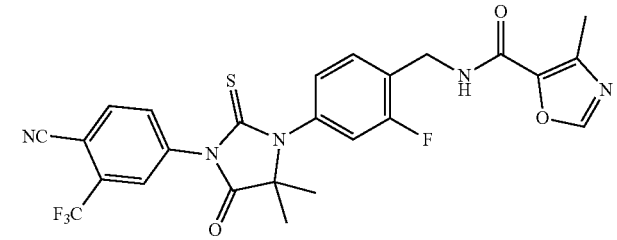 [SMILES: Cc1ncoc1C(=O)NCc1ccc(N2C(=S)N(c3ccc(C#N)c(C(F)(F)F)c3)C(=O)C2(C)C)cc1F] |
| 78 | 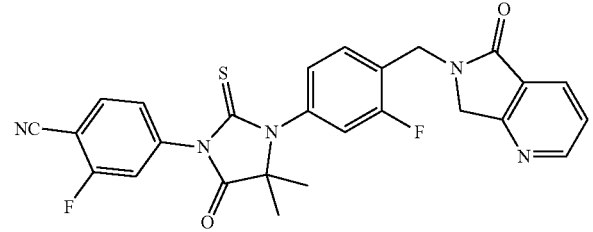 [SMILES: CC1(C)C(=O)N(c2ccc(C#N)c(F)c2)C(=S)N1c1ccc(CN2Cc3ncccc3C2=O)c(F)c1] |
| 79 | 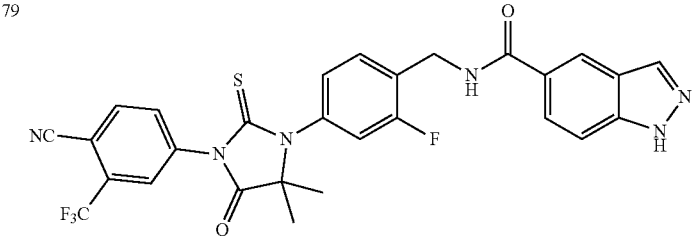 |
| 80 | 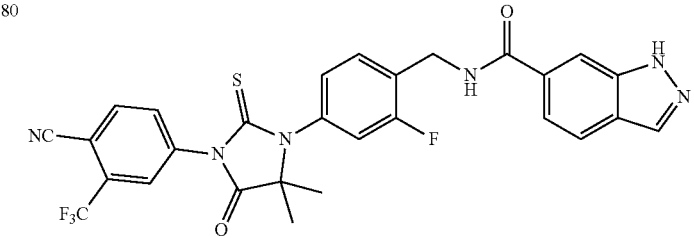 |
| 81 | 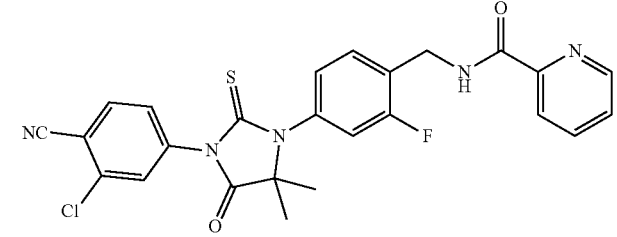 [SMILES: CC1(C)C(=O)N(c2ccc(C#N)c(Cl)c2)C(=S)N1c1ccc(CNC(=O)c2ccccn2)c(F)c1] |

TABLE 1-continued

| No. | Structure |
|---|---|
| 82 | 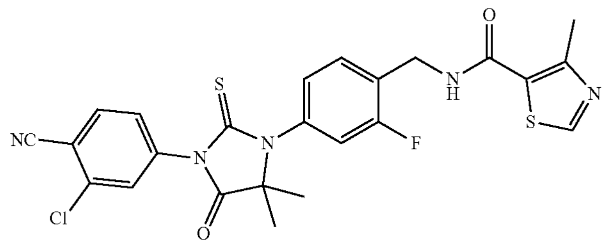 [SMILES: Cc1ncsc1C(=O)NCc1ccc(N2C(=S)N(c3ccc(C#N)c(Cl)c3)C(=O)C2(C)C)cc1F] |
| 83 | 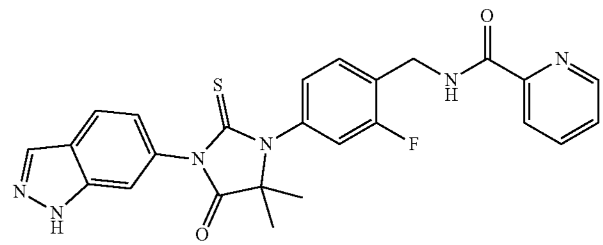 [SMILES: CC1(C)C(=O)N(c2ccc3cn[nH]c3c2)C(=S)N1c1ccc(CNC(=O)c2ccccn2)c(F)c1] |
| 84 | 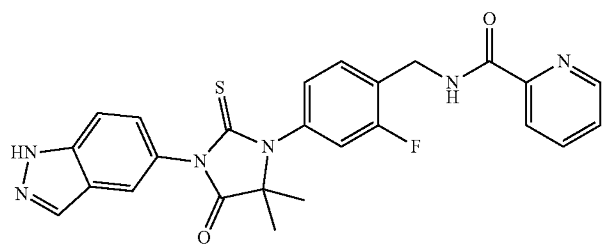 [SMILES: CC1(C)C(=O)N(c2ccc3[nH]ncc3c2)C(=S)N1c1ccc(CNC(=O)c2ccccn2)c(F)c1] |
| 85 | 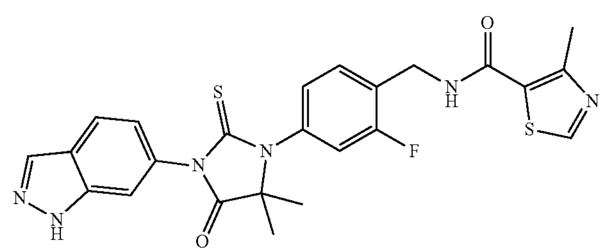 [SMILES: Cc1ncsc1C(=O)NCc1ccc(N2C(=S)N(c3ccc4cn[nH]c4c3)C(=O)C2(C)C)cc1F] |
| 86 | 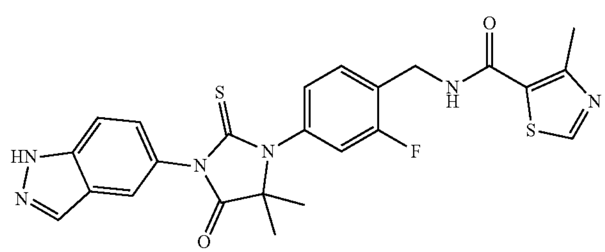 [SMILES: Cc1ncsc1C(=O)NCc1ccc(N2C(=S)N(c3ccc4[nH]ncc4c3)C(=O)C2(C)C)cc1F] |
| 87 | 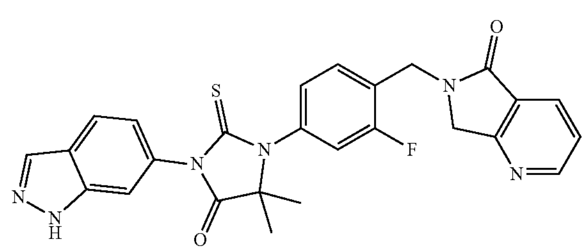 [SMILES: CC1(C)C(=O)N(c2ccc3cn[nH]c3c2)C(=S)N1c1ccc(CN2Cc3ncccc3C2=O)c(F)c1] |

TABLE 1-continued

| No. | Structure |
|-----|-----------|
| 88  | 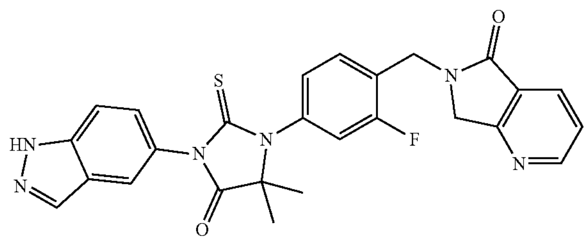 [SMILES: CC1(C)C(=O)N(c2ccc3[nH]ncc3c2)C(=S)N1c1ccc(CN2Cc3ncccc3C2=O)c(F)c1]          |
| 89  | 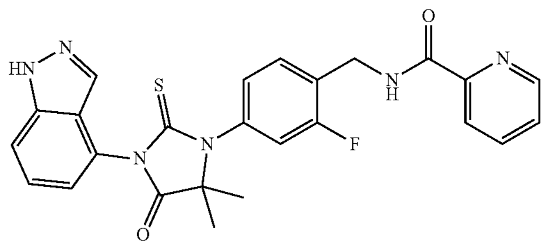 [SMILES: CC1(C)C(=O)N(c2cccc3[nH]ncc23)C(=S)N1c1ccc(CNC(=O)c2ccccn2)c(F)c1]          |
| 90  | 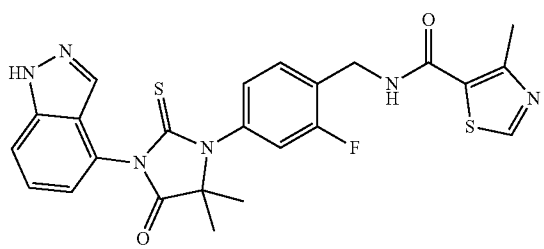 [SMILES: Cc1ncsc1C(=O)NCc1ccc(N2C(=S)N(c3cccc4[nH]ncc34)C(=O)C2(C)C)cc1F]          |
| 91  | 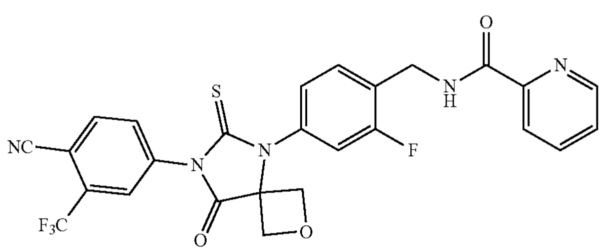 [SMILES: N#Cc1ccc(N2C(=O)C3(COC3)N(c3ccc(CNC(=O)c4ccccn4)c(F)c3)C2=S)cc1C(F)(F)F]          |
| 92  | 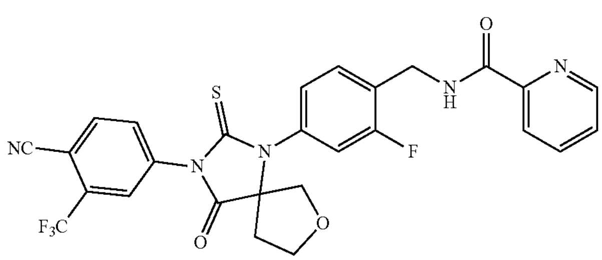 [SMILES: N#Cc1ccc(N2C(=O)C3(CCOC3)N(c3ccc(CNC(=O)c4ccccn4)c(F)c3)C2=S)cc1C(F)(F)F]          |
| 93  | 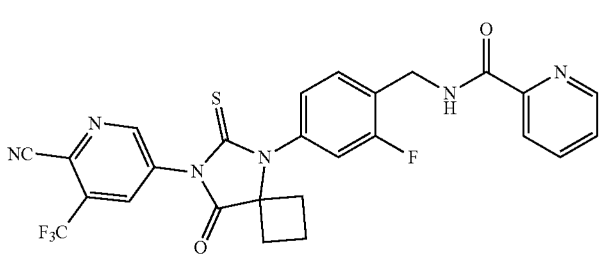 [SMILES: N#Cc1ncc(N2C(=O)C3(CCC3)N(c3ccc(CNC(=O)c4ccccn4)c(F)c3)C2=S)cc1C(F)(F)F]          |

TABLE 1-continued

| No. | Structure |
|---|---|
| 94 | 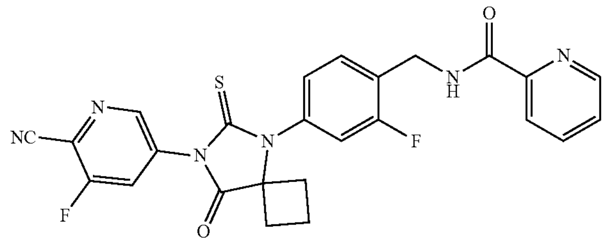 [SMILES: N#Cc1ncc(N2C(=O)C3(CCC3)N(c3ccc(CNC(=O)c4ccccn4)c(F)c3)C2=S)cc1F] |
| 95 | 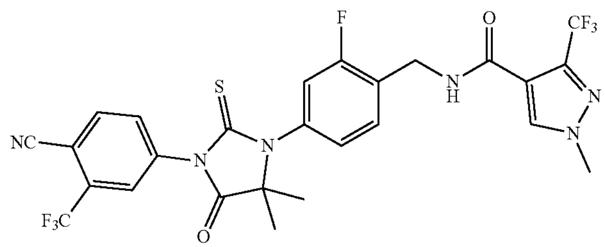 [SMILES: Cn1cc(C(=O)NCc2ccc(N3C(=S)N(c4ccc(C#N)c(C(F)(F)F)c4)C(=O)C3(C)C)cc2F)c(C(F)(F)F)n1] |
| 96 | 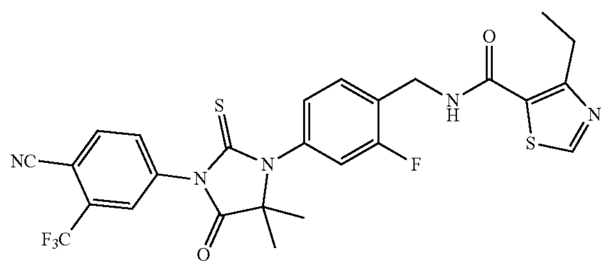 [SMILES: CCc1ncsc1C(=O)NCc1ccc(N2C(=S)N(c3ccc(C#N)c(C(F)(F)F)c3)C(=O)C2(C)C)cc1F] |
| 97 | 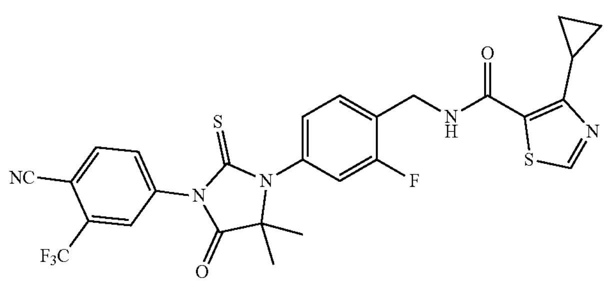 [SMILES: CC1(C)C(=O)N(c2ccc(C#N)c(C(F)(F)F)c2)C(=S)N1c1ccc(CNC(=O)c2scnc2C2CC2)c(F)c1] |
| 98 | 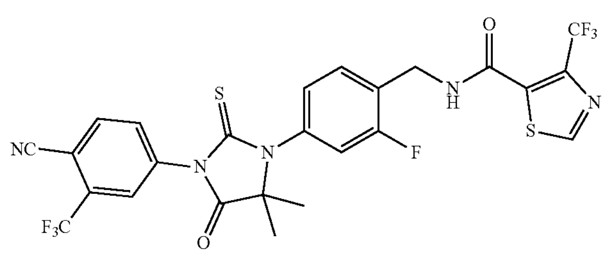 [SMILES: CC1(C)C(=O)N(c2ccc(C#N)c(C(F)(F)F)c2)C(=S)N1c1ccc(CNC(=O)c2scnc2C(F)(F)F)c(F)c1] |
| 99 | 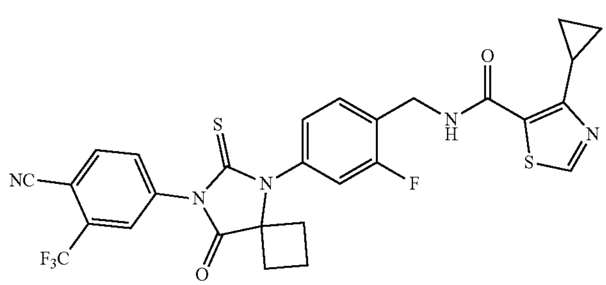 [SMILES: N#Cc1ccc(N2C(=O)C3(CCC3)N(c3ccc(CNC(=O)c4scnc4C4CC4)c(F)c3)C2=S)cc1C(F)(F)F] |

TABLE 1-continued

| No. | Structure |
|---|---|
| 100 | 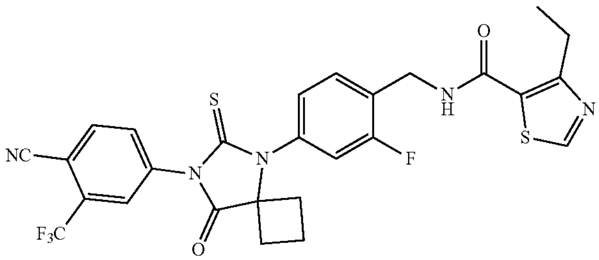 [SMILES: CCc1ncsc1C(=O)NCc1ccc(N2C(=S)N(c3ccc(C#N)c(C(F)(F)F)c3)C(=O)C23CCC3)cc1F] |
| 101 | 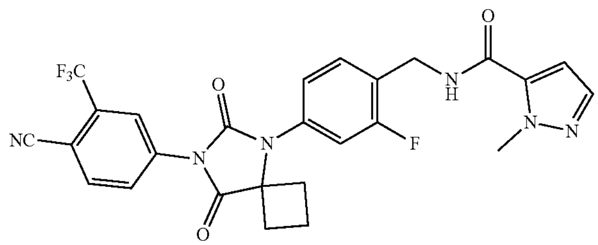 [SMILES: Cn1nccc1C(=O)NCc1ccc(N2C(=O)N(c3ccc(C#N)c(C(F)(F)F)c3)C(=O)C23CCC3)cc1F] |
| 102 | 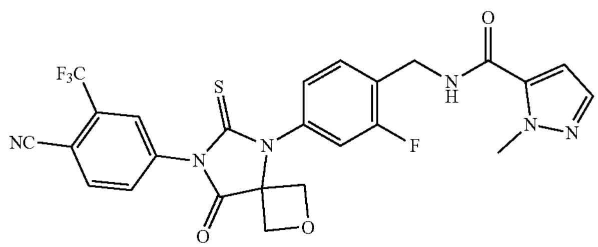 [SMILES: Cn1nccc1C(=O)NCc1ccc(N2C(=S)N(c3ccc(C#N)c(C(F)(F)F)c3)C(=O)C23COC3)cc1F] |
| 103 | 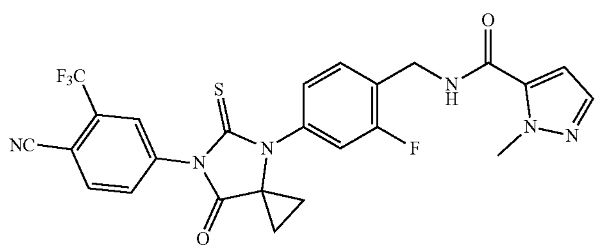 [SMILES: Cn1nccc1C(=O)NCc1ccc(N2C(=S)N(c3ccc(C#N)c(C(F)(F)F)c3)C(=O)C23CC3)cc1F] |
| 104 | 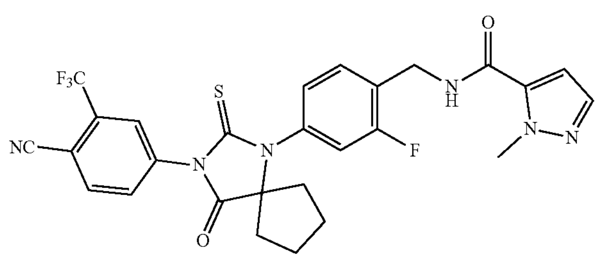 [SMILES: Cn1nccc1C(=O)NCc1ccc(N2C(=S)N(c3ccc(C#N)c(C(F)(F)F)c3)C(=O)C23CCCC3)cc1F] |
| 105 | 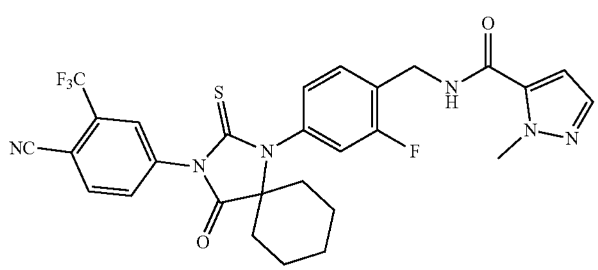 [SMILES: Cn1nccc1C(=O)NCc1ccc(N2C(=S)N(c3ccc(C#N)c(C(F)(F)F)c3)C(=O)C23CCCCC3)cc1F] |

TABLE 1-continued
| No. | Structure |
|---|---|
| 106 | 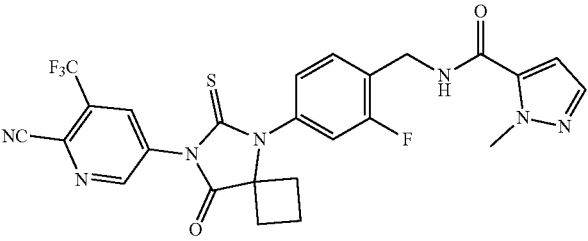 [SMILES: Cn1nccc1C(=O)NCc1ccc(N2C(=S)N(c3cnc(C#N)c(C(F)(F)F)c3)C(=O)C23CCC3)cc1F] |
| 107 | 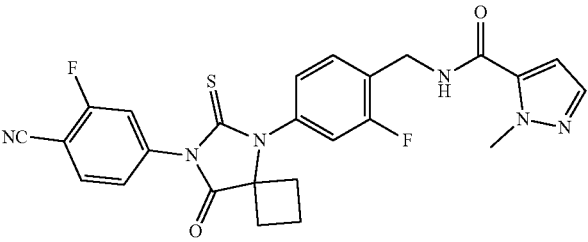 [SMILES: Cn1nccc1C(=O)NCc1ccc(N2C(=S)N(c3ccc(C#N)c(F)c3)C(=O)C23CCC3)cc1F] |
| 108 | 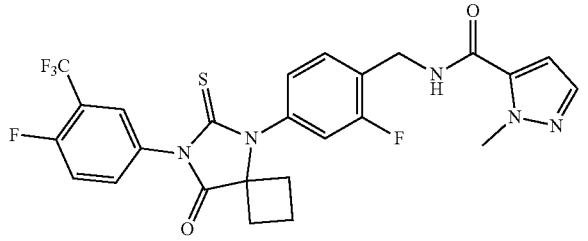 [SMILES: Cn1nccc1C(=O)NCc1ccc(N2C(=S)N(c3ccc(F)c(C(F)(F)F)c3)C(=O)C23CCC3)cc1F] |
| 109 | 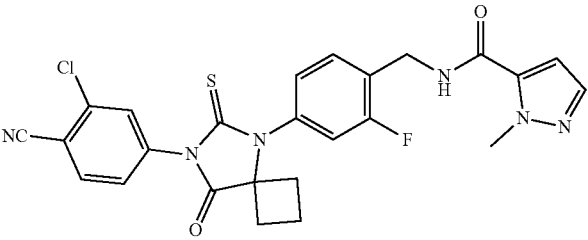 [SMILES: Cn1nccc1C(=O)NCc1ccc(N2C(=S)N(c3ccc(C#N)c(Cl)c3)C(=O)C23CCC3)cc1F] |
| 110 | 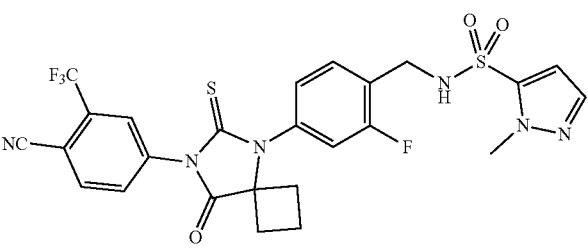 [SMILES: Cn1nccc1S(=O)(=O)NCc1ccc(N2C(=S)N(c3ccc(C#N)c(C(F)(F)F)c3)C(=O)C23CCC3)cc1F] |
| 111 | 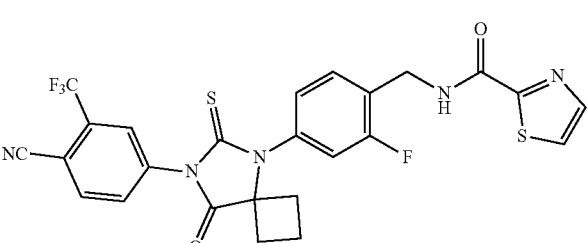 |

TABLE 1-continued

| No. | Structure |
|-----|-----------|
| 112 | 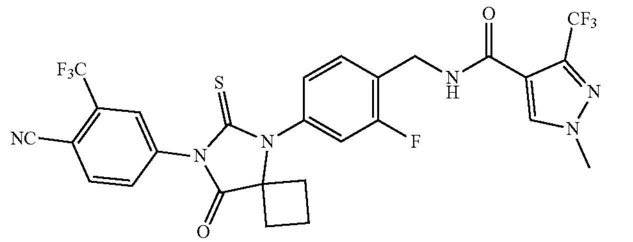 [SMILES: Cn1cc(C(=O)NCc2ccc(N3C(=S)N(c4ccc(C#N)c(C(F)(F)F)c4)C(=O)C34CCC4)cc2F)c(C(F)(F)F)n1] |
| 113 | 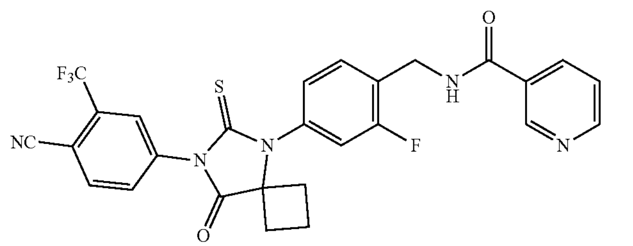 [SMILES: N#Cc1ccc(N2C(=O)C3(CCC3)N(c3ccc(CNC(=O)c4cccnc4)c(F)c3)C2=S)cc1C(F)(F)F] |
| 114 | 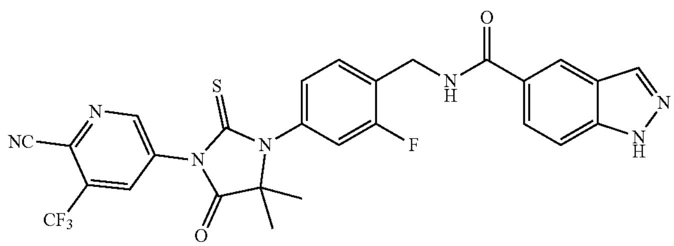 |
| 115 | 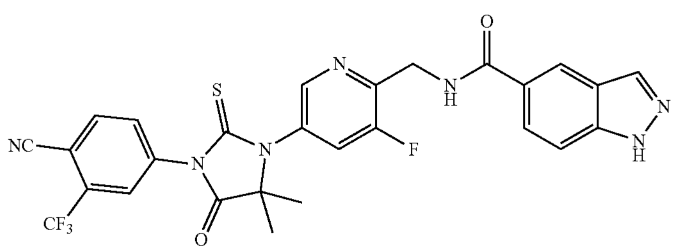 [SMILES: CC1(C)C(=O)N(c2ccc(C#N)c(C(F)(F)F)c2)C(=S)N1c1cnc(CNC(=O)c2ccc3[nH]ncc3c2)c(F)c1] |
| 116 | 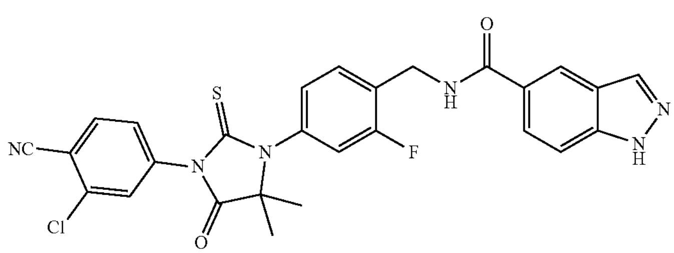 [SMILES: CC1(C)C(=O)N(c2ccc(C#N)c(Cl)c2)C(=S)N1c1ccc(CNC(=O)c2ccc3[nH]ncc3c2)c(F)c1] |
| 117 | 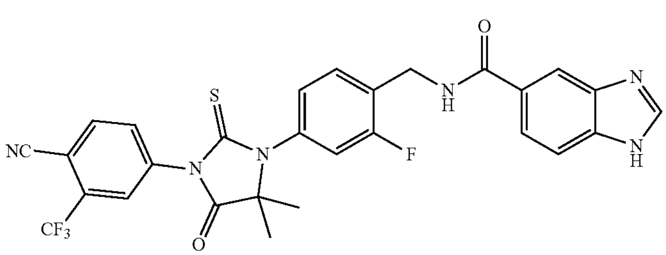 |

TABLE 1-continued

| No. | Structure |
|-----|-----------|
| 118 | 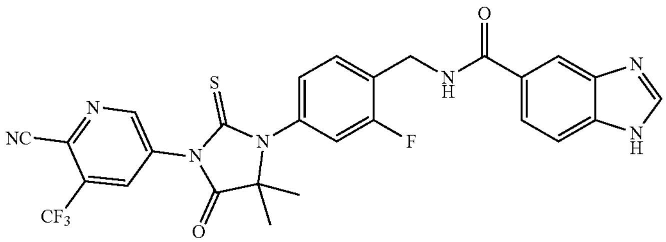 [SMILES: CC1(C)C(=O)N(c2cnc(C#N)c(C(F)(F)F)c2)C(=S)N1c1ccc(CNC(=O)c2ccc3[nH]cnc3c2)c(F)c1] |
| 119 | 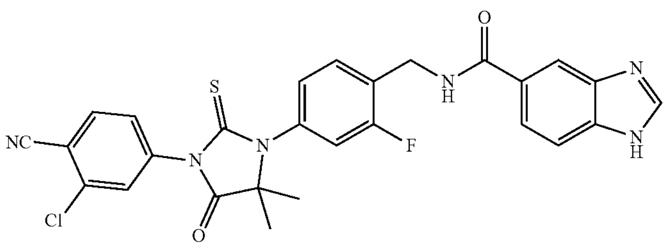 [SMILES: CC1(C)C(=O)N(c2ccc(C#N)c(Cl)c2)C(=S)N1c1ccc(CNC(=O)c2ccc3[nH]cnc3c2)c(F)c1] |
| 120 | 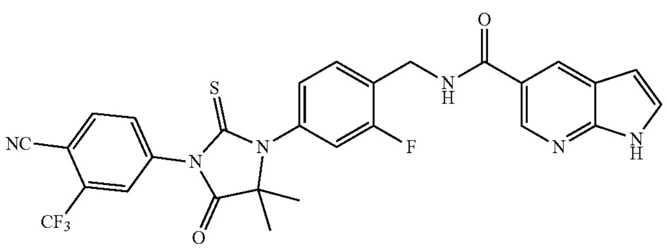 |
| 121 | 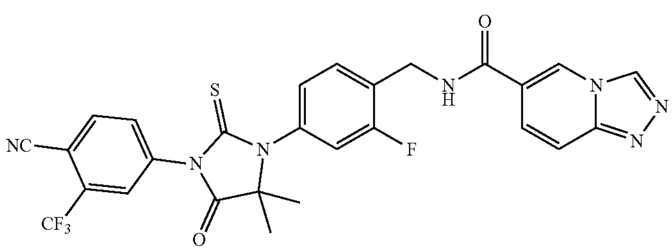 |
| 122 | 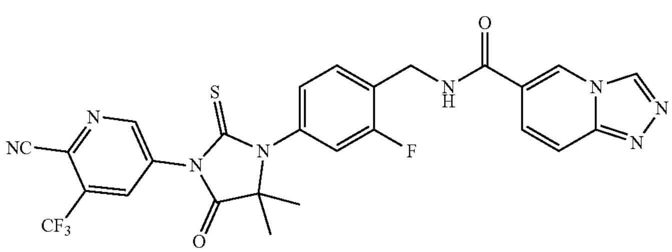 [SMILES: CC1(C)C(=O)N(c2cnc(C#N)c(C(F)(F)F)c2)C(=S)N1c1ccc(CNC(=O)c2ccc3nncn3c2)c(F)c1] |
| 123 | 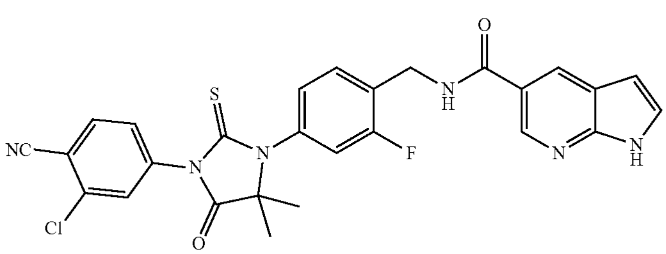 [SMILES: CC1(C)C(=O)N(c2ccc(C#N)c(Cl)c2)C(=S)N1c1ccc(CNC(=O)c2cnc3[nH]ccc3c2)c(F)c1] |

TABLE 1-continued

| No. | Structure |
|-----|-----------|
| 124 | 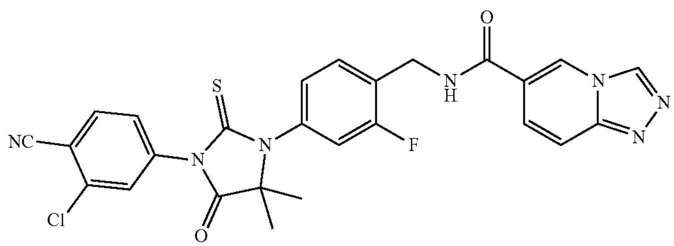 [SMILES: CC1(C)C(=O)N(c2ccc(C#N)c(Cl)c2)C(=S)N1c1ccc(CNC(=O)c2ccc3nncn3c2)c(F)c1] |
| 125 | 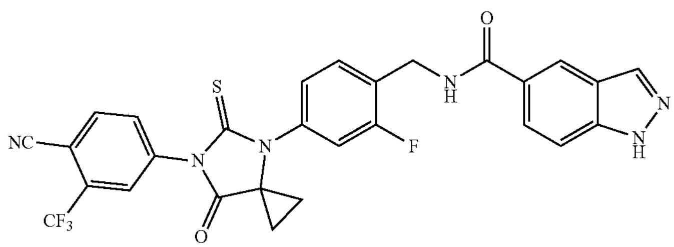 |
| 126 | 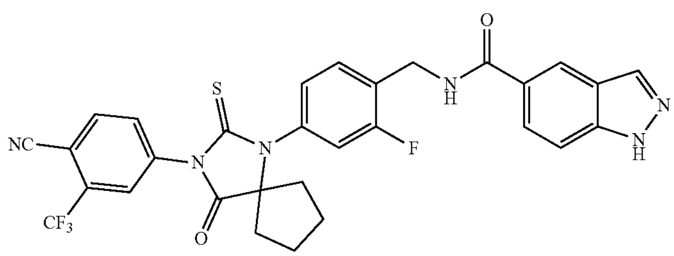 |
| 127 | 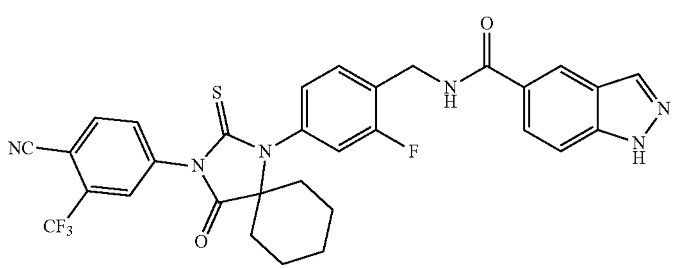 [SMILES: N#Cc1ccc(N2C(=O)C3(CCCCC3)N(c3ccc(CNC(=O)c4ccc5[nH]ncc5c4)c(F)c3)C2=S)cc1C(F)(F)F] |
| 128 | 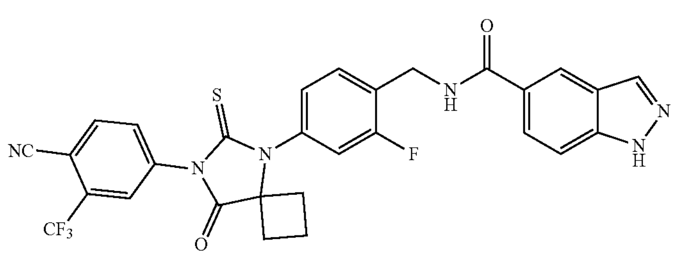 |
| 129 | 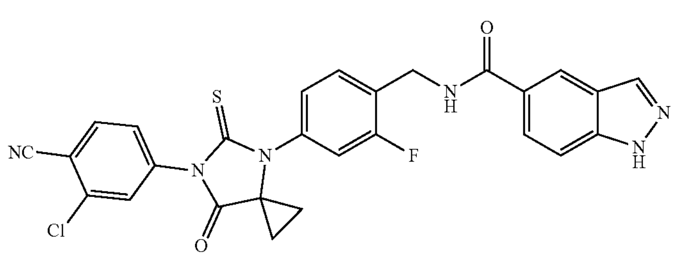 [SMILES: N#Cc1ccc(N2C(=O)C3(CC3)N(c3ccc(CNC(=O)c4ccc5[nH]ncc5c4)c(F)c3)C2=S)cc1Cl] |

TABLE 1-continued
| No. | Structure |
|---|---|
| 130 | 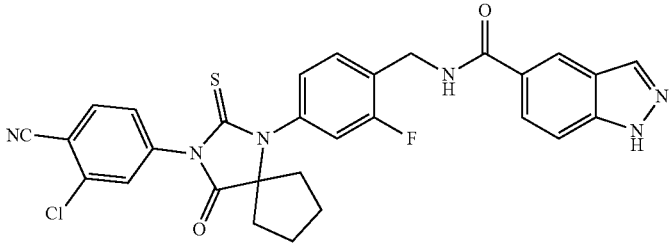 [SMILES: N#Cc1ccc(N2C(=O)C3(CCCC3)N(c3ccc(CNC(=O)c4ccc5[nH]ncc5c4)c(F)c3)C2=S)cc1Cl] |
| 131 | 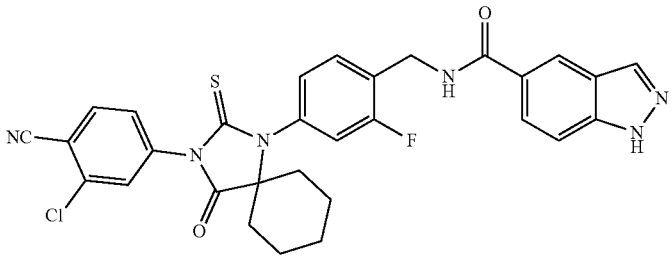 [SMILES: N#Cc1ccc(N2C(=O)C3(CCCCC3)N(c3ccc(CNC(=O)c4ccc5[nH]ncc5c4)c(F)c3)C2=S)cc1Cl] |
| 132 | 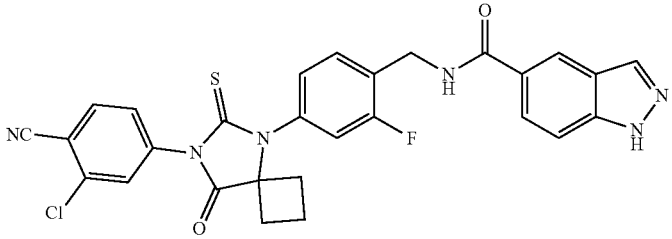 [SMILES: N#Cc1ccc(N2C(=O)C3(CCC3)N(c3ccc(CNC(=O)c4ccc5[nH]ncc5c4)c(F)c3)C2=S)cc1Cl] |
| 133 | 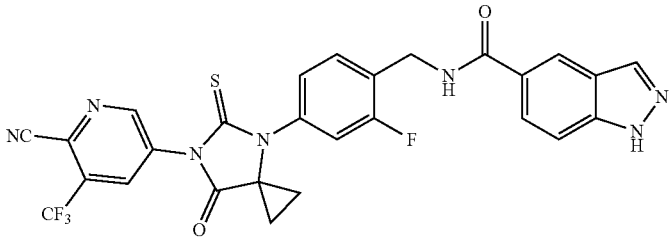 [SMILES: N#Cc1ncc(N2C(=O)C3(CC3)N(c3ccc(CNC(=O)c4ccc5[nH]ncc5c4)c(F)c3)C2=S)cc1C(F)(F)F] |
| 134 | 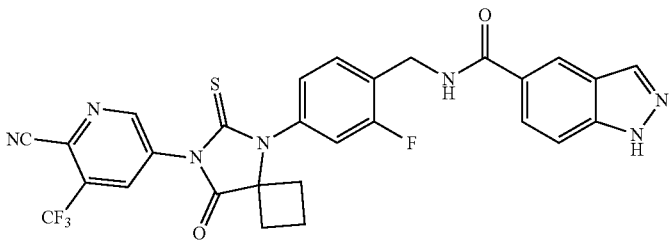 [SMILES: N#Cc1ncc(N2C(=O)C3(CCC3)N(c3ccc(CNC(=O)c4ccc5[nH]ncc5c4)c(F)c3)C2=S)cc1C(F)(F)F] |
| 135 | 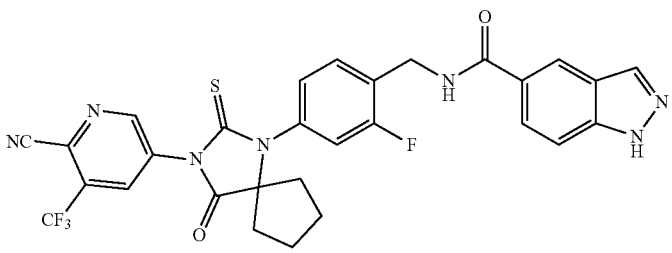 [SMILES: N#Cc1ncc(N2C(=O)C3(CCCC3)N(c3ccc(CNC(=O)c4ccc5[nH]ncc5c4)c(F)c3)C2=S)cc1C(F)(F)F] |

TABLE 1-continued
| No. | Structure |
|---|---|
| 136 | 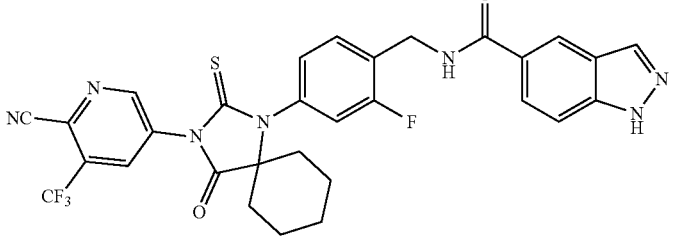 |
| 137 | 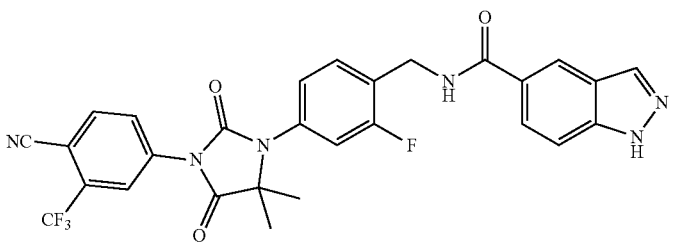 [SMILES: CC1(C)C(=O)N(c2ccc(C#N)c(Cl)c2)C(=O)N1c1ccc(CNC(=O)c2ccc3[nH]ncc3c2)c(F)c1] |
| 138 | 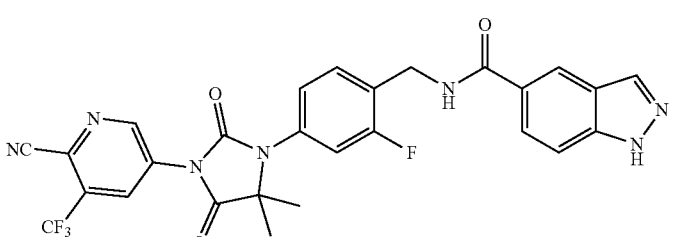 |
| 139 | 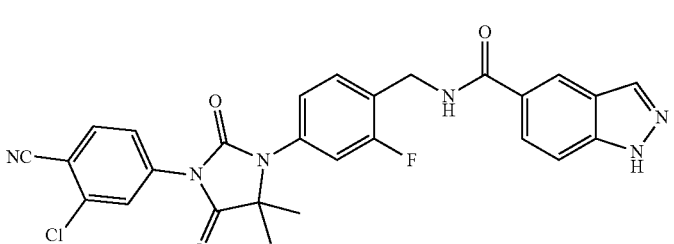 |
| 140 | 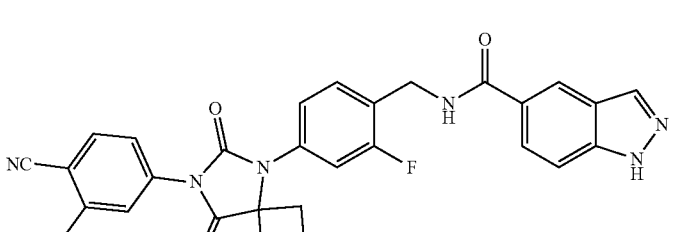 |
| 141 | 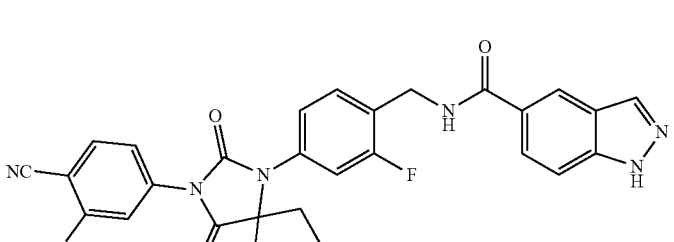 |

TABLE 1-continued

| No. | Structure |
|---|---|
| 142 | 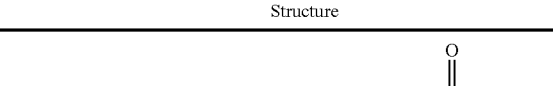 |

Methods of Treatment

It is contemplated that the compounds described herein antagonize AR and/or GR activity. As such, also provided is a method of treating or preventing diseases or conditions that are mediated by the AR and/or GR. In one embodiment, the disease is cancer, and the treatment comprises administering an effective amount of a compound or composition as described herein to an individual in need thereof. As used herein, "treatment" or "treating" is an approach for obtaining a beneficial or desired result, such as a clinical result. For purposes of this disclosure, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cancer. In certain embodiments, treatment of a disease or condition with a compound of the disclosure or a pharmaceutically acceptable salt, stereoisomer, mixture of stereoisomers, solvate, or tautomer thereof is accompanied by no or fewer side effects than are associated with currently available therapies for the disease or condition and/or improves the quality of life of the individual.

The term "cancer," as used herein refers to an abnormal growth of cells which tend to proliferate in an uncontrolled way and, in some cases, to metastasize (spread). The types of cancer include, but are not limited to, solid tumors, such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

As used herein, the term "cancer" refers to a class of diseases of mammals characterized by uncontrolled cellular growth. The term "cancer" is used interchangeably with the terms "tumor," "solid tumor," "malignancy," "hyperproliferation" and "neoplasm." Cancer includes all types of hyperproliferative growth, hyperplasic growth, neoplastic growth, cancerous growth or oncogenic processes, metastatic tissues or malignantly transformed cells, tissues, or organs, irrespective of histopathologic type or stage of invasiveness. Illustrative examples include, lung, prostate, head and neck, breast and colorectal cancer, melanomas and gliomas (such as a high grade glioma, including glioblastoma multiforme (GBM), the most common and deadliest of malignant primary brain tumors in adult humans).

The phrase "solid tumor" includes, for example, lung cancer, head and neck cancer, brain cancer, oral cancer, colorectal cancer, breast cancer, prostate cancer, pancreatic cancer, and liver cancer. Other types of solid tumors are named for the particular cells that form them, for example, sarcomas formed from connective tissue cells (for example, bone cartilage, fat), carcinomas formed from epithelial tissue cells (for example, breast, colon, pancreas) and lymphomas formed from lymphatic tissue cells (for example, lymph nodes, spleen, thymus). Treatment of all types of solid tumors regardless of naming convention is within the scope of this disclosure.

The cancer can be a blood cancer, lung cancer, breast cancer, fallopian tube cancer, brain cancer, head and neck cancer, esophageal cancer, ovarian cancer, pancreatic cancer, peritoneal cancer, prostate cancer or skin cancer, such as, but not limited to, liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoide, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or prostatic carcinoma.

Also provided is a method of treating or preventing bladder cancer, breast cancer, fallopian tube cancer, ovarian cancer, prostate cancer, non-small cell lung cancer, pancreatic cancer, peritoneal cancer, testicular cancer, endometrial cancer, or uterine cancer, comprising administering an effective amount of a compound or composition as described herein, or a pharmaceutically acceptable salt, stereoisomer, mixture of stereoisomers, solvate, or tautomer thereof, to an individual in need thereof. In certain embodiments, the cancer is prostate, breast, triple negative breast cancer, bladder, or liver cancer.

Also provided is a method of treating or preventing cancer, comprising administering an effective amount of a compound or composition as described herein, or a pharmaceutically acceptable salt, stereoisomer, mixture of stereoisomers, solvate, or tautomer thereof, in combination with an additional chemotherapeutic agent, to an individual in need thereof.

The compounds provided herein also modulate the function of the nuclear hormone receptors, particularly the androgen receptor, and include compounds which are, for example, selective antagonists of the androgen receptor (AR). Thus, the present compounds are useful in the treatment of AR-associated conditions. An "AR-associated condition," as used herein, denotes a condition or disorder which can be treated by modulating the function or activity of an AR in a subject, wherein treatment comprises prevention, partial alleviation or cure of the condition or disorder. Modulation can occur locally, for example, within certain tissues of the subject, or more extensively throughout a subject being treated for such a condition or disorder.

The compounds with potent antagonistic activity are used for the treatment of androgen related prostate cancer. Other, non-limiting examples include, treatment of a variety of male hormone-related conditions such as hypersexuality and sexual deviation; treatment of conditions including benign prostatic hyperplasia, acne vulgaris, androgenetic alopecia, and hirsutism; purposefully preventing or counteracting masculinization in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

Prostate cancer is one of the most common cancers in men around the world, and is one of the leading causes of cancer death in men in the United States. The androgen receptor antagonist drugs, such as flutamide and bicalutamide, were originally designed to avoid the side effects of hormone therapy but androgen agonism was observed for hydroxyflutamide (the active form of flutamide) and bicalutamide.

Compounds with potent antagonistic activity have been studied for the treatment of androgen related breast, bladder, liver, ovarian cancer, gastric or salivary duct carcinoma, and can be used for the treatment of triple negative breast cancer.

It is also contemplated that the compounds described herein are modulators, e.g., antagonists, of the glucocorticoid receptor (GR). Accordingly, compounds provided herein can be used as medicaments for the treatment and/or prevention of diseases which are associated with GR modulation.

In some embodiments, the compounds and compositions provided herein modulate cells, diseases or disorders, which are enzalutamide-resistant. In some embodiments, the compounds and compositions provided herein modulate cells, diseases or disorders, which are apalutamide-resistant.

Compositions

Compositions, including pharmaceutical compositions, of any of the compounds detailed herein are embraced by this disclosure. Thus, provided herein are pharmaceutical compositions comprising a compound of the disclosure, or a pharmaceutically acceptable salt, stereoisomer, mixture of stereoisomers, solvate, or tautomer thereof, and a pharmaceutically acceptable carrier or excipient. The pharmaceutical compositions provided herein may take a form suitable for oral, buccal, parenteral (e.g., intravenous, intramuscular, infusion or subcutaneous injection), nasal, topical or rectal administration, or a form suitable for administration by inhalation.

A compound as described herein may, in one aspect, be in a purified form. Compositions comprising a compound as described herein, or a pharmaceutically acceptable salt, stereoisomer, mixture of stereoisomers, solvate, or tautomer thereof, are provided, such as compositions of substantially pure compounds. In some embodiments, a composition comprising a compound as described herein, or a pharmaceutically acceptable salt, stereoisomer, mixture of stereoisomers, solvate, or tautomer thereof, is in substantially pure form. Unless otherwise stated, "substantially pure" refers to a composition which contains no more than 35% impurity, wherein the impurity denotes a compound other than the desired compound, or a pharmaceutically acceptable salt, stereoisomer, mixture of stereoisomers, solvate, or tautomer thereof, which comprises the majority of the composition. In one variation, a composition of substantially pure compound, or a pharmaceutically acceptable salt, stereoisomer, mixture of stereoisomers, solvate, or tautomer thereof, is provided wherein the composition contains no more than 25% impurity. In another variation, a composition of substantially pure compound, or a pharmaceutically acceptable salt, stereoisomer, mixture of stereoisomers, solvate, or tautomer thereof, is provided wherein the composition contains or no more than 20% impurity. In still another variation, a composition of substantially pure compound, or a pharmaceutically acceptable salt, stereoisomer, mixture of stereoisomers, solvate, or tautomer thereof, is provided wherein the composition contains or no more than 10% impurity. In a further variation, a composition of substantially pure compound, or a pharmaceutically acceptable salt, stereoisomer, mixture of stereoisomers, solvate, or tautomer thereof, is provided wherein the composition contains or no more than 5% impurity. In another variation, a composition of substantially pure compound, or a pharmaceutically acceptable salt, stereoisomer, mixture of stereoisomers, solvate, or tautomer thereof, is provided wherein the composition contains or no more than 3% impurity. In still another variation, a composition of substantially pure compound, or a pharmaceutically acceptable salt, stereoisomer, mixture of stereoisomers, solvate, or tautomer thereof, is provided wherein the composition contains or no more than 1% impurity. In a further variation, a composition of substantially pure compound, or a pharmaceutically acceptable salt, stereoisomer, mixture of stereoisomers, solvate, or tautomer thereof, is provided wherein the composition contains or no more than 0.5% impurity.

In certain embodiments, pharmaceutical compositions are formulated in any manner, including using one or more physiologically acceptable carriers comprising excipients and/or auxiliaries which facilitate processing of the active compounds into pharmaceutical compositions. In some embodiments, proper formulation is dependent upon the route of administration chosen. In various embodiments, any techniques, carriers, and excipients are used as suitable.

Provided herein are pharmaceutical compositions that include a compound described herein and a pharmaceutically acceptable diluent(s), excipient(s), and/or carrier(s). In addition, in some embodiments, the compounds described herein are administered as pharmaceutical compositions in which compounds described herein are mixed with other active ingredients, as in combination therapy.

A pharmaceutical composition, as used herein, refers to a mixture of a compound described herein with other chemical components, such as carriers, stabilizers, diluents, dispersing agents, suspending agents, thickening agents, and/or excipients. In certain embodiments, a pharmaceutical composition facilitates administration of the compound to an organism. In some embodiments, practicing the methods of treatment or use provided herein, includes administering or using a pharmaceutical composition comprising a therapeutically effective amount of a compound provided herein. In specific embodiments, the methods of treatment provided for herein include administering such a pharmaceutical composition to a mammal having a disease or condition to be treated. In one embodiment, the mammal is a human. In some embodiments, the therapeutically effective amount varies widely depending on the severity of the disease, the age and relative health of the subject, the potency of the compound used and other factors. In various embodiments, the compounds described herein are used singly or in combination with one or more therapeutic agents as components of mixtures.

In certain embodiments, the pharmaceutical compositions provided herein are formulated for intravenous injections. In certain aspects, the intravenous injection formulations provided herein are formulated as aqueous solutions, and, in some embodiments, in physiologically compatible buffers such as Hank's solution, Ringer's solution, or physiological saline buffer. In certain embodiments, the pharmaceutical compositions provided herein are formulated for transmucosal administration. In some embodiments, transmucosal formulations include penetrants appropriate to the barrier to be permeated. In certain embodiments, the pharmaceutical compositions provided herein are formulated for other parenteral injections, appropriate formulations include aqueous or nonaqueous solutions, and in one embodiment, with physiologically compatible buffers or excipients.

In certain embodiments, the pharmaceutical compositions provided herein are formulated for oral administration. In certain aspects, the oral formulations provided herein comprise compounds described herein that are formulated with pharmaceutically acceptable carriers or excipients. Such carriers enable the compounds described herein to be formulated as tablets, powders, pills, dragees, capsules, liquids, gels, syrups, elixirs, slurries, suspensions and the like, for oral ingestion by a patient to be treated.

In some embodiments, pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are optionally added, such as the cross-linked croscarmellose sodium, polyvinylpyrrolidone, agar, or alginic acid or a salt thereof such as sodium alginate.

In certain embodiments, provided herein is a pharmaceutical composition formulated as dragee cores with suitable coatings. In certain embodiments, concentrated sugar solutions are used in forming the suitable coating, and optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs and/or pigments are added to tablets, dragees and/or the coatings thereof for, e.g., identification or to characterize different combinations of active compound doses.

In certain embodiments, pharmaceutical compositions which are used include orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In certain embodiments, in soft capsules, the active compounds are dissolved or suspended in suitable liquids, such as fatty oils, liquid paraffin, or liquid polyethylene glycols. In addition, stabilizers are optionally added. In certain embodiments, the formulations for oral administration are in dosages suitable for such administration.

In certain embodiments, the pharmaceutical compositions provided herein are formulated for buccal or sublingual administration. In certain embodiments, buccal or sublingual compositions take the form of tablets, lozenges, or gels formulated in a conventional manner. In certain embodiments, parenteral injections involve bolus injection or continuous infusion. In some embodiments, formulations for injection are presented in unit dosage form, e.g., in ampoules or in multi-dose containers, with an added preservative. In some embodiments, the pharmaceutical composition described herein is in a form suitable for parenteral injection as a sterile suspensions, solutions or emulsions in oily or aqueous vehicles, and optionally contains formulatory agents such as suspending, stabilizing and/or dispersing agents. Pharmaceutical formulations for parenteral administration include aqueous solutions of the active compounds in water-soluble form. In some embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes.

In certain embodiments, aqueous injection suspensions contain substances which increase the viscosity of the suspension, such as sodium carboxymethyl cellulose, sorbitol, or dextran. Optionally, the suspensions also contain suitable stabilizers or agents which increase the solubility of the compounds to allow for the preparation of highly concentrated solutions. In alternative embodiments, the active ingredient is in powder form for constitution with a suitable vehicle, e.g., sterile pyrogen-free water, before use.

In some embodiments, the compounds described herein are administered topically. In specific embodiments, the compounds described herein are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and/or preservatives.

In certain embodiments, the pharmaceutical compositions provided herein are formulated for transdermal administration of compounds described herein. In some embodiments, administration of such compositions employs transdermal delivery devices and transdermal delivery patches. In certain embodiments, the compositions are lipophilic emulsions or buffered, aqueous solutions, dissolved and/or dispersed in a polymer or an adhesive. Such patches include those constructed for continuous, pulsatile, or on demand delivery of pharmaceutical agents. In some embodiments, transdermal delivery of the compounds described herein is accomplished by use of iontophoretic patches and the like. In certain embodiments, the rate of absorption is slowed by using rate-controlling membranes or by trapping the compound within a polymer matrix or gel. Conversely, absorption enhancers are optionally used to increase absorption. Absorption enhancer and carrier include absorbable pharmaceutically acceptable solvents that assist in passage of the compound through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In certain embodiments, the pharmaceutical compositions provided herein are formulated for administration by inhalation. In certain embodiments, in such pharmaceutical compositions formulated for inhalation, the compounds described herein are in a form as an aerosol, a mist or a powder. In some embodiments, pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In certain aspects of a pressurized aerosol, the dosage unit is determined by providing a valve to deliver a metered amount. In certain embodiments, capsules and cartridges of, such as, by way of example only, gelatin for use in an inhaler or insufflator is formulated containing a powder mix of the compound described herein and a suitable powder base such as lactose or starch.

In some embodiments, the compounds described herein are formulated in rectal compositions such as enemas, rectal gels, rectal foams, rectal aerosols, suppositories, jelly suppositories, or retention enemas. In certain embodiments, rectal compositions optionally contain conventional suppository bases such as cocoa butter or other glycerides, as well as synthetic polymers such as polyvinylpyrrolidone, PEG, and the like. In certain suppository forms of the compositions, a low-melting wax such as, but not limited to, a mixture of fatty acid glycerides, optionally in combination with cocoa butter is first melted.

In various embodiments provided herein, the pharmaceutical compositions are formulated in a conventional manner using one or more physiologically acceptable carriers comprising excipients and auxiliaries which facilitate processing of the active compounds into pharmaceutically acceptable preparations. In certain embodiments, proper formulation is dependent upon the route of administration chosen. In various embodiments, any of the techniques, carriers, and excipients is used as suitable. In some embodiments, pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

In certain embodiments, the pharmaceutical compositions include at least one pharmaceutically acceptable carrier, diluent or excipient and a compound described herein described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds described herein exist as tautomers. All tautomers are included within the scope of the compounds presented herein. Additionally, included herein are the solvated and unsolvated forms of the compounds described herein. Solvated compounds include those that are solvated with pharmaceutically acceptable solvents such as water, ethanol, and the like. The solvated forms of the compounds presented herein are also considered to be disclosed herein. In some embodiments, the pharmaceutical compositions described herein include other medicinal or pharmaceutical agents, carriers, adjuvants, such as preserving, stabilizing, wetting or emulsifying agents, solution promoters, salts for regulating the osmotic pressure, and/or buffers. In additional embodiments, the pharmaceutical compositions described herein also contain other therapeutically valuable substances.

Methods for the preparation of compositions containing the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. In various embodiments, the compositions are in liquid solutions or suspensions, solid forms suitable for solution or suspension in a liquid prior to use, or as emulsions. These compositions optionally contain minor amounts of nontoxic, auxiliary substances, such as wetting or emulsifying agents, pH buffering agents, and so forth.

In some embodiments, a composition comprising a compound described herein takes the form of a liquid where the agents are present in solution, in suspension or both. In some embodiments, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

Useful aqueous suspension optionally contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

Useful compositions optionally comprise an mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful compositions optionally include solubilizing agents to aid in the solubility of a compound described herein. The term "solubilizing agent" generally includes agents that result in formation of a micellar solution or a true solution of the agent. Solubilizing agents include certain acceptable nonionic surfactants, for example polysorbate 80, and ophthalmologically acceptable glycols, polyglycols, e.g., polyethylene glycol 400, and glycol ethers.

Useful compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Certain useful compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Some useful compositions optionally include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Certain useful compositions optionally one or more antioxidants to enhance chemical stability where required. Suitable antioxidants include, by way of example only, ascorbic acid and sodium metabisulfite.

In some embodiments, aqueous suspension compositions are packaged in single-dose non-reclosable containers. In alternative embodiments, multiple-dose reclosable containers are used, in which case it is typical to include a preservative in the composition.

In various embodiments, any delivery system for hydrophobic pharmaceutical compounds is employed. Liposomes and emulsions are examples of delivery vehicles or carriers for hydrophobic drugs. In certain embodiments, certain organic solvents such as N-methylpyrrolidone are employed. In some embodiments, the compounds are delivered using a sustained-release system, such as semipermeable matrices of solid hydrophobic polymers containing the therapeutic agent. Various sustained-release materials are utilized in the embodiments herein. In certain embodiments, sustained-release capsules release the compounds for a few weeks up to over 100 days. In some embodiments, depending on the chemical nature and the biological stability of the therapeutic reagent, additional strategies for protein stabilization are employed.

In certain embodiments, the formulations or compositions described herein benefit from and/or optionally comprise antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Dosing and Treatment Regimens

In certain embodiments, the compounds described herein are used in the preparation or manufacture of medicaments for the treatment of diseases or conditions that are mediated the AR and/or GR. In some embodiments, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. In some embodiments, amounts effective for this use will depend on the severity and course of the disease or condition, previous therapy, the patients health status, weight, and response to the drugs, and the judgment of the treating physician. In certain instances, it is considered appropriate for the caregiver to determine such therapeutically effective amounts by routine experimentation (including, but not limited to, a dose escalation clinical trial).

In certain prophylactic applications, compositions containing the compounds described herein are administered to a patient susceptible to or otherwise at risk of a particular disease, disorder or condition. In some embodiments, the amount administered is defined to be a "prophylactically effective amount or dose." In certain embodiments of this use, the precise amounts of compound administered depend on the patients state of health, weight, and the like. In some embodiments, it is considered appropriate for the caregiver to determine such prophylactically effective amounts by routine experimentation (e.g., a dose escalation clinical trial). In certain embodiments, when used in a patient, effective amounts for this use will depend on the severity and course of the disease, disorder or condition, previous therapy, the patients health status and response to the drugs, and the judgment of the treating physician.

In certain instances, a patients condition does not improve or does not significantly improve following administration of a compound or composition described herein and, upon the doctor's discretion the administration of the compounds is optionally administered chronically, that is, for an extended period of time, including throughout the duration of the patients life in order to ameliorate or otherwise control or limit the symptoms of the patients disease or condition.

In certain cases wherein the patients status does improve or does not substantially improve, upon the doctor's discretion the administration of the compounds are optionally given continuously;

alternatively, the dose of drug being administered is optionally temporarily reduced or temporarily suspended for a certain length of time (i.e., a "drug holiday"). In certain embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days.

The dose reduction during a drug holiday includes a reduction from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, once improvement of the patients conditions has occurred, a maintenance dose is administered if necessary. In some embodiments, the dosage, e.g., of the maintenance dose, or the frequency of administration, or both, are reduced, as a function of the symptoms, to a level at which the improved disease, disorder or condition is retained. In certain embodiments, however, patients are optionally given intermittent treatment on a long-term basis upon any recurrence of symptoms.

In certain embodiments, the amount of a given agent that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In certain embodiments, however, doses employed for adult human treatment is in the range of about 0.02 to about 5000 mg per day, in a specific embodiment about 1 to about 1500 mg per day. In various embodiments, the desired dose is conveniently presented in a single dose or as divided doses administered simultaneously (or over a short period of time) or at appropriate intervals, for example as two, three, four or more sub-doses per day.

In some embodiments, the pharmaceutical compositions described herein are in a unit dosage form suitable for single administration of precise dosages. In some instances, in unit dosage form, the formulation is divided into unit doses containing appropriate quantities of one or more compound. In certain embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In alternative embodiments, multiple-dose reclosable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In certain embodiments, the daily dosages appropriate for the compounds described herein described herein are from about 0.01 to about 20 mg/kg per body weight. In some embodiments, an indicated daily dosage in the larger subject, including, but not limited to, humans, is in the range from about 0.5 mg to about 1500 mg, conveniently administered in divided doses, including, but not limited to, up to four times a day or in extended release form. In certain embodiments, suitable unit dosage forms for oral administration comprise from about 1 to about 500 mg active ingredient. The foregoing ranges are merely suggestive, as the number of variables in regard to an individual treatment regime is large, and considerable excursions from these recommended values are not uncommon. In certain embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

In certain embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. In certain embodiments, compounds exhibiting high therapeutic indices are preferred. In some embodiments, the data obtained from cell culture assays and animal studies is used in formulating a range of dosage for use in human. In specific embodiments, the dosage of such compounds lies within a range of circulating concentrations that include the $ED_{50}$ with minimal toxicity. In certain embodiments, the dosage varies within this range depending upon the dosage form employed and the route of administration utilized.

Combination Therapy

Compounds described herein (e.g., compounds of Formula I-XVIII) can also be used in combination with other active ingredients. Such combinations are selected based on the condition to be treated, cross-reactivities of ingredients and pharmaco-properties of the combination. In one embodiment, the disclosure provides a use of a compound as described herein used in combination with another agent or therapy method, such as another cancer treatment. For example, when treating cancer, the compositions can be combined with other anti-cancer compounds (such as paclitaxel or rapamycin).

It is also possible to combine a compound of the disclosure with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic," i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-cancer effect denotes an anti-cancer effect that is greater than the predicted purely additive effects of the individual compounds of the combination.

Administration of the compounds and compositions of the present disclosure to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described active agent(s). These therapies include but are not limited to chemotherapy, radiotherapy, immunotherapy, gene therapy and surgery.

In some embodiments, provided herein is a method for the treatment of cancer, comprising administering to a subject in need of treatment a therapeutically-effective amount of a compound or composition described herein in combination with ionizing radiation or one or more chemotherapeutic agents. In some embodiments, the compound described herein is administered simultaneously with ionizing radiation or one or more chemotherapeutic agents. In other embodiments, the compound described herein is administered sequentially with ionizing radiation or one or more chemotherapeutic agents.

In certain embodiments, provided herein is a method for the treatment of cancer, which includes administering to a subject in need of treatment a therapeutically-effective amount of a compound or composition described herein in combination with ionizing radiation and one or more chemotherapeutic agents. In some embodiments, the compound described herein is administered simultaneously with ionizing radiation and one or more chemotherapeutic agents. In other embodiments, the compound described herein is administered sequentially with ionizing radiation and one or more chemotherapeutic agents.

Cancer therapies can also include a variety of combination therapies with both chemical and radiation based treatments. Combination chemotherapies include the use of chemotherapeutic agents such as, cisplatin, etoposide, irinotecan, camptostar, topotecan, paclitaxel, docetaxel, epothilones, taxotere, tamoxifen, 5-fluorouracil, methoxtrexate, temozolomide, cyclophosphamide, SCH 66336, R115777, L778,123, BMS 214662, IRESSA® (gefitinib), TARCEVAR® (erlotinib hydrochloride), antibodies to EGFR, GLEEVEC® (imatinib), intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, Mitomycin-C, L-Asparaginase, teniposide, 17α-Ethinylestradiol, Diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesterone acetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, Avastin, herceptin, Bexxar, Velcade, Zevalin, Trisenox, Xeloda, Vinorelbine, Porfimer, Erbitux® (cetuximab), Liposomal, Thiotepa, Altretamine, Melphalan, Trastuzumab, Lerozole, Fulvestrant, Exemestane, Fulvestrant, Ifosfomide, Rituximab, C225, Campath, carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, paclitaxel, gemcitabine, navelbine, farnesyl-protein transferase inhibitors, transplatinum, 5-fluorouracil, vincristine, vinblastine and methotrexate, or any analog or derivative variant of the foregoing.

Other factors that cause DNA damage, such as radiotherapy, have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (e.g., 3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

In yet another embodiment, the secondary treatment is a secondary gene therapy in which a therapeutic polynucleotide is administered before, after, or at the same time a first chemotherapeutic agent. Delivery of the chemotherapeutic agent in conjunction with a vector encoding a gene product will have a combined anti-hyperproliferative effect on target tissues.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

In one embodiment, a compound as described herein is administered in combination with a BET inhibitor. BET inhibitors are a class of drugs with anti-cancer, immunosuppressive, and other effects in clinical trials in the United States and Europe and widely used in research. These molecules reversibly bind the bromodomains of Bromodomain and Extra-Terminal motif (BET) proteins BRD2, BRD3, BRD4, and BRDT, and prevent protein-protein interaction between BET proteins and acetylated histones and transcription factors. BET inhibitors include, but are not limited to, JQ1, I-BET 161 (GSK1210151A), I-BET 762 (GSK525762), OTX-015, TEN-010, CPI-203, CPI-0610, MS436, linone, LYS294002, RVX2135, FT-1101, BAY1238097, INCB054329, TEN-010, GSK2820151, ZEN003694, BAY-299, BMS-986158, ABBV-075, GS-5829, and PLX51107.

In another embodiment, a compound of the invention may also be combined with a CDK inhibitor. A CDK (cyclin-dependent kinase) inhibitor is any chemical that inhibits the function of CDKs. They are used to treat cancers by preventing overproliferation of cancer cells. The US FDA approved the first drug of this type, palbociclib (Ibrance), a CDK4/6 inhibitor, in February 2015, for use in postmenopausal women with breast cancer that is estrogen receptor positive and HER2 negative. In one embodiment, the CDK inhibitor may be selected from, but not limited to, ribociclib, palbociclib, abemaciclib, P1446A-05, trilaciclib, favopiridol, olomucine, roscovitine, dinaciclib, PD-0332991, SNS-032, LY-2835219, R547, LEE011, AT7519, AZD5438, and AG-024322.

Administration of the compound or composition as described herein may precede or follow the other anti-cancer agent or treatment by intervals ranging from minutes to weeks. In embodiments where the other anti-cancer agent and expression construct are applied separately, one would generally ensure that a significant period of time did not elapse between the time of each delivery, such that the agent and expression construct would still be able to exert an advantageously combined effect on a cell. For example, in such instances, it is contemplated that one may contact a cell, tissue or organism with two, three, four or more modalities substantially simultaneously (i.e., within less than about a minute) with the active agent(s). In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 6 hours, about 8 hours, about 9 hours, about 12 hours, about 15 hours, about 18 hours, about 21 hours, about 24 hours, about 28 hours, about 31 hours, about 35 hours, about 38 hours, about 42 hours, about 45 hours, to about 48 hours or more prior to and/or after administering the active agent(s). In certain other embodiments, an agent may be administered within from about 1 day, about 2 days, about 3 days, about 4 days, about 5 days, about 6 days, about 8 days, about 9 days, about 12 days, about 15 days, about 16 days, about 18 days, about 20 days, to about 21 days prior to and/or after administering the active agent(s). In some situations, it may be desirable to extend the time period for treatment significantly, however, where several weeks (e.g., about 1, about 2, about 3, about 4, about 6, or about 8 weeks or more) lapse between the respective administrations.

Kits

Kits for use to achieve anti-cancer effects comprising a compound or composition described herein are provided. In certain embodiments, the kit comprises a unit dose of a compound or composition described herein and instructions for administering the same. In certain aspects, the kit further comprises a second drug suitable for anti-cancer therapy, or instructions for co-administering an additional anti-cancer therapy (such as radiation or gene therapy). In another aspect, kits for use to achieve anti-cancer effects comprise a low dose (e.g., less than about 500 mg/day, or less than about 400 mg/day, or less than about 300 mg/day, or less than about 200 mg/day) of a compound or composition described herein and a second drug suitable for anti-cancer therapy. In yet another variation, kits for use to achieve anti-cancer effects comprise a high dose (e.g., greater than about 500 mg/day) of a compound or composition as described herein and a second drug suitable for anti-cancer therapy.

Methods of Manufacturing a Medicament

In a further aspect of the disclosure, use of the compounds and compositions described herein in the manufacture of a medicament is provided. In particular, the manufacture of a medicament for use in the treatment of cancer are provided.

EXAMPLES

The disclosure is further illustrated by the following examples. The examples below are non-limiting are merely representative of various aspects of the disclosure. Solid and dotted wedges within the structures herein disclosed illustrate relative stereochemistry, with absolute stereochemistry depicted only when specifically stated or delineated.

Compounds having the structure of Formula I, or any sub-formula described herein can be synthesized using standard synthetic techniques known to those of skill in the art. Compounds of the present disclosure can be synthesized using the general synthetic procedures set forth in the examples that follow.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Abbreviations used in the instant specification, particularly in the schemes and examples, are as follows:
ACN acetonitrile
AcOH acetic acid
AIBN 2,2'-azobisisobutyronitrile
BMIM 1-butyl-3-methylimidazolium
Boc tert-butyl carbamate
BOP (benzotriazol-1-yloxy)tris(dimethylamino)phosphonium hexfluorophosphate
BuLi butyllithium
Cbz benzyl carbamate
CSS charcoal stripped serum
° C. degrees Celsius
DBU 1,8-diazabicyclo[5.4.0]undec-7-ene
DCC N,N'-dicyclohexylcarbodiimide
DCE 1,2-dichloroethane
DCM dichloromethane
DEAD diethyl azodicarboxylate
DIAD diisopropyl azodicarboxylate
DIBAL or DIBAL-H diisobutylaluminum hydride
DIEA or DIPEA diisopropylethylamine
DMA dimethylacetamide
DMAP 4-(dimethylamino)pyridine
DME ethylene glycol dimethyl ether
DMF dimethylformamide
DMSO dimethyl sulfoxide EDC N-(3-dimethylaminopropyl)-N'-ethylcarbodiimide
EDCI 1-(3-dimethylaminopropyl)-3-ethylcarbodiimide hydrochloride
Et ethyl
Et$_2$O diethyl ether
Et$_3$N triethylamine
EtOAc ethyl acetate
EtOH ethyl alcohol
eq equivalents
h or hr hour(s)
HATU O-(7-azabenzotriazol-1-yl)-N,N,N',N'-tetramethyluronium hexafluorophosphate
HBTU (2-(1H-benzotriazol-1-yl)-1,1,3,3-tetramethyluronium hexafluorophosphate
HCl hydrochloric acid
HOBt 1-hydroxybenzotriazole monohydrate
HPLC high performance liquid chromatography
KCN potassium cyanide
LCMS or LC-MS high pressure liquid chromatography with mass spectrometer
LDA lithium diisopropylamide
LiOH lithium hydroxide
LHMDS or LiHMDS lithium hexamethyl disilazide
M molar
Me methyl
MeCN acetonitrile
MeOH methyl alcohol
mg milligram(s)
min minute(s)
mmol millimole(s)
MOM methoxymethyl
NaCN sodium cyanide
NaHMDS sodium hexamethyl disilazide
NaOH sodium hydroxide
NaOtBu sodium tert-butoxide
NBS N-bromosuccinimide
NH$_4$Cl ammonium chloride
NMP N-methyl pyrrolidone
DMA N,N-dimethylacetamide
PBS phosphate buffered saline
Pd/C palladium on charcoal
Pd$_2$(dba)$_3$ tris(dibenzylideneacetone)dipalladium
Pd(dppf)Cl$_2$ [1,1'-bis(diphenylphosphino)ferrocene]dichloropalladium
Pd(OAc)$_2$ palladium diacetate
Pd(PPh$_3$)$_4$ tetrakis(triphenylphosphine)palladium
PPh$_3$ triphenyl phosphine
p-TsOH para-toluenesulfonic acid
rt or RT room temperature
TBAF tetrabutylammonium fluoride
TBDMSCl tert-butyldimethylsilyl chloride
TBTU 2-(1H-benzotriazole-1-yl)-N,N,N',N'-tetramethyluronium tetrafluoroborate
t-Bu tert-butyl
TEA triethylamine
TEMPO 2,2,6,6-tetramethyl-1-piperdinyloxy, free radical
TFA trifluoroacetic acid
THF tetrahydrofuran
TLC thin layer chromatography
TMSCl trimethylsilyl chloride Compounds as described herein may be prepared according to the process outlined in Schemes 1-3 below.

Scheme 1

Accordingly, a suitably substituted compound of formula A, where Y, X, R$^1$ and t are as defined herein, a known compound or compound prepared by known methods, may be reacted with thiophosgene B or phenyl chlorothionocarbonate, in the presence of a suitably selected base such as Et$_3$N, DIEA, DMAP, K$_2$CO$_3$, Cs$_2$CO$_3$, or similar, in a suitably selected solvent or mixture of solvents such as DCM, THF, 1,4-dioxane, water, or similar, at a temperature between 0 to about 130° C., to yield the corresponding compound of formula C, Scheme 1.

Scheme 2

A suitably substituted compound of formula D, a known compound or compound prepared by known methods, may be reacted with phthalimide E in the presence of a suitably selected base such as NaOH, KOH, K₂CO₃, or similar, in a suitably selected solvent or mixture of solvents such as DCM, THF, 1,4-dioxane, DMF, EtOH, water, or similar, at a temperature between 0 to about 130° C., to yield the corresponding compound of formula F. The compound of formula F may then be reacted with amino acid G in the presence of catalytic to stoichiometric amounts of copper(I) iodide, with a suitably selected base such as Et₃N, DIEA, or similar, in a suitably selected solvent or mixture of solvents such as DCM, THF, 1,4-dioxane, DMF, water, or similar, at a temperature between 0 to 100° C., to yield the corresponding compound of formula H. The compound of formula H may then be reacted with methyl iodide, with a suitably selected base such as Cs₂CO₃, K₂CO₃, TEA, DIEA, or similar, in a suitably selected solvent or mixture of solvents such as DCM, THF, DMF, or similar, at a temperature between 0 to 60° C., to yield the corresponding compound of formula J, Scheme 2.

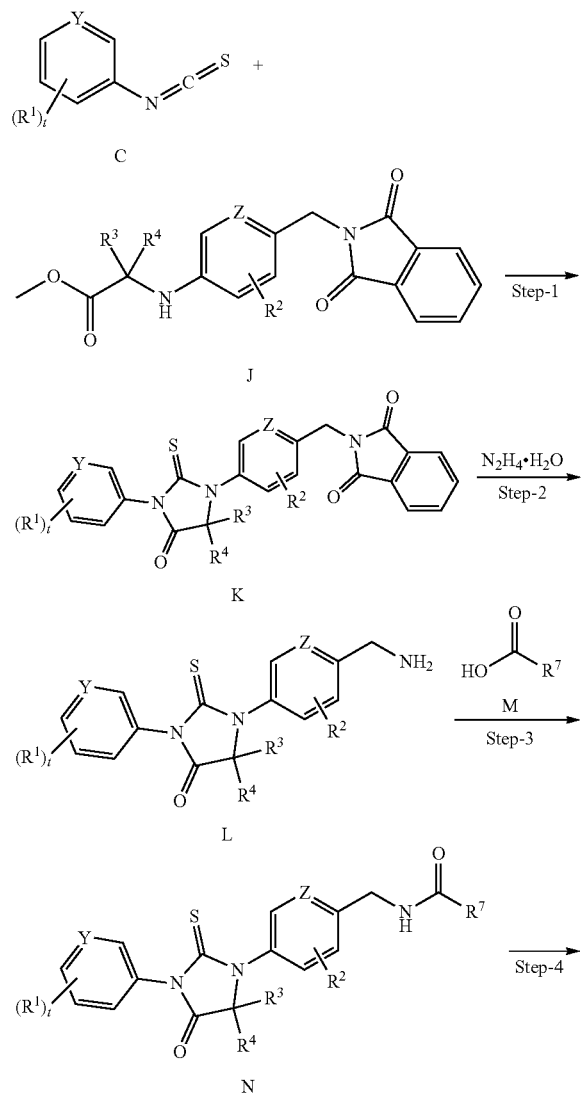

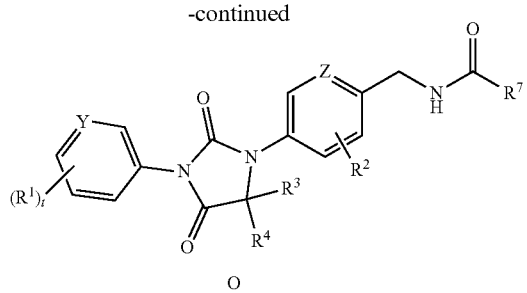

The compound of formula C may then be reacted with the compound of formula J with a suitably selected base such as DMAP, Et₃N, DIEA, or similar, in a suitably selected solvent or mixture of solvents such as DMF, NMP, toluene, xylene, or similar, at a temperature from about 20 to 180° C., to yield the corresponding compound of formula K. The compound of formula K may then be reacted with hydrazine hydrate in a suitably selected solvent or mixture of solvents such as THF, 1,4-dioxane, MeOH, EtOH, water, or similar, at a temperature from about 20 to 100° C., to yield the corresponding compound of formula L. The compound of formula L may then be reacted with carboxylic acid M in the presence of a suitably selected coupling agent such as CDI, EDC, HOBt, HBTU, HATU, or similar, with a suitably selected base such as Et₃N, DIEA, or similar, in a suitably selected solvent or mixture of solvents such as DCM, THF, 1,4-dioxane, DMF, or similar, at a temperature from about 0 to 50° C., to yield the corresponding compound of formula N. The compound of formula N may then be reacted with H₂O₂, SOCl₂, NaIO₄, RuCl₃, or similar in a suitably selected solvent or mixture of solvents such as ACN, CCl₄, DMF, THF, water, or similar, at a temperature from about 0 to 50° C., to yield the corresponding compound of formula O, Scheme 3.

Synthetic Examples

¹H NMR spectra was recorded on a Bruker Avance 400 MHz spectrometer. Spectra are referenced to residual chloroform (δ 7.26, 1H), DMSO (δ 2.54, 1H) or methanol (δ 3.34, 1H) unless otherwise noted. Chemical shifts are reported in ppm (δ); multiplicities are indicated by s (singlet), d (doublet), t (triplet), q (quartet), quint (quintet), sext (sextet), m (multiplet) and br (broad). Coupling constants, J, are reported in Hertz (Hz). Analytical HPLC was performed on an Agilent 1200 HPLC with an Agilent G1365D diode array detector using an Agilent Eclipse XDB-C18 (4.6×150 mm, 5 μm) column. Analytical LCMS was performed on an Agilent 6410 triple quadrupole LCMS. Commercially available reagents and solvents were used as received unless otherwise indicated.

Example 1. Preparation of 4-(3-(4-(aminomethyl)-3-fluorophenyl)-4,4-dimethyl-5-oxo-2-thioxoimidazolidin-1-yl)-2-(trifluoromethyl)benzonitrile

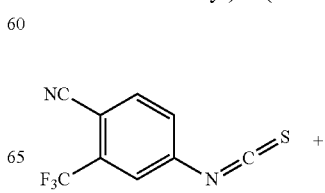

87

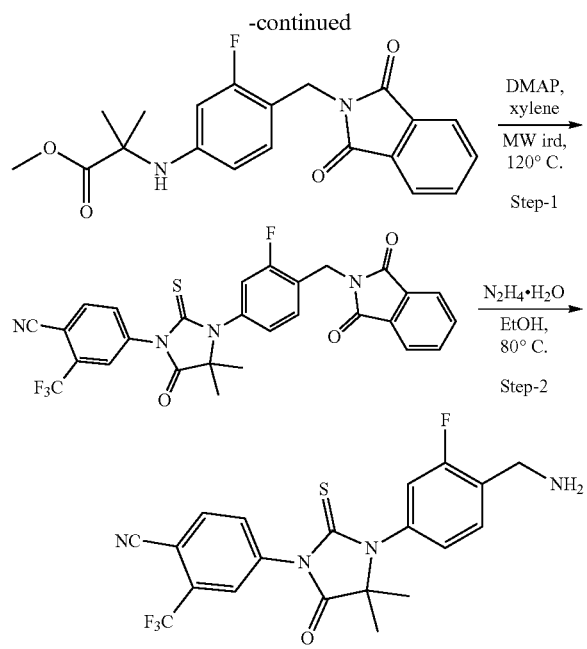

Step-1: Preparation of 4-(3-(4-((1,3-dioxoisoindo-lin-2-yl)methyl)-3-fluorophenyl)-4,4-dimethyl-5-oxo-2-thioxo imidazolidin-1-yl)-2-(trifluoromethyl)benzonitrile To a stirred solution of methyl 2-(4-((1,3-dioxoisoindolin-2-yl)methyl)-3-fluorophenylamino)-2-methylpropanoate (2.5 g, 6.76 mmol, 1 eq) in xylene (7 mL) were successively added 4-isothiocyanato-2-(trifluoromethyl)benzonitrile (3.41 g, 14.9 mmol, 2.5 eq) and DMAP (0.826 g, 6.76 mmol, 1 eq) and the resulting mixture was heated to 120° C. via microwave irradiation. After 1 h, the reaction mixture was diluted with EtOAc (400 mL). The organic layer was washed with water (100 mL×3), brine (100 mL), dried over $Na_2SO_4$, filtered and concentrated under reduced pressure to obtain a crude product which was purified by CombiFlash chromatography to afford the title compound. Analytical data: LC-MS 567 [M+H]$^+$; $^1$H NMR (400 MHz, methanol-d$_4$) δ 8.39 (d, J=8.33 Hz, 1H), 8.28 (s, 1H), 8.11-8.04 (m, 1H), 7.95-7.91 (m, 2H), 7.91-7.85 (m, 2H), 7.57-7.49 (m, 1H), 7.35 (dd, J=10.74, 1.53 Hz, 1H), 7.21 (d, J=7.89 Hz, 1H), 4.91-4.87 (m, 2H), 1.45-1.47 (m, 6H).

Step-2: Preparation of 4-(3-(4-(aminomethyl)-3-fluorophenyl)-4,4-dimethyl-5-oxo-2-thioxoimidazo-lidin-1-yl)-2-(trifluoromethyl)benzonitrile To a stirred solution of 4-(3-(4-((1,3-dioxoisoindolin-2-yl)methyl)-3-fluorophenyl)-4,4-dimethyl-5-oxo-2-thioxo-imidazolidin-1-yl)-2-(trifluoromethyl)benzonitrile (6.3 g, 11.1 mmol, 1 eq) in ethanol (100 mL) was added hydrazine hydrate (6 mL) and the resulting mixture was heated at 100° C. for 2 h. The reaction was monitored by TLC. After completion, the reaction mixture was concentrated under reduced pressure. The crude residue was diluted with water (300 mL) and extracted with EtOAc (500 mL×3). The combined organic layers were washed with brine (200 mL), dried over $Na_2SO_4$, filtered and concentrated under reduced pressure to obtain a crude product which was purified by CombiFlash chromatography to afford the title compound. Analytical data: LC-MS 437 [M+H]$^+$.

Example 2. Preparation of amide derivatives of 4-(3-(4-(aminomethyl)-3-fluorophenyl)-4,4-dimethyl-5-oxo-2-thioxoimidazolidin-1-yl)-2-(trifluoromethyl)benzonitrile (Method 1)

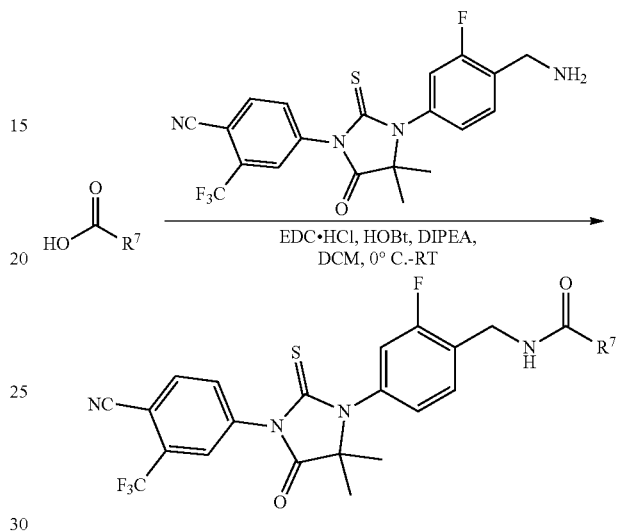

To a stirred solution of the appropriate carboxylic acid (1 eq) in DCM (50 vol) were added EDC.HCl (1.2 eq) and HOBt (1.2 eq) at 0° C. and the resulting mixture was stirred at same temperature for 10 min. DIPEA (4 eq) and 4-(3-(4-(aminomethyl)-3-fluorophenyl)-4,4-dimethyl-5-oxo-2-thio-xoimidazolidin-1-yl)-2-(trifluoromethyl)benzonitrile (1 eq) were then successively added and the resulting mixture was stirred at RT for 2 h. The reaction was monitored by TLC. After completion, the reaction mixture was diluted with DCM (200 vol). The organic layer was washed with saturated aqueous $NaHCO_3$ solution (80 vol), saturated aqueous $NH_4Cl$ solution (80 vol), water (80 vol), brine (50 vol), dried over $Na_2SO_4$, filtered and concentrated under reduced pressure to afford a crude product which was purified by SFC to afford the amide. Compounds 6, 7, 10-15 were prepared following this procedure.

Analytical Data: Compound 6—LC-MS 521 [M+H]$^+$; $^1$H NMR (methanol-d$_4$) δ 8.19-8.12 (m, 2H), 8.02-7.95 (m, 1H), 7.44 (t, J=8.3 Hz, 1H), 7.26-7.17 (m, 2H), 4.49 (s, 2H), 1.57 (s, 6H), 1.24 (s, 9H). Compound 7—LC-MS 507 [M+H]$^+$; $^1$H NMR (methanol-d$_4$) δ 8.19-8.12 (m, 2H), 7.99 (dd, J=8.3, 2.0 Hz, 1H), 7.49 (t, J=8.3 Hz, 1H), 7.27-7.18 (m, 2H), 4.48 (s, 2H), 2.52 (p, J=6.8 Hz, 1H), 1.57 (s, 6H), 1.16 (d, J=6.9 Hz, 6H). Compound 10—LC-MS 556 [M+H]$^+$; $^1$H NMR (methanol-d$_4$) δ 8.53-8.46 (m, 1H), 8.19-8.12 (m, 2H), 8.02-7.95 (m, 1H), 7.86-7.77 (m, 1H), 7.54 (t, J=8.1 Hz, 1H), 7.42 (d, J=7.8 Hz, 1H), 7.33 (dd, J=7.6, 5.1 Hz, 1H), 7.27-7.16 (m, 2H), 4.53 (s, 2H), 3.80 (d, J=7.1 Hz, 2H), 1.56 (s, 6H). Compound 11—LC-MS 505 [M+H]$^+$; $^1$H NMR (methanol-d$_4$) δ 8.19-8.12 (m, 2H), 7.99 (dd, J=8.6, 2.0 Hz, 1H), 7.51 (t, J=8.2 Hz, 1H), 7.28-7.18 (m, 2H), 4.50 (s, 2H), 1.65 (tt, J=8.1, 4.6 Hz, 1H), 1.57 (s, 6H), 0.89 (dt, J=5.9, 3.2 Hz, 2H), 0.79 (dq, J=10.7, 4.2, 3.7 Hz, 2H). Compound 12—LC-MS 542 [M+H]$^+$; $^1$H NMR (methanol-d$_4$) δ 9.03 (d, J=2.3 Hz, 1H), 8.70 (dd, J=4.9, 1.7 Hz, 1H), 8.30 (dt, J=8.1, 1.9 Hz, 1H), 8.19-8.12 (m, 2H), 7.99 (dd, J=8.3, 2.0

Hz, 1H), 7.65-7.52 (m, 2H), 7.26 (td, J=10.7, 2.0 Hz, 2H), 4.73 (s, 2H), 1.58 (s, 6H). Compound 13—LC-MS 542 [M+H]$^+$; $^1$H NMR (methanol-d$_4$) δ 8.74-8.68 (m, 2H), 8.19-8.12 (m, 2H), 8.02-7.95 (m, 1H), 7.87-7.80 (m, 2H), 7.60 (t, J=8.1 Hz, 1H), 7.31-7.20 (m, 2H), 4.72 (s, 2H), 1.57 (s, 6H). Compound 14—LC-MS 543 [M+H]$^+$; $^1$H NMR (methanol-d$_4$) δ 9.30 (s, 1H), 9.04 (d, J=5.1 Hz, 1H), 8.19-8.13 (m, 2H), 8.11 (dd, J=5.2, 1.5 Hz, 1H), 7.98 (dd, J=8.2, 2.0 Hz, 1H), 7.58 (t, J=8.1 Hz, 1H), 7.24 (ddd, J=16.9, 9.3, 2.1 Hz, 2H), 4.76 (s, 2H), 1.57 (s, 6H). Compound 15—LC-MS 543 [M+H]$^+$; $^1$H NMR (methanol-d$_4$) δ 9.29 (s, 1H), 9.21 (s, 2H), 8.16 (d, J=7.45 Hz, 2H), 8.00 (s, 1H), 7.63 (s, 1H), 7.22-7.32 (m, 2H), 4.73 (s, 2H), 1.58 (s, 6H).

Example 2. (Method 2)

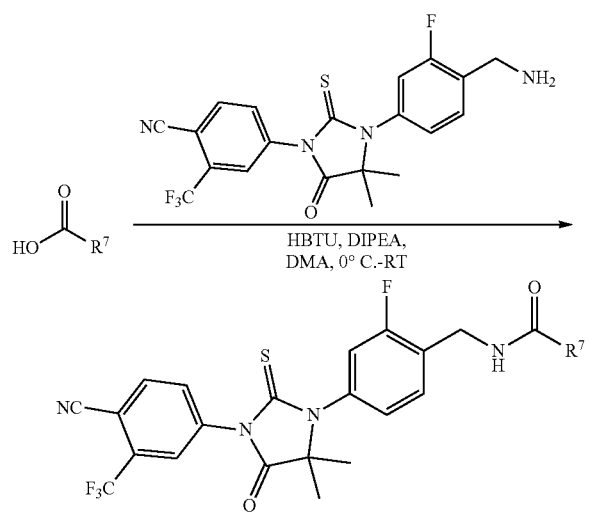

To a stirred solution of the appropriate carboxylic acid (1 eq) in DMA (30-40 vol) was added HBTU (1.2 eq) at 0° C. and the resulting mixture was stirred at same temperature for 10 min. DIPEA (2.2 eq) and 4-(3-(4-(aminomethyl)-3-fluorophenyl)-4,4-dimethyl-5-oxo-2-thioxoimidazolidin-1-yl)-2-(trifluoromethyl)benzonitrile (1 eq) were then successively added and the resulting mixture was stirred at RT for 2 h. The reaction was monitored by TLC. After completion, H$_2$O (50 vol) was added and the resulting precipitate was filtered through a Buchner funnel. The crude material was purified by SFC to afford the amide. Compounds 2-5, 8, 9, 40-48, 52, 54, 60 were prepared following this procedure.

Analytical Data: Compound 2—LC-MS 548 [M+H]$^+$; $^1$H NMR (methanol-d$_4$) δ 8.19-8.12 (m, 2H), 8.02-7.95 (m, 2H), 7.87 (d, J=3.1 Hz, 1H), 7.59 (t, J=8.0 Hz, 1H), 7.30-7.19 (m, 2H), 4.72 (s, 2H), 1.57 (s, 6H). Compound 3—LC-MS 531 [M+H]$^+$; $^1$H NMR (methanol-d$_4$) δ 8.19-8.12 (m, 2H), 7.98 (dd, J=8.3, 1.9 Hz, 1H), 7.59 (t, J=8.1 Hz, 1H), 7.30-7.19 (m, 3H), 7.12 (s, 1H), 4.70 (s, 2H), 1.57 (s, 6H). Compound 4—LC-MS 545 [M+H]$^+$; $^1$H NMR (methanol-d$_4$) δ 8.19-8.12 (m, 2H), 7.99 (dd, J=8.2, 2.0 Hz, 1H), 7.59 (t, J=8.1 Hz, 1H), 7.29-7.19 (m, 3H), 7.05-7.00 (m, 1H), 4.68 (s, 2H), 4.03 (s, 3H), 1.57 (s, 6H). Compound 5—LC-MS 548 [M+H]$^+$; $^1$H NMR (methanol-d$_4$) δ 9.15 (s, 1H), 8.46 (s, 1H), 8.19-8.12 (m, 2H), 7.99 (dd, J=8.3, 2.0 Hz, 1H), 7.59 (t, J=8.1 Hz, 1H), 7.31-7.20 (m, 2H), 4.69 (s, 2H), 1.57 (s, 6H). Compound 8—LC-MS 542 [M+H]$^+$; $^1$H NMR (methanol-d$_4$) δ 8.66 (d, J=4.8 Hz, 1H), 8.19-8.09 (m, 3H), 7.98 (dq, J=8.0, 3.8, 2.6 Hz, 2H), 7.61-7.52 (m, 2H), 7.24 (ddd, J=16.8, 9.3, 2.0 Hz, 2H), 4.76 (s, 2H), 1.57 (s, 6H). Compound 9—LC-MS 562 [M+H]$^+$; $^1$H NMR (methanol-d$_4$) δ 8.97 (d, J=3.0 Hz, 1H), 8.19-8.12 (m, 2H), 8.03-7.95 (m, 1H), 7.58 (t, J=8.2 Hz, 1H), 7.31-7.20 (m, 2H), 4.66 (d, J=3.1 Hz, 2H), 2.66 (d, J=3.1 Hz, 3H), 1.57 (d, J=3.1 Hz, 6H). Compound 40—LC-MS 556 [M+H]$^+$; $^1$H NMR (methanol-d$_4$) δ 8.44 (d, J=3.95 Hz, 1H), 8.12-8.19 (m, 2H), 7.98 (d, J=8.33 Hz, 1H), 7.74 (d, J=7.89 Hz, 1H), 7.61 (s, 1H), 7.38-7.47 (m, 1H), 7.18-7.30 (m, 2H), 4.71 (s, 2H), 2.61 (s, 3H), 1.57 (s, 6H). Compound 41—LC-MS 519 [M+H]$^+$; $^1$H NMR (methanol-d$_4$) δ 8.13-8.20 (m, 2H), 7.99 (d, J=8.77 Hz, 1H), 7.51 (s, 1H), 7.17-7.28 (m, 2H), 4.49 (s, 2H), 3.35 (s, 1H), 1.57 (s, 6H), 1.34-1.40 (m, 1H), 1.29 (br s, 2H), 1.09-1.14 (m, 3H). Compound 42—LC-MS 545 [M+H]$^+$; $^1$H NMR (methanol-d$_4$) δ 8.15 (d, J=4.38 Hz, 2H), 7.95-8.02 (m, 1H), 7.57 (s, 1H), 7.48 (d, J=1.75 Hz, 1H), 7.20-7.29 (m, 2H), 6.84 (d, J=1.75 Hz, 1H), 4.66 (s, 2H), 4.13 (s, 3H), 1.57 (s, 6H). Compound 43—LC-MS 555 [M+H]$^+$; $^1$H NMR (methanol-d$_4$) δ 8.09-8.19 (m, 2H), 7.99 (s, 1H), 7.63 (s, 1H), 7.39 (s, 1H), 7.34 (s, 1H), 7.20-7.29 (m, 4H), 4.67 (s, 2H), 2.40 (s, 3H), 1.58 (s, 6H). Compound 44—LC-MS 545 [M+H]$^+$; $^1$H NMR (methanol-d$_4$) δ 8.15 (d, J=4.38 Hz, 2H), 7.98 (d, J=8.77 Hz, 1H), 7.80 (br s, 1H), 7.66 (br s, 1H), 7.57 (t, J=8.11 Hz, 1H), 7.19-7.28 (m, 2H), 4.64 (s, 2H), 3.94 (s, 3H), 1.57 (s, 6H). Compound 45—LC-MS 562 [M+H]$^+$; $^1$H NMR (methanol-d$_4$) δ 8.12-8.20 (m, 3H), 7.99 (s, 1H), 7.58 (s, 1H), 7.20-7.29 (m, 2H), 4.66 (s, 2H), 2.73 (s, 3H), 1.57 (s, 6H). Compound 46—LC-MS 576 [M+H]$^+$; $^1$H NMR (methanol-d$_4$) δ 8.72 (br s, 1H), 8.15 (d, J=6.58 Hz, 2H), 7.94-8.02 (m, 1H), 7.56 (t, J=8.11 Hz, 1H), 7.16-7.30 (m, 2H), 4.60-4.67 (m, 2H), 2.68 (s, 3H), 2.59 (s, 3H), 1.57 (s, 6H). Compound 47—LC-MS 559 [M+H]$^+$; $^1$H NMR (methanol-d$_4$) δ 8.16 (d, J=7.02 Hz, 2H), 7.99 (d, J=7.89 Hz, 1H), 7.76 (s, 1H), 7.60 (d, J=9.21 Hz, 2H), 7.19-7.33 (m, 4H), 4.60 (br s, 2H), 1.58 (s, 6H). Compound 48—LC-MS 557 [M+H]$^+$; $^1$H NMR (methanol-d$_4$) δ 8.77 (br s, 1H), 8.15 (d, J=6.14 Hz, 2H), 7.95-8.01 (m, 1H), 7.60 (t, J=8.33 Hz, 1H), 7.53 (d, J=4.39 Hz, 1H), 7.18-7.29 (m, 2H), 4.60 (s, 2H), 2.63 (s, 3H), 1.57 (s, 6H). Compound 52—LC-MS 519 [M+H]$^+$; $^1$H NMR (methanol-d$_4$) δ 8.20-8.14 (m, 2H), 8.00 (dd, J=8.4, 2.0 Hz, 1H), 7.47 (t, J=8.3 Hz, 1H), 7.26-7.18 (m, 2H), 4.52 (s, 2H), 1.57 (s, 6H), 1.40-1.30 (m, 3H), 1.39 (s, 3H), 0.65 (m, 1H). Compound 54—LC-MS 532 [M+H]$^+$; $^1$H NMR (methanol-d$_4$) δ 8.45 (s, 1H), 8.23 (s, 1H), 8.15 (d, J=4.4 Hz, 2H), 8.00 (s, 1H), 7.56 (s, 1H), 7.17-7.29 (m, 2H), 4.59 (s, 2H), 1.57 ppm (s, 6H). Compound 60—LC-MS 532 [M+H]$^+$; $^1$H NMR (methanol-d$_4$) δ 8.34 (s, 1H), 8.15 (d, J=4.4 Hz, 2H), 8.00 (s, 1H), 7.77 (s, 1H), 7.58 (s, 1H), 7.25 (s, 2H), 4.59 (s, 2H), 1.57 ppm (s, 6H).

Example 2. (Method 3)

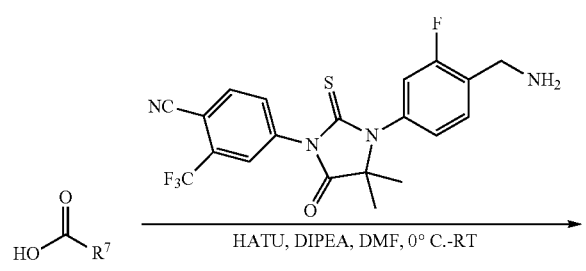

-continued

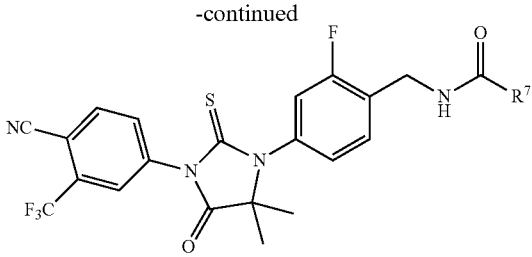

To a stirred solution of the appropriate carboxylic acid (1.5 eq) in DMF (30-40 vol) was added HATU (2 eq) at 0° C. and the resulting mixture was stirred at same temperature for 30 min. DIPEA (6 eq) and 4-(3-(4-(aminomethyl)-3-fluorophenyl)-4,4-dimethyl-5-oxo-2-thioxoimidazolidin-1-yl)-2-(trifluoromethyl)benzonitrile (1 eq) were then successively added and the resulting mixture was stirred at RT for 16 h. The reaction was monitored by TLC. After completion, $H_2O$ (50 vol) was added and the resulting precipitate was filtered through a Buchner funnel. The crude material was purified by SFC to afford the amide. Compounds 62, 63, 79, 80 were prepared following this procedure.

Analytical Data: Compound 62—LC-MS 547 [M+H]$^+$; $^1$H NMR (methanol-$d_4$) δ 8.16 (d, J=6.6 Hz, 2H), 7.99 (d, J=7.5 Hz, 1H), 7.61 (s, 1H), 7.20-7.30 (m, 2H), 4.71 (s, 2H), 2.62 ppm (s, 3H), 1.58 (s, 6H). Compound 63—LC-MS 534 [M+H]$^+$; $^1$H NMR (methanol-$d_4$) δ 8.12-8.20 (m, 2H), 7.99 (s, 1H), 7.53 (s, 1H), 7.18-7.28 (m, 2H), 4.51 (s, 2H), 3.82 (d, J=8.3 Hz, 2H), 3.65 (t, J=7.9 Hz, 2H), 3.42 (p, J=7.7 Hz, 1H), 2.54 (s, 3H), 1.57 ppm (s, 6H). Compound 79—LC-MS 581 [M+H]$^+$; $^1$H NMR (methanol-$d_4$) δ 8.40 (s, 1H), 8.16 (dd, J=8.5, 6.1 Hz, 3H), 7.99 (dd, J=8.3, 1.9 Hz, 1H), 7.93 (dd, J=8.9, 1.7 Hz, 1H), 7.61 (t, J=7.7 Hz, 2H), 7.31-7.19 (m, 2H), 4.75 (d, J=4.4 Hz, 1H), 1.58 (s, 6H). Compound 80—LC-MS 581 [M+H]$^+$; $^1$H NMR (methanol-$d_4$) δ 8.19-8.09 (m, 4H), 7.99 (dd, J=8.2, 2.0 Hz, 1H), 7.88 (d, J=8.5 Hz, 1H), 7.69-7.57 (m, 2H), 7.31-7.20 (m, 2H), 4.75 (s, 2H), 1.58 (s, 6H).

Example 3. Preparation of amide derivatives of 4-(3-(4-(aminomethyl)-3-fluorophenyl)-4,4-dimethyl-2,5-dioxoimidazolidin-1-yl)-2-(trifluoromethyl)benzonitrile

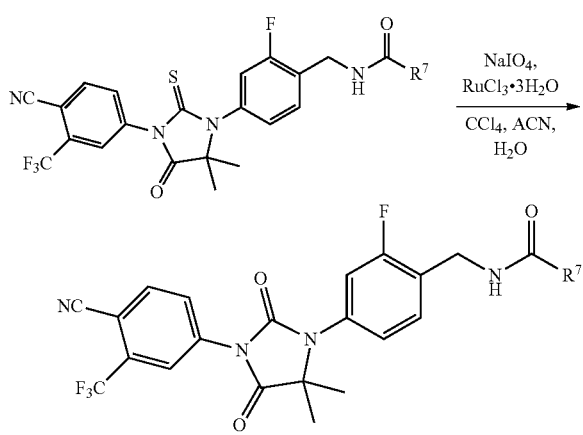

To a stirred solution of the appropriate thiohydantoin (1 eq) in a mixture of $CCl_4$ (20 vol), $H_2O$ (40 vol), ACN (20 vol) was added $NaIO_4$ (2 eq) at 0° C. and the mixture was stirred for 10 min. $RuCl_3 \cdot 3H_2O$ (0.05 eq) was then added and resultant mixture was stirred at RT for 3 h. The reaction was monitored by TLC. Upon completion, the reaction mixture was quenched with a solution of saturated aqueous sodium thiosulfate (100 vol) and extracted with EtOAc (200 vol). The organic layer was washed with saturated aqueous $NaHCO_3$ solution (100 vol), water (100 vol), brine (80 vol), dried over $Na_2SO_4$, filtered and concentrated under reduced pressure to afford a crude product which was purified by SFC to afford the hydantoin. Compounds 1, 20, 23, 24, 28, 29 were prepared following this procedure.

Analytical Data: Compound 1—LC-MS 529 [M+H]$^+$; $^1$H NMR (methanol-$d_4$) δ 8.25 (s, 1H), 8.17-8.07 (m, 2H), 7.57 (t, J=8.2 Hz, 1H), 7.33-7.21 (m, 3H), 7.02 (s, 1H), 4.65 (s, 2H), 4.02 (s, 3H), 1.56 (s, 6H). Compound 20—LC-MS 491 [M+H]$^+$; $^1$H NMR (methanol-$d_4$) δ 8.25 (s, 1H), 8.18-8.07 (m, 2H), 7.46 (t, J=8.3 Hz, 1H), 7.31-7.21 (m, 2H), 4.46 (s, 2H), 2.51 (p, J=6.9 Hz, 1H), 1.56 (s, 6H), 1.15 (d, J=6.9 Hz, 6H). Compound 23—LC-MS 526 [M+H]$^+$; $^1$H NMR (methanol-$d_4$) δ δ 8.69-8.62 (m, 1H), 8.25 (s, 1H), 8.17-8.06 (m, 3H), 7.98 (td, J=7.7, 1.8 Hz, 1H), 7.61-7.50 (m, 2H), 7.27 (ddd, J=17.2, 9.3, 2.1 Hz, 2H), 4.74 (s, 2H), 1.56 (s, 6H). Compound 24—LC-MS 489 [M+H]$^+$; $^1$H NMR (methanol-$d_4$) δ 8.25 (s, 1H), 8.18-8.07 (m, 2H), 7.49 (t, J=8.3 Hz, 1H), 7.31-7.21 (m, 2H), 4.48 (s, 2H), 1.64 (tt, J=8.3, 4.5 Hz, 1H), 1.56 (s, 6H), 0.93-0.83 (m, 2H), 0.79 (dt, J=8.3, 3.3 Hz, 2H). Compound 28—LC-MS 532 [M+H]$^+$; $^1$H NMR (methanol-$d_4$) δ 9.15 (s, 1H), 8.45 (s, 1H), 8.25 (d, J=1.7 Hz, 1H), 8.17-8.07 (m, 2H), 7.57 (t, J=8.2 Hz, 1H), 7.29 (td, J=10.2, 9.5, 4.4 Hz, 2H), 4.66 (s, 2H), 1.57 (s, 6H). Compound 29—LC-MS 526 [M+H]$^+$; $^1$H NMR (methanol-$d_4$) δ 9.02 (d, J=2.3 Hz, 1H), 8.70 (dd, J=4.9, 1.7 Hz, 1H), 8.33-8.22 (m, 2H), 8.18-8.07 (m, 2H), 7.63-7.52 (m, 2H), 7.34-7.23 (m, 2H), 4.70 (s, 2H), 1.57 (s, 6H).

Example 4. Preparation of 4-(3-(4-(aminomethyl)phenyl)-4,4-dimethyl-5-oxo-2-thioxoimidazolidin-1-yl)-2-(trifluoromethyl)benzonitrile

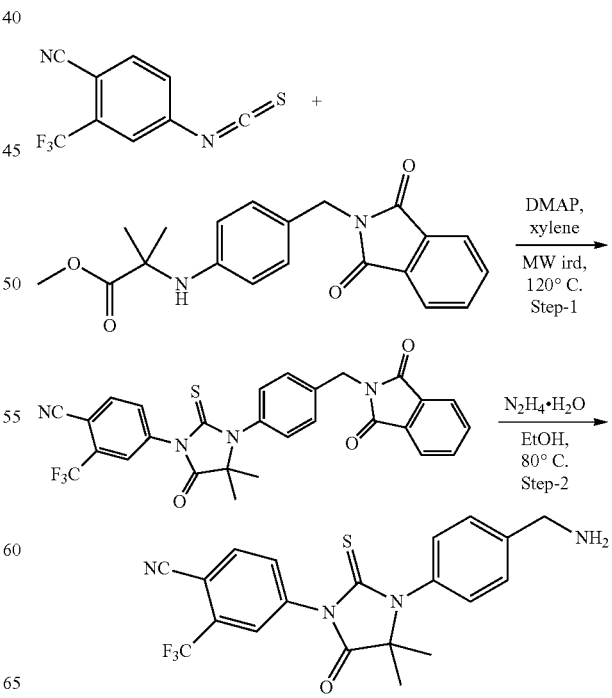

Step-1: Preparation of 4-(3-(4-((1,3-dioxoisoindolin-2-yl)methyl)phenyl)-4,4-dimethyl-5-oxo-2-thioxoimidazolidin-1-yl)-2-(trifluoromethyl)benzonitrile To a stirred solution of methyl 2-(4-((1,3-dioxoisoindolin-2-yl)methyl)phenylamino)-2-methylpropanoate (2.5 g, 7.1 mmol, 1 eq) in xylene (10 mL) were successively added 4-isothiocyanato-2-(trifluoromethyl)benzonitrile (4.05 g, 17.7 mmol, 2.5 eq) and DMAP (0.869 g, 7.1 mmol, 1 eq) and the resulting mixture was heated 120° C. via microwave irradiation. After 1 h, the reaction mixture was diluted with EtOAc (400 mL). The organic layer was washed with water (100 mL×3), brine (100 mL), dried over $Na_2SO_4$, filtered and concentrated under reduced pressure to obtain a crude product which was purified by CombiFlash chromatography to afford the title compound. Analytical data: LC-MS 549 $[M+H]^+$; $^1H$ NMR (400 MHz, methanol-$d_4$) δ 8.12-8.17 (m, 2H), 7.95-8.01 (m, 1H), 7.87-7.92 (m, 2H), 7.79-7.85 (m, 2H), 7.52-7.60 (m, 2H), 7.32-7.39 (m, 2H), 4.90-4.95 (m, 2H), 1.49-1.57 (m, 6H).

Step-2: Preparation of 4-(3-(4-(aminomethyl)phenyl)-4,4-dimethyl-5-oxo-2-thioxoimidazolidin-1-yl)-2-(trifluoromethyl)benzonitrile To a stirred solution of 4-(3-(4-((1,3-dioxoisoindolin-2-yl)methyl)phenyl)-4,4-dimethyl-5-oxo-2-thioxoimidazolidin-1-yl)-2-(trifluoromethyl)benzonitrile (3.7 g, 6.74 mmol, 1 eq) in ethanol (20 mL) was added hydrazine hydrate (4 mL) and the resulting mixture was heated at 100° C. for 2 h. The reaction was monitored by TLC. After completion, the reaction mixture was concentrated under reduced pressure. The crude material was diluted with water (150 mL) and extracted with EtOAc (200 mL×3). The combined organic layers were washed with brine (150 mL), dried over $Na_2SO_4$, filtered and concentrated under reduced pressure to obtain a crude product which was purified by CombiFlash chromatography to afford the title compound. Analytical data: LC-MS 419 $[M+H]^+$.

Example 5. Preparation of amide derivatives of 4-(3-(4-(aminomethyl)phenyl)-4,4-dimethyl-5-oxo-2-thioxoimidazolidin-1-yl)-2-(trifluoromethyl)benzonitrile

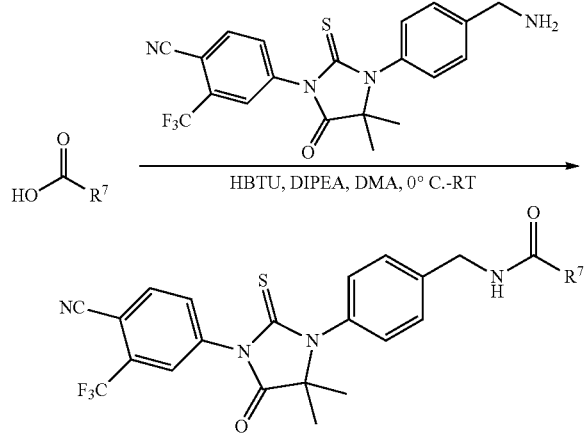

To a stirred solution of the appropriate carboxylic acid (1 eq) in DMA (30-40 vol) was added HBTU (1.2 eq) at 0° C. and the resulting mixture was stirred at the same temperature for 10 min. DIPEA (2.2 eq) and 4-(3-(4-(aminomethyl)phenyl)-4,4-dimethyl-5-oxo-2-thioxoimidazolidin-1-yl)-2-(trifluoromethyl)benzonitrile (1 eq) were then successively added to the reaction mixture and the resulting mixture was stirred at RT for 2 h. The reaction was monitored by TLC. After completion, $H_2O$ (50 vol) was added and the resulting precipitate was filtered through a Buchner funnel. The crude product was purified by reversed-phase HPLC to afford the amide. Compounds 16, 18, 19, 22, 39 were prepared following this procedure.

Analytical Data: Compound 16—LC-MS 538 $[M+H]^+$; $^1H$ NMR (methanol-$d_4$) δ 8.53-8.46 (m, 1H), 8.15 (d, J=8.0 Hz, 2H), 8.03-7.95 (m, 1H), 7.80 (td, J=7.7, 1.8 Hz, 1H), 7.48 (d, J=8.0 Hz, 2H), 7.42 (d, J=7.8 Hz, 1H), 7.35 (d, J=8.3 Hz, 2H), 7.31 (d, J=6.4 Hz, 1H), 4.49 (s, 2H), 3.81 (s, 2H), 1.55 (s, 6H). Compound 18—LC-MS 530 $[M+H]^+$; $^1H$ NMR (methanol-$d_4$) δ 9.15 (s, 1H), 8.45 (s, 1H), 8.19-8.12 (m, 2H), 8.02-7.95 (m, 1H), 7.54 (d, J=8.1 Hz, 2H), 7.38 (d, J=8.3 Hz, 2H), 4.65 (s, 2H), 1.56 (s, 6H). Compound 19—LC-MS 525 $[M+H]^+$; $^1H$ NMR (methanol-$d_4$) δ 8.96 (d, J=4.9 Hz, 2H), 8.15 (d, J=7.9 Hz, 2H), 8.02-7.95 (m, 1H), 7.64 (t, J=4.9 Hz, 1H), 7.57 (d, J=8.0 Hz, 2H), 7.41-7.34 (m, 2H), 4.73 (s, 2H), 1.55 (s, 6H). Compound 22—LC-MS 527 $[M+H]^+$; $^1H$ NMR (methanol-$d_4$) δ 8.15 (d, J=8.2 Hz, 2H), 7.99 (dd, J=8.0, 2.0 Hz, 1H), 7.55 (d, J=8.0 Hz, 2H), 7.37 (d, J=8.0 Hz, 2H), 7.24 (s, 1H), 7.02 (s, 1H), 4.63 (m, 2H), 4.03 (s, 3H), 1.56 (s, 6H). Compound 39—LC-MS 544 $[M+H]^+$; $^1H$ NMR (methanol-$d_4$) δ 8.97 (s, 1H), 8.12-8.19 (m, 2H), 7.99 (d, J=8.3 Hz, 1H), 7.53-7.57 (m, J=8.3 Hz, 2H), 7.36-7.41 (m, J=8.3 Hz, 2H), 4.62 (s, 2H), 2.68 (s, 3H), 1.56 (s, 6H).

Example 6. Preparation of amide derivatives of 4-(3-(4-(aminomethyl)phenyl)-4,4-dimethyl-2,5-dioxoimidazolidin-1-yl)-2-(trifluoromethyl)benzonitrile

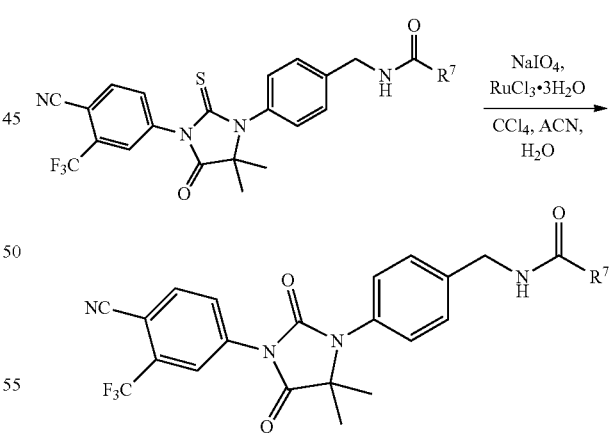

To a stirred solution of the appropriate thiohydantoin (1 eq) in a mixture of $CCl_4$ (20 vol), $H_2O$ (40 vol), ACN (20 vol) was added $NaIO_4$ (2 eq) at 0° C. and the mixture was stirred for 10 min. $RuCl_3 \cdot 3H_2O$ (0.05 eq) was then added and resultant mixture was stirred at RT for 3 h. The reaction was monitored by TLC. Upon completion, the reaction mixture was quenched with saturated aqueous sodium thiosulfate (100 vol) and extracted with EtOAc (200 vol). The organic layer was washed with saturated aqueous $NaHCO_3$ solution (100 vol), water (100 vol), brine (80 vol), dried over Na$_2$SO$_4$, filtered and concentrated under reduced pressure to afford a crude product which was purified by reversed-phase HPLC to afford the hydantoin. Compounds 17, 27, 33 were prepared following this procedure.

Analytical Data: Compound 17—LC-MS 511 [M+H]$^+$; $^1$H NMR (methanol-d$_4$) δ 8.25 (s, 1H), 8.17-8.07 (m, 2H), 7.53 (d, J=8.1 Hz, 2H), 7.40 (d, J=8.3 Hz, 2H), 7.23 (s, 1H), 7.02 (s, 1H), 4.61 (s, 2H), 4.02 (s, 3H), 1.54 (s, 6H). Compound 27—LC-MS 514 [M+H]$^+$; $^1$H NMR (methanol-d$_4$) δ 9.15 (s, 1H), 8.44 (s, 1H), 8.25 (s, 1H), 8.17-8.07 (m, 2H), 7.52 (d, J=8.0 Hz, 2H), 7.41 (d, J=7.9 Hz, 2H), 4.63 (s, 2H), 1.54 (s, 6H). Compound 33—LC-MS 509 [M+H]$^+$; $^1$H NMR (methanol-d$_4$) δ 8.96 (d, J=5.3 Hz, 2H), 8.25 (s, 1H), 8.12 (s, 2H), 7.64 (s, 1H), 7.52-7.58 (m, J=8.3 Hz, 2H), 7.36-7.43 (m, J=8.3 Hz, 2H), 4.71 (s, 2H), 1.54 ppm (s, 6H).

Example 7. Preparation of 4-(3-(4-(aminomethyl)-3-chlorophenyl)-4,4-dimethyl-5-oxo-2-thioxoimidazolidin-1-yl)-2-(trifluoromethyl)benzonitrile

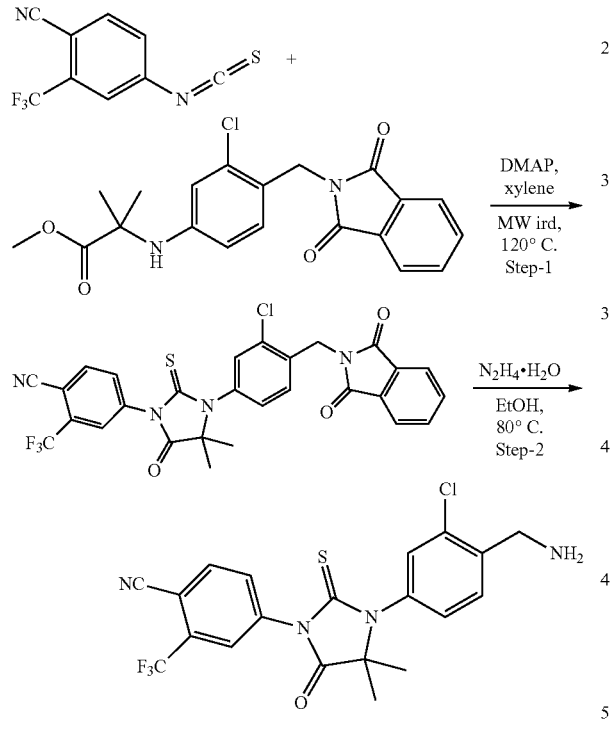

Step-1: Preparation of 4-(3-(3-chloro-4-((1,3-dioxoisoindolin-2-yl)methyl)phenyl)-4,4-dimethyl-5-oxo-2-thioxoimidazolidin-1-yl)-2-(trifluoromethyl)benzonitrile To a stirred solution of methyl 2-(3-chloro-4-((1,3-dioxoisoindolin-2-yl)methyl)phenylamino)-2-methylpropanoate (2.5 g, 6.46 mmol, 1 eq) in xylene (8 mL) were successively added 4-isothiocyanato-2-(trifluoromethyl)benzonitrile (3.68 g, 16.1 mmol, 2.5 eq) and DMAP (0.802 g, 6.46 mmol, 1 eq) and the resulting mixture was heated to 120° C. via microwave irradiation. After 1 h, the reaction mixture was diluted with EtOAc (400 mL). The organic layer was washed with water (100 mL×2), brine (100 mL), dried over Na$_2$SO$_4$, filtered and concentrated under reduced pressure to obtain a crude product which was purified by CombiFlash chromatography to afford the title compound. Analytical data: LC-MS 583 [M+H]$^+$; $^1$H NMR (400 MHz, CDCl$_3$) δ 8.00-7.94 (m, 1H), 7.94-7.89 (m, 2H), 7.84-7.74 (m, 3H), 7.42-7.35 (m, 2H), 7.26 (s, 1H), 7.16 (dd, J=8.33, 2.19 Hz, 1H), 5.01-5.07 (m, 2H), 1.54-1.59 (m, 6H).

Step-2: Preparation of 4-(3-(4-(aminomethyl)-3-chlorophenyl)-4,4-dimethyl-5-oxo-2-thioxoimidazolidin-1-yl)-2-(trifluoromethyl)benzonitrile To a stirred solution of 4-(3-(3-chloro-4-((1,3-dioxoisoindolin-2-yl)methyl)phenyl)-4,4-dimethyl-5-oxo-2-thioxoimidazolidin-1-yl)-2-(trifluoromethyl)benzonitrile (3 g, 7.75 mmol, 1 eq) in ethanol (30 mL) was added hydrazine hydrate (3 mL) and the resulting mixture was heated at 100° C. for 2 h. The reaction was monitored by TLC. After completion, the reaction mixture was concentrated under reduced pressure. The crude material was diluted with water (150 mL) and extracted with EtOAc (150 mL×3). The combined organic layers were washed with brine (100 mL), dried over Na$_2$SO$_4$, filtered and concentrated under reduced pressure to obtain a crude product which was purified by CombiFlash chromatography to afford the title compound. Analytical data: LC-MS 453 [M+H]+.

Example 8. Preparation of amide derivatives of 4-(3-(4-(aminomethyl)-3-chlorophenyl)-4,4-dimethyl-5-oxo-2-thioxoimidazolidin-1-yl)-2-(trifluoromethyl)benzonitrile (Method 1)

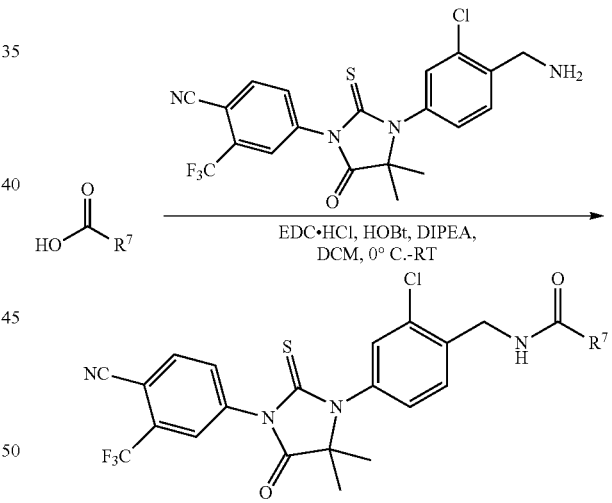

To a stirred solution of the appropriate carboxylic acid (1 eq) in DCM (50 vol) were added EDC.HCl (1.2 eq) and HOBt (1.2 eq) at 0° C. and the resulting mixture was stirred at the same temperature for 10 min. DIPEA (4 eq) and 4-(3-(4-(aminomethyl)-3-chlorophenyl)-4,4-dimethyl-5-oxo-2-thioxoimidazolidin-1-yl)-2-(trifluoromethyl)benzonitrile (1 eq) were then successively added to the reaction mixture and the resulting mixture was stirred at RT for 2 h. The reaction was monitored by TLC. After completion, the reaction mixture was diluted with DCM (200 vol). The organic layer was washed with saturated aqueous NaHCO$_3$ solution (80 vol), saturated aqueous NH$_4$Cl solution (80 vol), water (80 vol), brine (50 vol), dried over Na$_2$SO$_4$, filtered and concentrated under reduced pressure to afford a crude product which was purified by reversed-phase HPLC to afford the amide. Compound 34 was prepared following this procedure. Analytical Data: LC-MS 572 [M+H]+; 1H NMR (methanol-d4) δ 8.50 (d, J=4.38 Hz, 1H), 8.13-8.20 (m, 2H), 7.99 (d, J=9.65 Hz, 1H), 7.78-7.84 (m, 1H), 7.57 (d, J=7.89 Hz, 1H), 7.51 (d, J=1.75 Hz, 1H), 7.43 (d, J=8.33 Hz, 1H), 7.29-7.36 (m, 2H), 4.57 (s, 2H), 3.83 (s, 2H), 1.56 (s, 6H).

Example 8. (Method 2)

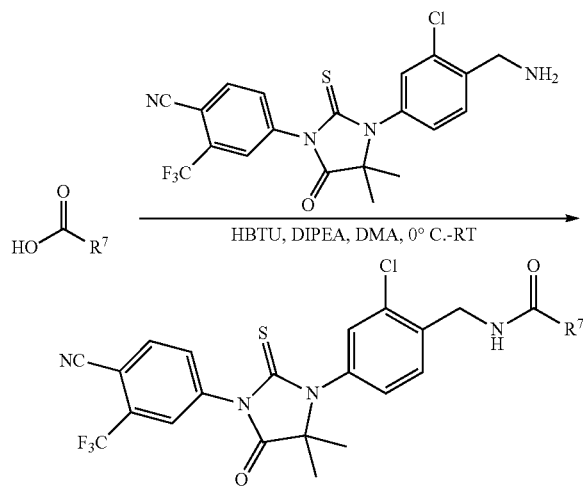

To a stirred solution of the appropriate carboxylic acid (1 eq) in DMA (30-40 vol) was added HBTU (1.2 eq) at 0° C. and the resulting mixture was stirred at same temperature for 10 min. DIPEA (2.2 eq) and 4-(3-(4-(aminomethyl)-3-chlorophenyl)-4,4-dimethyl-5-oxo-2-thioxoimidazolidin-1-yl)-2-(trifluoromethyl)benzonitrile (1 eq) were then successively added and the resulting mixture was stirred at RT for 2 h. The reaction was monitored by TLC. After completion, H2O (50 vol) was added and the resulting precipitate was filtered through a Buchner funnel. The crude material was purified by reversed-phase HPLC to afford the amide. Compounds 25, 26, 31, 32 were prepared following this procedure.

Analytical Data: Compound 25—LC-MS 564 [M+H]+; 1H NMR (methanol-d4) δ 9.16 (s, 1H), 8.49 (s, 1H), 8.16 (d, J=7.8 Hz, 2H), 7.99 (dd, J=8.3, 1.9 Hz, 1H), 7.64-7.52 (m, 2H), 7.37 (dd, J=8.3, 2.1 Hz, 1H), 4.73 (s, 2H), 1.57 (s, 6H). Compound 26—LC-MS 561 [M+H]+; 1H NMR (methanol-d4) δ 8.19-8.12 (m, 2H), 7.99 (dd, J=8.5, 2.0 Hz, 1H), 7.61 (d, J=8.2 Hz, 1H), 7.53 (d, J=2.1 Hz, 1H), 7.35 (dd, J=8.0, 2.1 Hz, 1H), 7.25 (s, 1H), 7.04 (s, 1H), 4.71 (s, 2H), 4.03 (s, 3H), 1.57 (s, 6H). Compound 31—LC-MS 559 [M+H]+; 1H NMR (methanol-d4) δ 8.98 (d, J=4.82 Hz, 2H), 8.13-8.18 (m, 2H), 7.99 (d, J=7.89 Hz, 1H), 7.66 (t, J=5.04 Hz, 1H), 7.61 (d, J=8.33 Hz, 1H), 7.55 (d, J=2.19 Hz, 1H), 7.35 (dd, J=8.11, 1.97, 1H), 4.81 (s, 2H), 1.57 (s, 6H). Compound 32—LC-MS 578 [M+H]+; 1H NMR (methanol-d4) δ 8.99 (s, 1H), 8.13-8.20 (m, 2H), 8.00 (s, 1H), 7.59 (d, J=7.89 Hz, 1H), 7.55 (d, J=1.75 Hz, 1H), 7.37 (d, J=8.33 Hz, 1H), 4.70 (s, 2H), 2.68 (s, 3H), 1.58 (s, 6H).

Example 9. Preparation of 5-(3-(4-(aminomethyl)-3-chlorophenyl)-4,4-dimethyl-5-oxo-2-thioxoimidazolidin-1-yl)-3-(trifluoromethyl)picolinonitrile

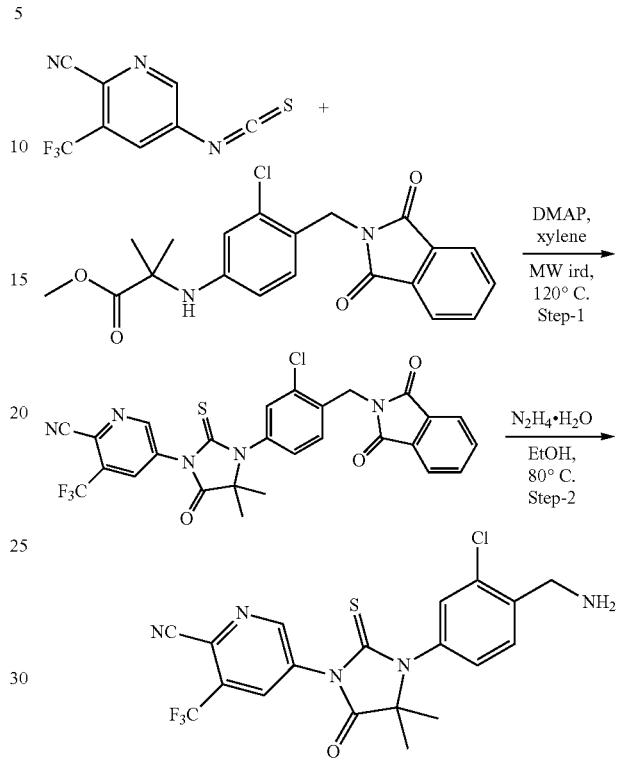

Step-1: Preparation of 5-(3-(3-chloro-4-((1,3-dioxoisoindolin-2-yl)methyl)phenyl)-4,4-dimethyl-5-oxo-2-thioxoimidazolidin-1-yl)-3-(trifluoromethyl) picolinonitrile To a stirred solution of methyl 2-(3-chloro-4-((1,3-dioxoisoindolin-2-yl)methyl)phenylamino)-2-methylpropanoate (1 g, 2.6 mmol, 1 eq) in xylene (7 mL) were successively added 5-isothiocyanato-3-(trifluoromethyl)picolinonitrile (1.48 g, 6.46 mmol, 2.5 eq) and DMAP (0.378 g, 3.1 mmol, 1.2 eq) and the resulting mixture was heated to 120° C. via microwave irradiation. After 1 h, the reaction mixture was diluted with EtOAc (300 mL). The organic layer was washed with water (100 mL×2), brine (100 mL), dried over Na2SO4, filtered and concentrated under reduced pressure to obtain a crude product which was purified by CombiFlash chromatography to afford the title compound. Analytical data: LC-MS 584 [M+H]+; 1H NMR (400 MHz, DMSO-d6) δ 8.80 (s, 1H), 7.98-7.94 (m, 2H), 7.90 (dd, J=5.26, 3.07 Hz, 3H), 7.53-7.43 (m, 2H), 7.37-7.28 (m, 2H), 4.93-4.87 (m, 2H), 1.56-1.50 (m, 6H).

Step-2: Preparation of 5-(3-(4-(aminomethyl)-3-chlorophenyl)-4,4-dimethyl-5-oxo-2-thioxoimidazolidin-1-yl)-3-(trifluoromethyl)picolinonitrile To a stirred solution of 5-(3-(3-chloro-4-(1,3-dioxoisoindolin-2-yl)methyl)phenyl)-4,4-dimethyl-5-oxo-2-thioxoimidazolidin-1-yl)-3-(trifluoromethyl)picolinonitrile (1.5 g, 2.57 mmol, 1 eq) in ethanol (25 mL) was added hydrazine hydrate (1.5 mL) and the resulting mixture was heated at 100° C. for 1 h. The reaction was monitored by TLC. After completion, the reaction mixture was concentrated under reduced pressure. The crude material was diluted with water (150 mL) and extracted with EtOAc (150 mL×3). The combined organic layers were washed with brine (100 mL), dried over Na$_2$SO$_4$, filtered and concentrated under reduced pressure to obtain a crude product which was purified by CombiFlash chromatography to afford the title compound. Analytical data: LC-MS 454 [M+H]$^+$.

Example 10. Preparation of amide derivatives of 5-(3-(4-(aminomethyl)-3-chlorophenyl)-4,4-dimethyl-5-oxo-2-thioxoimidazolidin-1-yl)-3-(trifluoromethyl)picolinonitrile (Method 1)

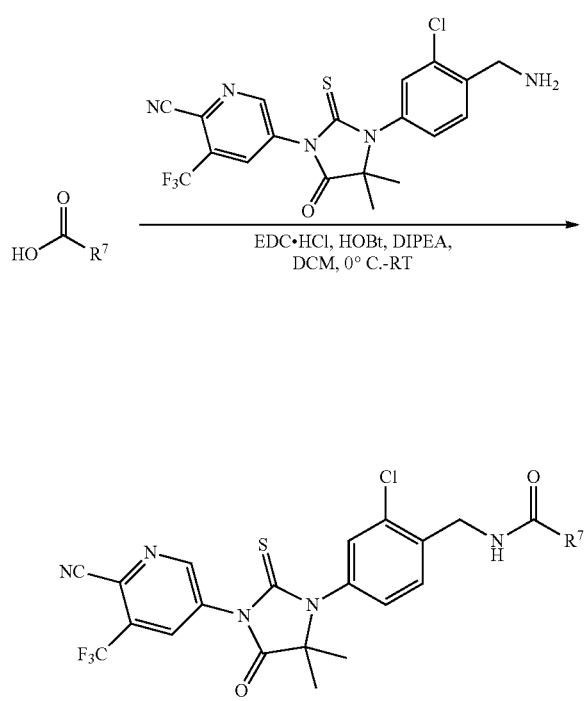

To a stirred solution of the appropriate carboxylic acid (1 eq) in DCM (50 vol) were added EDC.HCl (1.2 eq) and HOBt (1.2 eq) at 0° C. and the resulting mixture was stirred at the same temperature for 10 min. DIPEA (4 eq) and 5-(3-(4-(aminomethyl)-3-chlorophenyl)-4,4-dimethyl-5-oxo-2-thioxoimidazolidin-1-yl)-3-(trifluoromethyl)picolinonitrile (1 eq) were then successively added to the reaction mixture and the resulting mixture was stirred at RT for 2 h. The reaction was monitored by TLC. After completion, the reaction mixture was diluted with DCM (200 vol). The organic layer was washed with saturated NaHCO$_3$ solution (80 vol), sat. NH$_4$Cl solution (80 vol), water (80 vol), brine (50 vol), dried over Na$_2$SO$_4$, filtered and concentrated under reduced pressure to afford a crude product which was purified by reversed-phase chromatography to afford the amide. Compound 35 was prepared following this procedure. Analytical data: LC-MS 573 [M+H]$^+$; $^1$H NMR (methanol-d$_4$) δ 9.17 (s, 1H), 8.68 (s, 1H), 8.50 (br s, 1H), 7.78-7.84 (m, 1H), 7.58 (d, J=8.33 Hz, 1H), 7.51 (d, J=1.75 Hz, 1H), 7.43 (d, J=7.45 Hz, 1H), 7.34 (d, J=6.58 Hz, 2H), 4.57 (s, 2H), 3.84 (s, 2H), 1.58 (s, 6H).

Example 10. (Method 2)

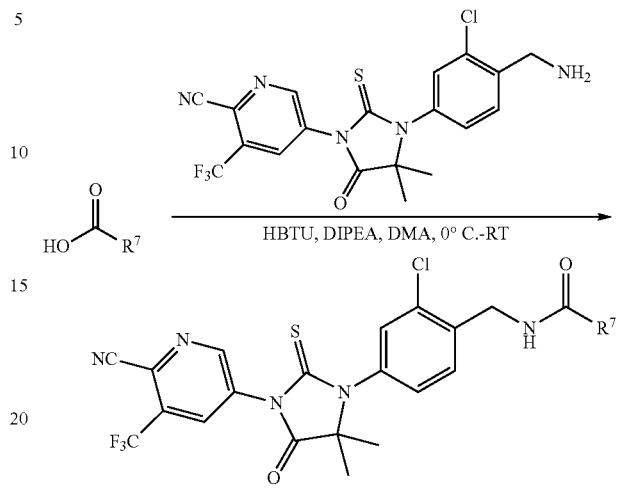

To a stirred solution of the appropriate carboxylic acid (1 eq) in DMA (30-40 vol) was added HBTU (1.2 eq) at 0° C. and the resulting mixture was stirred at the same temperature for 10 min. DIPEA (2.2 eq) and 5-(3-(4-(aminomethyl)-3-chlorophenyl)-4,4-dimethyl-5-oxo-2-thioxoimidazolidin-1-yl)-3-(trifluoromethyl)picolinonitrile (1 eq) were then successively added and the resulting mixture was stirred at RT for 2 h. The reaction was monitored by TLC. After completion, H$_2$O (50 vol) was added and the resulting precipitate was filtered through a Buchner funnel. The crude product obtained was purified by reversed-phase chromatography to afford the amide. Compounds 30, 36, 37, 38 were prepared following this procedure.

Analytical Data: Compound 30—LC-MS 560 [M+H]$^+$; $^1$H NMR (methanol-d$_4$) δ 9.17 (d, J=2.2 Hz, 1H), 8.98 (d, J=4.9 Hz, 2H), 8.68 (d, J=2.1 Hz, 1H), 7.70-7.56 (m, 2H), 7.55 (d, J=2.1 Hz, 1H), 7.35 (dd, J=8.1, 2.1 Hz, 1H), 4.82 (s, 2H), 1.59 (s, 6H). Compound 36—LC-MS 565 [M+H]$^+$; $^1$H NMR (methanol-d$_4$) δ 9.16 (s, 2H), 8.68 (d, J=2.19 Hz, 1H), 8.49 (s, 1H), 7.61 (d, J=7.89 Hz, 1H), 7.55 (d, J=1.75 Hz, 1H), 7.38 (d, J=1.75 Hz, 1H), 4.73 (s, 2H), 1.59 (s, 6H). Compound 37—LC-MS 562 [M+H]$^+$; $^1$H NMR (methanol-d$_4$) δ 9.17 (s, 1H), 8.68 (s, 1H), 7.62 (d, J=8.33 Hz, 1H), 7.54 (d, J=1.75 Hz, 1H), 7.37-7.35 (m, 1H), 7.25 (s, 1H), 7.04 (s, 1H), 4.71 (s, 2H), 4.03 (s, 3H), 1.59 (s, 6H). Compound 38—LC-MS 579 [M+H]$^+$; $^1$H NMR (methanol-d$_4$) δ 9.17 (s, 1H), 8.99 (s, 1H), 8.68 (s, 1H), 7.60 (d, J=8.33 Hz, 1H), 7.55 (d, J=2.19 Hz, 1H), 7.34-7.40 (m, 1H), 4.70 (s, 2H), 2.69 (s, 3H), 1.59 (s, 6H).

Example 11. Preparation of 5-(3-(4-(aminomethyl)-3-fluorophenyl)-4,4-dimethyl-5-oxo-2-thioxoimidazolidin-1-yl)-3-(trifluoromethyl)picolinonitrile

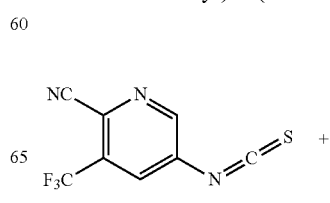

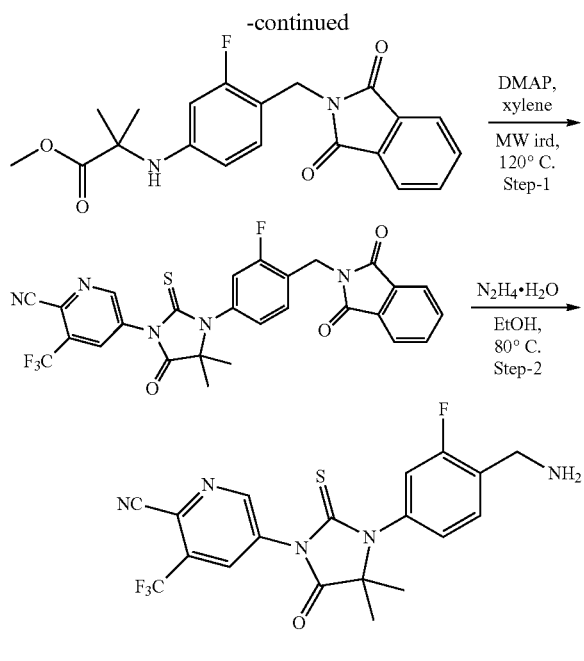

Example 12. Preparation of amide derivatives of 5-(3-(4-(aminomethyl)-3-fluorophenyl)-4,4-dimethyl-5-oxo-2-thioxoimidazolidin-1-yl)-3-(trifluoromethyl)picolinonitrile

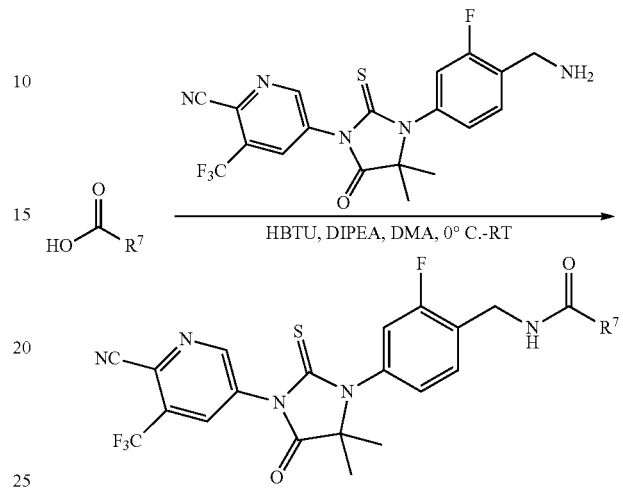

Step-1: Preparation of 5-(3-(4-((1,3-dioxoisoindolin-2-yl)methyl)-3-fluorophenyl)-4,4-dimethyl-5-oxo-2-thioxoimidazolidin-1-yl)-3-(trifluoromethyl)picolinonitrile To a stirred solution of methyl 2-(4-((1,3-dioxoisoindolin-2-yl)methyl)-3-fluorophenylamino)-2-methylpropanoate (1 g, 2.6 mmol, 1 eq) in xylene (4 mL) were successively added 5-isothiocyanato-3-(trifluoromethyl)picolinonitrile (1.54 g, 6.46 mmol, 2.5 eq) and DMAP (0.322 g, 2.6 mmol, 1 eq) and the resulting mixture was heated to 120° C. via microwave irradiation. After 1 h, the reaction mixture was diluted with EtOAc (300 mL). The organic layer was washed with water (100 mL×2), brine (100 mL), dried over $Na_2SO_4$, filtered and concentrated under reduced pressure to obtain a crude product which was purified by CombiFlash chromatography to afford the title compound. Analytical data: LC-MS 568 [M+H]$^+$; $^1$H NMR (400 MHz, DMSO-$d_6$) δ 7.89 (br s, 3H), 7.77 (d, J=2.63 Hz, 3H), 7.05 (s, 3H), 5.01 (s, 2H), 1.56 (s, 6H).

Step-2: Preparation of 5-(3-(4-(aminomethyl)-3-fluorophenyl)-4,4-dimethyl-5-oxo-2-thioxoimidazolidin-1-yl)-3-(trifluoromethyl)picolinonitrile To a stirred solution of 5-(3-(4-((1,3-dioxoisoindolin-2-yl)methyl)-3-fluorophenyl)-4,4-dimethyl-5-oxo-2-thioxoimidazolidin-1-yl)-3-(trifluoromethyl)picolinonitrile (0.55 g, 0.97 mmol, 1 eq) in ethanol (10 mL) was added hydrazine hydrate (0.55 mL) and the resulting mixture was heated at 100° C. for 1 h. The reaction was monitored by TLC. After completion, the reaction mixture was concentrated under reduced pressure. The crude material was diluted with water (150 mL) and extracted with EtOAc (150 mL×3). The combined organic layers were washed with brine (100 mL), dried over $Na_2SO_4$, filtered and concentrated under reduced pressure to obtain a crude product which was purified by CombiFlash chromatography to afford the title compound. Analytical data: LC-MS 438 [M+H]$^+$.

To a stirred solution of the appropriate carboxylic acid (1 eq) in DMA (30-40 vol) was added HBTU (1.2 eq) at 0° C. and the resulting mixture was stirred at the same temperature for 10 min. DIPEA (2.2 eq) and 5-(3-(4-(aminomethyl)-3-fluorophenyl)-4,4-dimethyl-5-oxo-2-thioxoimidazolidin-1-yl)-3-(trifluoromethyl)picolinonitrile (1 eq) were then successively added and the resulting mixture was stirred at RT for 2 h. The reaction was monitored by TLC. After completion, $H_2O$ (50 vol) was added and the resulting precipitate was filtered through a Buchner funnel. The crude product obtained was purified by reversed-phase chromatography to afford the amide. Compounds 49, 50, 51 were prepared following this procedure.

Analytical Data: Compound 49—LC-MS 546 [M+H]$^+$; $^1$H NMR (methanol-$d_4$) δ 9.16 (s, 1H), 8.67 (s, 1H), 7.61 (s, 1H), 7.24 (s, 3H), 7.03 (s, 1H), 4.59 (s, 2H), 4.03 (s, 3H), 1.59 (s, 6H). Compound 50—LC-MS 543 [M+H]$^+$; $^1$H NMR (methanol-$d_4$) δ 9.16 (s, 1H), 8.67 (s, 1H), 7.61 (s, 1H), 7.24 (s, 3H), 7.03 (s, 1H), 4.59 (s, 2H), 4.03 (s, 3H), 1.59 (s, 6H). Compound 51—LC-MS 563 [M+H]$^+$; $^1$H NMR (methanol-$d_4$) δ 9.16 (s, 1H), 8.97 (s, 1H), 8.67 (s, 1H), 7.59 (s, 1H), 7.25 (t, J=8.11 Hz, 2H), 4.67 (s, 2H), 2.67 (s, 3H), 1.59 (s, 7H).

Example 13. Preparation of 4-(3-(6-(aminomethyl)-5-fluoropyridin-3-yl)-4,4-dimethyl-5-oxo-2-thioxo imidazolidin-1-yl)-2-(trifluoromethyl)benzonitrile

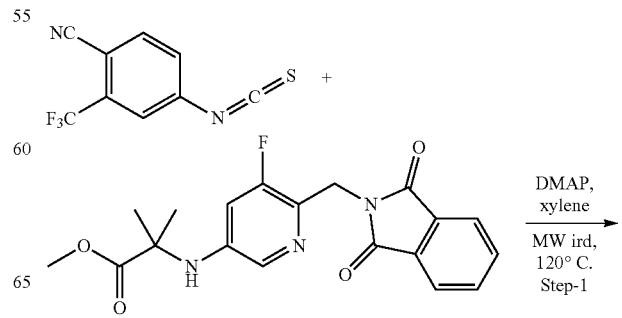

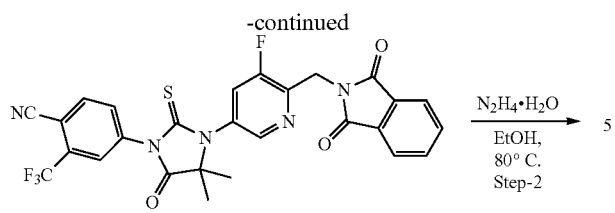

Example 14. Preparation of amide derivatives of 4-(3-(6-(aminomethyl)-5-fluoropyridin-3-yl)-4,4-dimethyl-5-oxo-2-thioxo imidazolidin-1-yl)-2-(trifluoromethyl)benzonitrile

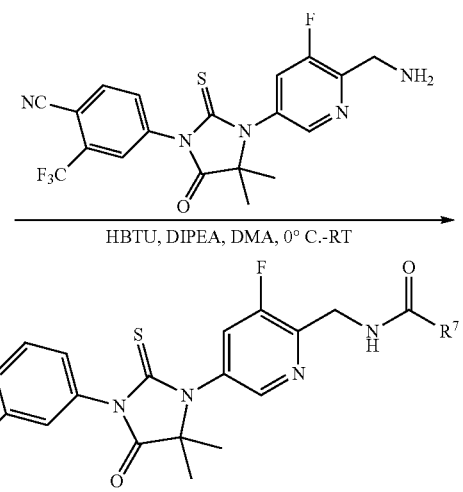

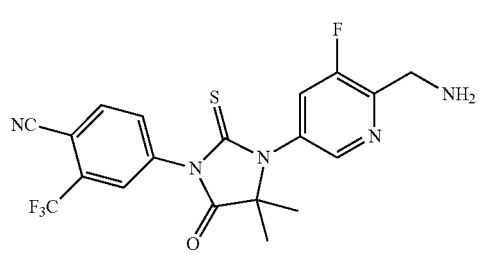

Step-1: Preparation of 4-(3-(6-((1,3-dioxoisoindolin-2-yl)methyl)-5-fluoropyridin-3-yl)-4,4-dimethyl-5-oxo-2-thioxoimidazolidin-1-yl)-2-(trifluoromethyl)benzonitrile To a stirred solution of methyl 2-(6-((1,3-dioxoisoindolin-2-yl)methyl)-5-fluoropyridin-3-ylamino)-2-methylpropanoate (1.5 g, 4.0 mmol, 1 eq) in xylene (5 mL) were successively added 5-isothiocyanato-3-(trifluoromethyl)benzonitrile (2.3 g, 10.0 mmol, 2.5 eq) and DMAP (0.50 g, 4.0 mmol, 1 eq) and the resulting mixture was heated to 120° C. via microwave irradiation. After 1 h, the reaction mixture was diluted with EtOAc (300 mL). The organic layer was washed with water (100 mL×2), brine (100 mL), dried over $Na_2SO_4$, filtered and concentrated under reduced pressure to obtain a crude product which was purified by CombiFlash chromatography to afford the title compound. Analytical data: LC-MS 568 [M+H]$^+$

Step-2: Preparation of 4-(3-(6-(aminomethyl)-5-fluoropyridin-3-yl)-4,4-dimethyl-5-oxo-2-thioxo imidazolidin-1-yl)-2-(trifluoromethyl)benzonitrile To a stirred solution of 4-(3-(6-((1,3-dioxoisoindolin-2-yl)methyl)-5-fluoropyridin-3-yl)-4,4-dimethyl-5-oxo-2-thioxoimidazolidin-1-yl)-2-(trifluoromethyl)benzonitrile (1.2 g, 2.1 mmol, 1 eq) in ethanol (25 mL) was added hydrazine hydrate (1.2 mL) and the resulting mixture was heated at 100° C. for 1 h. The reaction was monitored by TLC. After completion, the reaction mixture was concentrated under reduced pressure. The crude material was diluted with water (150 mL) and extracted with EtOAc (300 mL×3). The combined organic layers were washed with brine (100 mL), dried over $Na_2SO_4$, filtered and concentrated under reduced pressure to obtain a crude product which was purified by CombiFlash chromatography to afford the title compound. Analytical data: LC-MS 438 [M+H]$^+$.

To a stirred solution of the appropriate carboxylic acid (1 eq) in DMA (30-40 vol) was added HBTU (1.2 eq) at 0° C. and the resulting mixture was stirred at the same temperature for 10 min. DIPEA (2.2 eq) and 4-(3-(6-(aminomethyl)-5-fluoropyridin-3-yl)-4,4-dimethyl-5-oxo-2-thioxoimidazolidin-1-yl)-2-(trifluoromethyl)benzonitrile (1 eq) were then successively added to the reaction mixture and the resulting mixture was stirred at RT for 2 h. The reaction was monitored by TLC. After completion, $H_2O$ (50 vol) was added and the resulting precipitate was filtered through a Buchner funnel. The crude product obtained was purified by reversed-phase chromatography to afford the amide. Compounds 53, 55, 56 were prepared following this procedure.

Analytical Data: Compound 53—LC-MS 543 [M+H]$^+$; $^1$H NMR (methanol-$d_4$) δ 8.67 (d, J=4.82 Hz, 1H), 8.44-8.49 (m, 1H), 8.11-8.22 (m, 3H), 7.98-8.03 (m, 2H), 7.83 (dd, J=10.09, 1.75 Hz, 1H), 7.58 (d, J=1.75 Hz, 1H), 4.60 (s, 2H), 1.61 (s, 6H). Compound 55—LC-MS 563 [M+H]$^+$; $^1$H NMR (methanol-$d_4$) δ 8.98 (s, 1H), 8.43-8.49 (m, 1H), 8.17 (d, J=5.70 Hz, 2H), 8.00 (d, J=8.33 Hz, 1H), 7.82 (dd, J=10.09, 1.75, 1H), 4.60 (s, 2H), 2.70 (s, 3H), 1.61 (s, 6H). Compound 56—LC-MS 546 [M+H]$^+$; $^1$H NMR (methanol-$d_4$) δ 8.83 (br s, 1H), 8.46 (s, 1H), 8.41 (d, J=7.89 Hz, 1H), 8.29 (s, 1H), 8.08 (d, J=7.89 Hz, 1H), 7.93 (d, J=10.52 Hz, 1H), 7.37 (s, 1H), 7.01 (s, 1H), 4.70 (d, J=5.26 Hz, 2H), 3.96 (s, 2H), 1.56 (s, 6H).

Example 15. Preparation of 4-(5-(4-(aminomethyl)-3-fluorophenyl)-8-oxo-6-thioxo-5,7-diazaspiro[3.4]octan-7-yl)-2-(trifluoromethyl)benzonitrile

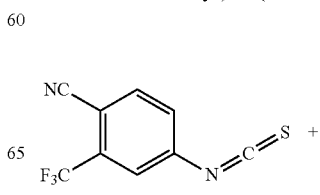

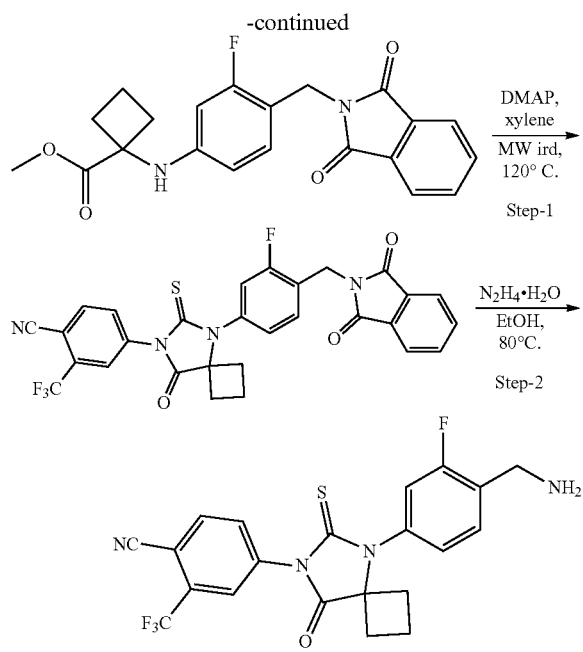

Step-1: Preparation of 4-(5-(4-((1,3-dioxoisoindolin-2-yl)methyl)-3-fluorophenyl)-8-oxo-6-thioxo-5,7-diazaspiro[3.4]octan-7-yl)-2-(trifluoromethyl)benzonitrile To a stirred solution of methyl 1-(4-((1,3-dioxoisoindolin-2-yl)methyl)-3-fluorophenylamino) cyclobutanecarboxylate (1 g, 2.6 mmol, 1 eq) in xylene (4 mL) were successively added 4-isothiocyanato-2-(trifluoromethyl)benzonitrile (1.5 g, 6.5 mmol, 2.5 eq) and DMAP (0.322 g, 2.6 mmol, 1 eq) and the resulting mixture was heated to 120° C. via microwave irradiation. After 1 h, the reaction mixture was diluted with EtOAc (400 mL). The organic layer was washed with water (100 mL×3), brine (100 mL), dried over Na$_2$SO$_4$, filtered and concentrated under reduced pressure to obtain a crude product which was purified by CombiFlash chromatography to afford the title compound. Analytical data: LC-MS 579 [M+H]$^+$; $^1$H NMR (400 MHz, CDCl$_3$) δ 7.94-8.02 (m, 2H), 7.88-7.94 (m, 2H), 7.84 (s, 1H), 7.74-7.78 (m, 1H), 7.58 (s, 1H), 7.05-7.13 (m, 2H), 5.00-5.07 (m, 2H), 2.63 (d, J=12.3 Hz, 1H), 2.53 (d, J=12.7 Hz, 1H), 2.3-2.2 (m, 2H), 1.75-1.65 (m, 2H).

Step-2: Preparation of 4-(5-(4-(aminomethyl)-3-fluorophenyl)-8-oxo-6-thioxo-5,7-diazaspiro[3.4]octan-7-yl)-2-(trifluoromethyl)benzonitrile To a stirred solution of 4-(5-(4-((1,3-dioxoisoindolin-2-yl)methyl)-3-fluorophenyl)-8-oxo-6-thioxo-5,7-diazaspiro[3.4]octan-7-yl)-2-(trifluoromethyl)benzonitrile (0.4 g, 0.692 mmol, 1 eq) in ethanol (10 mL) was added hydrazine hydrate (0.4 mL) and the resulting mixture was heated at 80° C. for 2 h. The reaction was monitored by TLC. After completion, the reaction mixture was concentrated under reduced pressure. The crude residue was diluted with water (300 mL) and extracted with EtOAc (500 mL×3). The combined organic layers were washed with brine (200 mL), dried over Na$_2$SO$_4$, filtered and concentrated under reduced pressure to obtain a crude product which was purified by CombiFlash chromatography to afford the title compound. Analytical data: LC-MS 449 [M+H]+.

Example 16. Preparation of amide derivatives of 4-(5-(4-(aminomethyl)-3-fluorophenyl)-8-oxo-6-thioxo-5,7-diazaspiro[3.4]octan-7-yl)-2-(trifluoromethyl)benzonitrile

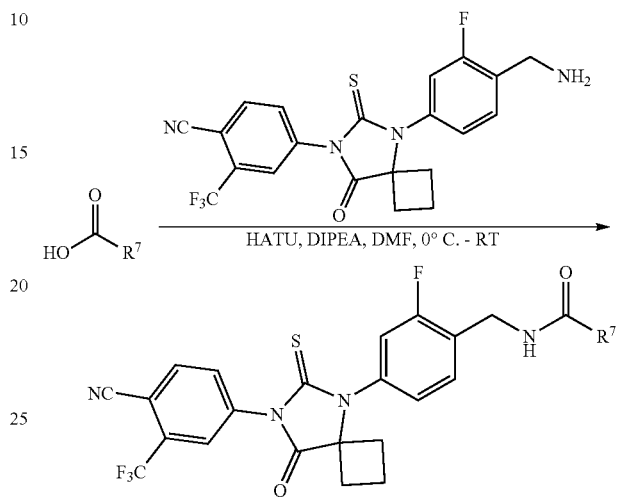

To a stirred solution of appropriate carboxylic acid (2 eq) in DMF (50 vol) was added HATU (2 eq) at 0° C. and the resulting mixture was stirred at same temperature for 30 min. DIPEA (5 eq) and 4-(5-(4-(aminomethyl)-3-fluorophenyl)-8-oxo-6-thioxo-5,7-diazaspiro[3.4]octan-7-yl)-2-(trifluoromethyl) benzonitrile (1 eq) were then successively added and the resulting mixture was stirred at RT for 2 h. The reaction was monitored by TLC. After completion, H$_2$O (50 vol) was added and the resulting precipitate was filtered through a Buchner funnel. The crude material was purified by SFC to afford the amide. Compounds 64, 65, 73 were prepared following this procedure.

Analytical Data: Compound 64—LC-MS 554 [M+H]$^+$; $^1$H NMR (methanol-d$_4$) δ 8.67 (d, J=4.8 Hz, 1H), 8.18-8.10 (m, 3H), 8.03-7.93 (m, 2H), 7.66-7.53 (m, 2H), 7.26 (ddd, J=16.8, 9.2, 2.0 Hz, 2H), 3.93 (t, J=4.1 Hz, 2H), 2.70-2.50 (m, 4H), 2.10 (tt, J=16.3, 8.2 Hz, 1H), 1.68-1.57 (m, 1H). Compound 65—LC-MS 574 [M+H]$^+$; $^1$H NMR (DMSO-d$_6$) δ 9.08 (s, 1H), 8.88 (br s, 1H), 8.38 (d, J=8.3 Hz, 1H), 8.24 (s, 1H), 8.05 (d, J=8.3 Hz, 1H), 7.57 (t, J=8.3 Hz, 1H), 7.36 (d, J=10.5 Hz, 1H), 7.30 (d, J=6.6 Hz, 1H), 4.56 (br s, 2H), 2.63 (s, 3H), 2.45-2.4 (m, 2H), 1.96 (d, J=10.1 Hz, 2H), 1.54 (br s, 2H). Compound 73—LC-MS 557 [M+H]$^+$; $^1$H NMR (methanol-d$_4$) δ 8.12-8.19 (m, 2H), 7.95-8.00 (m, 1H), 7.62 (t, J=8.1 Hz, 1H), 7.48 (d, J=2.2 Hz, 1H), 7.22-7.32 (m, 2H), 6.86 (d, J=1.8 Hz, 1H), 4.68 (s, 2H), 4.14 (s, 3H), 2.63-2.70 (m, 2H), 2.57 (d, J=10.1 Hz, 2H), 2.12 (d, J=11.4 Hz, 1H), 1.62 (d, J=11.0 Hz, 1H).

Example 17. Preparation of 2-fluoro-4-isothiocyanatobenzonitrile

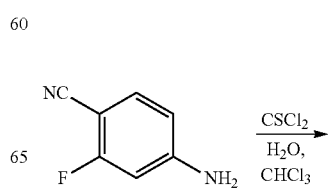

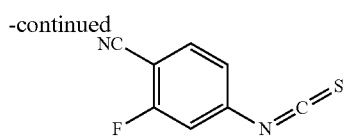

To a stirred solution of 4-amino-2-fluorobenzonitrile (5 g, 36.8 mmol, 1 eq) in H₂O (200 mL) chloroform (50 mL) mixture was added thiophosgene (3 mL, 40.4 mmol, 1.1 eq) slowly and the mixture was stirred at RT for 5 h. The reaction was monitored by TLC. After completion, the reaction mixture was diluted with water (300 mL) and extracted with DCM (200 mL×3). The combined organic layers were washed with water (200 mL), brine (200 mL), dried over Na₂SO₄, filtered and concentrated under reduced pressure to afford the title compound. Analytical data: ¹H NMR (400 MHz, DMSO-d₆) δ 8.02 (t, J=7.9 Hz, 1H), 7.76 (dd, J=10.3, 1.5 Hz, 1H), 7.44-7.53 (m, 1H).

Example 18. Preparation of 4-(3-(4-(aminomethyl)-3-fluorophenyl)-4,4-dimethyl-5-oxo-2-thioxoimidazolidin-1-yl)-2-fluorobenzonitrile

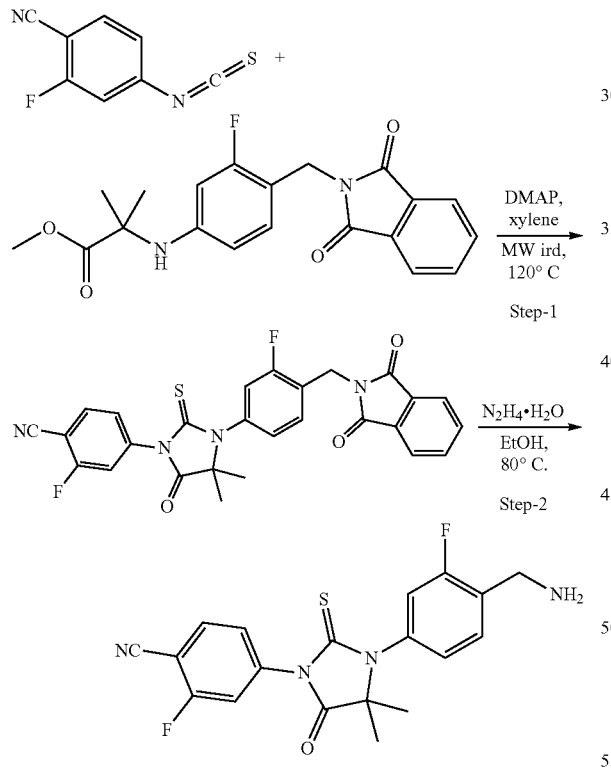

Step-1: Preparation of 4-(3-(4-((1,3-dioxoisoindolin-2-yl)methyl)-3-fluorophenyl)-4,4-dimethyl-5-oxo-2-thioxoimidazolidin-1-yl)-2-fluorobenzonitrile To a stirred solution of methyl 2-(4-((1,3-dioxoisoindolin-2-yl)methyl)-3-fluorophenylamino)-2-methylpropanoate (1 g, 2.7 mmol, 1 eq) in xylene (7 mL) were successively 2-fluoro-4-isothiocyanatobenzonitrile (1.44 g, 8.0 mmol, 3 eq) and DMAP (0.322 g, 2.7 mmol, 1 eq) and the resulting mixture was heated to 120° C. via microwave irradiation. After 1 h, the reaction mixture was diluted with EtOAc (400 mL). The organic layer was washed with water (100 mL×3), brine (100 mL), dried over Na₂SO₄, filtered and concentrated under reduced pressure to obtain a crude product which was purified by CombiFlash chromatography to afford the title compound. Analytical data: LC-MS 517 [M+H]⁺; ¹H NMR (400 MHz, DMSO-d₆) δ 8.14 (s, 1H), 7.91-7.96 (m, 2H), 7.84-7.90 (m, 2H), 7.80 (d, J=10.1 Hz, 1H), 7.58 (d, J=8.3 Hz, 1H), 7.53 (s, 1H), 7.36 (d, J=11.0 Hz, 1H), 7.20 (d, J=7.9 Hz, 1H), 4.89 (s, 2H), 1.47-1.54 (m, 6H).

Step-2: Preparation of 4-(3-(4-(aminomethyl)-3-fluorophenyl)-4,4-dimethyl-5-oxo-2-thioxoimidazolidin-1-yl)-2-fluorobenzonitrile To a stirred solution of 4-(3-(4-((1,3-dioxoisoindolin-2-yl)methyl)-3-fluorophenyl)-4,4-dimethyl-5-oxo-2-thioxoimidazolidin-1-yl)-2-fluorobenzonitrile (1.5 g, 3.43 mmol, 1 eq) in ethanol (15 mL) was added hydrazine hydrate (1.5 mL) and the resulting mixture was heated at 100° C. for 2 h. The reaction was monitored by TLC. After completion, the reaction mixture was concentrated under reduced pressure. The crude residue was diluted with water (300 mL) and extracted with EtOAc (500 mL×3). The combined organic layers were washed with brine (200 mL), dried over Na₂SO₄, filtered and concentrated under reduced pressure to obtain a crude product which was purified by CombiFlash chromatography to afford the title compound. Analytical data: LC-MS 387 [M+H]⁺.

Example 19. Preparation of amide derivatives of 4-(3-(4-(aminomethyl)-3-fluorophenyl)-4,4-dimethyl-5-oxo-2-thioxoimidazolidin-1-yl)-2-fluorobenzonitrile

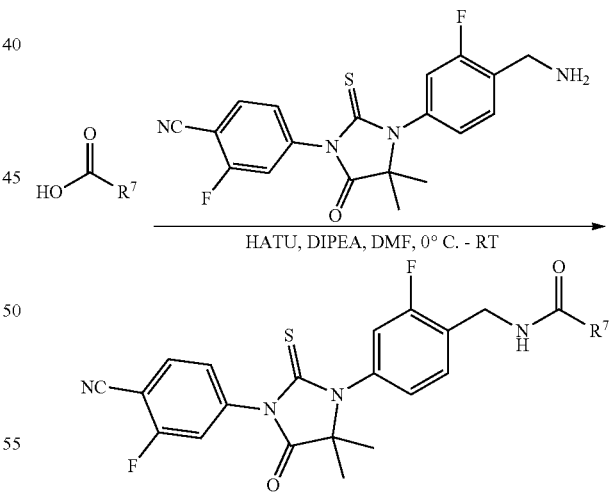

To a stirred solution of the appropriate carboxylic acid (1 eq) in DMF (30-40 vol) was added HATU (2 eq) at 0° C. and the resulting mixture was stirred at same temperature for 20 min. DIPEA (5 eq) and 4-(3-(4-(aminomethyl)-3-fluorophenyl)-4,4-dimethyl-5-oxo-2-thioxoimidazolidin-1-yl)-2-fluorobenzonitrile (0.5 eq) were then successively added and the resulting mixture was stirred at RT for 2 h. The reaction was monitored by TLC. After completion, H₂O (50 vol) was added and the resulting precipitate was filtered through a Buchner funnel. The crude material was purified by SFC to afford the amide. Compounds 68-71, 74 were prepared following this procedure.

Analytical Data: Compound 68—LC-MS 512 [M+H]+; $^1$H NMR (methanol-$d_4$) δ 8.97 (s, 1H), 7.85-7.95 (m, 1H), 7.58 (s, 3H), 7.24 (s, 2H), 4.66 (s, 2H), 2.67 (s, 3H), 1.56 (s, 6H). Compound 69—LC-MS 492 [M+H]+; $^1$H NMR (methanol-$d_4$) δ 8.66 (br s, 1H), 8.13 (d, J=7.9 Hz, 1H), 7.98 (d, J=1.8 Hz, 1H), 7.90 (d, J=7.0 Hz, 1H), 7.61-7.67 (m, 1H), 7.49-7.60 (m, 3H), 7.16-7.28 (m, 2H), 4.75 (s, 2H), 1.55 (s, 6H). Compound 70—LC-MS 512 [M+H]+; $^1$H NMR (methanol-$d_4$) δ 8.18 (s, 1H), 7.91 (d, J=7.0 Hz, 1H), 7.49-7.66 (m, 3H), 7.17-7.29 (m, 2H), 4.66 (s, 2H), 2.73 (s, 3H), 1.55 (s, 6H). Compound 71—LC-MS 505 [M+H]+; $^1$H NMR (methanol-$d_4$) δ 6.93 (s, 1H), 6.61-6.68 (m, 1H), 6.56 (d, J=1.8 Hz, 1H), 6.42 (d, J=7.5 Hz, 1H), 6.35 (s, 1H), 6.20-6.30 (m, 5H), 3.69 (s, 2H), 1.41 (s, 3H), 0.58 (s, 6H). Compound 74—LC-MS 495 [M+H]+; $^1$H NMR (methanol-$d_4$) δ 7.88-7.95 (m, 1H), 7.63 (dd, J=10.1, 1.8 Hz, 1H), 7.50-7.61 (m, 2H), 7.48 (d, J=2.2 Hz, 1H), 7.20-7.28 (m, 3H), 6.84 (d, J=1.8 Hz, 1H), 4.65 (s, 2H), 4.13 (s, 3H), 1.58 (m, 6H).

Example 20. Preparation of 4-(3-(4-(aminomethyl)-3-fluorophenyl)-4,4-dimethyl-5-oxo-2-thioxoimidazolidin-1-yl)-2-(trifluoromethyl)benzonitrile

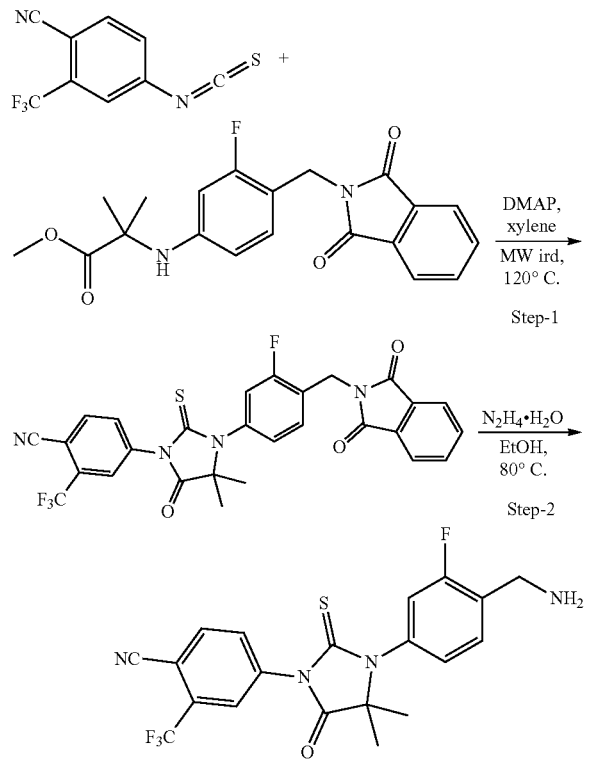

Step-1: Preparation of 4-(3-(4-((1,3-dioxoisoindolin-2-yl)methyl)-3-fluorophenyl)-4,4-dimethyl-5-oxo-2-thioxoimidazolidin-1-yl)-2-(trifluoromethyl) benzonitrile To a stirred solution of methyl 2-(4-((1,3-dioxoisoindolin-2-yl)methyl)-3-fluorophenylamino)-2-methylpropanoate (2.5 g, 6.76 mmol, 1 eq) in xylene (7 mL) were successively added 4-isothiocyanato-2-(trifluoromethyl)benzonitrile (3.41 g, 14.9 mmol, 2.5 eq) and DMAP (0.826 g, 6.76 mmol, 1 eq) and the resulting mixture was heated to 120° C. via microwave irradiation. After 1 h, the reaction mixture was diluted with EtOAc (400 mL). The organic layer was washed with water (100 mL×3), brine (100 mL), dried over $Na_2SO_4$, filtered and concentrated under reduced pressure to obtain a crude product which was purified by CombiFlash chromatography to afford the title compound. Analytical data: LC-MS 567 [M+H]+; $^1$H NMR (400 MHz, methanol-$d_4$) δ 8.39 (d, J=8.33 Hz, 1H), 8.28 (s, 1H), 8.11-8.04 (m, 1H), 7.95-7.91 (m, 2H), 7.91-7.85 (m, 2H), 7.57-7.49 (m, 1H), 7.35 (dd, J=10.74, 1.53 Hz, 1H), 7.21 (d, J=7.89 Hz, 1H), 4.91-4.87 (m, 2H), 1.45-1.47 (m, 6H).

Step-2: Preparation of 4-(3-(4-(aminomethyl)-3-fluorophenyl)-4,4-dimethyl-5-oxo-2-thioxoimidazolidin-1-yl)-2-(trifluoromethyl)benzonitrile To a stirred solution of 4-(3-(4-((1,3-dioxoisoindolin-2-yl)methyl)-3-fluorophenyl)-4,4-dimethyl-5-oxo-2-thioxoimidazolidin-1-yl)-2-(trifluoromethyl)benzonitrile (6.3 g, 11.1 mmol, 1 eq) in ethanol (100 mL) was added hydrazine hydrate (6 mL) and the resulting mixture was heated at 100° C. for 2 h. The reaction was monitored by TLC. After completion, the reaction mixture was concentrated under reduced pressure. The crude residue was diluted with water (300 mL) and extracted with EtOAc (500 mL×3). The combined organic layers were washed with brine (200 mL), dried over $Na_2SO_4$, filtered and concentrated under reduced pressure to obtain a crude product which was purified by CombiFlash chromatography to afford the title compound. Analytical data: LC-MS 437 [M+H]+.

Example 21. Preparation of amine derivatives of 4-(3-(4-(aminomethyl)-3-fluorophenyl)-4,4-dimethyl-5-oxo-2-thioxoimidazolidin-1-yl)-2-(trifluoromethyl)benzonitrile

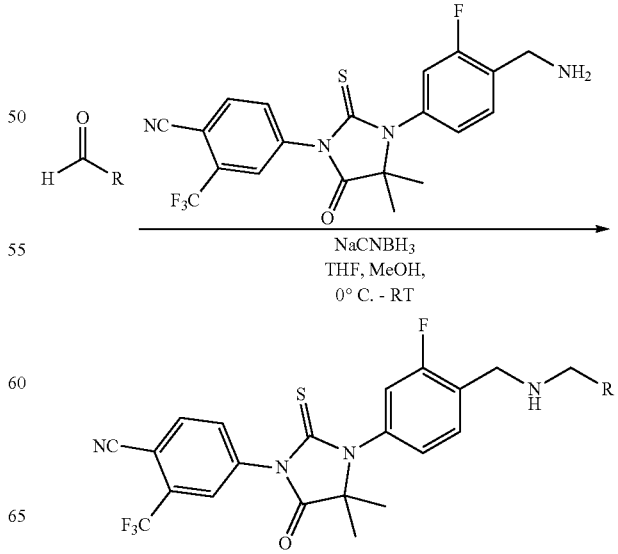

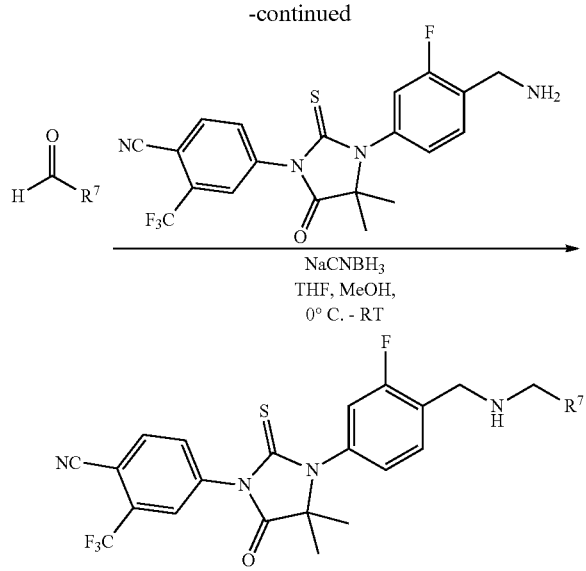

To a stirred solution of the appropriate aldehyde (1.2 eq) in MeOH (2 mL) and THF (1 mL) was added 4-(3-(4-(aminomethyl)-3-fluorophenyl)-4,4-dimethyl-5-oxo-2-thioxoimidazolidin-1-yl)-2-(trifluoromethyl)benzonitrile (1 eq) and the mixture was stirred at RT for 2 h. NaCNBH$_3$ (3.0 eq) was then added to the mixture at 0° C. slowly and the resultant mixture was stirred at RT for 4 h. The reaction was monitored by TLC. After completion, the reaction mixture was diluted with EtOAc (200 vol). The organic layer was water (80 vol), brine (50 vol), dried over Na$_2$SO$_4$, filtered and concentrated under reduced pressure to afford a crude product which was purified by SFC to afford the title compound. Compounds 57, 58, 59 were prepared following this procedure.

Analytical Data: Compound 57—LC-MS 528 [M+H]$^+$; $^1$H NMR (methanol-d$_4$) δ 8.48 (d, J=6.14 Hz, 2H), 8.11-8.20 (m, 2H), 7.95-8.02 (m, 1H), 7.63 (s, 1H), 7.47 (d, J=6.14 Hz, 2H), 7.16-7.26 (m, 2H), 3.84-3.95 (m, 4H), 1.57 (s, 6H). Compound 58—LC-MS 528 [M+H]$^+$; $^1$H NMR (methanol-d$_4$) δ 8.57 (br s, 1H), 8.16 (d, J=3.95 Hz, 2H), 7.99 (d, J=9.65 Hz, 1H), 7.85 (br s, 1H), 7.69 (br s, 1H), 7.50 (d, J=7.45 Hz, 1H), 7.36 (br s, 1H), 7.25-7.33 (m, 2H), 4.16 (d, J=7.89 Hz, 4H), 1.58 (s, 6H). Compound 59—LC-MS 528 [M+H]$^+$; $^1$H NMR (methanol-d$_4$) δ 8.65 (br s, 1H), 8.56 (br s, 1H), 8.11-8.21 (m, 2H), 7.93-8.03 (m, 2H), 7.70 (t, J=8.11 Hz, 1H), 7.51 (d, J=7.89 Hz, 1H), 7.28-7.40 (m, 2H), 4.20 (br s, 4H), 1.59 (s, 6H).

Example 22. Preparation of N-(4-(3-(4-cyano-3-(trifluoromethyl)phenyl)-5,5-dimethyl-2,4-dioxoimidazolidin-1-yl)-2-fluorobenzyl)pyrimidine-4-carboxamide, Compound 21

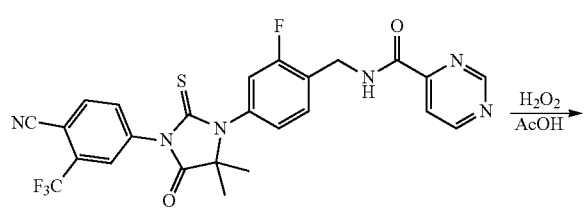

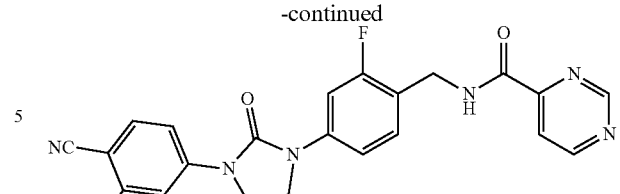

To a stirred solution of N-(4-(3-(4-cyano-3-(trifluoromethyl)phenyl)-5,5-dimethyl-4-oxo-2-thioxoimidazolidin-1-yl)-2-fluorobenzyl)pyrimidine-4-carboxamide (25 mg, 0.047 mmol) in AcOH (0.7 mL) was added H$_2$O$_2$ (30% in water, 0.7 mL) and the resulting mixture was stirred at RT for 16 h. The reaction was monitored by TLC. Upon completion, the reaction mixture was diluted in water (10 mL) and made alkaline with saturated aqueous NaHCO$_3$ solution (50 mL). The aqueous layer was then extracted with EtOAc (50 mL×2). The combined organic layers were washed with water (50 mL), brine (30 mL), dried over Na$_2$SO$_4$, filtered and concentrated under reduced pressure to afford a crude product which was purified by reversed-phase HPLC to afford the title compound. Analytical data: LC-MS 527 [M+H]$^+$; $^1$H NMR (400 MHz, methanol-d$_4$) δ 9.29 (s, 1H), 9.04 (d, J=5.1 Hz, 1H), 8.24 (s, 1H), 8.17-8.06 (m, 3H), 7.55 (t, J=8.2 Hz, 1H), 7.34-7.21 (m, 2H), 4.74 (s, 2H), 1.56 (s, 6H).

Example 23. Preparation of 4-(3-(3-fluoro-4-((2-oxopyrrolidin-1-yl)methyl)phenyl)-4,4-dimethyl-5-oxo-2-thioxoimidazolidin-1-yl)-2-(trifluoromethyl)benzonitrile, Compound 61

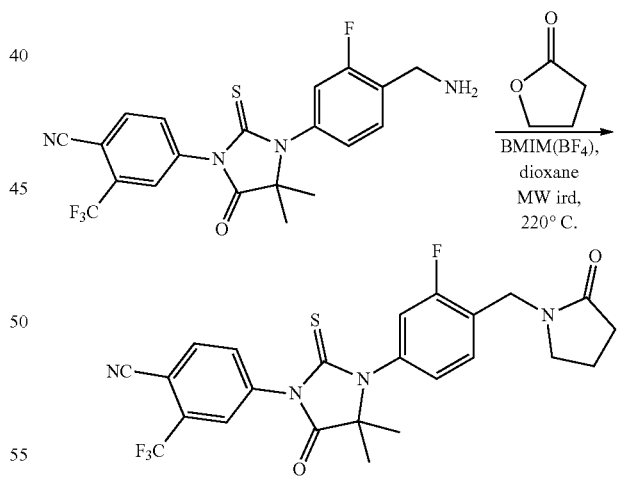

To a stirred solution of 4-(3-(4-(aminomethyl)-3-fluorophenyl)-4,4-dimethyl-5-oxo-2-thioxoimidazolidin-1-yl)-2-(trifluoromethyl)benzonitrile (0.200 g, 0.44 mmol, 1 eq) and dihydrofuran-2(3H)-one (0.04 g, 0.44 mmol, 1 eq) in 1,4-dioxane (3 mL) was added (BMIM)BF$_4$ (0.104 g, 0.44 mmol, 1 eq) and the mixture was heated to 220° C. via microwave irradiation. The reaction was monitored by TLC. After completion, the mixture was diluted with water (150 mL) and extracted with EtOAc (150 mL×3). The combined organic layers were washed with brine (100 mL), dried over Na$_2$SO$_4$, filtered and concentrated under reduced pressure to afford a crude residue which was purified by SFC to afford the title compound. Analytical data: LC-MS 505 [M+H]$^+$; $^1$H NMR (400 MHz, methanol-d$_4$) δ 8.16 (d, J=5.7 Hz, 2H), 8.00 (s, 1H), 7.49 (s, 1H), 7.20-7.31 (m, 2H), 4.60 (s, 2H), 3.46 (t, J=7.0 Hz, 2H), 2.46 (t, J=8.1 Hz, 2H), 2.01-2.12 (m, 2H), 1.58 (s, 6H).

Example 24. Preparation of 4-(3-(3-fluoro-4-((5-oxo-5H-pyrrolo[3,4-b]pyridin-6(7H)-yl)methyl)phenyl)-4,4-dimethyl-5-oxo-2-thioxoimidazolidin-1-yl)-2-(trifluoromethyl)benzonitrile, Compound 66

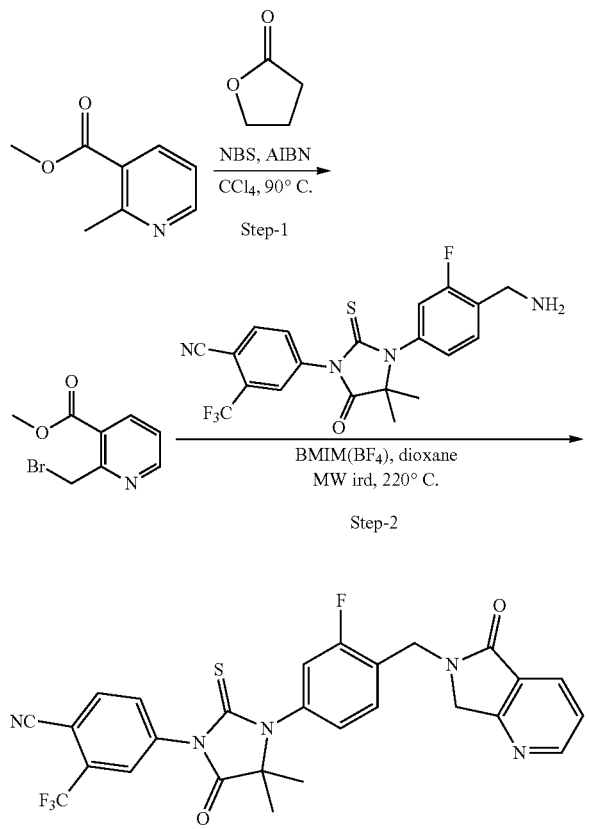

Step-1: Preparation of methyl 2-(bromomethyl)nicotinate

To a stirred solution of methyl 2-methylnicotinate (0.200 g, 0.44 mmol, 1 eq) and dihydrofuran-2(3H)-one (1.4 g, 9.26 mmol, 1 eq) in CCl$_4$ (10 mL) were added NBS (1.97 g, 11.1 mmol, 1.2 eq) and AIBN (0.45 g, 2.77 mmol, 1.1 eq) and the mixture was heated at 90° C. for 4 h. The reaction was monitored by TLC. After completion, the mixture was diluted with water (150 mL) and extracted with DCM (200 mL×2). The combined organic layers were washed with water (100 mL), brine (100 mL), dried over Na$_2$SO$_4$, filtered and concentrated under reduced pressure to afford a crude residue which was purified by CombiFlash chromatography to afford the title compound. Analytical data: LC-MS 231 [M+H]$^+$.

Step-2: Preparation of 4-(3-(3-fluoro-4-((5-oxo-5H-pyrrolo[3,4-b]pyridin-6(7H)-yl)methyl)phenyl)-4,4-dimethyl-5-oxo-2-thioxoimidazolidin-1-yl)-2-(trifluoromethyl)benzonitrile, Compound 66

To a stirred solution of 4-(3-(4-(aminomethyl)-3-fluorophenyl)-4,4-dimethyl-5-oxo-2-thioxoimidazolidin-1-yl)-2-(trifluoromethyl)benzonitrile (0.200 g, 0.46 mmol, 1 eq) in DMF (5 mL) were successively added K$_2$CO$_3$ (0.158 g, 1.14 mmol, 2.5 eq) and methyl 2-(bromomethyl)nicotinate (0.158 g, 0.69 mmol, 1.5 eq) at RT and the mixture was heated at 50° C. for 2 h. The reaction was monitored by TLC. After completion, the mixture was diluted with water (100 mL) and extracted with EtOAc (100 mL×3). The combined organic layers were washed with water (100 mL), brine (100 mL), dried over Na$_2$SO$_4$, filtered and concentrated under reduced pressure to afford a crude residue which was purified by SFC to afford the title compound. Analytical data: LC-MS 554 [M+H]$^+$; $^1$H NMR (400 MHz, methanol-d$_4$) δ 8.75 (d, J=4.8 Hz, 1H), 8.21 (d, J=7.9 Hz, 1H), 8.15 (d, J=6.6 Hz, 2H), 7.98 (d, J=8.3 Hz, 1H), 7.57 (t, J=6.8 Hz, 2H), 7.22-7.36 (m, 2H), 5.00 (s, 2H), 4.58 (s, 2H), 1.58 (s, 6H).

Example 25. Preparation of 4-(5-(3-fluoro-4-((5-oxo-5,7-dihydro-6H-pyrrolo[3,4-b]pyridin-6-yl)methyl)phenyl)-8-oxo-6-thioxo-5,7-diazaspiro[3.4]octan-7-yl)-2-(trifluoromethyl)benzonitrile, Compound 72

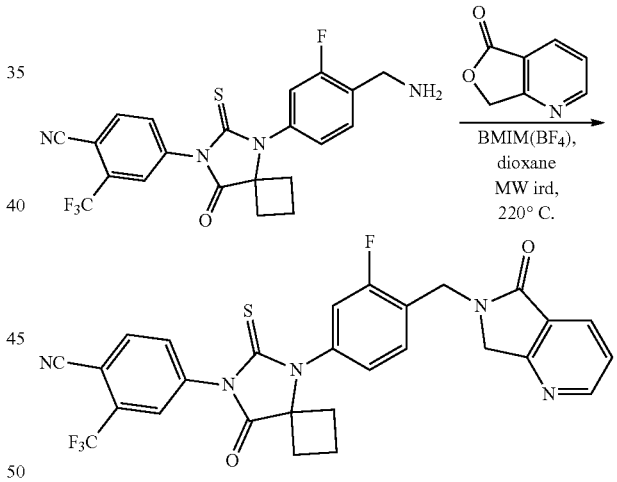

To a stirred solution of 4-(5-(4-(aminomethyl)-3-fluorophenyl)-8-oxo-6-thioxo-5,7-diazaspiro[3.4]octan-7-yl)-2-(trifluoromethyl)benzonitrile (0.300 g, 0.67 mmol, 1 eq) and furo[3,4-b]pyridin-5(7H)-one (0.136 g, 1.00 mmol, 1.5 eq) in 1,4-dioxane (3 mL) was added (BMIM)BF$_4$ (0.151 g, 0.67 mmol, 1 eq) and the mixture was heated to 220° C. via microwave irradiation. The reaction was monitored by TLC. After completion, the mixture was diluted with water (150 mL) and extracted with EtOAc (150 mL×3). The combined organic layers were washed with brine (100 mL), dried over Na$_2$SO$_4$, filtered and concentrated under reduced pressure to afford a crude residue which was purified by SFC to afford the title compound. Analytical data: LC-MS 566 [M+H]$^+$; $^1$H NMR (400 MHz, methanol-d$_4$) δ 8.75 (dd, J=5.0, 1.5 Hz, 1H), 8.22 (dd, J=7.9, 1.3 Hz, 1H), 8.10-8.18 (m, 2H), 7.98 (dd, J=7.9, 1.8 Hz, 1H), 7.55-7.65 (m, 2H), 7.26-7.37 (m, 2H), 5.03 (s, 2H), 2.64 (dd, J=8.8, 3.9 Hz, 2H), 2.49-2.61 (m, 2H), 2.16 (br s, 2H), 2.10 (br s, 2H).

Example 26. Preparation of N-(4-(5,5-dimethyl-4-oxo-2-thioxo-3-(3-(trifluoromethyl)phenyl)-imidazolidin-1-yl)-2-fluorobenzyl)-4-methylthiazole-5-carboxamide, Compound 76

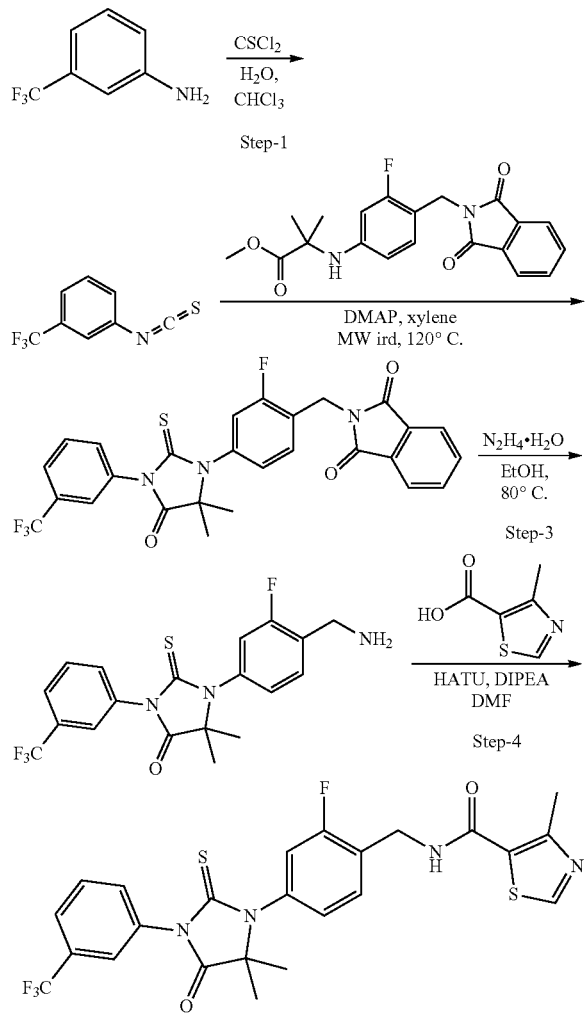

Step-1: Preparation of 1-isothiocyanato-3-(trifluoromethyl)benzene

To a reaction vessel with DCM (25 mL) was added a solution of bicarbonate (7.8 g, 93.0 mmol, 3 eq) in H₂O (25 mL) and the mixture was stirred at RT for 10 min. 3-(Trifluoromethyl) aniline (5 g, 31.0 mmol, 1 eq) was then added to the mixture at 0° C. followed by slow addition of thiophosgene (5.35 g, 46 mmol, 1.5 eq) and the mixture was stirred at RT for 16 h. The reaction was monitored by TLC. After completion, the reaction mixture was diluted with water (300 mL) and extracted with DCM (200 mL×3). The combined organic layers were washed with water (200 mL), brine (200 mL), dried over Na₂SO₄, filtered and concentrated under reduced pressure to afford the title compound.

Analytical data: $^1$H NMR (400 MHz, (CDCl$_3$) δ 7.52 (d, J=3.9 Hz, 1H), 7.49 (s, 1H), 7.47 (s, 1H), 7.40 (d, J=7.5 Hz, 1H).

Step-2: Preparation of 2-(4-(5,5-dimethyl-4-oxo-2-thioxo-3-(3-(trifluoromethyl)phenyl)imidazolidin-1-yl)-2-fluorobenzyl)isoindoline-1,3-dione To a stirred solution of methyl 2-(4-((1,3-dioxoisoindolin-2-yl)methyl)-3-fluorophenylamino)-2-methylpropanoate (0.50 g, 1.34 mmol, 1 eq) in xylene (37 mL) were successively added 1-isothiocyanato-3-(trifluoromethyl)benzene (0.68 g, 3.37 mmol, 2.5 eq) and DMAP (0.167 g, 1.34 mmol, 1 eq). The resulting mixture was heated to 120° C. via microwave irradiation. After 1 h, the reaction mixture was diluted with EtOAc (200 mL). The organic layer was washed with water (50 mL×2), brine (50 mL), dried over Na₂SO₄, filtered and concentrated under reduced pressure to obtain a crude product which was purified by CombiFlash chromatography to afford the title compound. Analytical data: LC-MS 542 [M+H]+.

Step-3: Preparation of 1-(4-(aminomethyl)-3-fluorophenyl)-5,5-dimethyl-2-thioxo-3-(3-(trifluoromethyl)phenyl)imidazolidin-4-one To a stirred solution of 2-(4-(5,5-dimethyl-4-oxo-2-thioxo-3-(3-(trifluoromethyl)phenyl) imidazolidin-1-yl)-2-fluorobenzyl)isoindoline-1,3-dione (0.75 g, 1.50 mmol, 1 eq) in ethanol (20 mL) was added hydrazine hydrate (0.75 mL) and the resulting mixture was heated at 100° C. for 1 h. The reaction was monitored by TLC. After completion, the reaction mixture was concentrated under reduced pressure. The crude residue was diluted with water (300 mL) and extracted with EtOAc (500 mL×3). The combined organic layers were washed with brine (200 mL), dried over Na₂SO₄, filtered and concentrated under reduced pressure to obtain a crude product which was purified by CombiFlash chromatography to afford the title compound. Analytical data: LC-MS 412 [M+H]+.

Step-4: Preparation of N-(4-(5,5-dimethyl-4-oxo-2-thioxo-3-(3-(trifluoromethyl) phenyl)-imidazolidin-1-yl)-2-fluorobenzyl)-4-methylthiazole-5-carboxamide, Compound 76

To a stirred solution of 4-methylthiazole-5-carboxylic acid (0.042 g, 0.291 mmol, 2 eq) in DMF (2 mL) was added HATU (0.066 g, 0.174 mmol, 1.2 eq) at 0° C. and the resulting mixture was stirred at same temperature for 30 min. DIPEA (0.047 g, 0.362 mmol, 2.5 eq) and 1-(4-(aminomethyl)-3-fluorophenyl)-5,5-dimethyl-2-thioxo-3-(3-(trifluoromethyl)phenyl)imidazolidin-4-one (0.060 g, 0.145 mmol, 1 eq) were then successively added and the resulting mixture was stirred at RT for 1 h. The reaction was monitored by TLC. After completion, H₂O (30 mL) was added and the resulting precipitate was filtered through a Buchner funnel. The crude material was purified by SFC to afford the title compound as a TFA salt. Analytical data: LC-MS 537 [M+H]$^+$; $^1$H NMR (methanol-d$_4$) δ 8.97 (s, 1H), 7.75-7.82 (m, 2H), 7.68-7.74 (m, 2H), 7.58 (s, 1H), 7.21-7.30 (m, 2H), 4.66 (s, 2H), 2.67 (s, 3H), 1.57 (s, 6H).

Example 27. Preparation of 2-fluoro-4-(3-(3-fluoro-4-((5-oxo-5,7-dihydro-6H-pyrrolo[3,4-b]pyridin-6-yl)methyl)phenyl)-4,4-dimethyl-5-oxo-2-thioxoimidazolidin-1-yl)benzonitrile, Compound 78

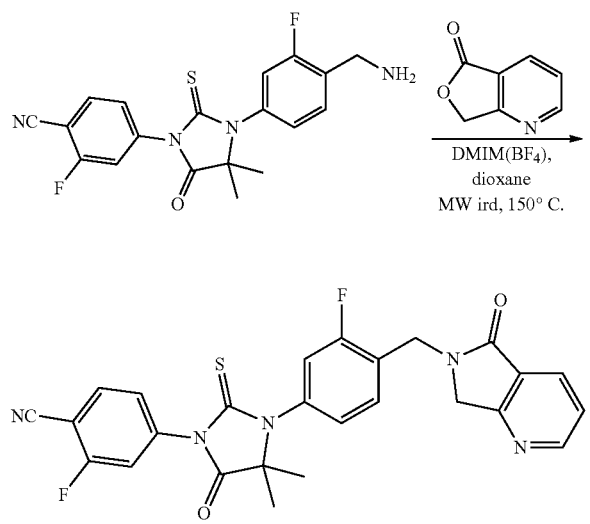

To a stirred solution of 4-(3-(4-(aminomethyl)-3-fluorophenyl)-4,4-dimethyl-5-oxo-2-thioxoimidazolidin-1-yl)-2-fluorobenzonitrile (0.300 g, 0.77 mmol, 1 eq) and furo[3,4-b]pyridin-5(7H)-one (0.157 g, 1.16 mmol, 1.5 eq) in 1,4-dioxane (3 mL) was added (BMIM)BF$_4$ (0.174 g, 0.77 mmol, 1 eq) and the mixture was heated to 150° C. via microwave irradiation for 1 h. The reaction was monitored by TLC. After completion, the mixture was diluted with water (150 mL) and extracted with EtOAc (150 mL×3). The combined organic layers were washed with brine (100 mL), dried over Na$_2$SO$_4$, filtered and concentrated under reduced pressure to afford a crude residue which was purified by SFC to afford the title compound. Analytical data: LC-MS 504 [M+H]$^+$; $^1$H NMR (400 MHz, methanol-d$_4$) δ 8.78-8.72 (m, 1H), 8.25-8.18 (m, 1H), 7.91 (t, J=7.7 Hz, 1H), 7.67-7.60 (m, 1H), 7.60-7.44 (m, 3H), 7.30 (d, J=10.4 Hz, 1H), 7.27-7.21 (m, 1H), 5.00 (s, 2H), 4.58 (s, 2H), 1.56 (s, 6H).

Example 28. Preparation of sulfonamide derivatives of 4-(3-(4-(aminomethyl)-3-fluorophenyl)-4,4-dimethyl-5-oxo-2-thioxoimidazolidin-1-yl)-2-(trifluoromethyl)benzonitrile

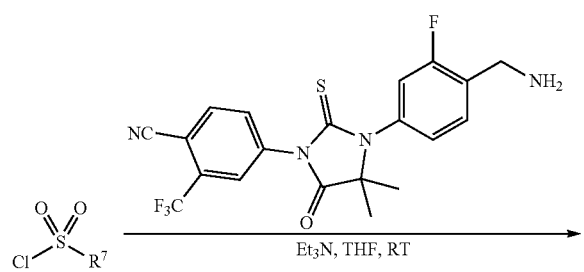

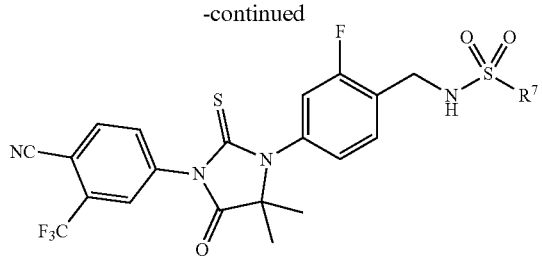

To a stirred solution of 4-(3-(4-(aminomethyl)-3-fluorophenyl)-4,4-dimethyl-5-oxo-2-thioxo imidazolidin-1-yl)-2-(trifluoromethyl)benzonitrile (1 eq) in THF (50 vol) was added triethylamine (2 eq) at 0° C. followed by addition of the appropriate sulphonyl chloride (1.25 eq). The resulting mixture was stirred at RT. The reaction was monitored by TLC. After completion, the reaction mixture was diluted with DCM (200 vol). The organic layer was washed with saturated aqueous NaHCO$_3$ solution (80 vol), water (80 vol), brine (50 vol), dried over Na$_2$SO$_4$, filtered and concentrated under reduced pressure to afford a crude product which was purified by SFC to afford the sulfonamide Compounds 67 and 75 were prepared following this procedure.

Analytical Data: Compound 67—LC-MS 598 [M+H]$^+$; $^1$H NMR (methanol-d$_4$) δ 8.95 (s, 1H), 8.12-8.19 (m, 2H), 7.94-8.02 (m, 1H), 7.46 (s, 1H), 7.10-7.19 (m, 2H), 4.36 (s, 2H), 2.57 (s, 3H), 1.55 (s, 6H). Compound 75—LC-MS 578 [M+H]$^+$; $^1$H NMR (methanol-d$_4$) δ 8.65 (d, J=4.8 Hz, 1H), 8.12-8.18 (m, 2H), 7.92-8.04 (m, 3H), 7.53 (s, 2H), 7.09-7.18 (m, 2H), 4.41 (s, 2H), 1.54 (s, 6H).

Example 29. Preparation of N-(4-(3-(4-cyano-3-(trifluoromethyl)phenyl)-5,5-dimethyl-4-oxo-2-thioxoimidazolidin-1-yl)-2-fluorobenzyl)-1-methyl-3-(trifluoromethyl)-1H-pyrazole-4-carboxamide, Compound 95

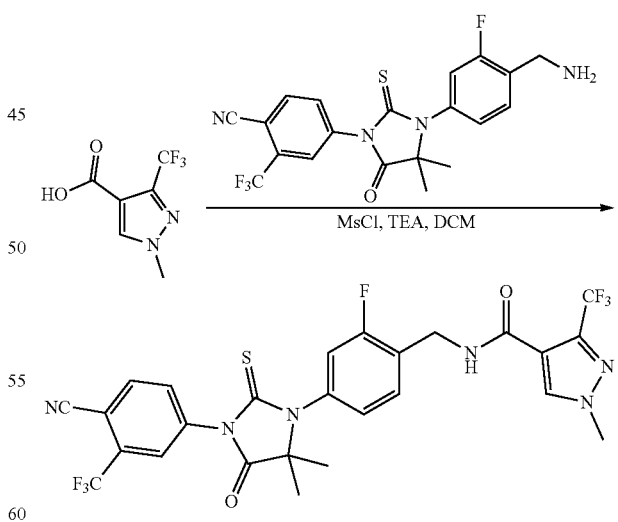

To a stirred solution of 1-methyl-3-(trifluoromethyl)-1H-pyrazole-4-carboxylic acid (200 mg, 1.03 mmol, 1 eq) in dichloromethane (20 mL) were added mesyl chloride (0.09 mL, 1.13 mmol, 1.1 eq) and triethylamine (0.31 mL, 2.26 mmol, 2.2 eq) at 0° C. and the mixture was stirred at same temperature for 30 min. 4-(3-(4-(aminomethyl)-3-fluorophenyl)-4,4-dimethyl-5-oxo-2-thioxoimidazolidin-1-yl)-2-(trifluoromethyl)benzonitrile (539 mg, 1.23 mmol, 1.2 eq) was then added to the mixture and the mixture was stirred at RT for 3 h. Upon completion, the reaction mixture was quenched with saturated solution of $NaHCO_3$ (30 mL) and extracted with DCM (30 mL×3) and water (50 mL). The combined organic layers were washed with brine (50 mL), dried over $Na_2SO_4$, filtered and concentrated under reduced pressure to obtain a crude product which was purified by reversed phase HPLC to afford the title compound.

Analytical Data: LC-MS 613 [M+H]$^+$; $^1$H NMR (400 MHz, DMSO-d$_6$) δ 8.84 (t, J=5.8 Hz, 1H), 8.40 (d, J=8.1 Hz, 1H), 8.29 (d, J=2.1 Hz, 1H), 8.07 (dd, J=8.3, 1.9 Hz, 1H), 7.53 (t, J=8.3 Hz, 1H), 7.32 (dd, J=10.5, 2.0 Hz, 1H), 7.24 (dd, J=8.2, 2.0 Hz, 1H), 4.51 (d, J=5.7 Hz, 2H), 3.95 (s, 3H), 1.52 (s, 6H).

It is understood that compounds from the Table 1 (e.g., 77, 81-94, 96-142) are synthesized using the General Synthetic Schemes 1 to 3 or using the experimental procedures as described above and the steps involved in the synthetic routes are clearly familiar to those skilled in the art, wherein the substituents described in compounds of Formula (I), (II), (III), (IV), (V), (VI), (VII), (VIII), (IX), (X), (XI), (XII), (XIII), (XIV), (XV), (XVI), (XVII), and (XVIII) herein can be varied with a choice of appropriate starting materials and reagents utilized in the steps presented.

Biological Example 1: AR Agonist and Antagonist Assay Methods

Human AR cDNA cloned into pCMV vector, GRE-LUC, and CMV-renilla-LUC were used to transfect cells. HEK-293 cells (ATCC) were plated at 120,000 cells per well of a 24 well plate in DME+5% csFBS (Fisher Scientific, Waltham, Mass.). The cells were transfected using Lipofectamine (Life Technologies, Carlsbad, Calif.) with 0.25 μg GRE-LUC, 0.010 μg CMV-LUC (renilla luciferase) and 25 ng of the AR. The cells were treated 24 hrs after transfection with test articles (9-concentration for $IC_{50}/EC_{50}$ calculations or 1 single concentration at 1 μM) in combination with 0.1 nM R1881 (antagonist assays) or alone (agonist assays). Luciferase assay was performed 48 hrs after transfection. Firefly luciferase assay values were normalized to renilla luciferase values and were graphed using graphpad prism software (La Jolla, Calif.). R1881 and enzalutamide were used as the positive control for agonist and antagonist assays, respectively. The $EC_{50}$ of R1881 in the AR agonist assay was 0.028 nM. The mean $IC_{50}$ of enzalutamide in the AR antagonist assays was 358 nM (n=4). The $IC_{50}$ or $EC_{50}$ values were determined using non-linear regression and three point logistics fitting. Results are presented in Table 2.

TABLE 2

Test compound activities in AR agonist and antagonist assays

| Compound No. | AR Agonist $IC_{50}$ (μM) | AR Antagonist % Inhibition (1 μM) | AR Antagonist $IC_{50}$ (μM) |
|---|---|---|---|
| 1 | >10.0 | ND | 0.968 |
| 2 | ND | ND | 0.031 |
| 3 | ND | ND | 0.180 |
| 4 | >10.0 | ND | 0.386 |
| 5 | ND | ND | 0.093 |
| 6 | >10.0 | ND | 0.778 |
| 7 | ND | ND | 0.180 |
| 8 | >10.0 | ND | 0.0472 |
| 9 | >10.0 | ND | 0.0491 |
| 11 | ND | ND | 0.120 |
| 12 | >10.0 | ND | 0.108 |
| 15 | ND | ND | 0.320 |
| 18 | >10.0 | ND | 0.358 |
| 19 | >10.0 | ND | 0.453 |
| 20 | ND | ND | 1.870 |
| 23 | ND | ND | 0.180 |
| 24 | ND | ND | 1.090 |
| 25 | ND | ND | 0.099 |
| 27 | ND | ND | 0.496 |
| 29 | ND | ND | 0.910 |
| 30 | ND | ND | 0.073 |
| 31 | ND | ND | 0.062 |
| 32 | ND | ND | 0.120 |
| 33 | ND | ND | 0.304 |
| 36 | ND | ND | 0.580 |
| 38 | ND | ND | 0.240 |
| 39 | ND | ND | 0.200 |
| 41 | ND | 88 | ND |
| 42 | ND | 95 | 0.077 |
| 43 | ND | 94 | ND |
| 44 | ND | ND | 0.120 |
| 45 | ND | 95 | 0.099 |
| 51 | ND | 93 | ND |
| 60 | ND | ND | 0.115 |
| 65 | ND | ND | 0.064 |
| 66 | ND | 90 | ND |
| 68 | ND | ND | 0.120 |
| 69 | ND | ND | 0.380 |
| 71 | ND | ND | 0.589 |
| 73 | ND | ND | 0.092 |
| 76 | ND | ND | >10.0 |

ND: not determined

Biological Example 2: AR Activity Assay Method (Gene Expression of TMPRSS2, PSA and FKBP5)

LNCaP (ATCC) or LNCaP-EnzR (MR49F was received from Dr. Martin Gleave, University of British Columbia) cells were plated in 96 well plates at 15,000-20,000 cells/well in RPMI+1% csFBS without phenol red. Cells were treated 2 days after plating and harvested 18 hours after treatment (for TMPRSS2) or 24 hours after treatment (for PSA and FKBP5). RNA was isolated (cells to ct kit, Life Technologies), cDNA synthesized (cells to ct kit), and expression of TMPRSS2, PSA or FKBP5 and expression of GAPDH were measured using realtime PCR primers and probes (TaqMan probes, Life Technologies) by realtime PCR (ABI 7900, Life Technologies). Relative expression was calculated using ddct method.

Figure 1B:
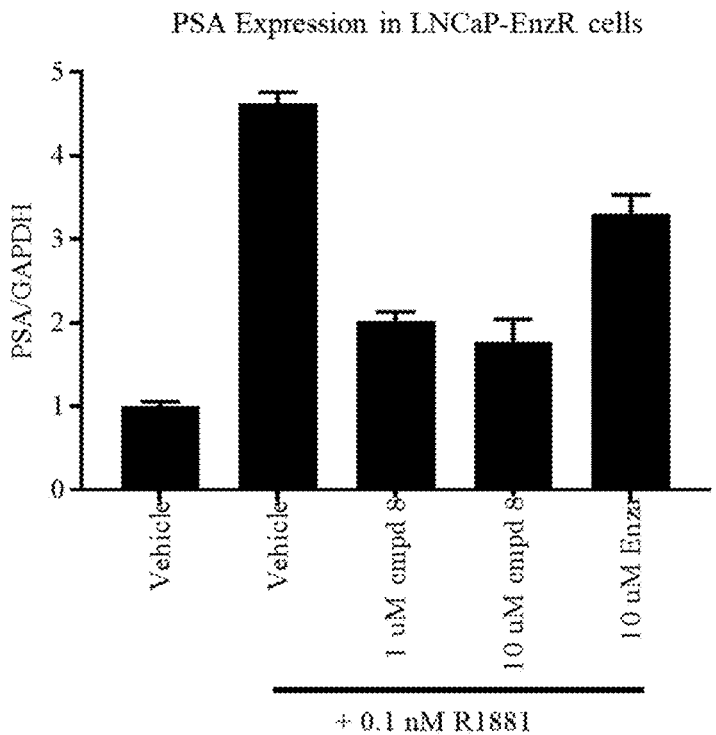
Figure 1C:
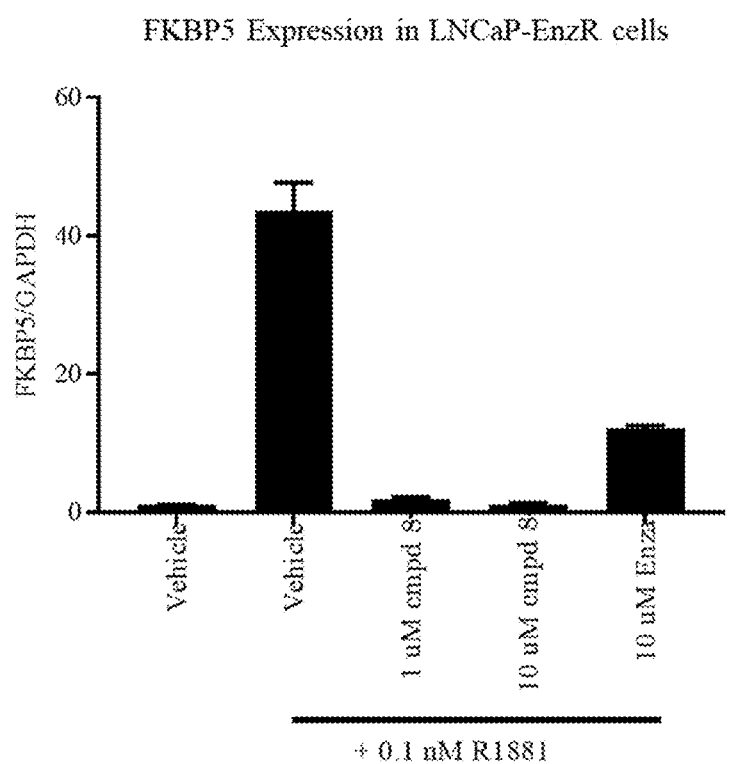

As shown in FIG. 1A, in the presence of 0.1 nM of R1881, two test compounds significantly inhibited TMPRSS2 expression at both 1 and 10 μM, similar to the inhibitory effects caused by enzalutamide treatment in LNCaP cells. In the enzalutamide resistant LNCaP cell line (LNCaP-EnzR), enzalutamide failed to reduce TMPRSS2 expression. Both test articles showed significant inhibitions at two concentrations tested (1 and 10 μM), suggesting these compounds have anti-AR effects in this enzalutamide-induced resistant cell line. As shown in FIGS. 1B and 1C, compound 8 similarly showed significant inhibition of PSA and FKBP5 gene expression, respectively, at the two concentrations tested (1 and 10 μM).

Biological Example 3: AR Nuclear Translocation Assay Method

COS cells plated in chamber slides in DME+5% csFBS without phenol red were transfected with 1 μM GFP-AR using lipofectamine reagent. Cells were treated with R1881 48 hours after transfection (after pre-treatment with compounds for 30 min). Four hours after treatment with R1881, cells were fixed, stained with DAPI (Fisher Scientific, Waltham, Mass.), and imaged using a confocal microscope (Zeiss microscope).

As shown in FIG. 2, AR is cytoplasmic in vehicle-treated cells and is nuclear in R1881-treated cells. One of the mechanisms of action of enzalutamide is preventing the translocation of the AR from the cytoplasm to the nucleus. As expected, AR is cytoplasmic in enzalutamide-treated samples. AR is nuclear in cells treated with Compounds 8 and 9.

Biological Example 4: GR Antagonist Assay Method

COS-7 cells (ATCC, Manassas, Va.) were plated in 24 well plates in DME+5% csFBS without phenol red at 70,000 cells/well. Once the cells attached to the plates (typically after overnight incubation after plating), they were transfected in OPTIMEM medium (Life Technologies) using lipofectamine reagent (Life Technologies) with 0.25 µg GRE-LUC, 25 ng pCR3.1 GR, and 10 ng CMV-renilla LUC per well. Twenty-four hours after transfection, the cells were fed with DME+5% csFBS without phenol red (Fisher Scientific, Waltham, Mass.) and treated with the test compounds (1 pM to 10 µM dose range) in the presence of 0.1 nM dexamethasone (Sigma, St. Louis, Mo.). Sixteen to twenty-four hours after treatment, a luciferase assay was performed using the Dual Luciferase assay kit (Promega, Madison, Wis.). Firefly luciferase values were normalized to Renilla luciferase numbers.

The $EC_{50}$ value of dexamethasone in the GR agonist assay was 0.26 nM. RU486 (Sigma, St. Louis, Mo.) was used as a positive control in the antagonist assay with an $IC_{50}$ value at 0.31 nM. Moderate inhibition by test articles was observed at 10 µM (Table 3).

TABLE 3

Inhibition by test compounds in GR antagonist assay

| Cmpd No. | 8 | 9 | 66 | 68 | RU486 |
|---|---|---|---|---|---|
| % of vehicle | 52% | 41% | 31% | 84% | 13% |

Additional compounds were tested in the GR antagonist assay. The $IC_{50}$ values were determined using non-linear regression and three point logistics fitting. Results are presented in Table 4.

TABLE 4

Additional compounds tested in GR antagonist assay

| Compound No. | GR Antagonist $IC_{50}$ (µM) |
|---|---|
| 2 | >10.0 |
| 3 | >10.0 |
| 5 | >10.0 |
| 6 | >10.0 |
| 7 | >10.0 |
| 11 | >10.0 |
| 12 | >10.0 |
| 15 | >10.0 |
| 18 | >10.0 |
| 19 | >10.0 |
| 20 | >10.0 |

TABLE 4-continued

Additional compounds tested in GR antagonist assay

| Compound No. | GR Antagonist $IC_{50}$ (µM) |
|---|---|
| 23 | >10.0 |
| 24 | >10.0 |
| 25 | >10.0 |
| 27 | >10.0 |
| 29 | >10.0 |
| 30 | >10.0 |
| 31 | >10.0 |
| 32 | >10.0 |
| 36 | >10.0 |
| 38 | >10.0 |
| 39 | >10.0 |
| 42 | >10.0 |
| 44 | >10.0 |
| 45 | >10.0 |
| 60 | >10.0 |
| 65 | >10.0 |
| 69 | >10.0 |
| 71 | >10.0 |
| 73 | 2.96 |
| 76 | 3.31 |

Certain compounds were screened in the GR antagonist assay at a single concentration. For these compounds, % inhibition at 10 µM was determined. Results are presented in Table 5. RU486 caused inhibition of 72.8% at 1 µM.

TABLE 5

Additional compounds tested in GR antagonist assay at single concentration

| Compound No. | GR Antagonism % inhibition at 10 µM |
|---|---|
| 14 | 22 |
| 33 | 3 |
| 40 | 48 |
| 43 | 0 |
| 47 | 46 |
| 50 | 69 |
| 51 | 35 |
| 52 | 56 |
| 53 | 66 |
| 54 | 56 |
| 55 | 58 |
| 62 | 0 |
| 63 | 0 |
| 74 | 17 |
| 75 | 40 |
| 78 | 0 |
| 79 | 75 |
| 80 | 38 |

Biological Example 5: GR Binding Assay Method

COS cells (ATCC) plated in 24 well plates at 70,000 cells/well in DME+5% csFBS without phenol red were transfected with 50 ng pCR3.1 GR using lipofectamine reagent. Cells were treated 48 hours after transfection with the compounds in combination with 0.1 nM $^3H$ dexamethasone (Perkin Elmer, Waltham, Mass.). Cells were pre-treated with test articles for 30 min before addition of dexamethasone. Four hours after treatment, cells were washed four times with ice cold PBS and the radioactivity was extracted with ice cold ethanol. Radioactivity extracted from the cells was counted using a scintillation counter. Compound 8 was tested in this assay.

Biological Example 6: Cell Proliferation Assays

LNCaP-abl (3,000 cells/well, received from Dr. Myles Brown, Dana Farber Cancer Institute), 22RV1 (1,000 cells/well), LNCaP (5,000 cells/well), or COS (3,000 cells/well) cells were plated in 96 well plates in 50 μl RPMI+10% FBS (Fisher Scientific, Waltham, Mass.). LNCaP, COS, and 22RV1 cells were obtained from ATCC. Cells were treated in RPMI+10% FBS with test articles, ranging from 1 nM to 10 μM. Three days later, viable cells (LNCaP-abl, 22RV1, and COS) were measured by CellTiter-Glo assay (Promega, Madison, Wis.). For LNCaP cells, medium containing test article was changed after 3 days of treatment, and after an additional 3 days of culture, viable cells were measured by CellTiter-Glo assay.

MR49F cells (Enzalutamide-resistant LNCaP cells) licensed from the University of Washington were cultured in RPMI+10% Fetal Bovine Serum (American Type Culture Collection, Manassas, Va.)+1% pencilling streptomycin+1 μM enzalutamide (MedKoo, N.C.). Cells were trypsinized, counted, and plated at 5,000 cells/well in 96 well plate in the growth medium (but lack enzalutamide). The outer wells of the 96 well plates were not used for treatment due to potential evaporation. Cells were treated with selected doses of the compounds with the final concentration of DMSO kept at 0.1%. The cells were re-treated three days later. At the end of six days of treatment, the cells were fixed using 40% w/v trichloroacetic acid and a sulforhodamine blue (SRB) assay was performed to determine the cell viability.

The LNCaP cell line is androgen responsive with AR and PSA expression. It contains a T877A mutation in the AR. The 22RV1 cell line is positive for AR and PSA with additional AR splice variants and is insensitive to androgen for cell proliferation. The LNCaP-abl cell line expresses both AR and GR but is insensitive to androgen for cell proliferation. COS-7 is used as an AR negative cell line in this experiment. Consistent with literature reports, enzalutamide has no inhibitory effects on cell proliferation in 22RV1, LNCaP-abl, or COS-7 cells up to 10 μM. Two test compounds showed various degree of inhibition in cell growth at high concentrations as listed in Table 6.

TABLE 6

Inhibition of cell proliferation by test compounds

| Cell Line | Compound 8 (% of vehicle at) | | Compound 9 (% of vehicle at) | | Enzalutamide (% of vehicle at) | |
| --- | --- | --- | --- | --- | --- | --- |
| | 3 μM | 10 μM | 3 μM | 10 μM | 3 μM | 10 μM |
| LNCaP | 63% | 19% | 55% | 21% | 89% | 54% |
| LNCaP-abl | 83% | 62% | 89% | 27% | 115% | 121% |
| 22RV1 | 87% | 90% | 77% | 41% | 90% | 94% |
| COS-7 | 99% | 91% | 92% | 99% | 92% | 95% |
| MR49F | ND | ND | 53% | 29% | 122% | 130% |

ND: not determined

Additional compounds were screened in LNCaP-abl cells. Results are presented in Table 7, with cell proliferation values given as percentage of vehicle control.

TABLE 7

Inhibition of LNCaP-abl cell proliferation by test compounds

| Compound No. | % of vehicle at 3 μM | % of vehicle at 10 μM |
| --- | --- | --- |
| 2 | 78 | 71 |
| 5 | 99 | 96 |
| 6 | 79 | 101 |
| 7 | 67 | 73 |
| 11 | 103 | 79 |
| 12 | 95 | 61 |
| 15 | 81 | 70 |
| 23 | 84 | 43 |
| 25 | 96 | 64 |
| 29 | 90 | 92 |
| 32 | 93 | 62 |
| 36 | 82 | 59 |
| 38 | 59 | 56 |
| 39 | 90 | 87 |
| 42 | 98 | 60 |
| 44 | 87 | 71 |
| 45 | 100 | 66 |
| 60 | 75 | 96 |
| 65 | 94 | 83 |
| 68 | 89 | 85 |
| 69 | 77 | 81 |
| 71 | 86 | 81 |
| 73 | 79 | 66 |
| 76 | 72 | 88 |

The invention claimed is:

1. A compound of Formula I:

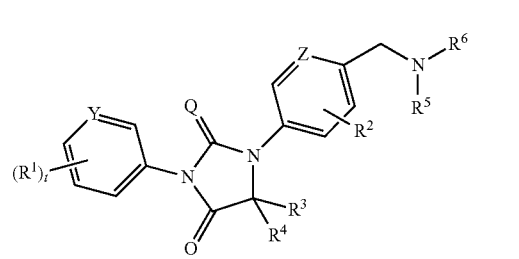

or a pharmaceutically acceptable salt, stereoisomer, mixture of stereoisomers, solvate, or tautomer thereof, wherein:

Y is N, CH, or $CR^1$;
Z is N or CH;
Q is O or S;
t is 0, 1 or 2;
each occurrence of $R^1$ is independently cyano, halo, $C_{1-6}$ alkyl, or $C_{1-6}$ haloalkyl; or two $R^1$ join to form an unsubstituted or substituted heteroaryl or unsubstituted or substituted aryl;
$R^2$ is hydrogen or halo;
$R^3$ and $R^4$ are each independently hydrogen, cyano, halo, or $C_{1-6}$ alkyl which may be further substituted with —OH, —$NH_2$, halo, or —$OCH_3$; or $R^3$ and $R^4$ join to form a $C_{3-10}$ cycloalkyl or 4-6-membered heterocyclyl;
$R^5$ is hydrogen or $C_{1-4}$ alkyl;
$R^6$ is —C(O)$R^7$, —S(O)$_2R^7$, —C(CH$_2$)$R^7$, —CH$_2R^7$, unsubstituted or substituted heteroaryl; or
$R^5$ and $R^6$ join together to form an unsubstituted or substituted bicyclic heterocyclyl or unsubstituted or substituted heteroaryl; and
$R^7$ is unsubstituted or substituted $C_{1-6}$ alkyl, unsubstituted or substituted $C_{3-10}$ cycloalkyl, unsubstituted or substituted heterocyclyl, unsubstituted or substituted aryl, unsubstituted or substituted heteroaryl, provided that the compound is not 5-(5-(4-((methyl(pyridin-4-ylmethyl)amino)methyl)phenyl)-8-oxo-6-thioxo-5,7-diazaspiro[3,4]octan-7-yl)-3-(trifluoromethyl)picolinonitrile, (2E)-3-[1-[[4-[3-[4-cyano-3-(trifluoromethyl)phenyl]-5,5-dimethyl-4-oxo-2-thioxo-1-imidazolidinyl]methyl]-1H-indol-5-yl]-N-hydroxy-2-propenamide, (2E)-3-[1-[[4-[3-[4-cyano-3-(trifluoromethyl)phenyl]-5,5-dimethyl-4-oxo-2-thioxo-1-imidazolidinyl]-2-fluorophenyl]methyl]-1H-indol-5-yl]-2-propenoic acid methyl ester, or (2E)-3-[1-[[4-[3-[4-cyano-3-(trifluoromethyl)phenyl]-5,5-dimethyl-4-oxo-2-thioxo-1-imidazolidinyl]-2-fluorophenyl]methyl]-1H-indol-5-yl]-2-propenoic acid.

2. The compound of claim 1, represented by Formula II:

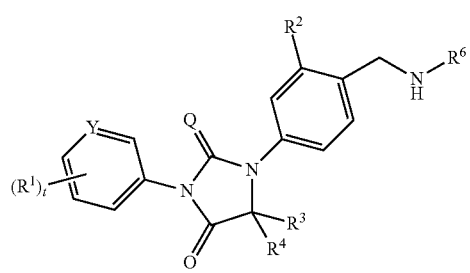

or a pharmaceutically acceptable salt, stereoisomer, mixture of stereoisomers, solvate, or tautomer thereof.

3. The compound of claim 1 or a pharmaceutically acceptable salt, stereoisomer, mixture of stereoisomers, solvate, or tautomer thereof, wherein Q is S.

4. The compound of claim 1 or a pharmaceutically acceptable salt, stereoisomer, mixture of stereoisomers, solvate, or tautomer thereof, wherein Q is O.

5. The compound of claim 1 or a pharmaceutically acceptable salt, stereoisomer, mixture of stereoisomers, solvate, or tautomer thereof, wherein $R^3$ and $R^4$ are each independently hydrogen, cyano, halo, or $C_{1-6}$ alkyl which may be further substituted with —OH, —NH$_2$, halo, or —OCH$_3$.

6. The compound of claim 1 or a pharmaceutically acceptable salt, stereoisomer, mixture of stereoisomers, solvate, or tautomer thereof, wherein $R^3$ and $R^4$ join to form a $C_{3-10}$ cycloalkyl or 4-6-membered heterocyclyl.

7. The compound of claim 1 or a pharmaceutically acceptable salt, stereoisomer, mixture of stereoisomers, solvate, or tautomer thereof, wherein $R^3$ and $R^4$ join to form a cyclopropyl, cyclobutyl, cyclopentyl, or cyclohexyl.

8. The compound of claim 1 or a pharmaceutically acceptable salt, stereoisomer, mixture of stereoisomers, solvate, or tautomer thereof, wherein $R^3$ and $R^4$ join to form a tetrahydrofuranyl or oxetanyl.

9. The compound of claim 1, represented by Formula III:

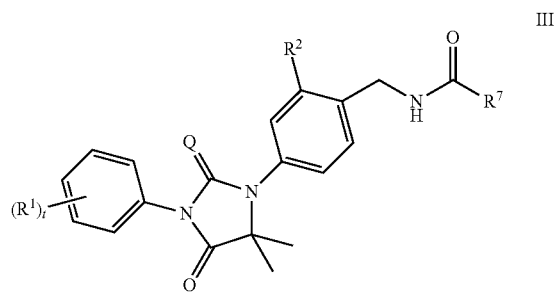

or a pharmaceutically acceptable salt, stereoisomer, mixture of stereoisomers, solvate, or tautomer thereof.

10. The compound of claim 1, represented by Formula IV:

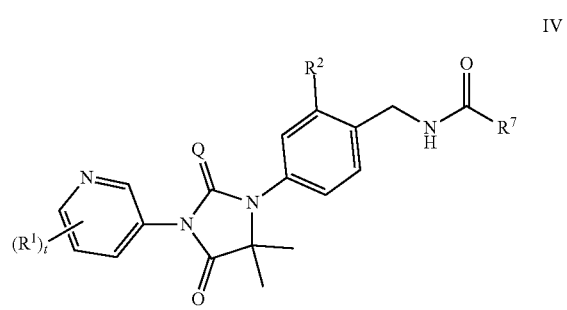

or a pharmaceutically acceptable salt, stereoisomer, mixture of stereoisomers, solvate, or tautomer thereof.

11. The compound of claim 1, represented by Formula V:

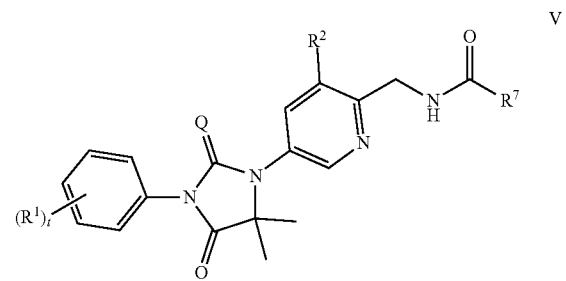

or a pharmaceutically acceptable salt, stereoisomer, mixture of stereoisomers, solvate, or tautomer thereof.

12. The compound of claim 1, represented by Formula VI:

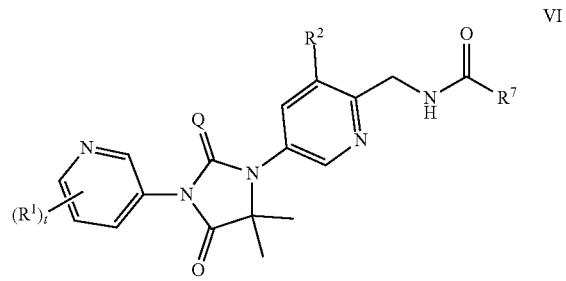

or a pharmaceutically acceptable salt, stereoisomer, mixture of stereoisomers, solvate, or tautomer thereof.

13. The compound of claim 1 or a pharmaceutically acceptable salt, stereoisomer, mixture of stereoisomers, solvate, or tautomer thereof, wherein t is 1 or 2.

14. The compound of claim 1, represented by Formula VII:

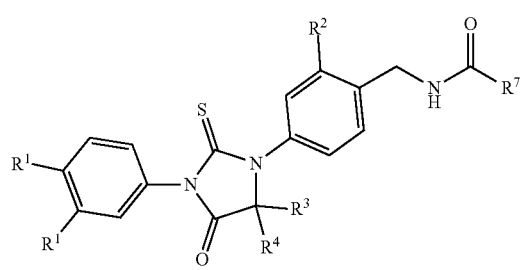

VII or a pharmaceutically acceptable salt, stereoisomer, mixture of stereoisomers, solvate, or tautomer thereof.

15. The compound of claim 1, represented by Formula VIII:

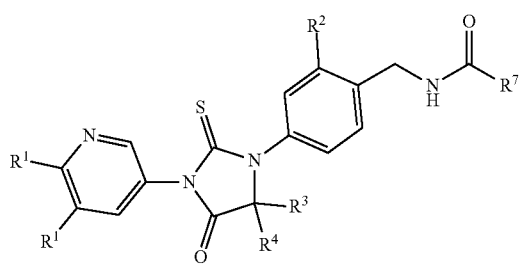

VIII or a pharmaceutically acceptable salt, stereoisomer, mixture of stereoisomers, solvate, or tautomer thereof.

16. The compound of claim 1, represented by Formula IX:

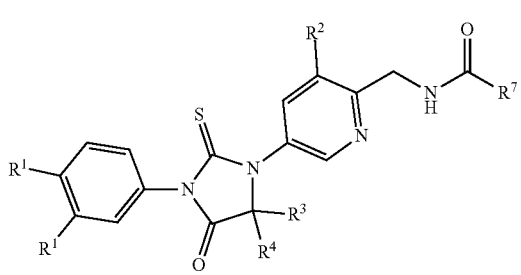

IX or a pharmaceutically acceptable salt, stereoisomer, mixture of stereoisomers, solvate, or tautomer thereof.

17. The compound of claim 1, represented by Formula X:

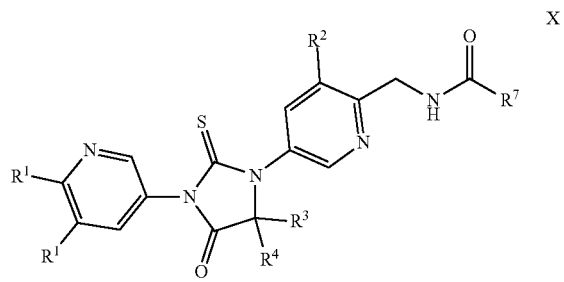

X or a pharmaceutically acceptable salt, stereoisomer, mixture of stereoisomers, solvate, or tautomer thereof.

18. The compound of claim 1, represented by Formula XI:

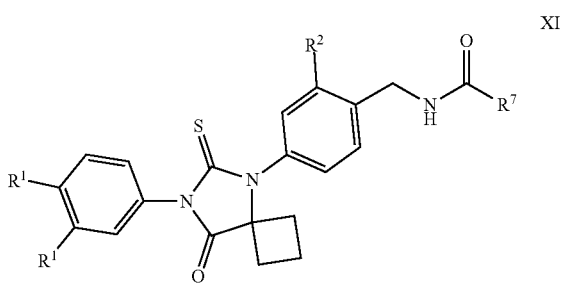

XI or a pharmaceutically acceptable salt, stereoisomer, mixture of stereoisomers, solvate, or tautomer thereof.

19. The compound of claim 1, represented by Formula XII:

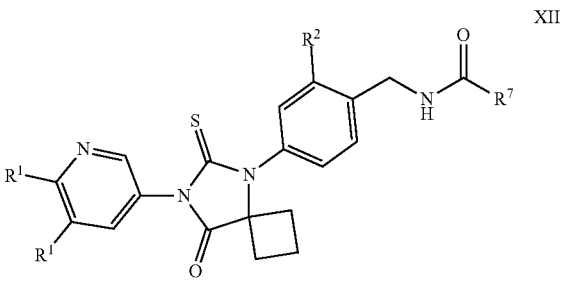

XII or a pharmaceutically acceptable salt, stereoisomer, mixture of stereoisomers, solvate, or tautomer thereof.

20. The compound of claim 1, represented by Formula XIII:

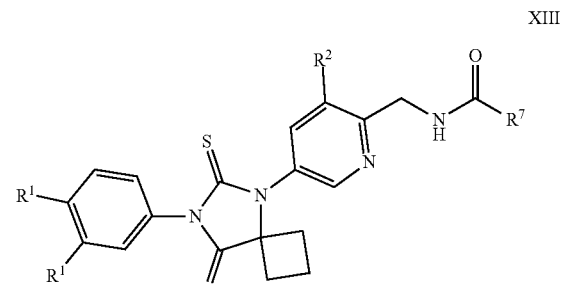

XIII or a pharmaceutically acceptable salt, stereoisomer, mixture of stereoisomers, solvate, or tautomer thereof.

21. The compound of claim 1, represented by Formula XIV:

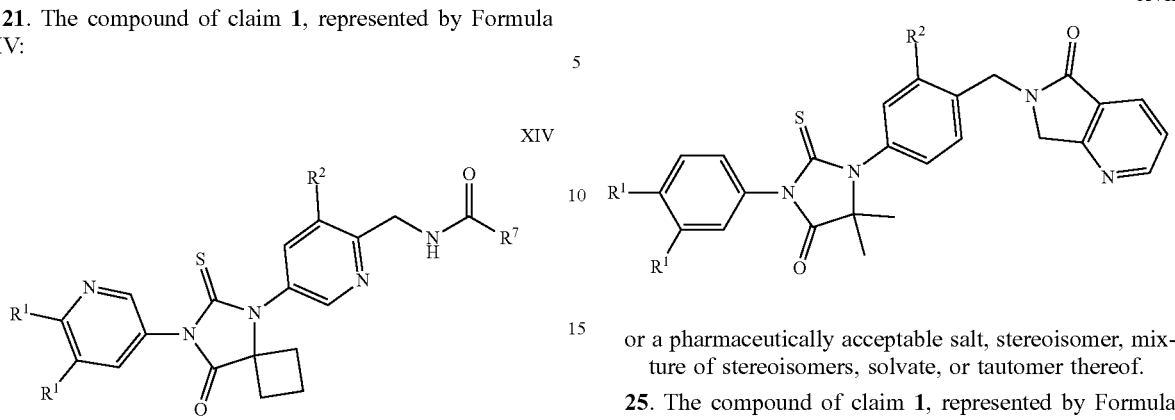

or a pharmaceutically acceptable salt, stereoisomer, mixture of stereoisomers, solvate, or tautomer thereof.

22. The compound of claim 1, represented by Formula XV:

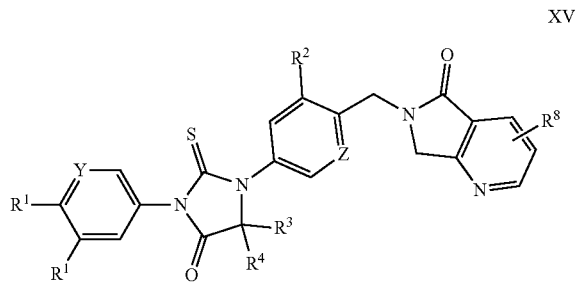

or a pharmaceutically acceptable salt, stereoisomer, mixture of stereoisomers, solvate, or tautomer thereof, wherein;

$R^8$ is hydrogen, $C_{1-4}$ alkyl or halogen.

23. The compound of claim 1, represented by Formula XVI:

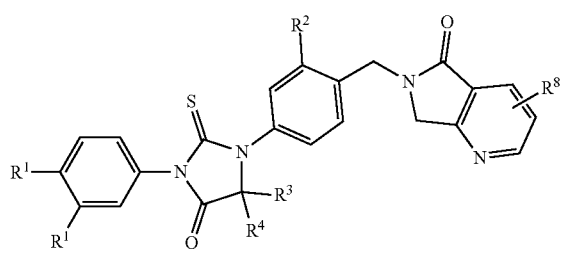

or a pharmaceutically acceptable salt, stereoisomer, mixture of stereoisomers, solvate, or tautomer thereof, wherein;

$R^8$ is hydrogen, $C_{1-4}$ alkyl or halogen.

24. The compound of claim 1, represented by Formula XVII:

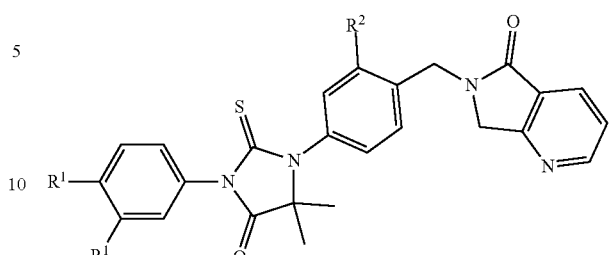

or a pharmaceutically acceptable salt, stereoisomer, mixture of stereoisomers, solvate, or tautomer thereof.

25. The compound of claim 1, represented by Formula XVIII:

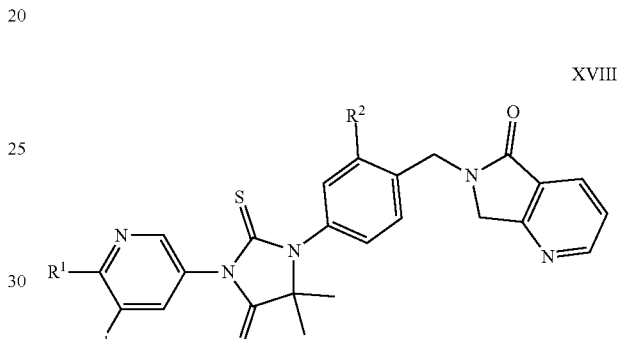

or a pharmaceutically acceptable salt, stereoisomer, mixture of stereoisomers, solvate, or tautomer thereof.

26. The compound of claim 1 or a pharmaceutically acceptable salt, stereoisomer, mixture of stereoisomers, solvate, or tautomer thereof, wherein, each $R^1$ is independently cyano, halo, $C_{1-6}$ alkyl, or $CF_3$.

27. A compound selected from:

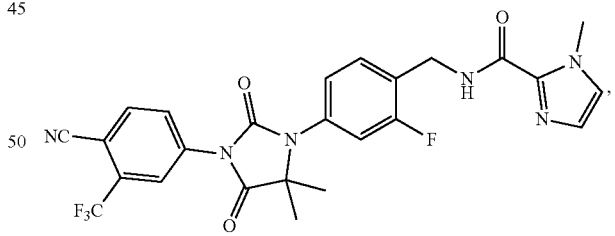

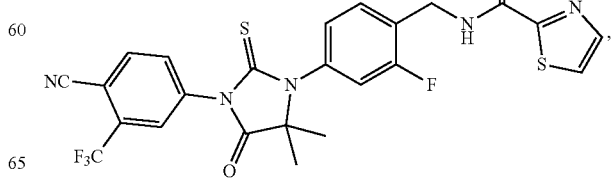

131
-continued
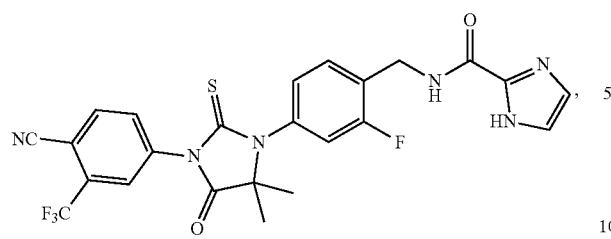
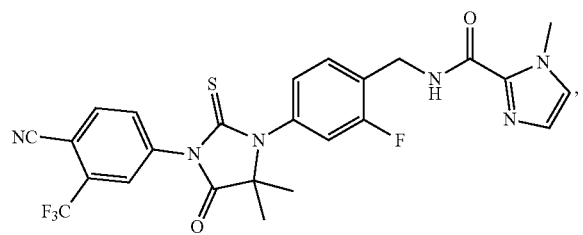
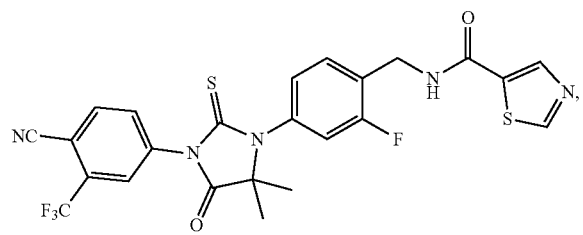
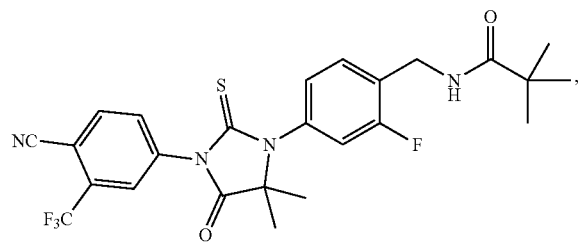
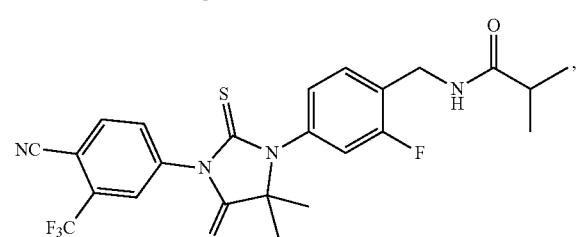
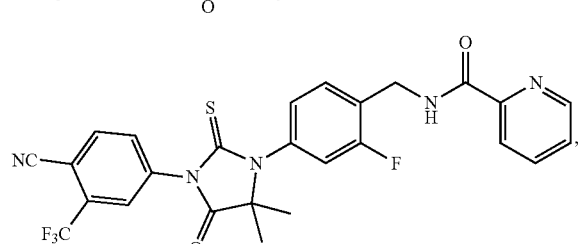
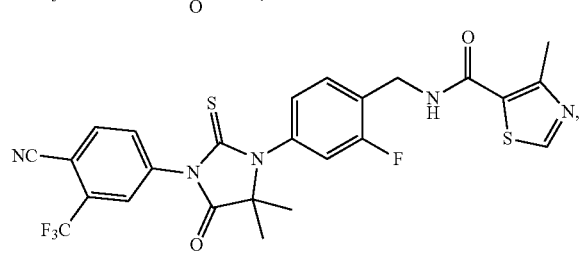
132
-continued
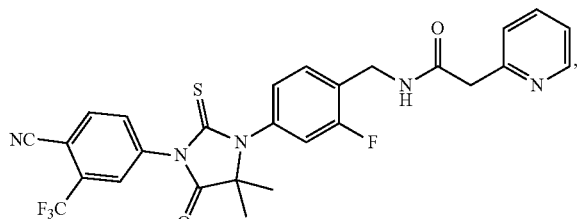
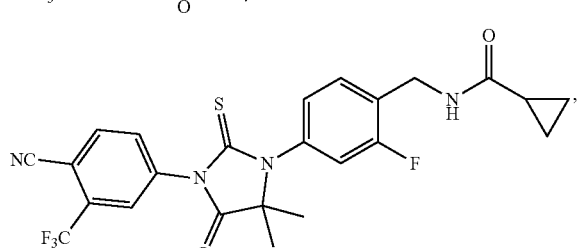
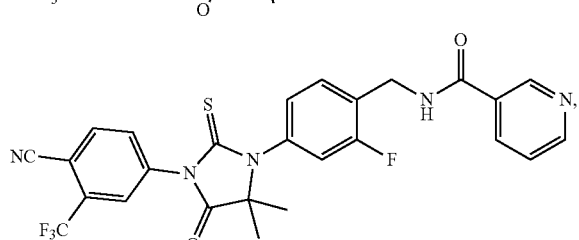
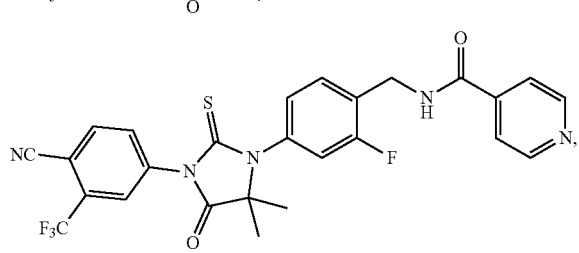
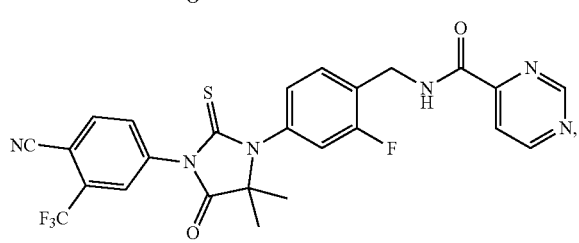
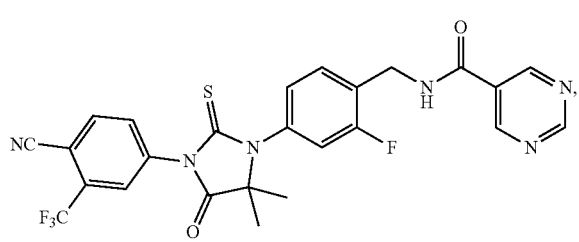
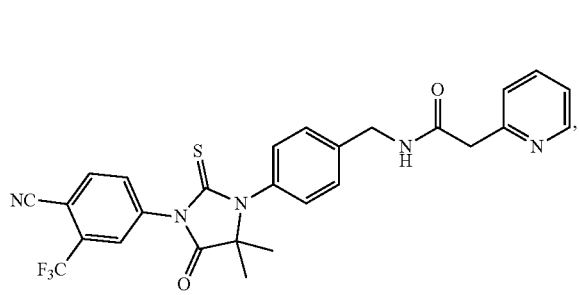

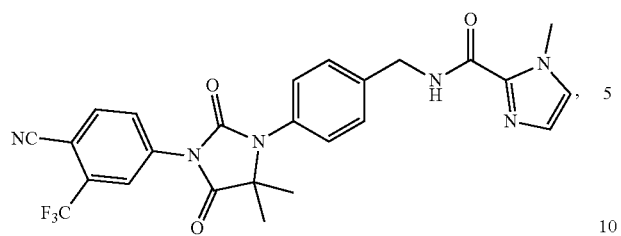
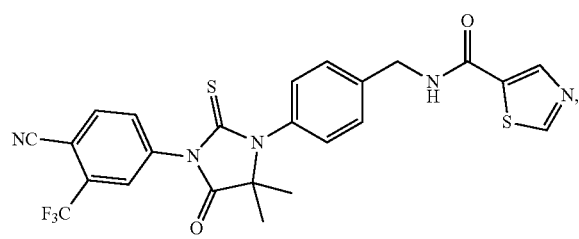
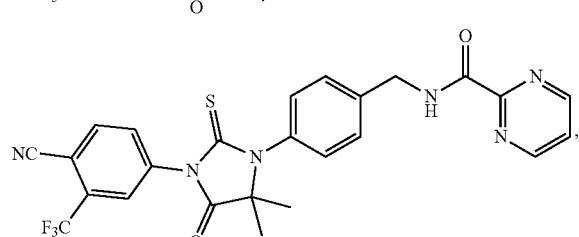
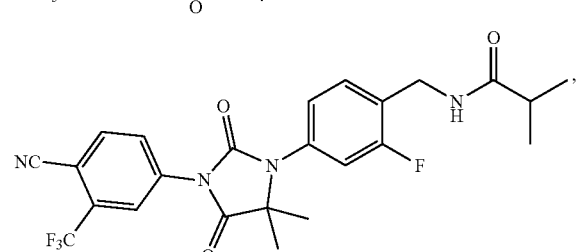
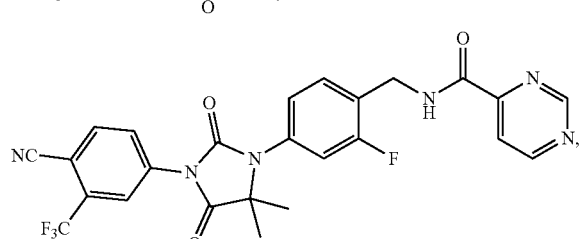
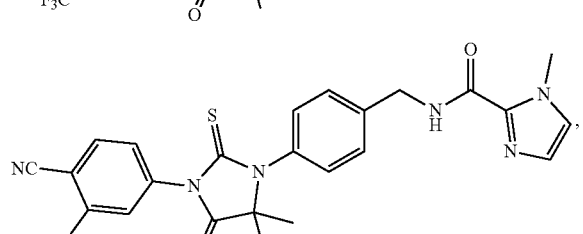
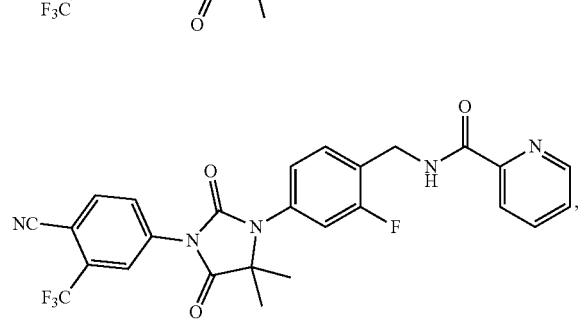
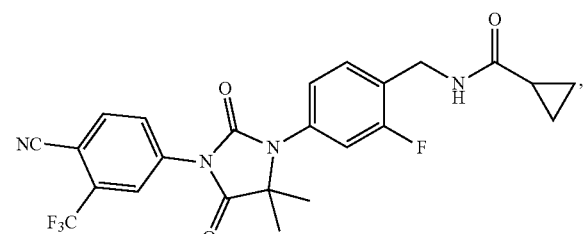
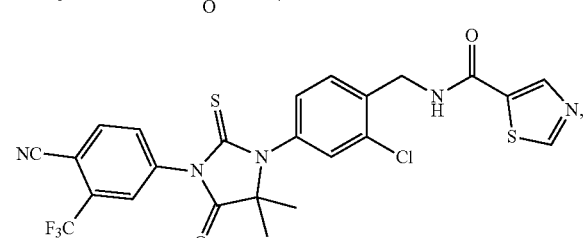
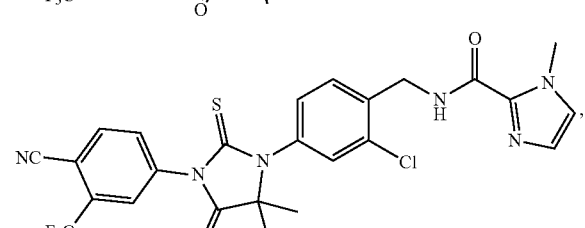
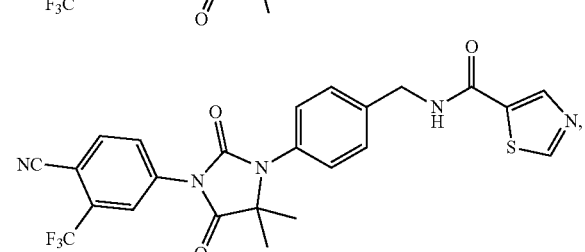
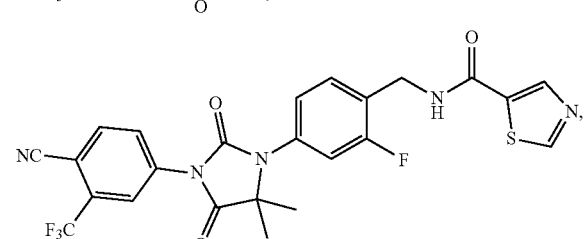
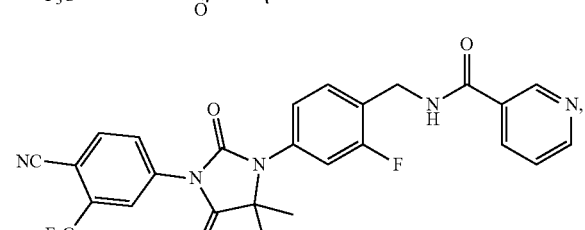
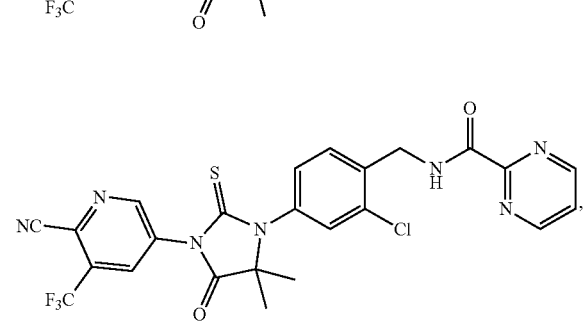

135
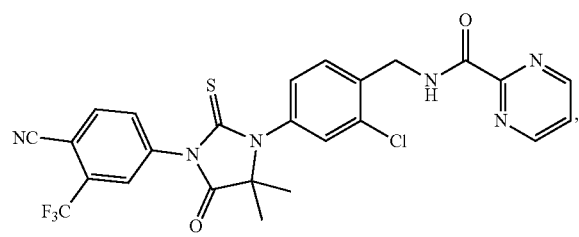
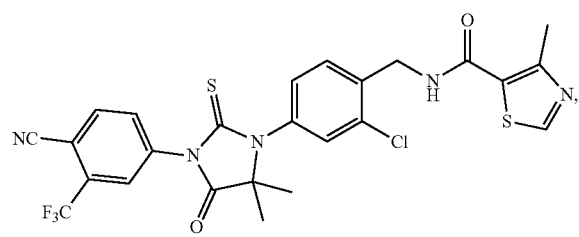
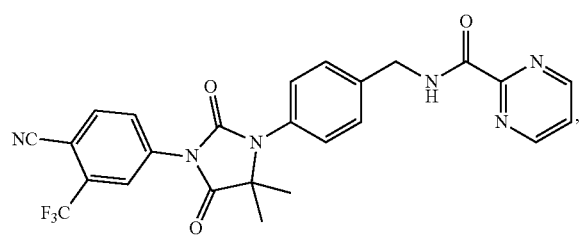
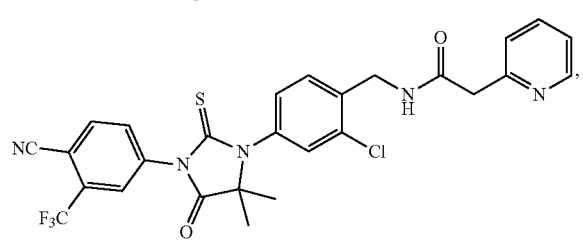
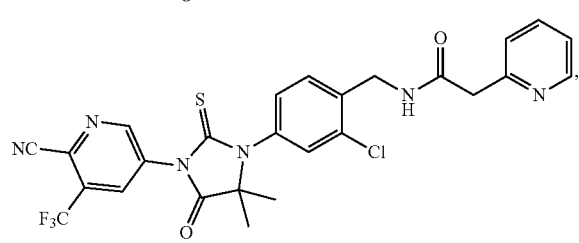
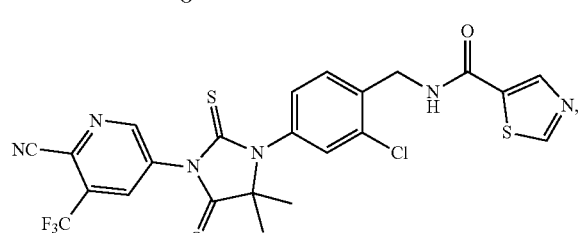
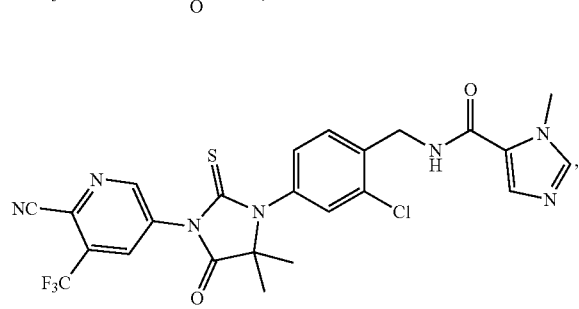
136
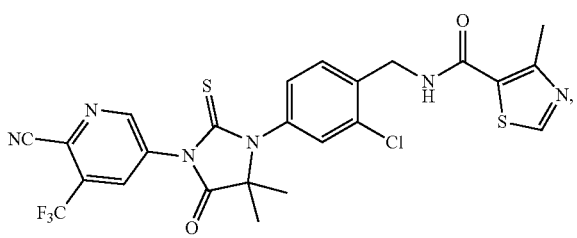
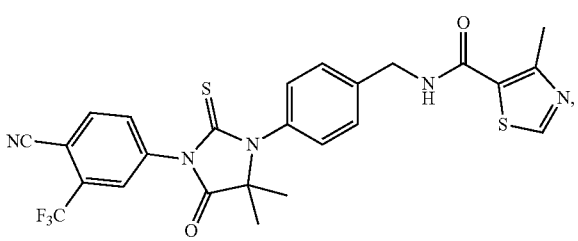
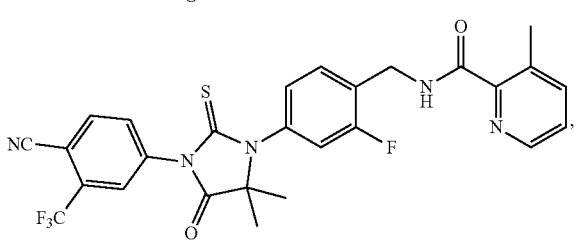
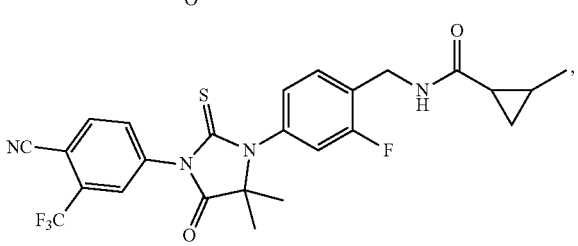
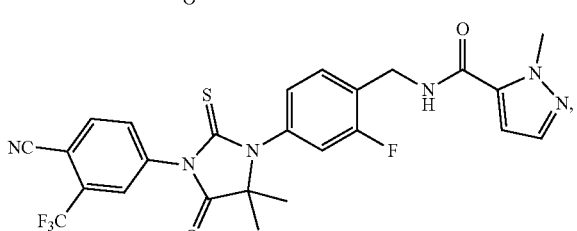
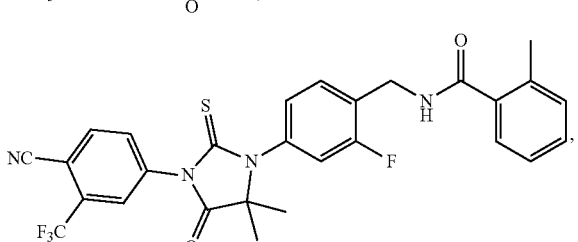
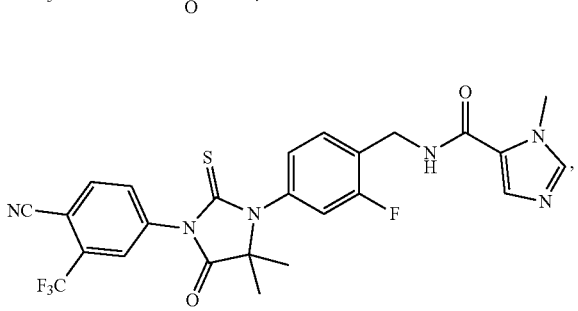

137
-continued
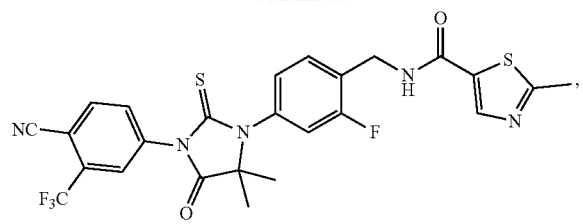
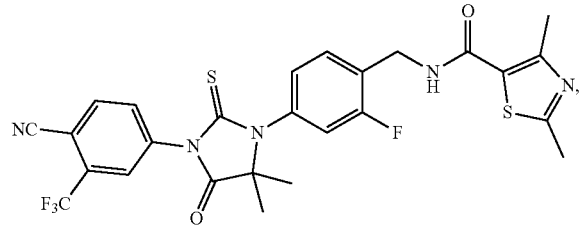
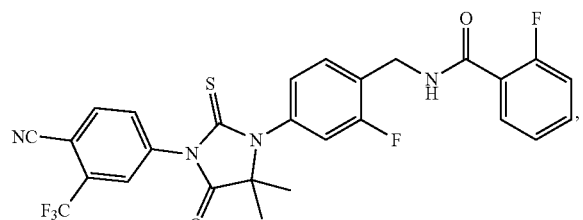
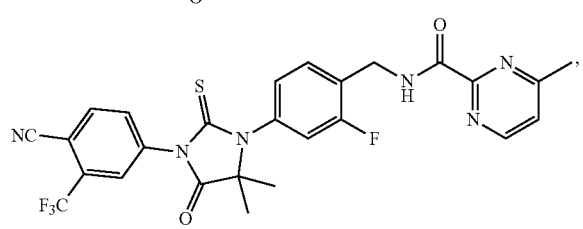
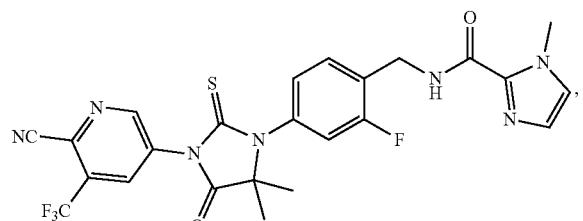
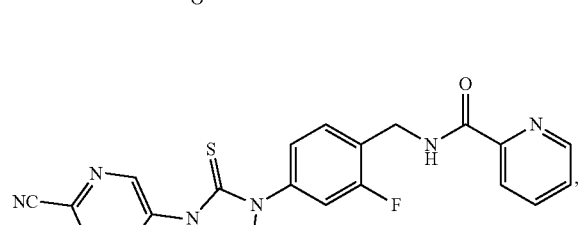
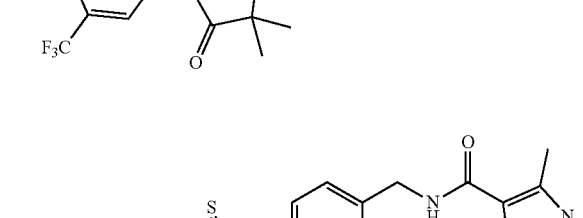
138
-continued
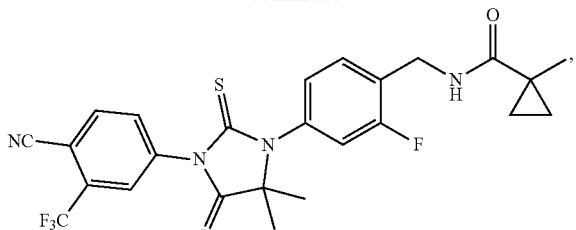
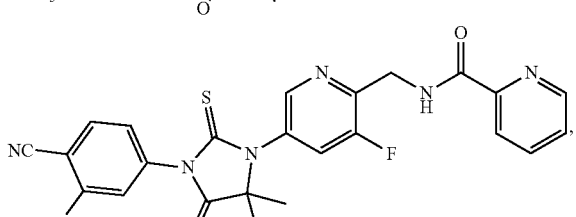
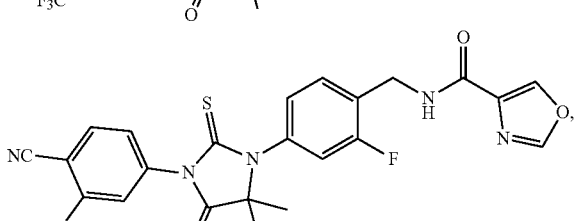
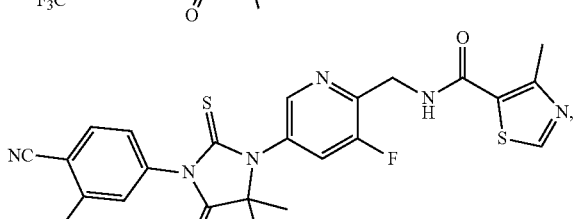
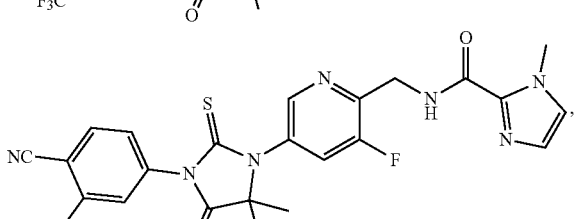
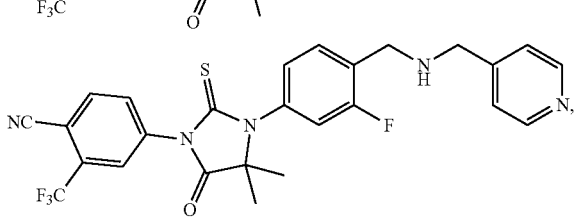
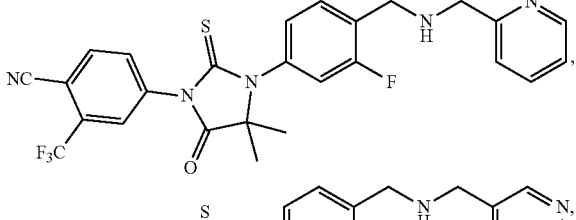
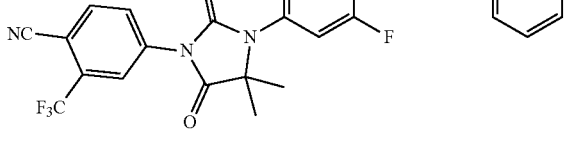

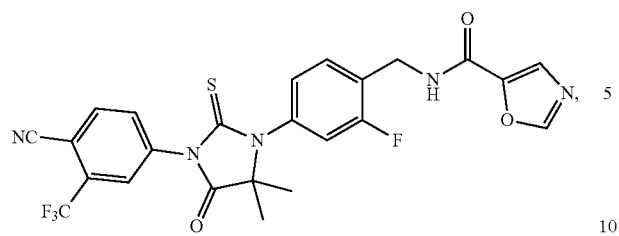
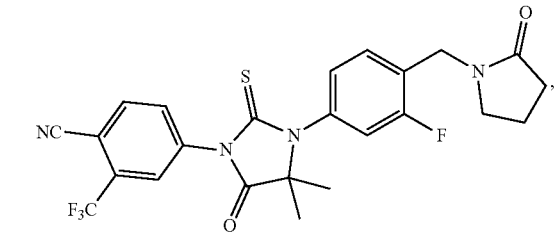
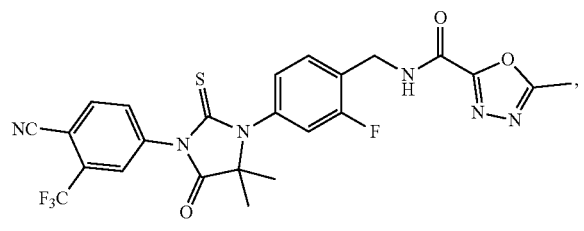
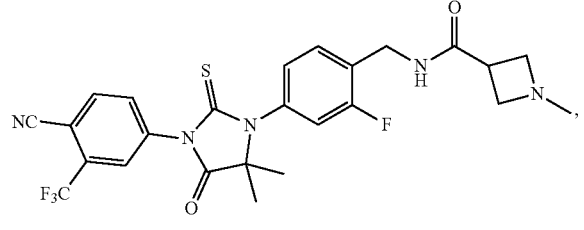
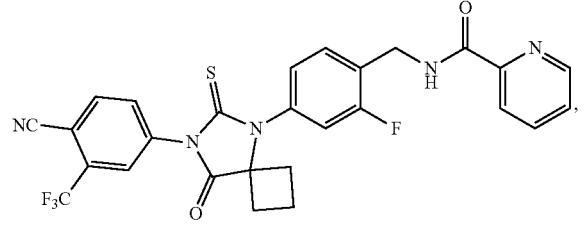
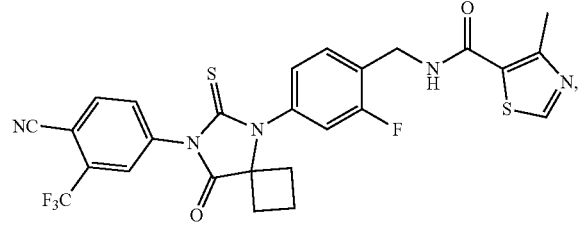
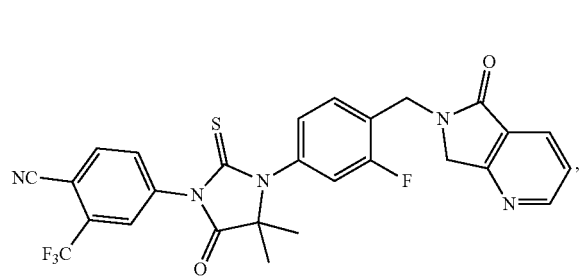
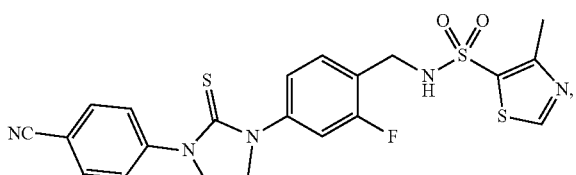
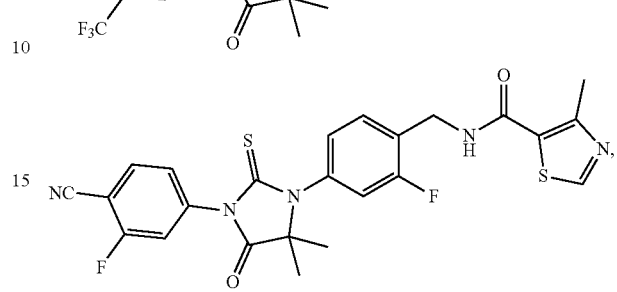
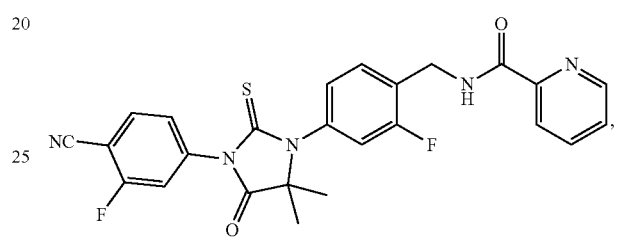
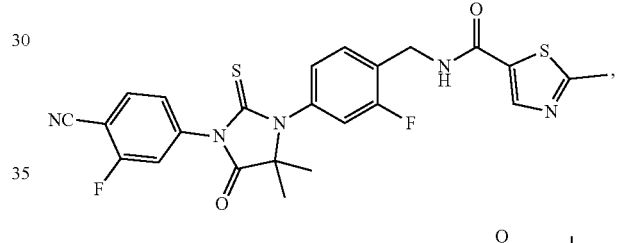
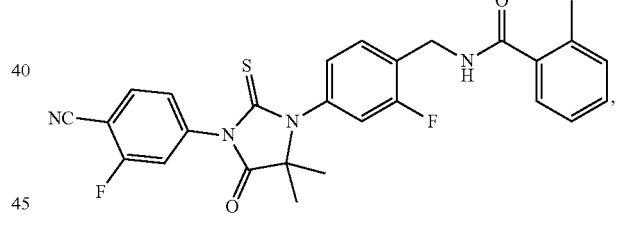
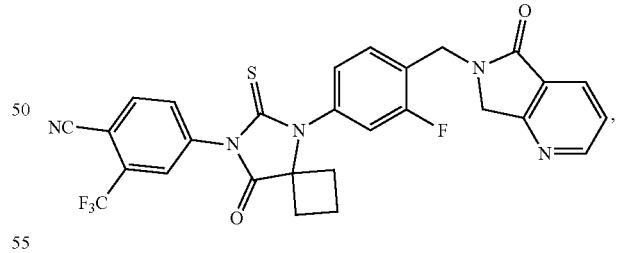
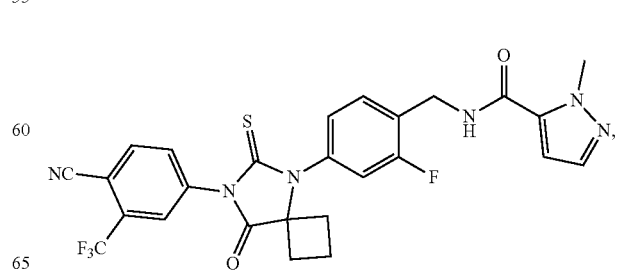

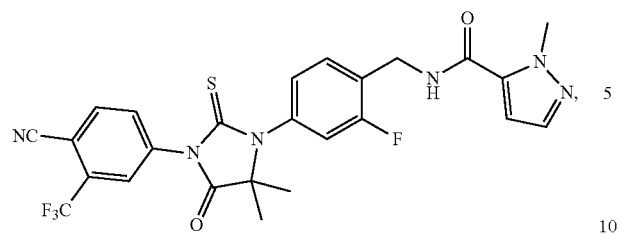
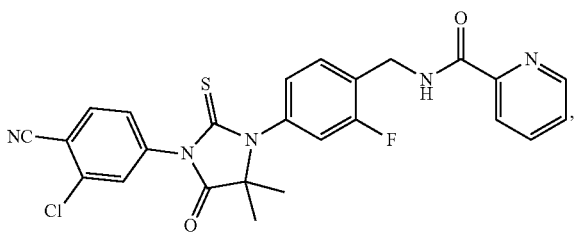
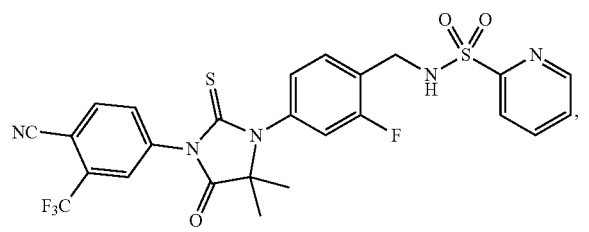
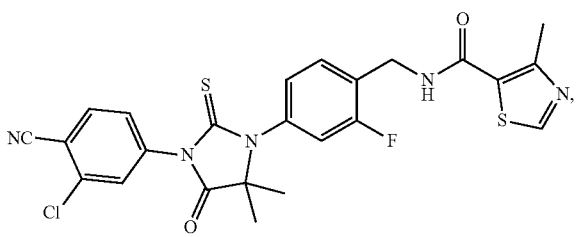
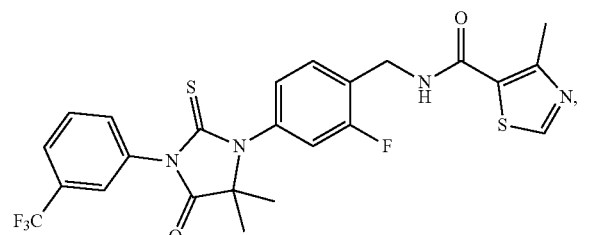
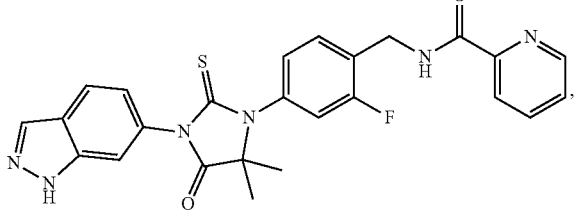
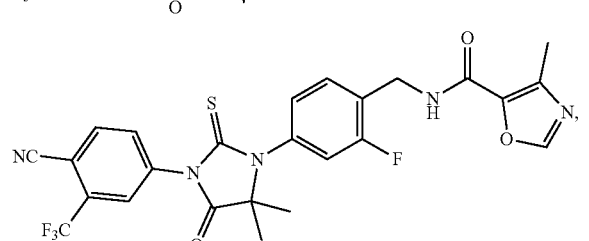
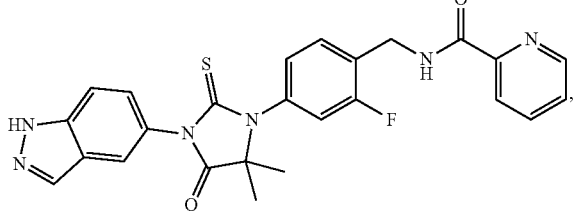
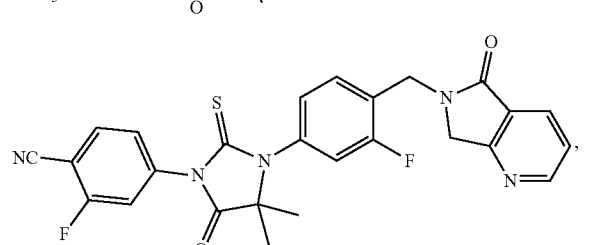
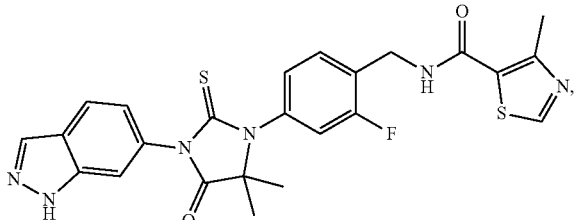
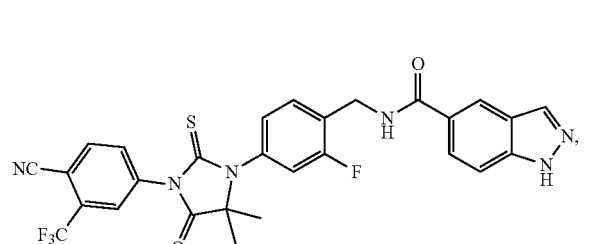
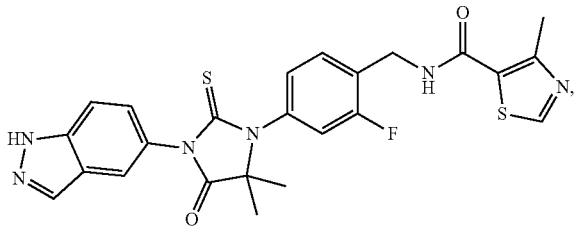
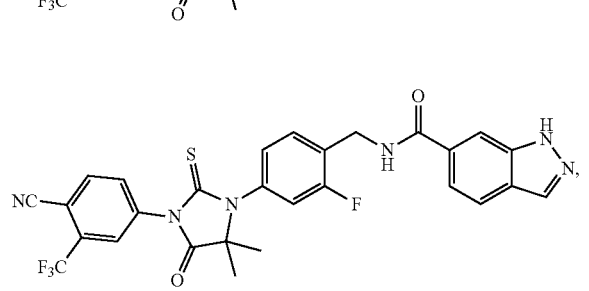
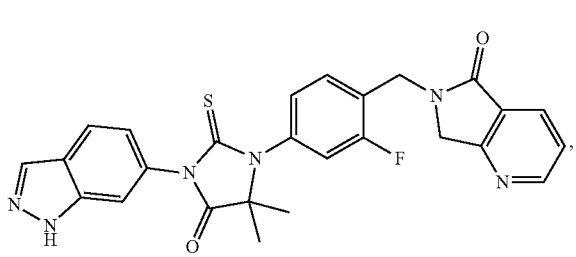

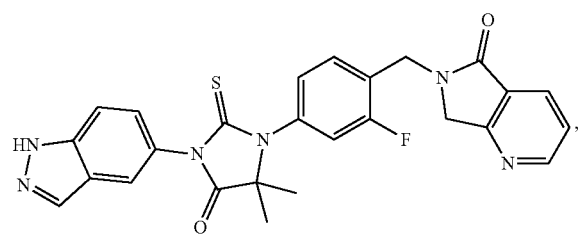
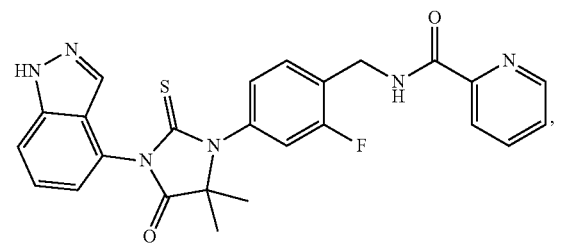
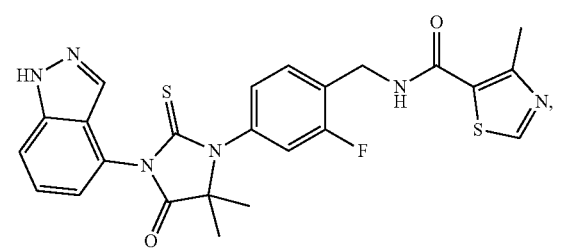
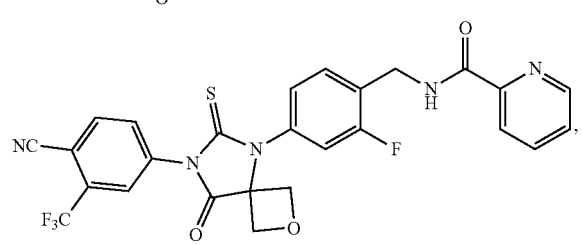
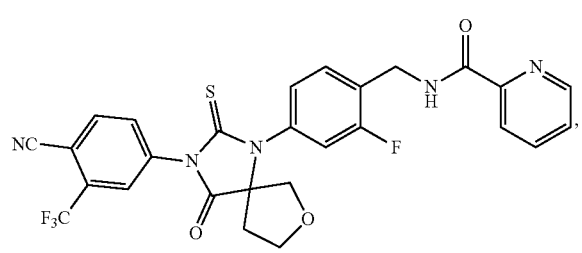
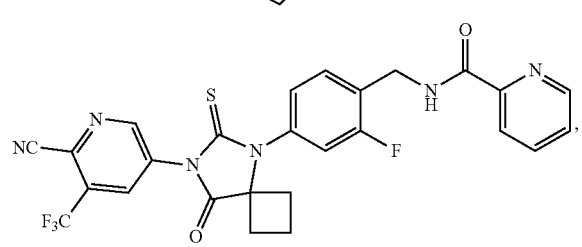
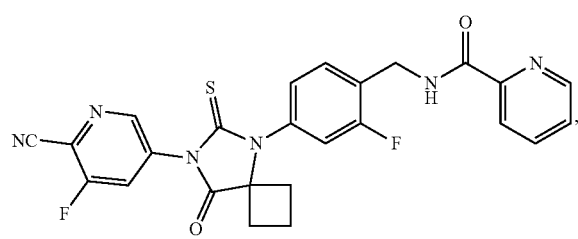
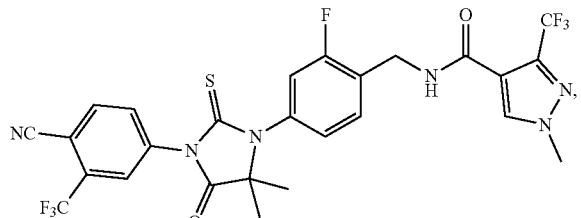
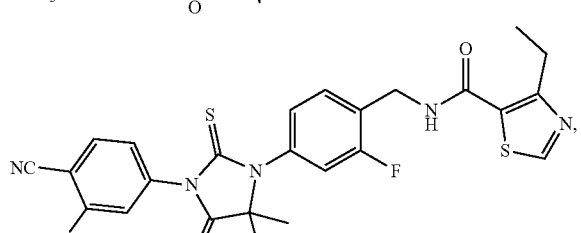
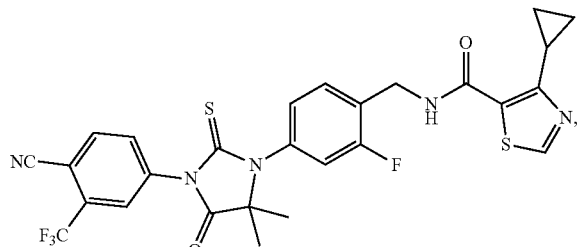
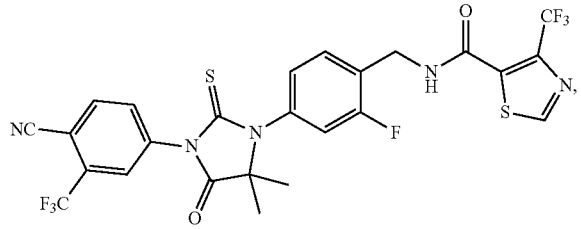
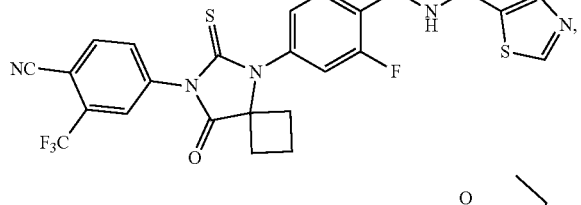
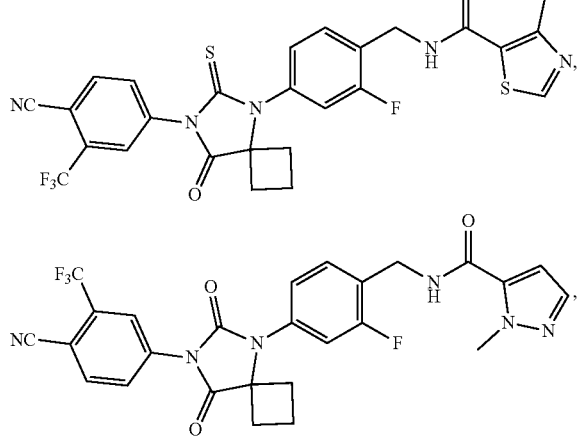

145
-continued
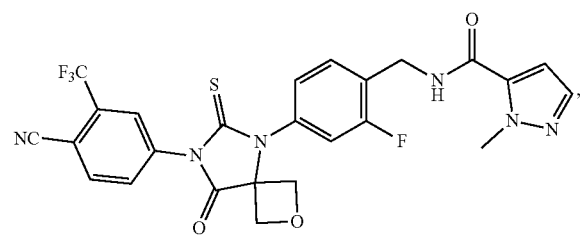
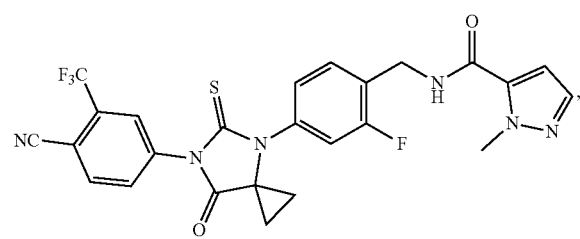
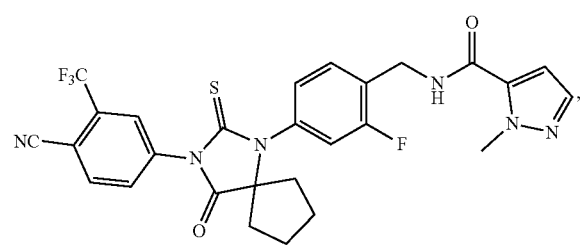
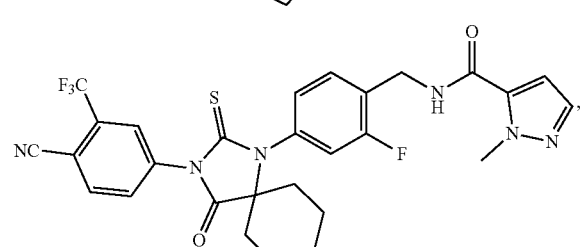
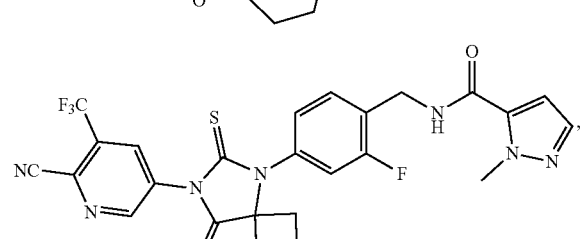
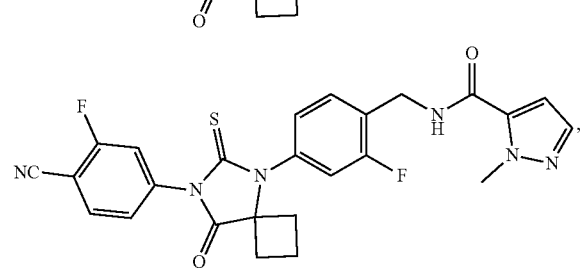
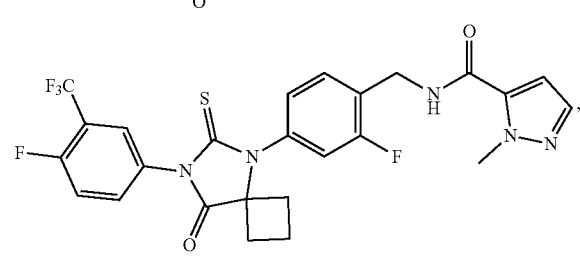
146
-continued
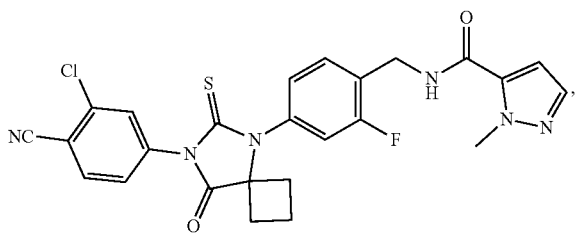
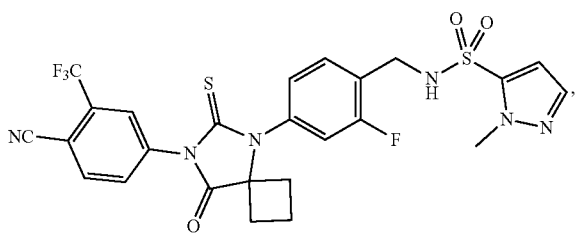
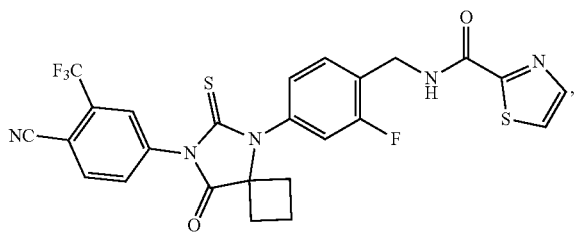
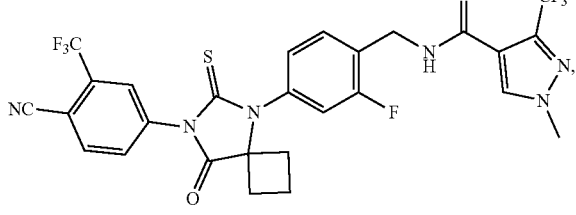
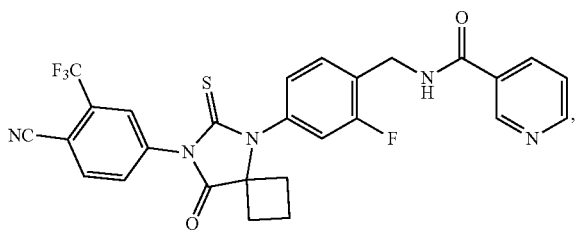
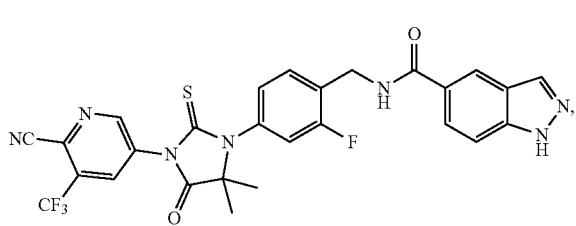
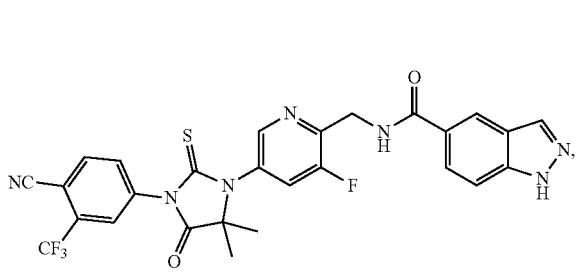

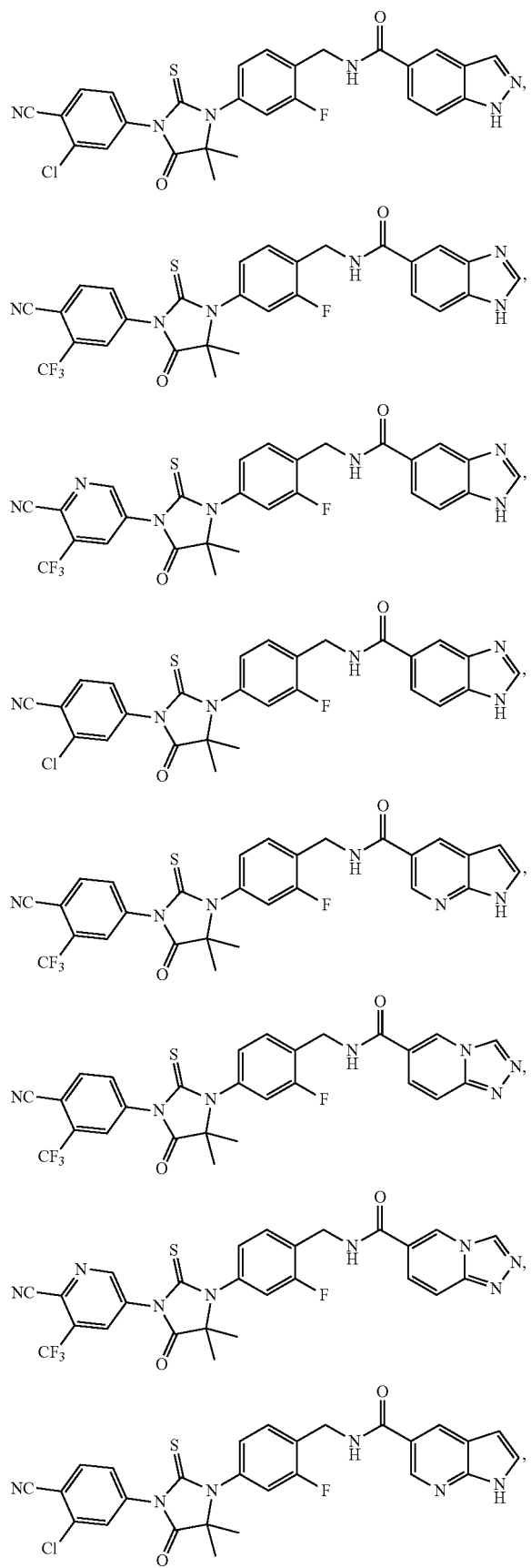
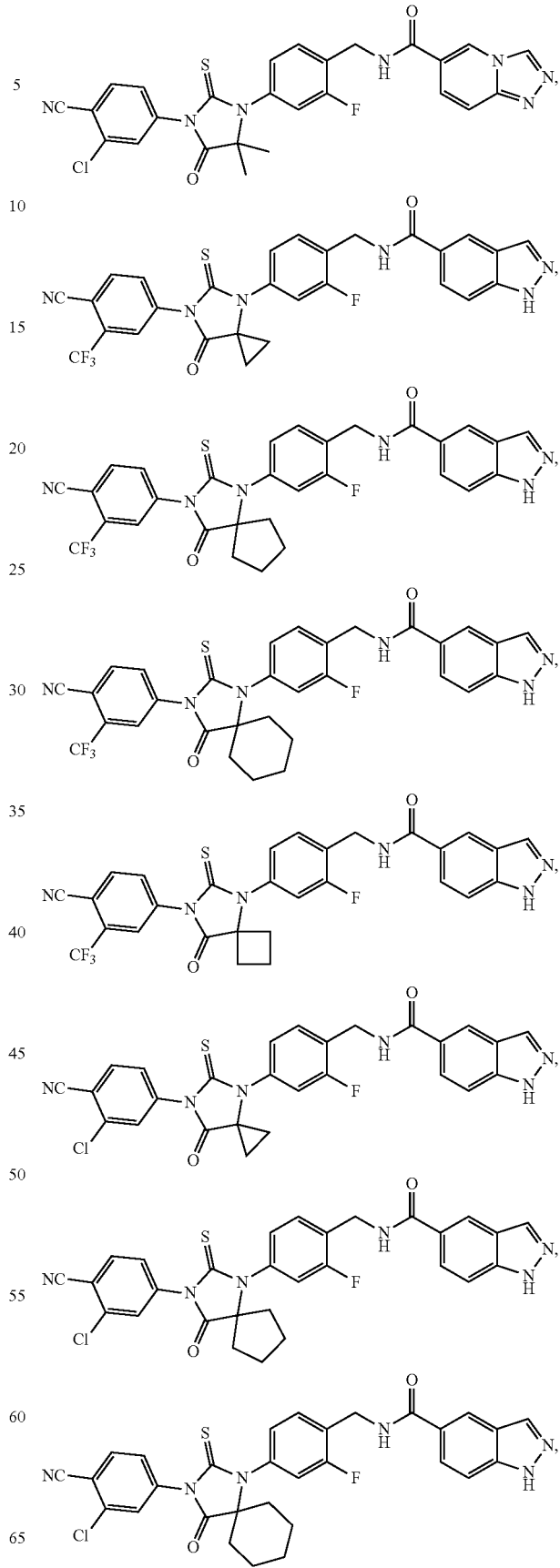

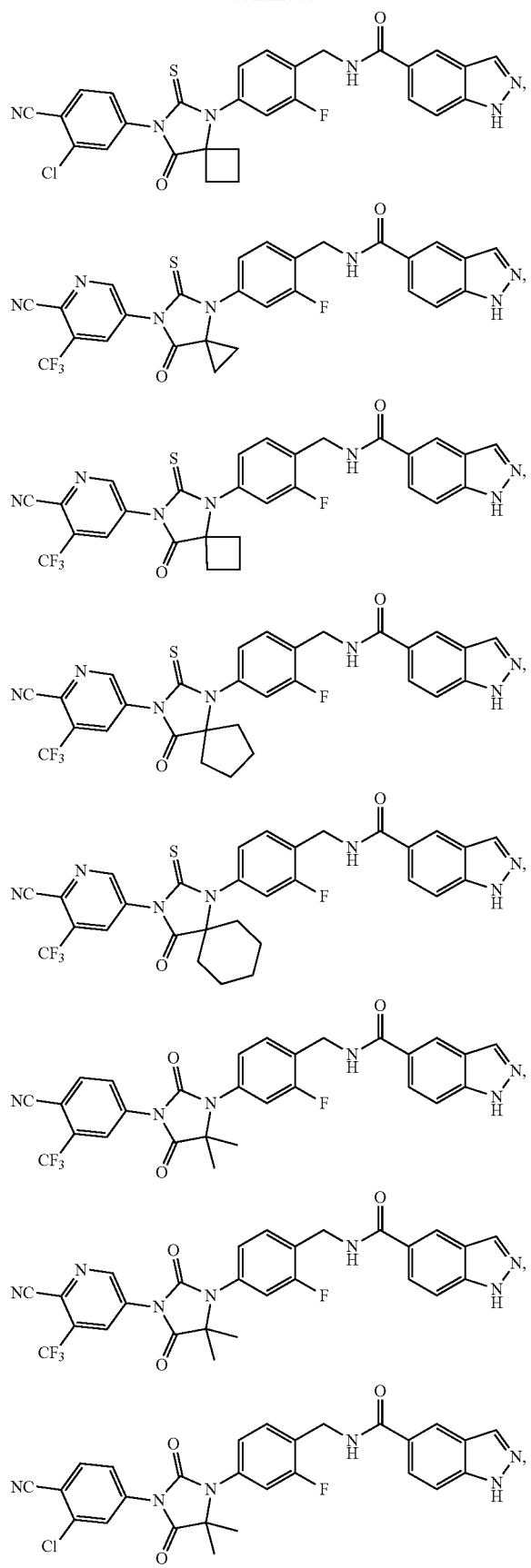
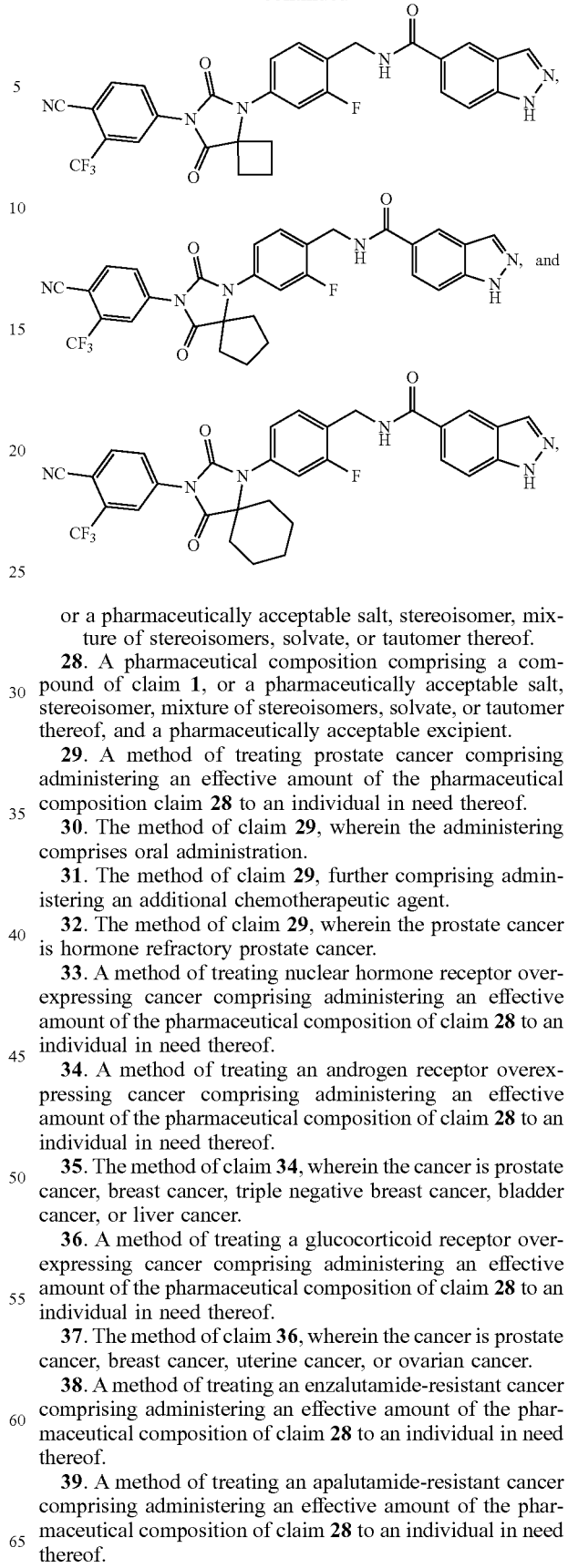

or a pharmaceutically acceptable salt, stereoisomer, mixture of stereoisomers, solvate, or tautomer thereof.

28. A pharmaceutical composition comprising a compound of claim 1, or a pharmaceutically acceptable salt, stereoisomer, mixture of stereoisomers, solvate, or tautomer thereof, and a pharmaceutically acceptable excipient.

29. A method of treating prostate cancer comprising administering an effective amount of the pharmaceutical composition claim 28 to an individual in need thereof.

30. The method of claim 29, wherein the administering comprises oral administration.

31. The method of claim 29, further comprising administering an additional chemotherapeutic agent.

32. The method of claim 29, wherein the prostate cancer is hormone refractory prostate cancer.

33. A method of treating nuclear hormone receptor overexpressing cancer comprising administering an effective amount of the pharmaceutical composition of claim 28 to an individual in need thereof.

34. A method of treating an androgen receptor overexpressing cancer comprising administering an effective amount of the pharmaceutical composition of claim 28 to an individual in need thereof.

35. The method of claim 34, wherein the cancer is prostate cancer, breast cancer, triple negative breast cancer, bladder cancer, or liver cancer.

36. A method of treating a glucocorticoid receptor overexpressing cancer comprising administering an effective amount of the pharmaceutical composition of claim 28 to an individual in need thereof.

37. The method of claim 36, wherein the cancer is prostate cancer, breast cancer, uterine cancer, or ovarian cancer.

38. A method of treating an enzalutamide-resistant cancer comprising administering an effective amount of the pharmaceutical composition of claim 28 to an individual in need thereof.

39. A method of treating an apalutamide-resistant cancer comprising administering an effective amount of the pharmaceutical composition of claim 28 to an individual in need thereof.

* * * * *